(12) United States Patent
Takeuchi et al.

(10) Patent No.: US 9,993,479 B2
(45) Date of Patent: Jun. 12, 2018

(54) TRK-INHIBITING COMPOUND

(71) Applicant: ONO PHARMACEUTICAL CO., LTD., Osaka-shi, Osaka (JP)

(72) Inventors: Jun Takeuchi, Osaka (JP); Satoshi Itadani, Osaka (JP); Kazuya Hashimura, Osaka (JP); Masahiro Ikura, Osaka (JP); Masato Higashino, Osaka (JP); Tetsuya Yasuhiro, Osaka (JP); Takeshi Nagaura, Osaka (JP)

(73) Assignee: ONO PHARMACEUTICAL CO., LTD., Osaka (JP)

(*) Notice: Subject to any disclaimer, the term of this patent is extended or adjusted under 35 U.S.C. 154(b) by 0 days. days.

(21) Appl. No.: 15/679,568

(22) Filed: Aug. 17, 2017

(65) Prior Publication Data

US 2017/0340634 A1 Nov. 30, 2017

Related U.S. Application Data

(63) Continuation of application No. 15/291,700, filed on Oct. 12, 2016, now Pat. No. 9,763,943, which is a (Continued)

(30) Foreign Application Priority Data

Feb. 19, 2013 (JP) ................................. 2013-029563
Jul. 5, 2013 (JP) ................................. 2013-141246

(51) Int. Cl.
*A61K 31/506* (2006.01)
*A61K 31/136* (2006.01)
*A61K 31/444* (2006.01)
*A61K 31/519* (2006.01)
*A61K 31/663* (2006.01)
*A61K 31/5377* (2006.01)
*A61K 45/06* (2006.01)
*C07D 213/75* (2006.01)
*C07D 239/47* (2006.01)
*C07D 401/14* (2006.01)
*C07D 401/12* (2006.01)
*C07D 405/14* (2006.01)
*C07D 409/14* (2006.01)
*C07D 471/04* (2006.01)
*C07D 487/04* (2006.01)

(52) U.S. Cl.
CPC .......... *A61K 31/506* (2013.01); *A61K 31/136* (2013.01); *A61K 31/444* (2013.01); *A61K 31/519* (2013.01); *A61K 31/5377* (2013.01); *A61K 31/663* (2013.01); *A61K 45/06* (2013.01); *C07D 213/75* (2013.01); *C07D 239/47* (2013.01); *C07D 401/12* (2013.01); *C07D 401/14* (2013.01); *C07D 405/14* (2013.01); *C07D 409/14* (2013.01); *C07D 471/04* (2013.01); *C07D 487/04* (2013.01)

(58) Field of Classification Search
CPC .. A61K 31/444; A61K 31/506; A61K 31/519; A61K 31/663; A61K 31/136; A61K 31/5377; A61K 45/06; C07D 213/75; C07D 401/12; C07D 401/14; C07D 239/47; C07D 471/04; C07D 487/04; C07D 405/14; C07D 409/14

See application file for complete search history.

(56) References Cited

U.S. PATENT DOCUMENTS 7,838,524 B2 11/2010 Lee et al.
7,838,541 B2 11/2010 Dumas et al.
(Continued)

FOREIGN PATENT DOCUMENTS

CN 101717373 A 6/2010
JP 2003-501420 A 1/2003
(Continued)

OTHER PUBLICATIONS

Ananya Mandal, MD, "How to prevent cancer", 2013, pp. 1-4, retrieved online at http://www.news-medical.net/health/How-to-prevent-cancer.aspx.*

(Continued)

*Primary Examiner* — Sarah Pihonak
(74) *Attorney, Agent, or Firm* — Foley & Lardner LLP

(57) ABSTRACT

The present invention provides a drug containing a compound having Trk-inhibiting activity as an active ingredient in prophylaxis and/or therapy for Trk-related diseases such as pain, pruritus, lower urinary tract dysfunction, asthma, allergic rhinitis, inflammatory bowel disease or Chagas disease. A compound represented by the general formula (I), wherein all symbols represent the same meanings as described in the specification, a salt thereof, an N-oxide thereof, a solvate thereof or a prodrug thereof is useful as a drug component having Trk-inhibiting activity in prophylaxis and/or therapy of diseases such as pain, pruritus, lower urinary tract dysfunction, asthma, allergic rhinitis, inflammatory bowel disease or Chagas disease.

(I)

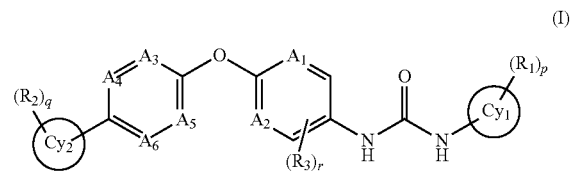

2 Claims, No Drawings

Related U.S. Application Data continuation of application No. 15/173,161, filed on Jun. 3, 2016, now Pat. No. 9,498,453, which is a continuation of application No. 14/768,727, filed as application No. PCT/JP2014/053683 on Feb. 18, 2014, now Pat. No. 9,463,192.

(56) References Cited

U.S. PATENT DOCUMENTS

| | | | |
|---|---|---|---|
| 8,188,133 | B2 | 5/2012 | Liberatore et al. |
| 8,207,166 | B2 | 6/2012 | Lee et al. |
| 8,242,147 | B2 | 8/2012 | Dumas et al. |
| 8,618,141 | B2 | 12/2013 | Dumas et al. |
| 2002/0025976 | A1 | 2/2002 | Chu et al. |
| 2003/0207870 | A1 | 11/2003 | Dumas et al. |
| 2006/0167247 | A1 | 7/2006 | Michelotti et al. |
| 2007/0078121 | A1 | 4/2007 | Flynn et al. |
| 2008/0214545 | A1 | 9/2008 | Lee et al. |
| 2008/0227783 | A1 | 9/2008 | Wan et al. |
| 2008/0227828 | A1 | 9/2008 | Dumas et al. |
| 2008/0261961 | A1 | 10/2008 | Flynn et al. |
| 2009/0105250 | A1 | 4/2009 | Sim et al. |
| 2009/0124633 | A1 | 5/2009 | Jonczyk et al. |
| 2009/0186930 | A1 | 7/2009 | Liberatore et al. |
| 2011/0015195 | A1 | 1/2011 | Dumas et al. |
| 2011/0129440 | A1 | 6/2011 | Tadikonda et al. |
| 2011/0136809 | A1 | 6/2011 | Lee et al. |
| 2011/0195110 | A1 | 8/2011 | Smith et al. |
| 2012/0202818 | A1 | 8/2012 | Tao et al. |
| 2012/0225057 | A1 | 9/2012 | Flynn et al. |
| 2012/0289552 | A1 | 11/2012 | Dumas et al. |
| 2015/0111865 | A1 | 4/2015 | Takeuchi et al. |
| 2016/0000783 | A1 | 1/2016 | Takeuchi et al. |

FOREIGN PATENT DOCUMENTS

| | | |
|---|---|---|
| JP | 2005-522448 A | 7/2005 |
| JP | 2006-519266 A1 | 8/2006 |
| JP | 2007-182433 A | 7/2007 |
| JP | 2007-535565 A | 12/2007 |
| JP | 2008-523071 A | 7/2008 |
| JP | 2008-525498 A | 7/2008 |
| JP | 2008-528585 A | 7/2008 |
| JP | 2009-503073 A | 1/2009 |
| JP | 2009-518298 A | 5/2009 |
| JP | 2009-533362 A | 9/2009 |
| JP | 2009-534450 A | 9/2009 |
| JP | 2011-502160 A | 1/2011 |
| WO | WO-03/068228 A1 | 8/2003 |
| WO | WO-2004/078128 A2 | 9/2004 |
| WO | WO-2004/078128 A3 | 9/2004 |
| WO | WO-2007/066784 A2 | 6/2007 |
| WO | WO-2007/076473 A2 | 7/2007 |
| WO | WO-2007/076473 A3 | 7/2007 |
| WO | WO-2008/131227 A1 | 10/2008 |
| WO | WO-2008/131276 A1 | 10/2008 |
| WO | WO-2010/057833 A1 | 5/2010 |
| WO | WO-2010/144522 A1 | 12/2010 |
| WO | WO-2013/161919 A1 | 10/2013 |
| WO | WO-2014/129431 A1 | 8/2014 |

OTHER PUBLICATIONS

Cao et. al., "Cancer research: past, present and future", Nature Reviews Cancer, 2011, Nature Publishing Group, vol. 11, pp. 749-754.*

Lemanske et. al., "Asthma: clinical expression and molecular mechanisms", J. Allergy Clin. Immunol., 2010, American Academy of Allergy, Asthma, and Immunology, vol. 125, pp. S95-S102.*
Leaf, "Why we're losing the war on cancer—and how to win it", Fortune, 2004, Time Inc., pp. 1-26.*
Botchkarev et al., "Neurotrophins in Skin Biology and Pathology", Journal of Investigative Dermatology, Jan. 2006, vol. 126, pp. 1719-1727.
Di Mola et. al., "Nerve growth factor and Trk high affinity receptor (TrkA) gene expression in inflammatory bowel disease", Gut, 2000, pp. 670-678.
Evans et al., "Proof of Concept Trial of Tanezumab for the Treatment of Symptoms Associated With Interstitial Cystitis", The Journal of Urology, May 2011, vol. 185, pp. 1716-1721.
Ghilardi et al. "Sustained blockade of neurotrophin receptors TrkA, TrkB and TrkC reduces non-malignant skeletal pain but not the maintenance of sensory and sympathetic nerve fibers", Bone, 2011, vol. 48, pp. 389-398.
Ghilardi et. al., "Administration of a tropomyosin receptor kinase inhibitor attenuates sarcoma-induced nerve sprouting, neuroma formation and bone cancer pain", Molecular Pain, Dec. 2010, pp. 1-12.
Hefti et al., "Novel class of pain drugs based on antagonism of NGF", Trends in Pharmacological Sciences, vol. 27, No. 2, Feb. 2006, pp. 85-91.
Huang et al. "Trk Receptors: Roles in Neuronal Signal Transduction", Annual Review of Biochemistry, Mar. 27, 2003, pp. 609-642.
International Search Report dated May 27, 2014 issued in PCT/JP2014/053683.
Katz et. al., "Efficacy and safety of tanezumab in the treatment of chronic low back pain", Pain, May 2011, pp. 2248-2258.
Lane et. al.,"Tanezumb for the Treatment of Pain from Osteoarthritis of the Knee", The New England Journal of Medicine, Oct. 2010, pp. 1521-1531.
Office Action issued in Singaporean Patent Application No. 11201506514Q dated May 3, 2016.
Raap et al., "The role of neurotrophins in the pathophysiology of allergic rhinitis", Current Opinion in Allergy and Clinical Immunology, 2010, pp. 8-13.
Scuri et al., "The Role of Neurotrophins in Inflammation and Allergy", Inflammation & Allergy-Drug Targets, 2010, pp. 173-180.
Shelton et. al., "Nerve growth factor mediates hyperalgesia and cachexia in auto-immune arthritis", Pain, Mar. 2005, pp. 8-16.
Sun et al., "Design, synthesis, and in vitro antitumor evaluation of novel diaryl ureas derivatives", European Journal of Medicinal Chemistry., vol. 45, 2010, pp. 2299-2306.
Wang et. al.,"Trk kinase inhibitors as new treatments for cancer and pain", Expert Opinion Therapeutic Patients, 2009, pp. 305-319.
Wild et al., "Antibodies to Nerve Growth Factor Reverse Established Tactile Allodynia in Rodent Models of Neuropathic Pain without Tolerance", The Journal of Pharmacology and Experimental Therapeutics, vol. 322, No. 1, Apr. 2007, pp. 282-287.
Zhu et. al. "Nerve Growth Factor Modulates TRPV1 Expression and Function and Mediates Pain in Chronic Pancreatitis", Gastroenterology, 2011, pp. 370-377.
Extended European Search Report for European Patent Application No. 14753934.0 dated Jun. 14, 2016.
Notification of Reasons for Refusal issued in Japanese Patent Application No. 2016-112809 dated Mar. 10, 2017.
Thress et al., "Identification and preclinical characterization of AZ-23, a novel, selective, and orally bioavailable inhibitor of the Trk kinase pathway", Mol Cancer Ther, 2009, vol. 8, No. 7, p. 1818-1827.
Tsukamoto et al., A novel, potent and selective pan-Trk inhibitor ONO-5390556, demonstrates therapeutic efficacy in cancer cells harboring the TrkA rearrangement, Cancer Research, 2015, vol. 75, No. 15, suppl. Abstract No. 788.

* cited by examiner

TRK-INHIBITING COMPOUND

CROSS REFERENCE TO RELATED APPLICATIONS

This application is a continuation of U.S. patent application Ser. No. 15/291,700, filed Oct. 12, 2016, which is a continuation of U.S. patent application Ser. No. 15/173,161, filed Jun. 3, 2016 (now U.S. Pat. No. 9,498,453), which is a continuation of U.S. patent application Ser. No. 14/768,727, filed Aug. 18, 2015 (now U.S. Pat. No. 9,463,192), which is a National Phase of PCT/JP2014/053683, filed Feb. 18, 2014, which claims priority to Japanese Application No. 2013-029563, filed Feb. 19, 2013 and Japanese Application No. 2013-141246, filed Jul. 5, 2013, the entireties of which are incorporated herein by reference.

TECHNICAL FIELD

The present invention relates to a Trk-inhibiting compound or a salt thereof and a medicament containing the same as an active ingredient. More specifically, the present invention relates to a Trk-inhibiting compound represented by the general formula (I):

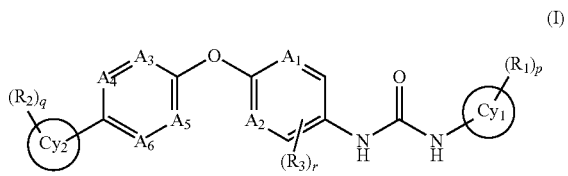

wherein all symbols represent the same meanings as described hereinbelow, and a salt thereof, an N-oxide thereof, a solvate thereof or a prodrug thereof (hereinafter referred to as "the present compound") and a medicament containing the same as an active ingredient.

BACKGROUND ART

The tropomyosin receptor kinase (hereinafter abbreviated as "Trk") family is classified as receptor tyrosine kinases and comprises TrkA which is a high-affinity receptor of nerve growth factor (hereinafter abbreviated as NGF), TrkB which is a high-affinity receptor of brain-derived neutrophic factor (BDNF) and neurotrophin (hereinafter abbreviated as NT)-4/5 and TrkC which is a high-affinity receptor of NT-3. All Trk receptors are highly expressed in nerve tissues and are involved in differentiation and maintenance of functions of nerve cells (see Non-Patent Document 1). Meanwhile it has been known that activation of TrkA in peripheral nerves by NGF initiates hyperalgesia (see Non-Patent Document 2) and based on clinical and non-clinical test results using anti-NGF antibodies and non-clinical test results using low-molecular weight Trk inhibitors, involvement of TrkA has been reported in nociceptive pain of osteoarthritis, chronic low back pain, rheumatoid arthritis, bone fracture, interstitial cystitis and chronic pancreatitis, neuropathic pain as well as cancer pain combining both types of pain described above (see Non-Patent Document 3 to 10). Moreover, Trk receptors are expressed on cancer cells such as neuroblastoma, prostate cancer and pancreatic cancer, inflammatory cells such as mast cells and eosinophils, immunocompetent cells such as T cells and B cells and keratinocytes and are reported to be potentially involved in proliferation, migration and metastasis of cancer cells, inflammatory diseases such as ulcerative colitis and Crohn's disease, allergic diseases such as asthma, rhinitis and atopic dermatitis and other diseases such as psoriasis (see Non-Patent Document 11 to 15). Therefore compounds having Trk-inhibiting activity may be applied to therapy of nociceptive pain, neuropathic pain and pain combining both types of pain, cancer, inflammatory diseases, allergic diseases and psoriasis.

Accordingly it is expected that development of Trk-inhibiting agents may provide novel types of prophylactic and/or therapeutic agents for pain and the like.

Meanwhile Patent Document 1 discloses a method for treating or preventing a disease in a human or other mammal regulated by tyrosine kinase, comprising administering, to a human or other mammal in need thereof, a compound of the following formula (Ia), a salt thereof, an isomer thereof or a prodrug.

The general formula (Ia) is as follows:

wherein Aa is selected from the group consisting of the following (i) to (iii) and the like;

(i) phenyl, optionally substituted with 1 to 3 substituents independently selected from the group consisting of $Ra^1$, $ORa^1$, a halogen and the like;

(ii) naphthyl, optionally substituted with 1 to 3 substituents independently selected from the group consisting of $Ra^1$, $ORa^1$, a halogen and the like;

(iii) a 5- to 6-membered monocyclic heteroaryl group, optionally substituted with 1 to 3 substituents independently selected from the group consisting of $Ra^1$, $ORa^1$, a halogen and the like and having 1 to 3 heteroatoms independently selected from the group consisting of O, N and S;

Ba is selected from the group consisting of the following (i) to (iii) and the like;

(i) phenyl, optionally substituted with 1 to 3 substituents independently selected from the group consisting of -La-Ma, $C_1$-$C_5$ linear or branched alkyl, halogen and the like;

(ii) naphthyl, optionally substituted with 1 to 3 substituents independently selected from the group consisting of -La-Ma, a $C_1$-$C_5$ linear or branched alkyl, a halogen and the like;

(iii) a 5- to 6-membered monocyclic heteroaryl group, optionally substituted with 1 to 3 substituents independently selected from the group consisting of -La-Ma, a $C_1$-$C_5$ linear or branched alkyl, a halogen and the like and having 1 to 3 heteroatoms independently selected from the group consisting of O, N and S;

La is selected from the group consisting of —$(CH_2)_{ma}$—O—$(CH_2)_{la}$—, —$(CH_2)_{ma}$—C(O)—$(CH_2)_{la}$— and the like, wherein the variables ma and la are integers independently selected from 0 to 4;

Ma is selected from the group consisting of the following (i) to (iii) and the like;

(i) phenyl, optionally substituted with 1 to 3 substituents independently selected from the group consisting of $Ra^1$, $ORa^1$, a halogen and the like;

(ii) naphthyl, optionally substituted with 1 to 3 substituents independently selected from the group consisting of $Ra^1$, $ORa^1$, a halogen and the like;

(iii) a 5- to 6-membered monocyclic heteroaryl group, optionally substituted with 1 to 3 substituents independently selected from the group consisting of $Ra^1$, $ORa^1$, a halogen and the like and having 1 to 3 heteroatoms independently selected from the group consisting of O, N and S;

wherein $Ra^1$ is independently selected from the group consisting of (a) a hydrogen, (b) a $C_1$-$C_6$ alkyl, (c) phenyl, (d) a 5- to 6-membered monocyclic heteroaryl or a 8- to 10-membered bicyclic heteroaryl both having 1 to 4 heteroatoms selected from the group consisting of O, N and S, (e) a $C_1$-$C_3$ alkyl-phenyl and (f) an alkyl-heteroaryl having 1 to 4 heteroatoms selected from the group consisting of O, N and S; $Ra^1$ is, when it is not a hydrogen, optionally substituted with 1 to 3 substituents independently selected from the group consisting of a $C_1$-$C_5$ linear, branched or cyclic alkyl, a $C_1$-$C_3$ alkoxy, hydroxy, amino, a $C_1$-$C_3$ alkylamino, a $C_2$-$C_6$ dialkylamino, a halogen, cyano and nitro; and the definitions of the groups are partially abstracted.

Patent Document 1 discloses that the compound therein inhibits KDR and thereby is used for a method of treatment of diseases mediated by VEGF induced signal transduction pathways in a human or other mammal, particularly retinopathy or retinopathy of prematurity. However, it is not disclosed or suggested that the compound disclosed therein has Trk-inhibiting activity and Patent Document 1 does not specifically disclose the present compound.

Patent Document 2 discloses that a compound represented by the general formula (Ib):

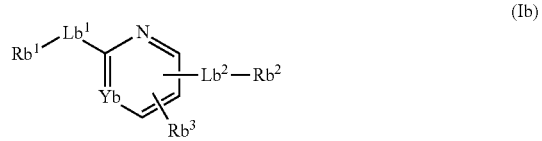

wherein:
Yb is N or CH;
$Lb^1$ is a bond, —O—, —S—, —SO—, —SO$_2$— or the like;
$Lb^2$ is a bond, —NHC(O)NH—, —NHC(O)— or the like;
$Rb^1$ is (i) $Rb^5$ or (ii) a $C_1$-$C_6$ alkyl optionally substituted with one or more halogen, $Rb^5$ or the like;
$Rb^2$ is (i) a $C_1$-$C_6$ alkyl or (ii) an aryl or heteroaryl, each of which is optionally substituted with one or more halogen, $Rb^9$, $ORb^9$, $SRb^9$, $N(Rb^9)_2$, $C(O)Rb^9$ or the like;
$Rb^3$ is a hydrogen, a halogen, a $C_1$-$C_6$ alkyl or the like;
$Rb^5$ is a cycloalkyl, a heterocycle, an aryl or a heteroaryl, each of which is optionally substituted with one or more halogen, $ORb^6$, $N(Rb^6)_2$, $Rb^7$, $ORb^7$ or the like;
$Rb^7$ is a cycloalkyl, a heterocycle, an aryl or a heteroaryl, each of which is optionally substituted with one or more halogen, hydroxy, $N(Rb^6)_2$ or the like; and
each $Rb^6$ is independently a hydrogen or a $C_1$-$C_4$ alkyl (the definitions of the groups are partially abstracted), a tautomer, enantiomer, pharmaceutically acceptable salt, hydrate, solvate, complex or a prodrug thereof acts as an endogenous utrophin upregulator. However, it is not disclosed or suggested that the compounds have Trk-inhibiting activity. In addition, Patent Document 2 does not specifically disclose the present compound.

Further, Patent Document 3 discloses that a compound represented by the general formula (Ic):

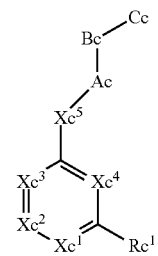

wherein:
Ac and Cc are each independently selected from the group consisting of an aryl and heteroaryl, both of which may be optionally substituted;
Bc is selected from the group consisting of —N(H)C(O)N(H)— and —N(H)C(O)N(H)CH$_2$—;
$Xc^1$ to $Xc^4$ are each selected from the group consisting of $C(Rc^2)$ and N and at least one of $Xc^1$ to $Xc^4$ is N;
$Rc^1$ is $C(Rc^3)$ $(Rc^4)$, $N(Rc^3)$, O or $S(O)_{mc}$; and
$Rc^1$ is selected from the group consisting of a heteroaryl and heterocycloalkyl, both of which may be optionally substituted (the definitions of the groups are partially abstracted), a salt or ester thereof or a prodrug thereof has B-Raf-inhibiting activity. However, it is not disclosed or suggested that the compounds have Trk-inhibiting activity. In addition, Patent Document 3 does not disclose the present compound.

None of the Trk-inhibiting compounds which have been known by now has a chemical structure characterized by "urea group-ring-O-ring-ring" as the compounds of the present invention.

Patent Document 1: WO 2003/068228
Patent Document 2: WO 2010/057833
Patent Document 3: WO 2007/076473
Non-Patent Document 1: Annual Review of Biochemistry, 72, 609-642, 2003
Non-Patent Document 2: Trends in Pharmacological Sciences, 27, 85-91, 2006
Non-Patent Document 3: New England Journal of Medicine, 363, 1521-1531, 2010
Non-Patent Document 4: Pain, 152, 2248-2258, 2011
Non-Patent Document 5: Journal of Urology, 185, 1716-1721, 2011
Non-Patent Document 6: Pain, 116, 8-16, 2005
Non-Patent Document 7: Bone, 48, 389-398, 2011
Non-Patent Document 8: Molecular Pain, 6, 87, 2010
Non-Patent Document 9: Journal of Pharmacological and Experimental Therapeutics, 322, 282-287, 2007
Non-Patent Document 10: Gastroenterology, 141, 370-377, 2011
Non-Patent Document 11: Expert Opinion Therapeutic Patents, 19, 305-319, 2009
Non-Patent Document 12: Gut, 46, 670-679, 2000
Non-Patent Document 13: Current Opinion in Allergy and Clinical Immunology, 10, 8-13, 2010
Non-Patent Document 14: Inflammation and Allergy Drug Targets, 9, 173-180, 2010
Non-Patent Document 15: Journal of Investigative Dermatology, 126, 1719-1727, 2006

DISCLOSURE OF THE INVENTION

An object of the present invention is to create a compound having selective Trk-inhibiting activity and find a compound useful as a prophylactic and/or therapeutic agent for various diseases typically including pain.

The present inventors have carried out exhaustive studies in order to find compounds which have selective Trk-inhibiting activity and can be prophylactic and/or therapeutic agents for various diseases typically including pain, and as a result have found that the compounds represented by the following general formula (I) have Trk-inhibiting action, have excellent kinase selectivity and can persistently inhibit NGF vascular hyper permeability, thereby completing the present invention.

Thus the present invention relates to the followings:

[1] A compound represented by the general formula (I):

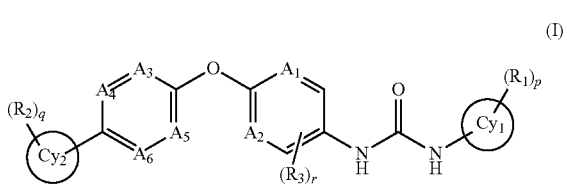

(I)

a compound represented by the general formula (I):
wherein:
a ring $Cy_1$ represents a C3-10 monocyclic carbocycle or bicyclic carbocycle or a 4- to 10-membered monocyclic heterocycle or bicyclic heterocycle;
a ring $Cy_1$ represents a 4- to 10-membered monocyclic heterocycle or bicyclic heterocycle excluding a heterocycle 1,3-thiazol-5-yl group;
$R_1$ represents:
(1) a halogen;
(2) a C1-6 alkyl group, C2-6 alkenyl group or C2-6 alkynyl group optionally substituted with a substituent selected from the group consisting of (i) a halogen and (ii) a hydroxy group;
(3) a C5-6 monocyclic carbocycle optionally substituted with one or two $R_5$ groups;
(4) a 5- to 6-membered monocyclic heterocycle optionally substituted with one or two $R_5$ groups;
(5) —S(O)$_{m1}$—R$_6$;
(6) —SO$_2$NR$_7$R$_8$;
(7) —C(O) OR$_9$;
(8) —NR$_{10}$C(O)R$_{11}$;
(9) —C(O)NR$_{12}$R$_{13}$;
(10) —OR$_{14}$;
(11) —NR$_{15}$R$_{16}$;
(12) a cyano group; or
(13) a nitro group;
$R_5$ represents:
(1) a halogen;
(2) —S(O)$_{m2}$—R$_{17}$;
(3) —SO$_2$NR$_{18}$R$_{19}$;
(4) —C(O)OR$_{20}$;
(5) —NR$_{21}$C(O)R$_{22}$;
(6) —C(O)NR$_{23}$R$_{24}$;
(7) —OR$_{25}$;
(8) —NR$_{26}$R$_{27}$;
(9) a cyano group;
(10) a nitro group; or
(11) a C1-3 alkyl group optionally substituted with a substituent selected from the group consisting of (i) a halogen, (ii) a hydroxy group and (iii) an oxo group;
when two $R_5$ groups are present, the $R_5$ groups may be independently the same or different;

when, further, two $R_5$ groups are respectively and independently a C1-3 alkyl group or a hydroxy group and the $R_5$ groups are attached to carbon atoms adjacent to each other on the C5-6 monocyclic carbocycle or the 5- to 6-membered monocyclic heterocycle, the $R_5$ groups may together form a ring;
$R_6$ to $R_{27}$ respectively and independently represent (1) a hydrogen atom or (2) a C1-6 alkyl group optionally substituted with (i) a halogen or (ii) a hydroxy group;
when $R_{18}$ and $R_{19}$ are respectively and independently a C1-6 alkyl group, $R_{18}$ and $R_{19}$ groups may together form a ring;
$R_2$ represents:
(1) a halogen;
(2) a C1-6 alkyl group optionally substituted with (i) a halogen or (ii) a hydroxy group;
(3) a C3-6 cycloalkyl group optionally substituted with (i) a halogen or (ii) a hydroxy group;
(4) a C1-6 alkoxy group optionally substituted with a halogen;
(5) —NR$_{28}$R$_{29}$;
(6) a 3- to 7-membered monocyclic heterocycle; or
(7) —O-(3- to 7-membered monocyclic heterocycle);
$R_{28}$ and $R_{29}$ respectively and independently represent (1) a hydrogen atom or (2) a C1-6 alkyl group optionally substituted with (i) a halogen or (ii) a hydroxy group;
$A_1$ and $A_2$ respectively and independently represent =CR$_3$— or =N—;
$A_3$, $A_4$, $A_5$ and $A_6$ respectively and independently represent =CR$_4$— or =N—;
$R_3$ and $R_4$ respectively and independently represent a hydrogen atom or a halogen;
m1 represents an integer of 0 to 2;
m2 represents an integer of 0 to 2;
p represents an integer of 0 to 7;
q represents an integer of 0 to 7;
r represents an integer of 0 to 2;
provided that when p, q and r respectively represent an integer of 2 or more, $R_1$, $R_2$ and $R_3$ groups may be respectively and independently the same or different, a salt thereof, an N-oxide thereof, a solvate thereof or a prodrug thereof;

[2] the compound according to the above [1], wherein the ring $Cy_2$ is a 5- to 10-membered monocyclic aromatic heterocycle or bicyclic aromatic heterocycle excluding a heterocycle 1,3-thiazol-5-yl group;

[3] the compound according to the above [1] or [2], wherein the ring $Cy_2$ is a pyridine ring, a pyrimidine ring, a pyrazolopyrimidine ring, an imidazopyridazine ring, an imidazopyridine ring, a pyrrolopyridine ring, an imidazopyrazine ring or a pyrazolopyridine ring;

[4] the compound according to any one of the above [1] to [3], wherein one of $A_1$ and $A_2$ is =N— and the other is =CH— or both are =N— and $A_3$, $A_4$, $A_5$ and $A_6$ are =CH—;

[5] the compound according to the above [1], wherein the general formula (I) is represented by the general formula (I-i) or the general formula (I-ii):

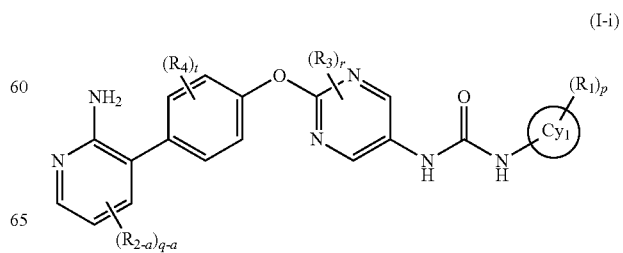

(I-i)

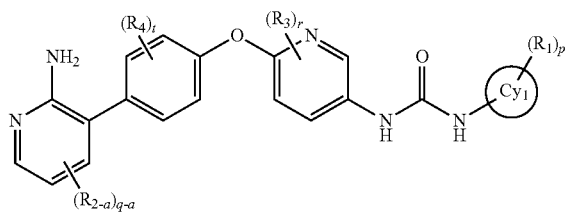

wherein $R_{2-a}$ represents the same meaning as $R_2$; q-a represents an integer of 0 to 3; t represents an integer of 0 to 4; and other symbols represent the same meanings as those described in the above [1], provided that when q-a and t represent an integer of 2 or more, $R_{2-a}$ and $R_4$ groups may be respectively and independently the same or different;

[6] the compound according to the above [5], wherein $R_{2-a}$ is a 3- to 7-membered monocyclic heterocycle;

[7] the compound according to the above [1], wherein the general formula (I) is represented by the general formula (I-iii) or the general formula (I-iv):

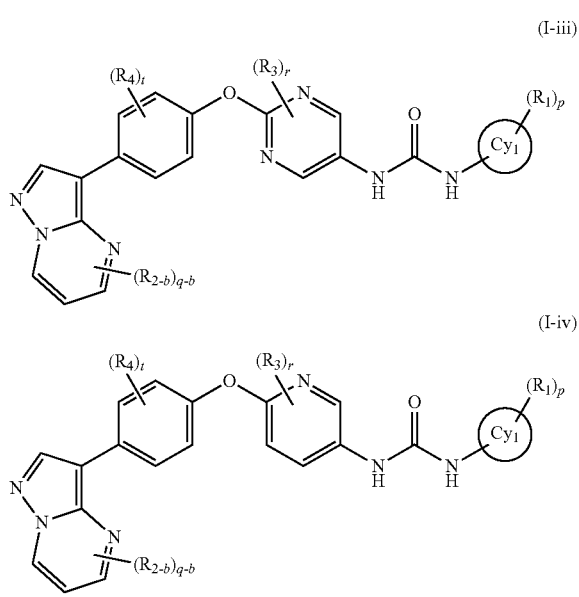

wherein $R_{2-b}$ represents the same meaning as $R_2$; q-b represents an integer of 0 to 4; and other symbols represent the same meanings as those described in the above [1] and [5], provided that when q-b represents an integer of 2 or more, $R_{2-b}$ groups may be respectively and independently the same or different;

[8] the compound according to the above [7], wherein $R_{2-b}$ is a 3- to 7-membered monocyclic heterocycle;

[9] the compound according to any one of the above [1] to [8], wherein the ring $Cy_1$ is a benzene ring or a 5- to 6-membered monocyclic aromatic heterocycle;

[10] the compound according to the above [9], wherein the ring $Cy_1$ is a benzene ring, a pyridine ring or a pyrazole ring;

[11] a pharmaceutical composition including the compound represented by the general formula (I) according to the above [1], a salt thereof, an N-oxide thereof, a solvate thereof or a prodrug thereof as an active ingredient;

[12] the composition according to the above [11], which is a Trk inhibitor;

[13] the composition according to the above [11], which is a prophylactic and/or therapeutic agent for Trk-related disease;

[14] the composition according to the above [13], wherein the Trk-related disease is pain, pruritus, lower urinary tract dysfunction, asthma, allergic rhinitis, inflammatory bowel disease or Chagas disease;

[15] the composition according to the above [14], wherein the pain is pain of osteoarthritis, cancer pain, chronic low back pain, low back pain of osteoporosis, pain of bone fracture, pain of rheumatoid arthritis, neuropathic pain, postherpetic pain, pain of diabetic neuropathy, fibromyalgia, pain of pancreatitis, pain of interstitial cystitis, pain of endometriosis, pain of irritable bowel syndrome, migraine, postoperative pain or pain of pulpitis;

[16] a medicament which is a combination of the compound represented by the general formula (I) according to the above [1], a salt thereof, an N-oxide thereof, a solvate thereof or a prodrug thereof and at least one selected from acetaminophen, a nonsteroid antiinflammatory drug, an opioid, an antidepressant, an antiepileptic agent, an N-methyl-D-aspartate antagonist, a muscle relaxant, an antiarrhythmic agent, a steroid and a bisphosphonate;

[17] a method for prophylaxis and/or therapy of Trk-related disease, including administering, to a patient, an effective amount of the compound represented by the general formula (I) according to the above [1], a salt thereof, an N-oxide thereof, a solvate thereof or a prodrug thereof;

[18] the compound represented by the general formula (I) according to the above [1], a salt thereof, an N-oxide thereof, a solvate thereof or a prodrug thereof for prophylaxis and/or therapy of Trk-related disease;

[19] a method for inhibiting Trk, including administering, to a patient, an effective amount of the compound represented by the general formula (I) according to the above [1], a salt thereof, an N-oxide thereof, a solvate thereof or a prodrug thereof;

[20] use of the compound represented by the general formula (I) according to the above [1], a salt thereof, an N-oxide thereof, a solvate thereof or a prodrug thereof for manufacturing a prophylactic and/or therapeutic agent for Trk-related disease;

[21] the compound according to any one of the above [1] to [5], which is:

(1) 1-(2-(1H-pyrazol-1-yl)-5-(trifluoromethyl)phenyl)-3-(2-(4-(2-amino-5-chloropyridin-3-yl)phenoxy)pyrimidin-5-yl)urea, (2) 1-(2-(4-(2-amino-5-chloropyridin-3-yl)phenoxy)pyrimidin-5-yl)-3-(2-(4-methyl-1H-1,2,3-triazol-1-yl)-5-(trifluoromethyl)phenyl)urea, (3) 1-(2-(4-(2-amino-5-chloropyridin-3-yl)phenoxy)pyrimidin-5-yl)-3-(5-(trifluoromethyl)-2-(3-(trifluoromethyl)-1H-pyrazol-1-yl)phenyl)urea, (4) 1-(2-(4-(2-amino-5-chloropyridin-3-yl)phenoxy)pyrimidin-5-yl)-3-(2-chloro-5-(trifluoromethyl)phenyl)urea, (5) 1-(2-(1H-pyrazol-1-yl)-5-(trifluoromethyl)phenyl-3-(6-(4-(2-amino-5-chloropyridin-3-yl)phenoxy)pyridin-3-yl)urea, (6) 1-(2-(1H-1,2,3-triazol-1-yl)-5-(trifluoromethyl)phenyl-3-(6-(4-(2-amino-5-chloropyridin-3-yl)phenoxy)pyridin-3-yl)urea, (7) 1-(6-(4-(2-amino-5-chloropyridin-3-yl)phenoxy)pyridin-3-yl)-3-(2-(pyridin-3-yl)-5-(trifluoromethyl)phenyl)urea, (8) 1-(2-(4-(2-amino-5-chloropyridin-3-yl)phenoxy)pyrimidin-5-yl)-3-(2-(1-methyl-1H-pyrazol-5-yl)-5-(trifluoromethyl)phenyl)urea,
(9) 1-(2-(1H-1,2,3-triazol-1-yl)-5-(trifluoromethyl)phenyl)-3-(2-(4-(2-amino-5-fluoropyridin-3-yl)phenoxy)pyrimidin-5-yl)urea,
(10) 1-(2-(4-(2-amino-5-fluoropyridin-3-yl)phenoxy)pyrimidin-5-yl)-3-(2-(pyridin-3-yl)-5-(trifluoromethyl)phenyl)urea,
(11) 1-(2-(1H-pyrazol-1-yl)-4-(trifluoromethyl)phenyl)-3-(2-(4-(2-amino-5-chloropyridin-3-yl)phenoxy)pyrimidin-5-yl)urea,
(12) 1-(2-(4-(2-amino-5-chloropyridin-3-yl)phenoxy)pyrimidin-5-yl)-3-(2-fluoro-4-(trifluoromethyl)phenyl)urea,
(13) 1-(2-(4-(2-amino-5-chloropyridin-3-yl)phenoxy)pyrimidin-5-yl)-3-(2-chloro-4-(trifluoromethyl)phenyl)urea,
(14) 1-(2-{4-[2-amino-5-(trifluoromethyl)-3-pyridinyl]phenoxy}-5-pyrimidinyl)-3-{5-(trifluoromethyl)-2-[3-(trifluoromethyl)-1H-pyrazol-1-yl]phenyl}urea,
(15) 1-{2-[4-(2-amino-5-chloro-3-pyridinyl)phenoxy]-5-pyrimidinyl}-3-[4-(trifluoromethyl)-2-biphenylyl]urea,
(16) 1-{2-[4-(2-amino-5-fluoro-3-pyridinyl)phenoxy]-5-pyrimidinyl}-3-[4-(trifluoromethyl)-2-biphenylyl]urea,
(17) 1-{2-[4-(2-amino-5-chloro-3-pyridinyl)phenoxy]-5-pyrimidinyl}-3-[2-(4-chloro-1H-pyrazol-1-yl)-5-(trifluoromethyl)phenyl]urea,
(18) 1-{2-[4-(2-amino-5-chloro-3-pyridinyl)phenoxy]-5-pyrimidinyl}-3-{5-chloro-2-[3-(trifluoromethyl)-1H-pyrazol-1-yl]phenyl}urea,
(19) 1-{2-[4-(2-amino-5-chloro-3-pyridinyl)phenoxy]-5-pyrimidinyl}-3-[2,4-bis(trifluoromethyl)phenyl]urea,
(20) 1-(2-{4-[2-amino-5-(trifluoromethyl)-3-pyridinyl]phenoxy}-5-pyrimidinyl)-3-[2-(4-chloro-1H-pyrazol-1-yl)-5-(trifluoromethyl)phenyl]urea,
(21) 1-{2-[4-(2-amino-5-fluoro-3-pyridinyl)phenoxy]-5-pyrimidinyl}-3-[2-(methylsulfonyl)-5-(trifluoromethyl)phenyl]urea,
(22) 1-(2-{4-[2-amino-5-(trifluoromethyl)-3-pyridinyl]phenoxy}-5-pyrimidinyl)-3-[2-(methylsulfonyl)-5-(trifluoromethyl)phenyl]urea,
(23) 1-{2-[4-(2-amino-5-chloro-3-pyridinyl)phenoxy]-5-pyrimidinyl}-3-[2-(methylsulfonyl)-5-(trifluoromethyl)phenyl]urea or
(24) 2-{[(2-{4-[2-amino-5-(trifluoromethyl)-3-pyridinyl]phenoxy}-5-pyrimidinyl)carbamoyl]amino}-N,N-dimethyl-4-(trifluoromethyl)benzenesulfonamide;
[22] the compound according to any one of the above [1] to [4] and the above [7], which is:
(1) 1-(2-(4-(5-(azetidin-1-yl)pyrazolo[1,5-a]pyrimidin-3-yl)phenoxy)pyrimidin-5-yl)-3-(2-(pyridin-3-yl)-5-(trifluoromethyl)phenyl)urea,
(2) 1-(2-(4-(5-(azetidin-1-yl)pyrazolo[1,5-a]pyrimidin-3-yl)phenoxy)pyrimidin-5-yl)-3-(2-(1-methyl-1H-pyrazol-5-yl)-5-(trifluoromethyl)phenyl)urea,
(3) 1-(2-(4-(5-methoxypyrazolo[1,5-a]pyrimidin-3-yl)phenoxy)pyrimidin-5-yl)-3-(2-(pyridin-3-yl)-5-(trifluoromethyl)phenyl)urea,
(4) 1-(2-(4-(pyrazolo[1,5-a]pyrimidin-3-yl)phenoxy)pyrimidin-5-yl)-3-(2-(pyridin-3-yl)-5-(trifluoromethyl)phenyl)urea,
(5) 1-(2-{4-[5-(dimethylamino)pyrazolo[1,5-a]pyrimidin-3-yl]phenoxy}-5-pyrimidinyl)-3-[2-(3-pyridinyl)-5-(trifluoromethyl)phenyl]urea,
(6) 1-(2-{4-[5-(dimethylamino)pyrazolo[1,5-a]pyrimidin-3-yl]phenoxy}-5-pyrimidinyl)-3-[2-(1-methyl-1H-pyrazol-5-yl)-5-(trifluoromethyl)phenyl]urea,
(7) 1-{2-[4-(5-methylpyrazolo[1,5-a]pyrimidin-3-yl)phenoxy]-5-pyrimidinyl}-3-[2-(3-pyridinyl)-5-(trifluoromethyl)phenyl]urea,
(8) 1-(2-{4-[5-(ethylamino)pyrazolo[1,5-a]pyrimidin-3-yl]phenoxy}-5-pyrimidinyl)-3-[3'-methyl-4-(trifluoromethyl)-2-biphenylyl]urea,
(9) 1-(2-{4-[5-(dimethylamino)pyrazolo[1,5-a]pyrimidin-3-yl]phenoxy}-5-pyrimidinyl)-3-[4-(trifluoromethyl)-2-biphenylyl]urea,
(10) 1-(2-{4-[5-(dimethylamino)pyrazolo[1,5-a]pyrimidin-3-yl]phenoxy}-5-pyrimidinyl)-3-[3'-methyl-4-(trifluoromethyl)-2-biphenylyl]urea or
(11) 1-(2-{4-[5-(dimethylamino)pyrazolo[1,5-a]pyrimidin-3-yl]phenoxy}-5-pyrimidinyl)-3-[2'-methyl-4-(trifluoromethyl)-2-biphenylyl]urea;
[23] an article of manufacture including (1) a pharmaceutical composition including the compound represented by the general formula (I) according to the above [1], a salt thereof, an N-oxide thereof, a solvate thereof or a prodrug thereof, (2) a container and (3) an instruction, a description, a package insert or a product label indicating that the composition can be used for prophylaxis and/or therapy of Trk-related disease;
[24] the article of manufacture according to the above [23], wherein the Trk-related disease is pain;
[25] an article of manufacture including (1) a pharmaceutical composition including the compound represented by the general formula (I) according to the above [1], a salt thereof, an N-oxide thereof, a solvate thereof or a prodrug thereof, (2) a container and (3) an instruction, a description, a package insert or a product label indicating that the composition can be used for prophylaxis and/or therapy of Trk-related disease in combination with acetaminophen, a nonsteroid antiinflammatory drug, an opioid, an antidepressant, an antiepileptic agent, an N-methyl-D-aspartate antagonist, a muscle relaxant, an antiarrhythmic agent, a steroid and/or a bisphosphonate;
[26] the article of manufacture according to the above [25], wherein the Trk-related disease is pain;
[27] an article of manufacture including (1) a pharmaceutical composition in the form of a combination drug including the compound represented by the general formula (I) according to the above [1], a salt thereof, an N-oxide thereof, a solvate thereof or a prodrug thereof and acetaminophen, a nonsteroid antiinflammatory drug, an opioid, an antidepressant, an antiepileptic agent, an N-methyl-D-aspartate antagonist, a muscle relaxant, an antiarrhythmic agent, a steroid and/or a bisphosphonate, (2) a container and (3) an instruction, a description, a package insert or a product label indicating that the composition can be used for prophylaxis and/or therapy of Trk-related disease; and
[28] the article of manufacture according to the above [27], wherein the Trk-related disease is pain;

Effect of the Invention

The present compound has Trk-inhibiting activity and excellent kinase selectivity. Further, the present compound persistently inhibits NGF vascular hyper permeability. Therefore the present compound can be a prophylactic and/or therapeutic agent for Trk-related diseases such as pain, pruritus, lower urinary tract dysfunction, asthma, allergic rhinitis, inflammatory bowel disease or Chagas disease.

BEST MODE FOR CARRYING OUT THE INVENTION

The present invention is hereinafter specifically described.
In the present invention, "a C3-10 monocyclic carbocycle or bicyclic carbocycle" may include, for example, cyclopropane, cyclobutane, cyclopentane, cyclohexane, cycloheptane, cyclooctane, cyclononane, cyclodecane, cyclopentene, cyclohexene, cycloheptene, cyclooctene, cyclopentadiene, cyclohexadiene, cycloheptadiene, cyclooctadiene, benzene, pentalene, perhydropentalene, azulene, perhydroazulene, indene, perhydroindene, indane, naphthalene, dihydronaphthalene, tetrahydronaphthalene and perhydronaphthalene rings.

In the present invention, "a 4- to 10-membered monocyclic heterocycle or bicyclic heterocycle" in the ring $Cy_1$ may include, for example, oxetane, azetidine, pyrrolidine, pyrrole, imidazole, triazole, tetrazole, pyrazole, pyridine, piperidine, piperazine, pyrazine, pyrimidine, pyridazine, azepine, diazepine, furan, pyran, oxepin, thiophene, thiopyran, thiepine, oxazole, isoxazole, triazole, isothiazole, furazan, oxadiazole, oxazine, oxadiazine, oxazepine, oxadiazepine, thiadiazole, thiazine, thiadiazine, thiazepine, thiadiazepine, indole, isoindole, indolizine, benzofuran, isobenzofuran, benzothiophene, isobenzothiophene, indazole, quinoline, isoquinoline, quinolidine, purine, phthalazine, pteridine, naphthyridine, quinoxaline, quinazoline, cinnoline, benzoxazole, benzothiazole, benzimidazole, benzodioxole, benzoxathiole, chromene, benzofurazan, benzothiadiazole, benzotriazole, pyrroline, pyrrolidine, imidazoline, imidazolidine, triazoline, triazolidine, tetrazoline, tetrazolidine, pyrazoline, pyrazolidine, dihydropyridine, tetrahydropyridine, dihydropyrazine, tetrahydropyrazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, dihydrofuran, tetrahydrofuran, dihydropyran, tetrahydropyran, dihydrooxepin, tetrahydrooxepin, perhydrooxepin, dihydrothiophene, tetrahydrothiophene, dihydrothiopyran, tetrahydrothiopyran, dihydrothiepine, tetrahydrothiepine, perhydrothiepine, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzoxathiane, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dioxolane, dioxane, dioxaindane, benzodioxane, thiochromane, dihydrobenzodioxine, dihydrobenzoxathiine, chromane, pyrazolopyrimidine, imidazopyridazine, imidazopyridine, pyrrolopyridine, imidazopyrazine, pyrazolopyridine, pyrazolopyrimidine, imidazopyridine and triazolopyridine rings.

In the present invention, "a 4- to 10-membered monocyclic heterocycle or bicyclic heterocycle excluding a heterocycle 1,3-thiazol-5-yl group" in the ring $Cy_2$ has the same meaning as "a 4- to 10-membered monocyclic heterocycle or bicyclic heterocycle" in the ring $Cy_1$ as described above, excluding the heterocycle 1,3-thiazol-5-yl group.

In the present invention, the compound wherein the ring $Cy_2$ is "a 4- to 10-membered monocyclic heterocycle or bicyclic heterocycle excluding a heterocycle 1,3-thiazol-5-yl group" corresponds to the compound of the general formula (I) excluding the compound of the following general formula (I'):

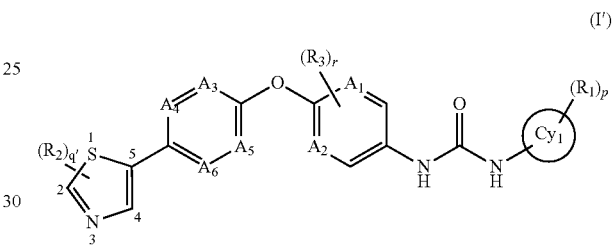

wherein q' represents an integer of 0 to 2 and other symbols represent the same meanings as those described in the above [1], provided that when q' represents 2, $R_2$ groups may be respectively and independently the same or different.

In the present invention, "a halogen" may include fluorine, chlorine, bromine and iodine.

In the present invention, "a C1-6 alkyl group" may include, for example, methyl, ethyl, n-propyl, isopropyl, n-butyl, sec-butyl, tert-butyl, isobutyl, pentyl, 1-methylbutyl, 2-methylbutyl, 3-methylbutyl, 1,1-dimethylpropyl, 1,2-dimethylpropyl, 2,2-dimethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 1-methyl-1-ethylpropyl, 2-methyl-2-ethylpropyl, 1-ethylbutyl, 2-ethylbutyl and 1,1-dimethylpentyl groups.

In the present invention, "a C2-6 alkenyl group" may include, for example, vinyl, 1-propenyl, 2-propenyl, 1-butenyl, 2-butenyl, 3-butenyl, 1-pentenyl, 2-pentenyl, 3-pentenyl, 4-pentenyl, 3-methyl-1-butenyl, 3-methyl-2-butenyl, 3-methyl-3-butenyl, 1-hexenyl, 2-hexenyl, 3-hexenyl, 4-hexenyl and 5-hexenyl groups.

In the present invention, "a C2-6 alkynyl group" may include, for example, ethynyl, 1-propynyl, 2-propynyl, 1-butynyl, 2-butynyl, 3-butynyl, 1-pentynyl, 2-pentynyl, 3-pentynyl, 4-pentynyl, 3-methyl-1-butynyl, 1-hexynyl, 2-hexynyl, 3-hexynyl, 4-hexynyl and 5-hexynyl groups.

In the present invention, "a C5-6 monocyclic carbocycle" may include, for example, cyclopentane, cyclohexane, cyclopentene, cyclohexene, cyclopentadiene, cyclohexadiene and benzene rings.

In the present invention, "a 5- to 6-membered monocyclic heterocycle" may include, for example, pyrrole, imidazole, triazole, tetrazole, pyrazole, pyridine, piperidine, piperazine, pyrazine, pyrimidine, pyridazine, furan, pyran, thiophene, thiopyran, oxazole, isoxazole, triazole, isothiazole, furazan, oxadiazole, oxazine, oxadiazine, thiadiazole, thiazine, thiadiazine, pyrroline, pyrrolidine, imidazoline, imidazolidine, triazoline, triazolidine, tetrazoline, tetrazolidine, pyrazoline, pyrazolidine, dihydropyridine, tetrahydropyridine, dihydropyrazine, tetrahydropyrazine, dihydropyrimidine, tetrahydropyrimidine, perhydropyrimidine, dihydropyridazine, tetrahydropyridazine, perhydropyridazine, dihydrofuran, tetrahydrofuran, dihydropyran, tetrahydropyran, dihydrothiophene, tetrahydrothiophene, dihydrothiopyran, tetrahydrothiopyran, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrothiadiazole, tetrahydrothiadiazole (thiadiazolidine), dihydrothiazine, tetrahydrothiazine, dihydrothiadiazine, tetrahydrothiadiazine, morpholine, thiomorpholine and oxathiane rings.

In the present invention, "a C1-3 alkyl group" includes methyl, ethyl, n-propyl and isopropyl groups.

In the present invention, "a C3-6 cycloalkyl group" includes cyclopropyl, cyclobutyl, cyclopentyl and cyclohexyl groups.

In the present invention, "a C1-6 alkoxy group" may include, for example, methoxy, ethoxy, propoxy, isopropoxy, butoxy, 1-methylpropoxy, tert-butoxy, isobutoxy, pentyloxy, 1-methylbutoxy, 2-methylbutoxy, 3-methylbutoxy, 1,1-dimethylpropoxy, 1,2-dimethylpropoxy, 2,2-dimethylpropoxy, hexyloxy, 1-methylpentyloxy, 2-methylpentyloxy, 3-methylpentyloxy, 4-methylpentyloxy, 1,1-dimethylbutoxy, 1,2-dimethylbutoxy, 1,3-dimethylbutoxy, 1-methyl-1-ethylpropoxy, 1-methyl-2-ethylpropoxy, 1,2-dimethylbutoxy, 2,2-dimethylbutoxy, 1-ethyl-2-methylpropoxy, 2-ethyl-2-methylpropoxy and 1-ethylbutoxy groups.

In the present invention, "a 3- to 7-membered monocyclic heterocycle" may include, for example, aziridine, oxetane, azetidine, pyrrole, imidazole, triazole, tetrazole, pyrazole, pyridine, piperidine, piperazine, pyrazine, pyrimidine, pyridazine, azepine, diazepine, furan, pyran, oxepin, thiophene, thiopyran, thiepine, oxazole, isoxazole, triazole, isothiazole, furazan, oxadiazole, oxazine, oxadiazine, oxazepine, oxadiazepine, thiadiazole, thiazine, thiadiazine, thiazepine, thiadiazepine, pyrroline, pyrrolidine, imidazoline, imidazolidine, triazoline, triazolidine, tetrazoline, tetrazolidine, pyrazoline, pyrazolidine, dihydropyridine, tetrahydropyridine, dihydropyrazine, tetrahydropyrazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, dihydrofuran, tetrahydrofuran, dihydropyran, tetrahydropyran, dihydrooxepin, tetrahydrooxepin, perhydrooxepin, dihydrothiophene, tetrahydrothiophene, dihydrothiopyran, tetrahydrothiopyran, dihydrothiepine, tetrahydrothiepine, perhydrothiepine, dihydrooxazole, tetrahydrooxazole (oxazolidine), dihydroisoxazole, tetrahydroisoxazole (isoxazolidine), dihydrothiazole, tetrahydrothiazole (triazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine and oxathiane rings.

In the present invention, "a 5- to 10-membered monocyclic aromatic heterocycle or bicyclic aromatic heterocycle excluding a heterocycle 1,3-thiazol-5-yl group" may include, for example, pyrrole, imidazole, triazole, tetrazole, pyrazole, pyridine, pyrazine, pyrimidine, pyridazine, azepine, diazepine, furan, oxepin, thiophene, thiepine, oxazole, isoxazole, isothiazole, furazan, oxadiazole, oxazepine, oxadiazepine, thiadiazole, indole, isoindole, indolizine, benzofuran, isobenzofuran, benzothiophene, isobenzothiophene, indazole, quinoline, isoquinoline, quinolidine, purine, phthalazine, pteridine, naphthyridine, quinoxaline, quinazoline, cinnoline, benzoxazole, benzothiazole, benzimidazole, benzofurazan, benzothiadiazole, benzotriazole, pyrazolopyrimidine, imidazopyridazine, imidazopyridine, pyrrolopyridine, imidazopyrazine, pyrazolopyridine, pyrazolopyrimidine, imidazopyridine and triazolopyridine rings.

In the present invention, "a 5- to 6-membered monocyclic aromatic heterocycle" may include, for example, pyrrole, imidazole, triazole, tetrazole, pyrazole, pyridine, pyrazine, pyrimidine, pyridazine, furan, thiophene, oxazole, isoxazole, triazole, isothiazole, furazan, oxadiazole and thiadiazole rings.

In the present invention, the phrase "when, further, two $R_5$ groups are respectively and independently a C1-3 alkyl group or a hydroxy group and the $R_5$ groups are attached to carbon atoms adjacent to each other on the C5-6 monocyclic carbocycle or the 5- to 6-membered monocyclic heterocycle, the $R_5$ groups may together form a ring" may indicate, for example, the following groups:

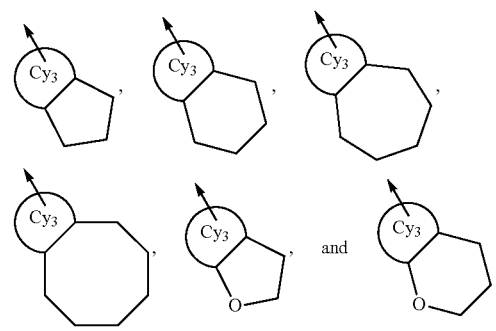

wherein a ring $Cy_3$ represents a C5-6 monocyclic carbocycle or a 5- to 6-membered monocyclic heterocycle and an arrow means binding to the ring $Cy_1$.

In the present invention, the phrase "$R_5$ is $—SO_2NR_{18}R_{19}$ and when $R_{18}$ and $R_{19}$ are respectively and independently a C1-6 alkyl group, $R_{18}$ and $R_{19}$ may together form a ring" may indicate, for example, the following groups:

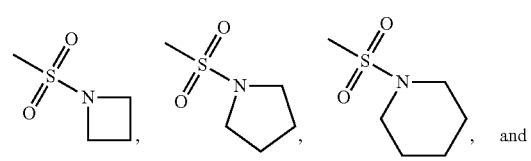

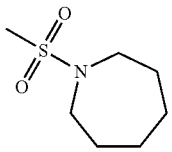

In the present invention, the ring $Cy_1$ is preferably a C5-6 monocyclic carbocycle or a 5- to 6-membered monocyclic heterocycle.

In the present invention, the ring $Cy_1$ is more preferably cyclopentane, cyclohexane, benzene, pyran, thiopyran, pyrrolidine, piperidine, piperazine, imidazoline, imidazolidine, morpholine, thiomorpholine or a 5- to 6-membered monocyclic aromatic heterocycle.

In the present invention, the ring $Cy_1$ is further preferably benzene or a 5- to 6-membered monocyclic aromatic heterocycle.

In the present invention, the ring $Cy_1$ is still more preferably a benzene, pyrrole, imidazole, pyrazole, pyridine, pyrazine, pyrimidine, pyridazine, furan, thiophene, oxazole, isoxazole, thiazole or isothiazole ring.

In the present invention, the ring $Cy_1$ is yet more preferably a benzene, imidazole, pyrazole, pyridine, pyrazine, pyrimidine or pyridazine ring.

In the present invention, the ring $Cy_1$ is yet still more preferably a benzene, pyrazole or pyridine ring.

In the present invention, the ring $Cy_1$ is the most preferably a benzene or pyridine ring.

In the present invention, the ring $Cy_1$ is preferably a 5-to 10-membered monocyclic aromatic heterocycle or bicyclic aromatic heterocycle excluding a heterocycle 1,3-thiazol-5-yl group.

In the present invention, the ring $Cy_2$ is more preferably a pyridine, pyrazine, pyrimidine, pyridazine, indole, isoindole, indolizine, benzofuran, isobenzofuran, benzothiophene, isobenzothiophene, indazole, quinoline, isoquinoline, quinolidine, purine, phthalazine, pteridine, naphthyridine, quinoxaline, quinazoline, cinnoline, benzoxazole, benzothiazole, benzimidazole, benzofurazan, benzothiadiazole, benzotriazole, pyrazolopyrimidine, imidazopyridazine, imidazopyridine, pyrrolopyridine, imidazopyrazine, pyrazolopyridine, pyrazolopyrimidine, imidazopyridine or triazolopyridine ring.

In the present invention, the ring $Cy_2$ is still more preferably a pyridine, pyrazine, pyrimidine, pyridazine, indole, isoindole, indolizine, indazole, quinoline, isoquinoline, quinolidine, purine, phthalazine, pteridine, naphthyridine, quinoxaline, quinazoline, cinnoline, benzoxazole, benzothiazole, benzimidazole, benzofurazan, benzothiadiazole, benzotriazole, pyrazolopyrimidine, imidazopyridazine, imidazopyridine, pyrrolopyridine, imidazopyrazine, pyrazolopyridine, pyrazolopyrimidine, imidazopyridine or triazolopyridine ring.

In the present invention, the ring $Cy_2$ is yet more preferably a pyridine, pyrazine, pyrimidine, pyridazine, pyrazolopyrimidine, imidazopyridazine, imidazopyridine, pyrrolopyridine, imidazopyrazine, pyrazolopyridine, pyrazolopyrimidine, imidazopyridine or triazolopyridine ring.

In the present invention, the ring $Cy_2$ is yet still more preferably a pyridine, pyrimidine, pyrazolopyrimidine, imidazopyridazine, imidazopyridine, pyrrolopyridine, imidazopyrazine or pyrazolopyridine ring.

In the present invention, the ring $Cy_2$ is the most preferably a pyridine or pyrazolopyrimidine ring.

In the present invention, $R_1$ is preferably (1) a halogen, (2) a C1-3 alkyl group optionally substituted with a halogen, (3) a benzene ring optionally substituted with one or two $R_5$ groups, (4) a 5- to 6-membered monocyclic aromatic heterocycle optionally substituted with one or two $R_5$ groups, (5) a methylsulfonyl group or (6) N,N-dimethylsulfonamide.

In the present invention, $R_1$ is more preferably (1) a halogen, (2) a methyl group, (3) a trifluoromethyl group, (4) a difluoromethyl group, (5) a monofluoromethyl group, (6) a trichloromethyl group, (7) a dichloromethyl group, (8) a monochloromethyl group, (9) a benzene ring optionally substituted with one or two $R_5$ groups, (10) a pyrrole, imidazole, triazole, tetrazole, pyrazole, pyridine, pyrazine, pyrimidine, pyridazine, furan, thiophene, oxazole, isoxazole, triazole, isothiazole, furazan, oxadiazole or thiadiazole ring optionally substituted with one or two $R_5$ groups, (11) a methylsulfonyl group or (12) N,N-dimethylsulfonamide.

In the present invention, $R_1$ is still more preferably (1) a halogen, (2) a methyl group, (3) a trifluoromethyl group, (4) a difluoromethyl group, (5) a monofluoromethyl group, (6) a benzene ring, (7) an indane ring, (8) a tolyl group, (9) a dimethylbenzene ring, (10) an imidazole, triazole, pyrazole or pyridine ring optionally substituted with one or two $R_5$ groups or (11) a methylsulfonyl group.

In the present invention, $R_1$ is yet more preferably (1) a halogen, (2) a trifluoromethyl group, (3) a difluoromethyl group, (4) a benzene ring, (5) an indane ring, (6) a tolyl group, (7) a dimethylbenzene ring, (8) an imidazole, triazole, pyrazole or pyridine ring optionally substituted with one or two methyl, difluoromethyl or trifluoromethyl groups or (9) a methylsulfonyl group.

In the present invention, $R_1$ is yet still more preferably (1) a trifluoromethyl group, (2) a difluoromethyl group, (3) a benzene ring, (4) a triazole, pyrazole or pyridine ring optionally substituted with one or two methyl, difluoromethyl or trifluoromethyl groups or (5) a methylsulfonyl group.

In the present invention, $R_1$ is the most preferably (1) a trifluoromethyl group or (2) a triazole, pyrazole or pyridine ring optionally substituted with one or two methyl, difluoromethyl or trifluoromethyl groups.

In the present invention, $R_5$ is preferably (1) a halogen, (2) a methyl group optionally substituted with a halogen or (3) a C1-3 alkyl group optionally substituted with a hydroxy group or an oxo group.

In the present invention, $R_5$ is more preferably a methyl group, a trifluoromethyl group, a difluoromethyl group, an acetyl group or a hydroxyethyl group.

In the present invention, $R_5$ is the most preferably a methyl group, a trifluoromethyl group or a difluoromethyl group.

In the present invention, $R_2$ is preferably (1) a halogen, (2) a C1-3 alkyl group optionally substituted with a halogen or a hydroxy group, (3) a C3-6 cycloalkyl group, (4) a C1-3 alkoxy group, (5) an amino group, (6) a methylamino, ethylamino, n-propylamino, isopropylamino, n-butylamino, sec-butylamino, tert-butylamino, isobutylamino or dimethylamino group optionally substituted with a hydroxy group, (7) a 3- to 7-membered monocyclic heterocycle or (8) —O-(3- to 7-membered monocyclic heterocycle).

In the present invention, $R_2$ is more preferably a halogen, a methyl group, a trifluoromethyl group, a difluoromethyl group, a monofluoromethyl group, a hydroxymethyl group, a hydroxyethyl group, a 2-methyl-hydroxyethyl group, a cyclopropyl group, a methoxy group, an ethoxy group, an amino group, a methylamino group, an ethylamino group, a dimethylamino group, a 2-methyl-2-hydroxypropylamino group, an oxetanyloxy group, an azetidine ring, a pyrrolidine ring or a piperidine ring.

In the present invention, $R_2$ is still more preferably a halogen, a methyl group, a cyclopropyl group, a methoxy group, an amino group, a dimethylamino group, an oxetanyloxy group, an azetidine ring, a pyrrolidine ring or a piperidine ring.

In the present invention, $R_2$ is yet more preferably a halogen, a methyl group, an amino group, an azetidine ring or a pyrrolidine ring.

In the present invention, $R_2$ is the most preferably fluorine, chlorine, a methyl group, an amino group or an azetidine ring.

In the present invention, $R_3$ is preferably hydrogen or fluorine and the most preferably hydrogen.

In the present invention, $R_4$ is preferably hydrogen or fluorine and the most preferably hydrogen.

In the present invention, $R_6$ is preferably a C1-3 alkyl group optionally substituted with a halogen.

In the present invention, $R_6$ is more preferably a methyl group, an ethyl group or a n-propyl group.

In the present invention, preferably $R_7$ and $R_8$ are respectively and independently a hydrogen atom or a C1-3 alkyl group optionally substituted with a hydroxy group.

In the present invention, more preferably $R_7$ and $R_8$ are respectively and independently a hydrogen atom, a methyl group, an ethyl group, a n-propyl group, an isopropyl group or a 2-hydroxypropyl group.

In the present invention, still more preferably $R_7$ and $R_8$ are respectively and independently a hydrogen atom, a methyl group, an ethyl group or a n-propyl group.

In the present invention, $R_9$ is preferably a hydrogen atom, a methyl group or an ethyl group.

In the present invention, preferably $R_{10}$ to $R_{16}$ are respectively and independently a hydrogen atom, a methyl group, an ethyl group or a n-propyl group.

In the present invention, $R_{17}$ is preferably a C1-3 alkyl group optionally substituted with a halogen.

In the present invention, $R_{17}$ is more preferably a methyl group, an ethyl group or a n-propyl group.

In the present invention, preferably $R_{18}$ and $R_{19}$ are respectively and independently a hydrogen atom or a C1-3 alkyl group optionally substituted with a hydroxy group.

In the present invention, more preferably $R_{18}$ and $R_{19}$ are respectively and independently a hydrogen atom, a methyl group, an ethyl group, a n-propyl group, an isopropyl group or a 2-hydroxypropyl group.

In the present invention, still more preferably $R_{18}$ and $R_{19}$ are respectively and independently a hydrogen atom, a methyl group, an ethyl group or a n-propyl group.

In the present invention, $R_{20}$ is preferably a hydrogen atom, a methyl group or an ethyl group.

In the present invention, preferably $R_{21}$ to $R_{29}$ are respectively and independently a hydrogen atom, a methyl group, an ethyl group or a n-propyl group.

In the present invention, m1 is preferably an integer of 2.

In the present invention, m2 is preferably an integer of 2.

In the present invention, p is preferably an integer of 0 to 3.

In the present invention, q is preferably an integer of 0 to 3.

In the present invention, r is preferably an integer of 0 to 1.

In the present invention, $R_{2-a}$ and $R_{2-b}$ respectively and independently have the same meaning as $R_2$ and preferable groups thereof are also the same as $R_2$.

In the present invention, q-a is preferably an integer of 0 to 1.

In the present invention, q-b is preferably an integer of 0 to 1.

In the present invention, the general formula (I) is preferably those having the combinations of preferable definitions for the ring $Cy_1$, the ring $Cy_2$, $R_1$, $R_2$, $R_3$, $R_4$, $R_5$, $R_{2-a}$, $R_{2-b}$, m1, m2, p, q, r, t, q-a and q-b.

In the present invention, the general formula (I) is more preferably the general formula (I-a) or the general formula (I-b):

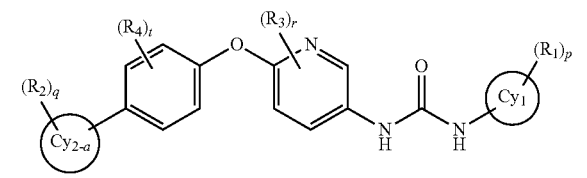

(I-a)

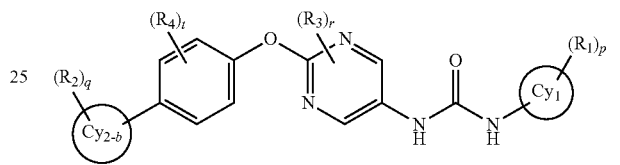

(I-b)

wherein a ring $Cy_{2-a}$ and a ring $Cy_{2-b}$ represent a 5- to 10-membered monocyclic aromatic heterocycle or bicyclic aromatic heterocycle excluding a heterocycle 1,3-thiazol-5-yl group, and other symbols represent the same meanings as those described in [1] and [5] above, a salt thereof, an N-oxide thereof, a solvate thereof or a prodrug thereof.

In the present invention, the general formula (I) is still more preferably the general formula (I-c) or the general formula (I-d):

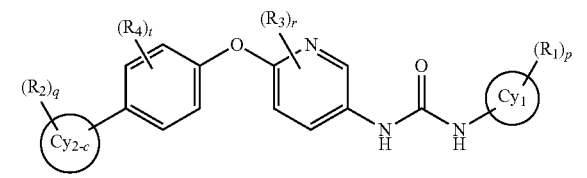

(I-c)

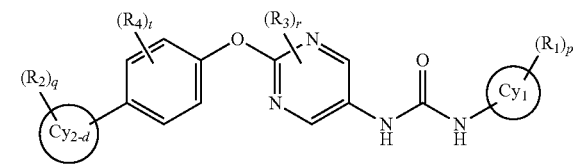

(I-d)

wherein a ring $Cy_{2-c}$ and a ring $Cy_{2-d}$ represent a pyridine ring, a pyrimidine ring, a pyrazolopyrimidine ring, an imidazopyridazine ring, an imidazopyridine ring, a pyrrolopyridine ring, an imidazopyrazine ring or a pyrazolopyridine ring, and other symbols represent the same meanings as those described in [1] and [5] above, a salt thereof, an N-oxide thereof, a solvate thereof or a prodrug thereof.

In the present invention, the general formula (I) is yet more preferably the general formula (I-e) or the general formula (I-f):

(I-e)

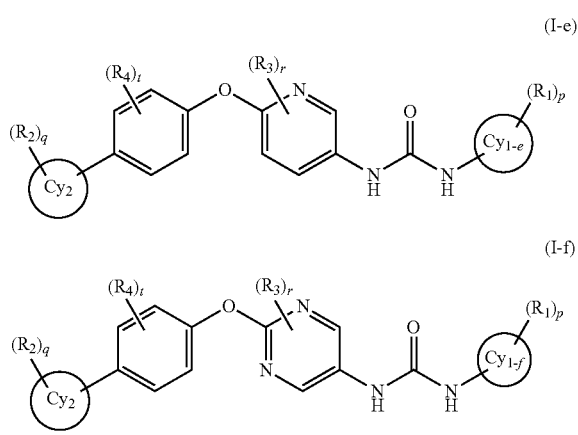

(I-f)

(I-k)

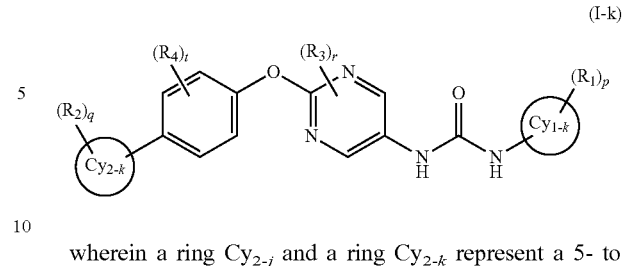

wherein a ring $Cy_{1-e}$ and a ring $Cy_{1-f}$ represent a benzene ring or a 5- to 6-membered monocyclic aromatic heterocycle, and other symbols represent the same meanings as those described in [1] and [5] above, a salt thereof, an N-oxide thereof, a solvate thereof or a prodrug thereof.

In the present invention, the general formula (I) is yet still more preferably the general formula (I-g) or the general formula (I-h):

(I-g)

(I-h)

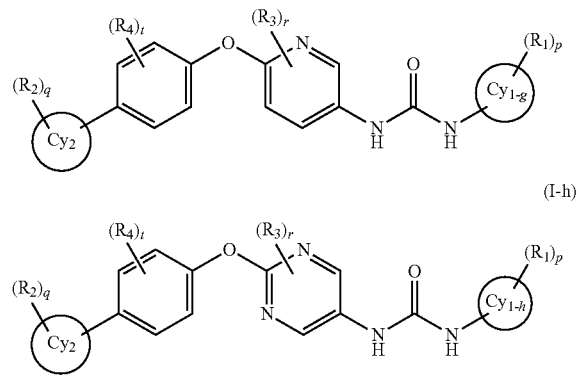

wherein a ring $Cy_{2-j}$ and a ring $Cy_{2-k}$ represent a 5- to 10-membered monocyclic aromatic heterocycle or bicyclic aromatic heterocycle excluding a heterocycle 1,3-thiazol-5-yl group; a ring $Cy_{1-j}$ and a ring $Cy_{1-k}$ represent a benzene ring or a 5- to 6-membered monocyclic aromatic heterocycle; and other symbols represent the same meanings as those described in [1] and [5] above, a salt thereof, an N-oxide thereof, a solvate thereof or a prodrug thereof.

In the present invention, the general formula (I) is yet still more preferably the general formula (I-m) or the general formula (I-n):

(I-m)

(I-n)

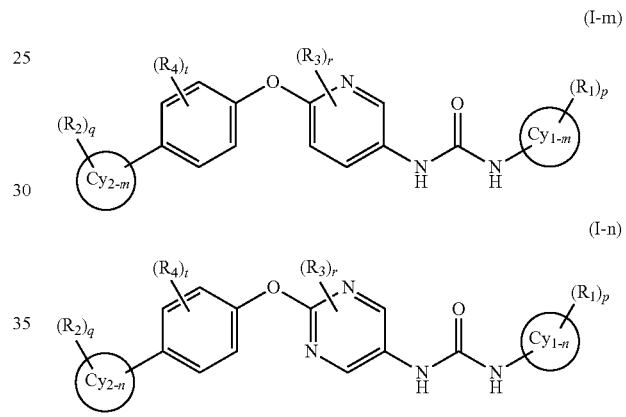

wherein a ring $Cy_{2-m}$ and a ring $Cy_{2-n}$ represent a pyridine ring, a pyrimidine ring, a pyrazolopyrimidine ring, an imidazopyridazine ring, an imidazopyridine ring, a pyrrolopyridine ring, an imidazopyrazine ring or a pyrazolopyridine ring; a ring $Cy_{1-m}$ and a ring $Cy_{1-n}$ represent a benzene ring, a pyridine ring or a pyrazole ring; and other symbols represent the same meanings as those described in [1] and [5] above, a salt thereof, an N-oxide thereof, a solvate thereof or a prodrug thereof.

In the present invention, the compound represented by the general formula (I-n) wherein $Cy_{2-n}$ is a pyrimidine ring is preferably the present compound of any of Example 16-1 to Example 16-8 as described hereinbelow, a salt thereof, an N-oxide thereof, a solvate thereof or a prodrug thereof.

In the present invention, the compound represented by the general formula (I-m) or the general formula (I-n) wherein the ring $Cy_{2-m}$ or $Cy_{2-n}$ is an imidazopyridazine ring is preferably the present compound of any of Example 22-1 to Example 22-67 as described hereinbelow, a salt thereof, an N-oxide thereof, a solvate thereof or a prodrug thereof.

In the present invention, the general formula (I-m) or the general formula (I-n) is preferably the present compound of any of Example 23-1 to Example 23-12 as described hereinbelow, a salt thereof, an N-oxide thereof, a solvate thereof or a prodrug thereof.

In the present invention, the general formula (I) is still more preferably the general formula (I-i) or the general formula (I-ii):

wherein a ring $Cy_{1-g}$ and a ring $Cy_{1-h}$ represent a benzene ring, a pyridine ring or a pyrazole ring, and other symbols represent the same meanings as those described in [1] and [5] above, a salt thereof, an N-oxide thereof, a solvate thereof or a prodrug thereof.

In the present invention, the general formula (I) is yet still more preferably the general formula (I-j) or the general formula (I-k):

(I-j)

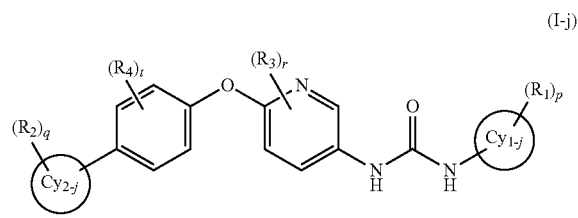

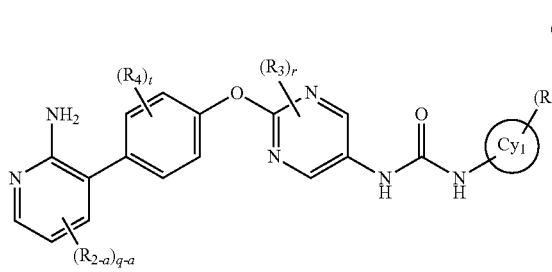
(I-i)

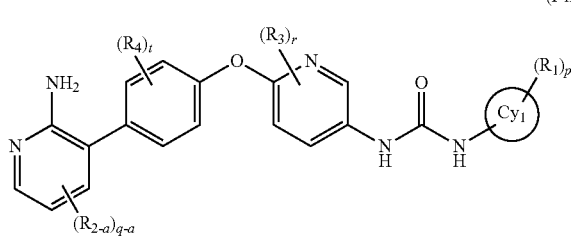
(I-ii)

wherein all symbols represent the same meanings as those described in [1] and [5] above, a salt thereof, an N-oxide thereof, a solvate thereof or a prodrug thereof.

In the present invention, the general formula (I-i) or the general formula (I-ii) is preferably the general formula (I-i-a) or the general formula (I-ii-b):

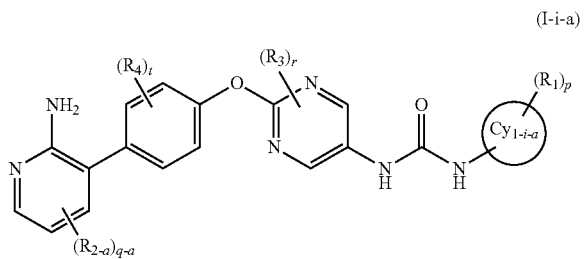
(I-i-a)

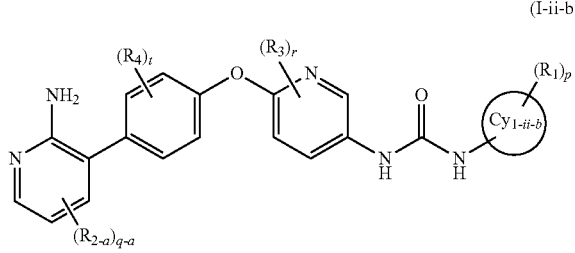
(I-ii-b)

wherein a ring $Cy_{1-i-a}$ and a ring $Cy_{1-ii-b}$ represent a benzene ring or a 5- to 6-membered monocyclic aromatic heterocycle and other symbols represent the same meanings as those described in [1] and [5] above, a salt thereof, an N-oxide thereof, a solvate thereof or a prodrug thereof.

In the present invention, the general formula (I-i) or the general formula (I-ii) is more preferably the general formula (I-i-c) or the general formula (I-ii-d):

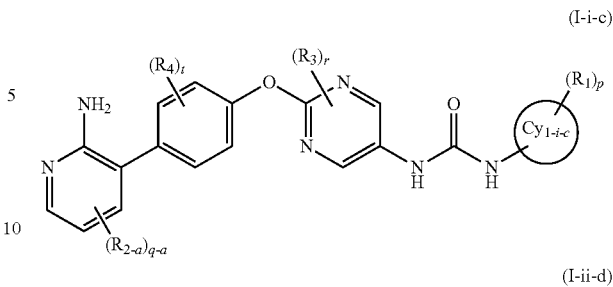
(I-i-c)

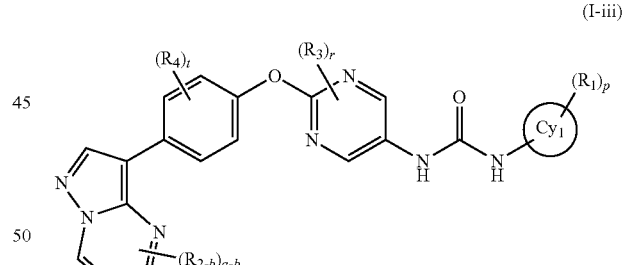
(I-ii-d)

wherein a ring $Cy_{1-i-c}$ and a ring $Cy_{1-ii-d}$ represent a benzene ring, a pyridine ring or a pyrazole ring and other symbols represent the same meanings as those described in [1] and [5] above, a salt thereof, an N-oxide thereof, a solvate thereof or a prodrug thereof.

In the present invention, the general formula (I-i) or the general formula (I-ii) is the most preferably the present compound of any of Example 7, Example 8-1 to Example 8-22, Example 9-1 to Example 9-3, Example 11, Example 12, Example 13-1 to Example 13-4, Example 14-1 to Example 14-20 and Example 15-1 to Example 15-251, a salt thereof, an N-oxide thereof, a solvate thereof or a prodrug thereof.

In the present invention, the general formula (I) is still more preferably the general formula (I-iii) or the general formula (I-iv):

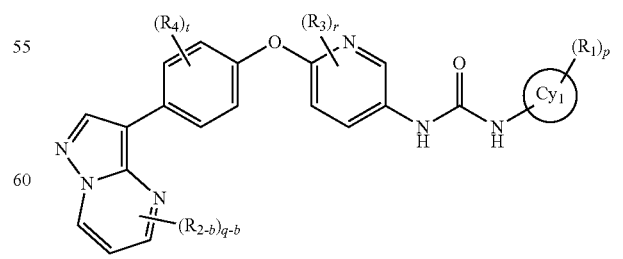
(I-iii)

(I-iv)

wherein all symbols represent the same meanings as those described in [1], [5] and [7] above, a salt thereof, an N-oxide thereof, a solvate thereof or a prodrug thereof.

In the present invention, the general formula (I-iii) or the general formula (I-iv) is preferably the general formula (I-iii-a) or the general formula (I-iv-b):

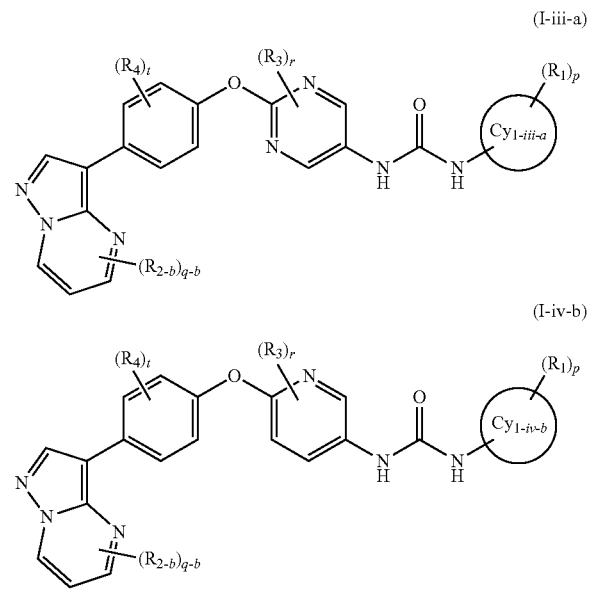

wherein a ring $CY_{1\text{-}iii\text{-}a}$ and a ring $Cy_{1\text{-}iv\text{-}b}$ represent a benzene ring or a 5- to 6-membered monocyclic aromatic heterocycle and other symbols represent the same meanings as those described in [1], [5] and [7] above, a salt thereof, an N-oxide thereof, a solvate thereof or a prodrug thereof.

In the present invention, the general formula (I-iii) or the general formula (I-iv) is more preferably the general formula (I-iii-c) or the general formula (I-iv-d):

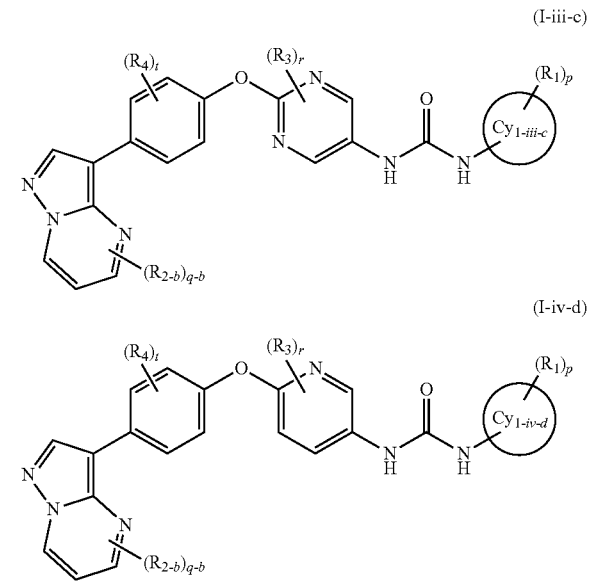

wherein a ring $Cy_{1\text{-}iii\text{-}c}$ and a ring $Cy_{1\text{-}iv\text{-}d}$ represent a benzene ring or a pyridine ring and other symbols represent the same meanings as those described in [1], [5] and [7] above, a salt thereof, an N-oxide thereof, a solvate thereof or a prodrug thereof.

In the present invention, the general formula (I-iii) or the general formula (I-iv) is the most preferably the present compound of any of Example 20 and Example 21-1 to Example 21-134 as described hereinbelow, a salt thereof, an N-oxide thereof, a solvate thereof or a prodrug thereof.

All isomers are encompassed by the present invention unless specifically stated. For example, an alkyl group, an alkenyl group, an alkynyl group and an alkoxy group comprise linear and branched groups. Further, rings, isomers in fused rings (E, Z, cis and trans forms), isomers due to asymmetric carbons (R and S forms, α and β forms, enantiomers, diastereomers), optically active substances with optical rotatory (D, L, d and l forms), polar substances by chromatographic separation (high-polarity substances, low-polarity substances), equilibrated compounds, rotational isomers, mixtures thereof with any proportions and racemic mixtures are all encompassed by the present invention. Isomers due to tautomeric properties are also encompassed by the present invention.

In the present invention, as is apparent to the one skilled in the art, unless otherwise stated the symbol:

indicates that the bond projects below the plane of the paper (i.e. α-configuration), the symbol:

indicates that the bond projects above the plane of the paper (i.e. β-configuration), the symbol:

indicates that the bond is the α-configuration or the β-configuration, and the symbol:

indicates that the bond is a mixture of the α-configuration and the β-configuration with any proportions.

[Salts]

The compound represented by the general formula (I) may be converted to a salt according to well known methods.

The salt is preferably a pharmaceutically acceptable salt.

The salt is preferably water soluble.

The salt may include, for example, acid addition salts, alkali metal salts, alkaline-earth metal salts, ammonium salts and amine salts.

The acid addition salt may include, for example, inorganic acid salts such as hydrochlorides, hydrobromides, hydroiodides, sulfates, phosphates and nitrates and organic acid salts such as acetates, lactates, tartrates, benzoates, citrates, methanesulfonates, ethanesulfonates, tri fluoroacetates, benzenesulfonates, toluenesulfonates, isethionates, glucuronates and gluconates.

The alkali metal salt may include, for example, potassium and sodium.

The alkaline-earth metal salt may include, for example, calcium and magnesium.

The ammonium salt may include, for example, tetramethylammonium.

The amine salt may include, for example, triethylamine, methylamine, dimethylamine, cyclopentylamine, benzylamine, phenethylamine, piperidine, monoethanolamine, diethanolamine, tris(hydroxymethyl)aminomethane, lysine, arginine and N-methyl-D-glucamine.

The present compound may be converted to an N-oxide according to any methods. The N-oxide represents the compound of the general formula (I) in which a nitrogen atom thereof is oxidized and specifically may be the compound represented by the general formula (I) wherein the nitrogen atom in $A_1$, $A_2$, $A_3$, $A_4$, $A_5$ or $A_6$, which is =N—, is oxidized. Alternatively, the N-oxide may be the compound represented by the general formula (I) wherein the nitrogen atom in $Cy_1$ and $Cy_{2-n}$ which are a nitrogen-containing heterocycle, is oxidized. Further, the N-oxide may be the compound represented by the general formula (I) wherein an amino group is oxidized.

The compound represented by the general formula (I) and a salt thereof may be converted to a solvate.

The solvate is preferably non-toxic and water soluble. Appropriate solvates may include, for example, solvates with water or an alcoholic solvent (e.g., ethanol).

[Prodrugs]

A prodrug of the compound represented by the general formula (I) refers to a compound that is converted to the compound represented by the general formula (I) by in vivo reaction with an enzyme or gastric acid. The prodrug of the compound represented by the general formula (I) may include, for example, compounds wherein an amino group in the compound represented by the general formula (I) is acylated, alkylated or phosphated (e.g., compounds wherein an amino group in the compound represented by the general formula (I) is derivatized to eicosanoyl, alanyl, pentylaminocarbonyl, (5-methyl-2-oxo-1,3-dioxolen-4-yl)methoxycarbonyl, tetrahydrofuranyl, pyrrolidylmethyl, pivaloyloxymethyl, acetoxymethyl or tert-butyl); compounds wherein a hydroxy group in the compound represented by the general formula (I) is acylated, alkylated, phosphated or borated (e.g., compounds wherein a hydroxy group in the compound represented by the general formula (I) is derivatized to acetyl, palmitoyl, propanoyl, pivaloyl, succinyl, fumaryl, alanyl or dimethylaminomethylcarbonyl); compounds wherein a carboxy group in the compound represented by the general formula (I) is esterified or amidated (e.g., compounds wherein a carboxy group in the compound represented by the general formula (I) is derivatized to ethyl ester, phenyl ester, carboxymethyl ester, dimethylaminomethyl ester, pivaloyloxymethyl ester, 1-{(ethoxycarbonyl) oxy}ethyl ester, phthalidyl ester, (5-methyl-2-oxo-1,3-dioxolen-4-yl)methyl ester, 1-{[(cyclohexyloxy)carbonyl] oxy}ethyl ester or methylamide) and the like. These compounds may be prepared according to the methods well known per se. The prodrug of the compound represented by the general formula (I) may be a hydrate or non-hydrate. The prodrug of the compound represented by the general formula (I) may be the one which is converted to the compound represented by the general formula (I) under physiological conditions described in "Iyakuhin no Kaihatsu (Development of Medicines)", vol. 7, "Bunshi Sekkei (Molecular Designs)", Hirokawa Shoten Co., 1990, pp. 163-198.

The atoms constituting the compound represented by the general formula (I) may respectively be substituted with isotopes thereof (e.g., $^2H$, $^3H$, $^{13}C$, $^{14}C$, $^{15}N$, $^{16}N$, $^{17}O$, $^{18}O$, $^{35}S$, $^{36}Cl$, $^{77}Br$, $^{125}I$ and the like).

[Production Method of the Present Compound]

The present compound represented by the general formula (I) can be produced according to well known methods, for example the methods described hereinbelow, equivalent methods thereof or methods described in Examples. In the production methods described hereinbelow, starting compounds may be salts. The salts may include those described as pharmaceutically acceptable salts of the general formula (I).

The present compound of the general formula (I) can be prepared, for example, according to the following reaction scheme:

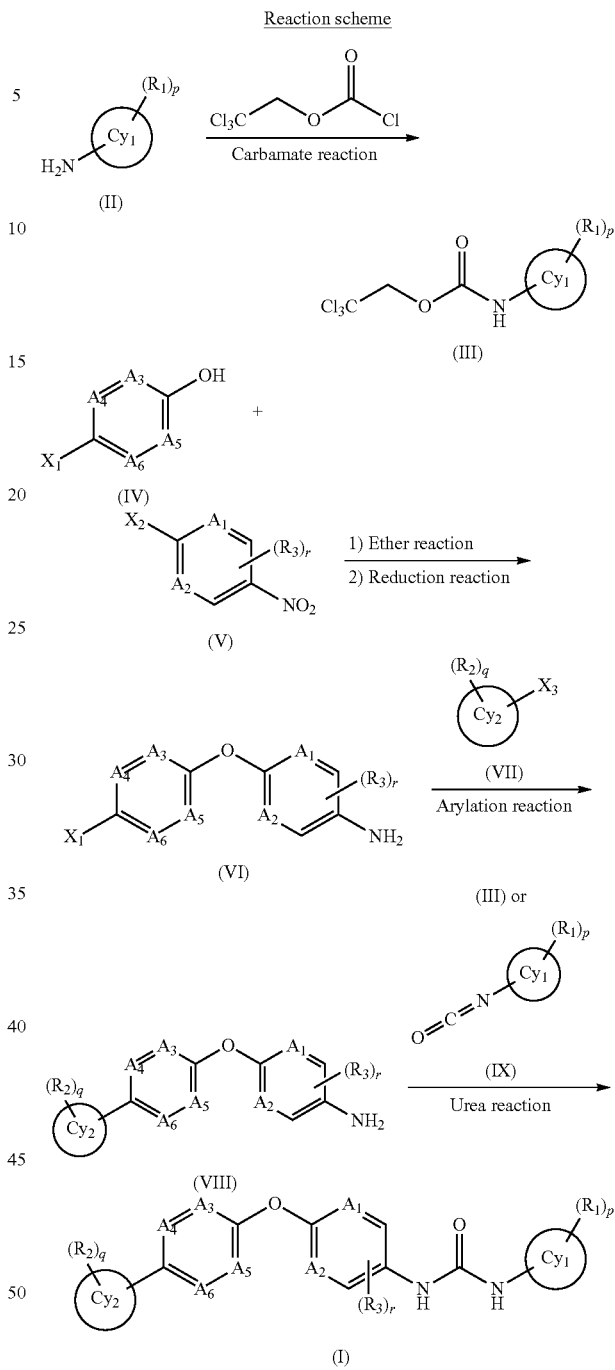

wherein $X_1$ represents a boronic acid group (—B(OH)$_2$) or a boronate ester group (—B(ORi) (ORii), wherein Ri and Rii represent a C1-3 alkyl group and Ri and Rii may together form a ring, such as 4,4,5,5-tetramethyl-1,3,2-dioxaborolan-2-yl); $X_2$ represents a halogen; $X_3$ represents a halogen; and other symbols represent the same meanings as those described in the above [1].

The present compound having an amino group, an ester group and a hydroxy group can be produced by carrying out the reactions up to urea derivatization reaction as indicated in the above reaction scheme with a compound which may be optionally protected with a protecting group conventionally used for the above-mentioned groups as described in, for example, "Comprehensive Organic Transformations: A Guide to Functional Group Preparations 2nd Edition (Richard C. Larock, John Wiley & Sons Inc, 1999)" followed by a well known deprotection reaction or the deprotection reaction described in, for example, "Comprehensive Organic Transformations: A Guide to Functional Group Preparations 2nd Edition (Richard C. Larock, John Wiley & Sons Inc, 1999)".

In the reaction scheme, the reaction step (carbamate derivatization reaction) of producing the compound represented by the general formula (III) from the compound represented by the general formula (II) is well known. The compound represented by the general formula (III) obtained thereby can be produced by, for example, allowing reaction of the compound represented by the general formula (II) with 2,2,2-trichloroethoxycarbonyl chloride in an organic solvent (e.g., pyridine, ethyl acetate, methylene chloride, dioxane, diethyl ether or an appropriately mixed solvent thereof) or in a mixed solvent of the organic solvent with water in the presence or absence of a base (e.g., 4-dimethylaminopyridine, pyridine, triethylamine, sodium hydrogen carbonate) at a temperature of about −20° C. to 80° C.

In the reaction scheme, the reaction step (etherification reaction, reduction reaction) of producing the compound represented by the general formula (VI) from the compound represented by the general formula (IV) is well known. The compound represented by the general formula (VI) obtained thereby can be produced by, for example, allowing reaction of the compound represented by the general formula (IV) and the compound represented by the general formula (V) in an organic solvent (e.g., dimethylsulfoxide, dimethylformamide, methanol, acetonitrile, tetrahydrofuran or an appropriately mixed solvent thereof) or in a mixed solvent of the organic solvent with water in the presence of a base (e.g., potassium fluoride, potassium carbonate, tripotassium phosphate, sodium hydroxide, sodium hydride, triethylamine) at a temperature of about 0° C. to 120° C. and subjecting the obtained compound to reaction under a hydrogen atmosphere in an organic solvent (e.g., methanol, ethanol, ethyl acetate, tetrahydrofuran, acetic acid, 1,2-dimethoxyethane or an appropriately mixed solvent thereof) or in a mixed solvent of the organic solvent with water in the presence of a catalyst (e.g., a silver catalyst (e.g., silver acetate), a platinum catalyst (e.g., platinum-carbon, platinum oxide), a rhodium catalyst (e.g., rhodium-carbon), an iron catalyst (e.g., iron acetate), a ruthenium catalyst (e.g., ruthenium-carbon), a palladium catalyst (e.g., palladium-carbon, palladium hydroxide), a zinc catalyst (zinc bromide, zinc iodide, zinc acetate), Raney nickel or an appropriately mixed catalyst thereof) at a temperature of from room temperature to about 80° C. or subjecting to reaction in an organic solvent (e.g., acetic acid, hydrochloric acid, ethanol, methanol, dimethylformamide, toluene or an appropriately mixed solvent thereof) or in a mixed solvent of the organic solvent with water in the presence of a catalyst (e.g., an iron catalyst (e.g., iron, iron chloride, iron-ammonium chloride), a zinc catalyst (e.g., zinc), a nickel catalyst (e.g., nickel chloride), an indium catalyst (e.g., indium), a tin catalyst (e.g., tin, tin chloride) or an appropriately mixed catalyst thereof) at a temperature of from room temperature to about 80° C.

In the reaction scheme, the reaction step (aryl derivatization reaction) of producing the compound represented by the general formula (VIII) from the compound represented by the general formula (VI) is well known. The compound represented by the general formula (VIII) obtained thereby can be produced by, for example, allowing reaction of the compound represented by the general formula (VI) and the compound represented by the general formula (VII) in an organic solvent (e.g., dimethylacetamide, dimethylformamide, an alcohol (e.g., methanol, ethanol, isopropyl alcohol), diethyl carbonate, dioxane, 1,2-dimethoxyethane, toluene or an appropriately mixed solvent thereof) or in a mixed solvent of the organic solvent with water, in the presence or absence of a base (e.g., caesium carbonate, potassium acetate, potassium carbonate, sodium carbonate, lithium-t-butoxide, silver carbonate, tripotassium phosphate, triethylamine or an appropriately mixed base thereof) in a catalyst (e.g., a palladium catalyst (e.g., palladium hydroxide, palladium acetate, bis(tri-t-butylphosphine)palladium, palladium(0) tetrakis(triphenylphosphine), bis(triphenylphosphine)dichloropalladium (II) or an appropriately mixed catalyst thereof)) at a temperature of from room temperature to about 120° C.

In the reaction scheme, the reaction step (urea derivatization reaction) of producing the present compound represented by the general formula (I) from the compound represented by the general formula (VIII) is the reaction carried out with the compound represented by the general formula (VIII) and the compound represented by the general formula (III) or general formula (IX) under the conditions described in Examples herein or under well known conditions.

In the reaction scheme, compounds used as starting materials and represented by the general formulae (II), (IV), (V), (VI) and (IX) are well known or can be easily produced according to well known methods, for example, the method described in "Comprehensive Organic Transformations: A Guide to Functional Group Preparations 2nd Edition (Richard C. Larock, John Wiley & Sons Inc, 1999)".

The present compound of the general formula (I) can be alternatively produced by subjecting to urea derivatization reaction the compound represented by the general formula (II) and a 2,2,2-trichloroethyl carbamate derivative produced from the compound represented by the general formula (VIII) in the above reaction scheme and 2,2,2-trichloroethoxycarbonyl chloride.

The present compounds represented by the general formula (I) other than those indicated above can be produced according to the methods described in Examples herein or to the combinations of well known methods, for example, the method described in "Comprehensive Organic Transformations: A Guide to Functional Group Preparations 2nd Edition (Richard C. Larock, John Wiley & Sons Inc, 1999)".

The respective reactions involving heating as described herein can be carried out, as apparent to a person skilled in the art, in a water bath, an oil bath, a sand bath or with microwave.

In the respective reactions as described herein, a reagent supported on a solid phase of a high-molecular weight polymer (e.g., polystyrene, polyacrylamide, polypropylene, polyethylene glycol) may be appropriately used.

In the respective reactions as described herein, reaction products can be purified by conventional purification means, e.g., by methods including distillation under normal or reduced pressure, high speed liquid chromatography using silica gel or magnesium silicate, thin layer chromatography, ion exchange resins, scavenger resins or column chromatography or washing and recrystallization. Purification may be carried out after each reaction step or may be carried out after more than one reaction steps.

[Toxicity]

The present compound has sufficiently low toxicity. The present compound does not cause, for example, hepatotoxicity or gastrointestinal dysfunction and has low brain transition. Thus the present compound can be used safely as a medicament.

[Application to Medicaments]

The present compound exhibits Trk-inhibiting activity and thus is useful as a prophylactic and/or therapeutic agent for Trk-related diseases e.g., pain, pruritus, lower urinary tract dysfunction, asthma, allergic rhinitis, inflammatory bowel disease and Chagas disease.

More specifically, pain may include, for example, pain of osteoarthritis, cancer pain, chronic low back pain, low back pain of osteoporosis, pain of bone fracture, pain of rheumatoid arthritis, neuropathic pain, postherpetic pain, pain of diabetic neuropathy, fibromyalgia, pain of pancreatitis, pain of interstitial cystitis, pain of endometriosis, pain of irritable bowel syndrome, migraine, postoperative pain, pain of pulpitis and the like. Pruritus may include systemic cutaneous pruritus, localized cutaneous pruritus, senile cutaneous pruritus, gestational pruritus, pruritus ani, vulvar pruritus and the like. Inflammatory bowel disease may include, for example, ulcerative colitis, Crohn's disease and the like.

The present compound is particularly useful as a prophylactic and/or therapeutic agent for pain.

The present compound may be administered as a combination drug with another drug in order to:
1) complement and/or enhance the prophylactic and/or therapeutic effect of the compound;
2) improve the kinetics and absorption and reduce the dosage of the compound; and/or
3) alleviate the side effect of the compound.

The combination drug of the present compound and another drug may be administered in the form of one formulation containing both components or may be administered as separate formulations. Administration of separate formulations may include simultaneous administration and sequential administration. In the sequential administration, the present compound may be first administered followed by another drug or another drug may be first administered followed by the present compound. The respective manners of administration may be the same or different.

The disease for which the combination drug exhibits the prophylactic and/or therapeutic effect is not particularly limited and may be the disease which may complement and/or enhance the prophylactic and/or therapeutic effect of the present compound.

Another drug for complementing and/or enhancing the prophylactic and/or therapeutic effect of the present compound for pain may include, for example, acetaminophen, a nonsteroid antiinflammatory drug, an opioid, an antidepressant, an antiepileptic agent, an N-methyl-D-aspartate antagonist, a muscle relaxant, an antiarrhythmic agent, a steroid and a bisphosphonate.

The nonsteroid antiinflammatory drug may include, for example, sasapyrine, sodium salicylate, aspirin, aspirin formulations such as those containing aspirin-dialuminate, diflunisal, indomethacin, suprofen, ufenamate, dimethylisopropylazulene, bufexamac, felbinac, diclofenac, tolmetin sodium, Clinoril, fenbufen, nabumetone, proglumetacin, indomethacin farnesil, acemetacin, proglumetacin maleate, amfenac sodium, mofezolac, etodolac, ibuprofen, ibuprofen piconol, naproxen, flurbiprofen, flurbiprofen axetil, ketoprofen, fenoprofen calcium, Tiaprofen, oxaprozin, pranoprofen, loxoprofen sodium, alminoprofen, zaltoprofen, mefenamic acid, aluminium mefenamate, tolfenamic acid, floctafenine, ketophenylbutazone, oxyphenbutazone, piroxicam, tenoxicam, ampiroxicam, Napageln ointment, epirizole, tiaramide hydrochloride, tinoridine hydrochloride, emorfazone, sulpyrine, Migrenin, Saridon, Sedes G, Amipylo-N, Sorbon, pilin cold remedies, acetaminophen, phenacetin, dimetotiazine mesilate, meloxicam, celecoxib, rofecoxib, valdecoxib, simetride-containing formulations and non-pilin cold remedies and the like.

The opioid may include, for example, codeine, fentanyl, hydromorphone, levorphanol, meperidine, methadone, morphine, oxycodone, oxymorphone, propoxyphene and the like.

The antidepressant may include, for example, tricyclic antidepressants (e.g., amitriptyline hydrochloride, imipramine hydrochloride, clomipramine hydrochloride, dosulepin hydrochloride, nortriptyline hydrochloride, lofepramine hydrochloride, trimipramine maleate, amoxapine), tetracyclic antidepressants (e.g., maprotiline hydrochloride, mianserin hydrochloride, setiptiline maleate), monoamine oxidase (MAO) inhibitors (safrazine hydrochloride), serotonin and noradrenaline reuptake inhibitors (SNRIs) (e.g., milnacipran hydrochloride, venlafaxine hydrochloride), selective serotonin reuptake inhibitors (SSRIs) (e.g., fluvoxamine maleate, paroxetine hydrochloride, fluoxetine hydrochloride, citalopram hydrochloride), serotonin reuptake inhibitors (e.g., trazodone hydrochloride) and the like.

The antiepileptic agent may include, for example, phenobarbital, Puridomin, phenytoin, ethosuximide, zonisamide, nitrazepam, clonazepam, carbamazepine, sodium valproate, acetazolamide, sulthiame and the like.

The N-methyl-D-aspartate antagonist may include, for example, ketamine hydrochloride, amantadine hydrochloride, memantine hydrochloride, dextromethorphan, methadone and the like.

The muscle relaxant may include, for example, succinylcholine, suxamethonium, vecuronium bromide, pancronium bromide, dantrolene sodium and the like.

The antiarrhythmic agent may include, for example, procainamide, disopyramide, cibenzoline, pirmenol, lidocaine, mexiletine, aprindine, pilsicainide, flecainide, propafenone, propranolol, atenolol, bisoprolol, amiodarone, sotalol, verapamil, diltiazem, bepridil and the like.

The steroid may include, for example, as external medicines, clobetasol propionate, diflorasone diacetate, fluocinonide, mometasone furoate, betamethasone dipropionate, betamethasone butyrate propionate, betamethasone valerate, difluprednate, budesonide, diflucortolone valerate, amcinonide, halcinonide, dexamethasone, dexamethasone propionate, dexamethasone valerate, dexamethasone acetate, hydrocortisone acetate, hydrocortisone butyrate, hydrocortisone butyrate propionate, deprodone propionate, prednisolone valerate acetate, fluocinolone acetonide, peclometasone propionate, triamcinolone acetonide, flumethasone pivalate, alclometasone dipropionate, clobetasone butyrate, prednisolone, beclomethasone propionate, fludroxycortide and the like.

As medicines for internal use or for injection, cortisone acetate, hydrocortisone, hydrocortisone sodium phosphate, hydrocortisone sodium succinate, fludrocortisone acetate, prednisolone, prednisolone acetate, prednisolone sodium succinate, prednisolone butylacetate, prednisolone sodium phosphate, halopredone acetate, methylprednisolone, methylprednisolone acetate, methylprednisolone sodium succinate, triamcinolone, triamcinolone acetate, triamcinolone acetonide, dexamethasone, dexamethasone acetate, dexamethasone sodium phosphate, dexamethasone palmitate, paramethasone acetate, betamethasone and the like may be included.

As inhalants, beclomethasone propionate, fluticasone propionate, budesonide, flunisolide, triamcinolone, ST-126P, ciclesonide, dexamethasone palmitate, mometasone furoate, prasterone sulfonate, deflazacort, methylprednisolone suleptanate, methylprednisolone sodium succinate and the like may be included.

The bisphosphonate may include, for example, etidronate, pamidronate, alendronate, risedronate, zoledronate, minodronate and the like.

The mass ratio of the present compound and another drugs is not particularly limited.

Any combination of two or more kinds of another drugs may be administered.

Another drugs for complementing and/or enhancing the prophylactic and/or therapeutic effect of the present compound may encompass not only those have been identified to date but also those will be identified in future based on the above mechanism.

The present compound or the combination drug of the present compound and another drugs which is used for the purpose described above is generally formulated as an appropriate pharmaceutical composition with a pharmaceutically acceptable carrier, and then administered systemically or topically by oral or parenteral administration.

The dosage may vary according to age, weight, symptoms, therapeutic effect, mode of administration, treatment period and the like and may be one to several oral administrations a day within the range of 1 mg to 1000 mg per dose per adult or one to several parenteral administrations a day within the range of 0.1 mg to 100 mg per dose or intravenous continuous administration for 1 hour to 24 hours a day per adult.

As described above, the dosage may vary according to various conditions, thus the sufficient dosage may be of course lower than the amount described above or the amount higher than the above may be required.

The present compound or the combination drug of the present compound and another drugs may be administered as an oral solid dosage form for internal use, an internal liquid medicine or an injection, an external medicine, a suppository, an ophthalmic solution or an inhalation for parenteral administration.

The oral solid dosage form for internal use may include tablets, pills, capsules, powders, granules and the like. Capsules may include hard capsules and soft capsules. Tablets may include sublingual tablets, oral patches, orally disintegrating tablets and the like.

In the solid dosage form for internal use, one or more active substances per se may be formulated or may be formulated after mixing thereof with a excipient (lactose, mannitol, glucose, microcrystalline cellulose, starch and the like), a binder (hydroxypropylcellulose, polyvinylpyrrolidone, magnesium aluminate metasilicate and the like), a disintegrant (calcium cellulose glycolate and the like), a lubricant (magnesium stearate and the like), a stabilizer, a solution adjuvant (glutamic acid, aspartic acid and the like) according to conventional methods. The solid dosage form may be optionally coated with a coating agent (sucrose, gelatin, hydroxypropylcellulose, hydroxypropyl methylcellulose phthalate and the like) and may be coated with two or more layers. The solid dosage form may further encompass capsules of an absorbable substance such as gelatin.

The internal liquid medicine may include pharmaceutically acceptable waters, suspensions, emulsions, syrups, elixirs and the like. In the liquid medicine, one or more active substances are dissolved, suspended or emulsified in a diluent of general use (purified water, ethanol or a mixed solution thereof). The liquid medicine may further contain a wetting agent, a suspending agent, an emulsifying agent, a sweetening agent, a flavouring agent, an aroma, a preservative, a buffering agent and the like.

The dosage form of the external medicine for parenteral administration may include, for example, ointments, gels, creams, cataplasms, plasters and pressure sensitive adhesives, liniments, atomized agents, inhalations, sprays, aerosols, ophthalmic solutions, nasal solutions and the like. The dosage forms contain one or more active substances and may be prepared according to well known methods or formulations which are generally used.

Atomized agents, inhalations and sprays may contain, in addition to a diluent which is generally used, a stabilizer such as sodium hydrogen sulfite and a buffering agent that confers isotonicity, e.g., sodium chloride, sodium citrate or an isotonicity agent such as citric acid. Methods for producing sprays are specifically described in, for example, U.S. Pat. Nos. 2,868,691 and 3,095,355.

The injection for parenteral administration may encompass injections in the form of solution, suspension, emulsion and solid that is dissolved or suspended in a solvent upon use. The injection may be used by dissolving, suspending or emulsifying one or more active substances in a solvent. The solvent may be, for example, distilled water for injection, saline, vegetable oil, propylene glycol, polyethylene glycol, alcohols such as ethanol and combinations thereof. The injection may further contain a stabilizer, a solution adjuvant (glutamic acid, aspartic acid, Polysorbate 80® and the like), a suspending agent, an emulsifying agent, a soothing agent, a buffering agent, a preservative and the like. The injection may be produced by sterilization in the final step or through aseptic technique. Aseptic solid agents, e.g., lyophilized products may be manufactured and dissolved in sterilized or aseptic distilled water or other solvents for injection before use.

Other compositions for parenteral administration may include suppositories for rectal administration and pessaries for vaginal administration which contain one or more active substances and are formulated according to conventional methods.

In the present invention, "an article of manufacture" comprises (1) a pharmaceutical composition including the present compound or a pharmaceutical composition in the form of a combination drug including the present compound with a concomitant drug other than the present compound, (2) a container containing the composition and (3) at least one of an instruction, a description, a package insert and a product label (including those corresponding to a label and a labeling in the United States), all of which indicate that the composition can be used for prophylaxis and/or therapy of Trk-related disease optionally in combination with an appropriate concomitant drug (preferably acetaminophen, a non-steroid antiinflammatory drug, an opioid, an antidepressant, an antiepileptic agent, an N-methyl-D-aspartate antagonist, a muscle relaxant, an antiarrhythmic agent, a steroid and/or a bisphosphonate).

The package insert as used herein means an official document attached to a medicament which provides necessary information for appropriate use of the medicament and corresponds to "Tenpu Bunsho" (also referred to as "Nougaki") in accordance with the Pharmaceutical Affairs Act in Japan, "Summary of Product Characteristics (SPC or SmPC)" in accordance with Directive in EU, "US Package Insert (USPI)" in accordance with Federal Regulations in the United States and equivalent documents elsewhere.

The information provided by these documents is specifically prescribed by Articles 52, 54 and 68 (4) and the like in the Pharmaceutical Affairs Act (see, if necessary, Notification Nos. 606 and 607 of Pharmaceutical Affairs Bureau as of 25 Apr. 1997 and/or related notifications) for "Tenpu Bunsho" in Japan, by Directive 2001/83/EC Article 11 and the like (see, if necessary, A guideline on SmPC and/or related guidelines) for Summary of Product Characteristics in EU, and by 21 CFR 201.100 and the like (see, if necessary, 21 CFR 201.57 and/or related Federal Regulations) for US Package Insert in the United States and generally includes information on indications, dosage and administration, method of administration, warnings and/or contraindications.

In the United States, 21 CFR 201 Subpart B requires that in addition to the US Package Insert, a label or a labeling (or labelling) should contain a part or all information provided on the US Package Insert. A label herein means the one directly provided on a container and a labeling means the concept encompassing the label, printing on packages and printed matters attached to articles of manufacture.

In the present invention, the term "container" means the one which directly accommodates the pharmaceutical composition comprising the present compound or the pharmaceutical composition in the form of a combination drug including the present compound with a concomitant drug other than the present compound and may also be referred to as "an immediate container", "an immediate wrapper", "an inner seal" or the like. The container includes, for example, cans/tins, bottles, boxes, ampoules, vials, tubes, unit dose containers for eye drops, paper, cloth, plastics, plastic bags, SP sheets, PTP sheets, plastic containers and the like.

The container containing the pharmaceutical composition therein is combined with at least one of an instruction, a description, a package insert and a product label (including the one corresponding to a label or labeling in the United Stated) as described above, and then may be generally packaged in an outer container or an outer wrapper and distributed to the market.

The present invention also discloses a method for advertisement of a pharmaceutical composition comprising the present compound or a pharmaceutical composition in the form of a combination drug including the present compound with a concomitant drug, the method including encouraging a target viewer to use the composition for prophylaxis and/or therapy of Trk-related disease.

The above method involves publicly distributing information that describes the value, particularly a health benefit of using, in prophylaxis and/or therapy for Trk-related diseases, the pharmaceutical composition including the present compound or the pharmaceutical composition in the form of the combination drug including the present compound with another concomitant drug. Such information is distributed through an appropriate advertising medium in addition to verbal communication. The advertising medium may be any of newspaper, magazines, television, radio, video, brochures, leaflets, posters, social networking systems, e-mail, electronic signboards, digital signage, internet advertisements (homepages/websites, banner advertisements and the like), outdoor advertisements (poster boards, neon signs, large screen displays and the like), transportation advertisements (advertisements suspended in trains, buses, cabs and the like, advertisements above windows and beside doors of trains, buses, cabs and the like, advertisements in stations), movie theatre slide advertisements (advertisements on screens in movie theatres), POP advertisements (advertisements at shop front and in shops), direct advertisements (direct mails, newspaper inserts, flyers), specialty advertisements (novelty advertisements such as calendars, pens and the like), other advertisements (skywriting, advertisements on benches and the like). A person skilled in the art can easily produce the advertising media.

Unless otherwise defined, all technical and scientific terms and abbreviations used herein have the same meanings as are usually understood by a person skilled in the art to which the present invention pertains.

The present application claims the priority of Japanese Patent Application Nos. 2013-029563 and 2013-141246 filed respectively on 19 Feb. 2013 and 5 Jul. 2013, the entire contents of which are incorporated herein by reference.

The contents of all Patent Document and Non-Patent Document or references explicitly cited herein may be entirely incorporated herein as a part of the present specification.

EXAMPLES

The present invention is hereinafter specifically described by way of Examples which do not limit the present invention.

The solvents indicated in brackets described in chromatographic separation and TLC sections indicate elution solvents or development solvents used and the proportions are expressed in volume ratio.

The solvents indicates in brackets described in NMR sections indicate the solvents used for measurements.

LC-MS/ELSD was carried out under the following conditions:

{Column: Waters ACQUITY $C_{18}$ (particle diameter: 1.7× $10^{-6}$ m; column length: 30×2.1 mm I.D.); flow rate: 1.0 mL/min; column temperature: 40° C.; mobile phase (A): 0.1% trifluoroacetic acid aqueous solution; mobile phase (B): 0.1% trifluoroacetic acid-acetonitrile solution; gradient (the ratio of mobile phase (A):mobile phase (B)): [0 min] 95:5; [0.1 min] 95:5; [1.2 min] 5:95; [1.4 min] 5:95; [1.41 min] 95:5; [1.5 min] 95:5; detector: UV(PDA), ELSD, MS}

The compounds described herein were named by using a computer programme generally according to IUPAC nomenclature system, ACD/Name®, or Chemdraw Ultra (version 12.0, Cambridge Soft), or according to IUPAC nomenclature system.

Example 1

1-(2-nitro-4-(trifluoromethyl)phenyl)-1H-pyrazole

To a solution of 1H-pyrazole (0.39 g) in dimethylsulfoxide (hereinafter abbreviated as DMSO) (5.2 mL) was added potassium tert-butoxide (0.7 g). The reaction mixture was stirred at room temperature for 40 minutes. To the reaction mixture was gradually added 1-fluoro-2-nitro-4-(trifluoromethyl)benzene (1.1 g) and the reaction mixture was further stirred for 90 minutes. The reaction mixture was poured with a saturated ammonium chloride aqueous solution and extracted with ethyl acetate. The obtained organic layer was washed with water and a saturated sodium chloride aqueous solution, dried over magnesium sulfate and then concentrated under reduced pressure. The obtained residue was purified on silica gel column chromatography (hexane:ethyl acetate=10:1→2:1) to give the titled compound having the following physical characteristics (0.43 g).

TLC: Rf 0.43 (Hexane:Ethyl Acetate=3:1);

$^1$H-NMR (DMSO-$d_6$): δ 6.61-6.64 (m, 1H), 7.82 (d, 1H), 8.07 (d, 1H), 8.20 (dd, 1H), 8.45-8.49 (m, 2H).

Example 2

2-(1H-pyrazol-1-yl)-5-(trifluoromethyl)aniline

To a solution of the compound produced in Example 1 (430 mg) in methanol (16 mL) was added palladium-carbon (5% wet, 380 mg). The reaction mixture was placed in a hydrogen atmosphere and stirred at room temperature for 6 hours. The reaction mixture was filtered through Celite (trade name) followed by concentration of the filtrate to give the titled compound having the following physical characteristics (357 mg).

TLC: Rf 0.56 (Hexane:Ethyl Acetate=3:1);
$^1$H-NMR (DMSO-$d_6$): δ 6.10 (s, 2H), 6.52-6.56 (m, 1H), 6.92 (dd, 1H), 7.19 (d, 1H), 7.45 (d, 1H), 7.79 (d, 1H), 8.21 (d, 1H).

Example 3

2,2,2-trichloroethyl(2-(1H-pyrazol-1-yl)-5-(trifluoromethyl)phenyl)carbamate

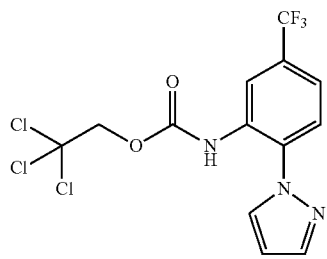 [SMILES: O=C(Nc1cc(C(F)(F)F)ccc1-n1cccn1)OCC(Cl)(Cl)Cl]

To a solution of the compound produced in Example 2 (356 mg) in ethyl acetate (8 mL) were added sodium hydrogen carbonate (400 mg) and 2,2,2-trichloroethyl carbonochloridate (430 mg). The reaction mixture was stirred at room temperature for 150 minutes. The reaction mixture was added with water and extracted with ethyl acetate. The obtained organic layer was dried over magnesium sulfate and then concentrated under reduced pressure. The obtained residue was purified on silica gel column chromatography (hexane:ethyl acetate=10:1→2:1) to give the titled compound having the following physical characteristics (610 mg).

TLC: Rf 0.60 (Hexane:Ethyl Acetate=3:1);
$^1$H-NMR (DMSO-$d_6$): δ 4.93 (s, 2H), 6.63-6.66 (m, 1H), 7.66 (dd, 1H), 7.88 (d, 1H), 7.94 (d, 1H), 8.29 (s, 1H), 8.42 (d, 1H), 10.6 (s, 1H).

Example 4

5-nitro-2-(4-(4,4,5,5-tetramethyl-1,3,2-dioxaborolan-2-yl)phenoxy)pyrimidine

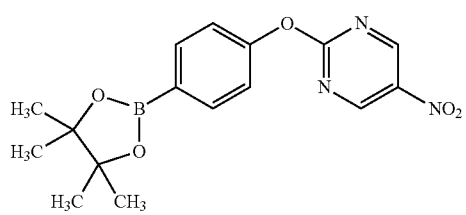 [SMILES: CC1(C)OB(c2ccc(Oc3ncc([N+](=O)[O-])cn3)cc2)OC1(C)C]

To a solution of 4-(4,4,5,5-tetramethyl-1,3,2-dioxaborolan-2-yl)phenol (10 g) in tetrahydrofuran (hereinafter abbreviated as THF) (91 mL) were added triethylamine (7 mL) and 2-chloro-5-nitropyrimidine (7.6 g). The reaction mixture was stirred at 0° C. for 1 hour. The reaction mixture was diluted in ethyl acetate and washed with a saturated sodium hydrogen carbonate aqueous solution, water and a saturated sodium chloride aqueous solution. The obtained organic layer was dried over sodium sulfate and then concentrated under reduced pressure to give the titled compound having the following physical characteristics (17 g).

TLC: Rf 0.45 (Hexane:Ethyl Acetate=4:1);
$^1$H-NMR (CDCl$_3$): δ 1.35 (s, 12H), 7.20 (d, 2H), 7.93 (d, 2H), 9.31 (s, 2H).

Example 5

2-(4-(4,4,5,5-tetramethyl-1,3,2-dioxaborolan-2-yl)phenoxy)pyrimidin-5-amine

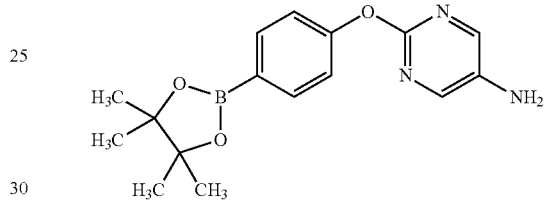

To a solution of the compound produced in Example 4 (17 g) in a mixture of ethanol (187 mL) and ethyl acetate (94 mL) was added palladium hydroxide (20% wet, 1.56 g). The reaction mixture was stirred in a hydrogen atmosphere at 35° C. for 4 hours. The reaction mixture was added with methanol (90 mL) and activated carbon (0.32 g) and stirred at room temperature for 5 minutes. The reaction mixture was filtered through Celite (trade name) followed by concentration of the filtrate. To the obtained residue was added an 1:1 mixed solvent of tert-butyl methyl ether/hexane and the precipitated solid was filtered to give the titled compound having the following physical characteristics (12.8 g).

TLC: Rf 0.29 (Hexane:Ethyl Acetate=1:1);
$^1$H-NMR (CDCl$_3$): δ 1.33 (s, 12H), 3.51 (br s, 2H), 7.14 (d, 2H), 7.85 (d, 2H), 8.06 (s, 2H).

Example 6

2-(4-(2-amino-5-chloropyridin-3-yl)phenoxy)pyrimidin-5-amine

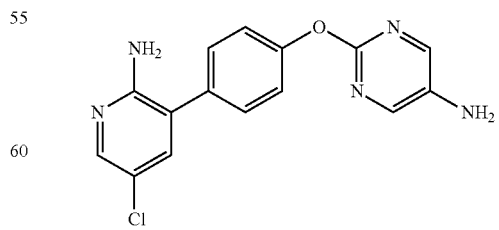

To a solution of the compound produced in Example 5 (1 g) in a mixture of 2-propanol (6.4 mL) and 1,2-dimethoxyethane (1.6 mL) were added 3-bromo-5-chloropyridin-2- amine (662 mg), potassium phosphate aqueous solution (2 M, 3.2 mL) and bis(triphenylphosphinepalladium) dichloride (112 mg). The reaction mixture was stirred in an argon atmosphere at 85° C. for 2 hours. The reaction mixture was cooled to room temperature, diluted in ethyl acetate and then washed with water. The obtained organic layer was back extracted with hydrochloric acid (0.5 M, 120 mL). The obtained aqueous layer was neutralized with a saturated sodium carbonate aqueous solution and extracted with ethyl acetate. The obtained organic layer was washed with a saturated sodium chloride aqueous solution, dried over sodium sulfate and then filtered. The obtained organic layer was concentrated to around 100 mL. The concentrated solution was purified on column chromatography (Fuji Silysia Chromatorex NH DM1020 (trade name), ethyl acetate) to give the titled compound having the following physical characteristics (857 mg).

TLC: Rf 0.32 (Dichloromethane:Ethyl Acetate:Methanol=8:4:1);

$^1$H-NMR (DMSO-d$_6$): δ 5.28 (br s, 2H), 5.82 (br s, 2H), 7.14 (d, 2H), 7.39 (d, 1H), 7.45 (d, 2H), 7.94 (d, 1H), 7.99 (s, 2H).

Example 7

1-(2-(1H-pyrazol-1-yl)-5-(trifluoromethyl)phenyl)-3-(2-(4-(2-amino-5-chloropyridin-3-yl)phenoxy)pyrimidin-5-yl)urea

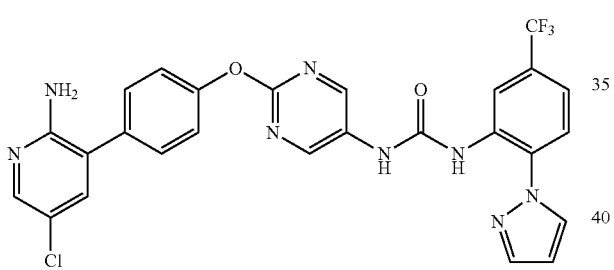

To a solution of the compound produced in Example 6 (400 mg) and the compound produced in Example 3 (513 mg) in N,N-dimethylacetamide (hereinafter abbreviated as DMA) (2.6 mL) was added triethylamine (0.018 mL). In an argon atmosphere, the reaction mixture was stirred at 65° C. for 21 hours. The reaction mixture was cooled to room temperature and then diluted in ethyl acetate. The obtained organic layer was washed three times with water and once with a saturated sodium chloride aqueous solution. The obtained organic layer was dried over sodium sulfate, filtered and then concentrated. The obtained residue was purified on silica gel column chromatography (dichloromethane:ethyl acetate=2:1) to give the present compound having the following physical characteristics (465 mg).

TLC: Rf 0.29 (Hexane:Ethyl Acetate=1:3);

$^1$H-NMR (DMSO-d$_6$): δ 5.86 (br s, 2H), 6.68 (dd, 1H), 7.27 (d, 2H), 7.42 (d, 1H), 7.46-7.56 (m, 3H), 7.75 (d, 1H), 7.92-7.99 (m, 2H), 8.41 (d, 1H), 8.58 (d, 1H), 8.70 (s, 2H), 9.71 (br s, 1H), 9.97 (br s, 1H).

Example 8

The similar procedure as Example 7 was carried out with a corresponding carbamate or isocyanate compound in place of the compound produced in Example 3 to give the present compounds having the following physical characteristics.

Example 8-1

1-(2-(4-(2-amino-5-chloropyridin-3-yl)phenoxy)pyrimidin-5-yl)-3-(2-(4-methyl-1H-1,2,3-triazol-1-yl)-5-(trifluoromethyl)phenyl)urea

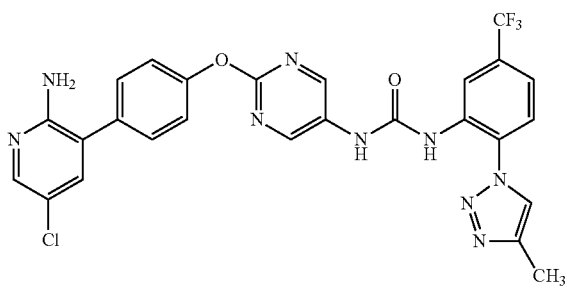 [SMILES: Cc1cn(-c2ccc(C(F)(F)F)cc2NC(=O)Nc2cnc(Oc3ccc(-c4cc(Cl)cnc4N)cc3)nc2)nn1]

TLC: Rf 0.21 (Hexane:Ethyl Acetate=1:3);

$^1$H-NMR (DMSO-d$_6$): δ 2.38 (s, 3H), 5.85 (s, 2H), 7.26 (d, 2H), 7.41 (d, 1H), 7.50 (d, 2H), 7.58 (dd, 1H), 7.69 (d, 1H), 7.94 (d, 1H), 8.39 (s, 1H), 8.58-8.61 (m, 1H), 8.68 (s, 2H), 8.76 (s, 1H), 9.69 (s, 1H).

Example 8-2

1-(2-(4-(2-amino-5-chloropyridin-3-yl)phenoxy)pyrimidin-5-yl)-3-(5-(trifluoromethyl)-2-(3-(trifluoromethyl)-1H-pyrazol-1-yl)phenyl)urea

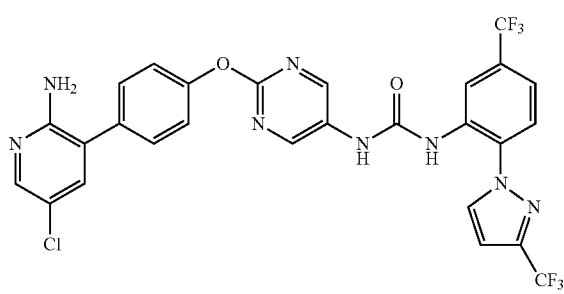

TLC: Rf 0.80 (Ethyl Acetate:Hexane=2:1);

$^1$H-NMR (DMSO-d$_6$): δ 5.85 (s, 2H), 7.12 (d, 1H), 7.26 (s, 2H), 7.42 (s, 1H), 7.51 (d, 2H), 7.58 (dd, 1H), 7.71 (d, 1H), 7.95 (d, 1H), 8.47 (s, 2H), 8.59 (s, 1H), 8.67 (s, 2H), 9.48 (s, 1H).

Example 8-3

1-(2-(1H-1,2,3-triazol-1-yl)-5-(trifluoromethyl)phenyl)-3-(2-(4-(2-amino-5-chloropyridin-3-yl)phenoxy)pyrimidin-5-yl)urea TLC: Rf 0.69 (Ethyl Acetate);

$^1$H-NMR (DMSO-d$_6$): δ 5.84 (s, 2H), 7.26 (d, 2H), 7.41 (d, 1H), 7.51 (d, 2H), 7.61 (dd, 1H), 7.74 (d, 1H), 7.95 (d, 1H), 8.09 (d, 1H), 8.57 (s, 1H), 8.67 (s, 3H), 8.71 (s, 1H), 9.65 (s, 1H).

Example 8-4

1-(2-(4-(2-amino-5-chloropyridin-3-yl)phenoxy)pyrimidin-5-yl)-3-(2-chloro-5-(trifluoromethyl)phenyl)urea

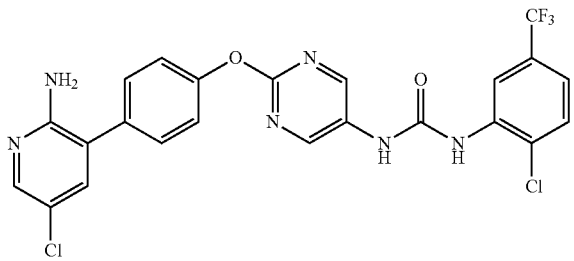 [SMILES: Nc1ncc(Cl)cc1-c1ccc(Oc2ncc(NC(=O)Nc3cc(C(F)(F)F)ccc3Cl)cn2)cc1]

TLC: Rf 0.52 (Hexane:Ethyl Acetate=1:2);
$^1$H-NMR (DMSO-d$_6$): δ 5.85 (s, 2H), 7.26 (d, 2H), 7.41 (d, 1H), 7.51 (d, 2H), 7.68 (dd, 1H), 7.86-7.89 (m, 1H), 7.94 (d, 1H), 8.42 (s, 1H), 8.74 (s, 2H), 8.79 (s, 1H), 9.76 (s, 1H).

Example 8-5

1-(2-(4-(2-amino-5-chloropyridin-3-yl)phenoxy)pyrimidin-5-yl)-3-(5-(trifluoromethyl)-2-(4-trifluoromethyl)-1H-pyrazol-1-yl)phenyl)urea TLC: Rf 0.36 (Hexane:Ethyl Acetate=1:2);
$^1$H-NMR (DMSO-d$_6$): δ 5.85 (s, 2H), 7.26 (d, 2H), 7.42 (d, 1H), 7.50 (d, 2H), 7.56 (dd, 1H), 7.76 (d, 1H), 7.95 (d, 1H), 8.38 (s, 1H), 8.54-8.59 (m, 1H), 8.69 (s, 2H), 8.98 (d, 2H), 9.75 (s, 1H).

Example 8-6

1-(2-(4-(2-amino-5-chloropyridin-3-yl)phenoxy)pyrimidin-5-yl)-3-(2-(3-(difluoromethyl)-1H-pyrazol-1-yl)-5-(trifluoromethyl)phenyl)urea TLC: Rf 0.27 (Hexane:Ethyl Acetate=1:2);
$^1$H-NMR (DMSO-d$_6$): δ 5.85 (s, 2H), 6.90-6.96 (m, 1H), 7.14 (t, 1H), 7.26 (d, 2H), 7.41 (d, 1H), 7.50 (d, 2H), 7.53-7.59 (m, 1H), 7.72 (d, 1H), 7.95 (d, 1H), 8.41-8.46 (m, 1H), 8.53 (s, 1H), 8.68 (s, 2H), 8.95 (s, 1H), 9.66 (s, 1H).

Example 8-7

1-(2-(4-(2-amino-5-chloropyridin-3-yl)phenoxy)pyrimidin-5-yl)-3-(5-(trifluoromethyl)-2-(3-(trifluoromethyl)-1H-1,2,4-triazol-1-yl)phenyl)urea TLC: Rf 0.62 (Hexane:Ethyl Acetate=1:2);
$^1$H-NMR (DMSO-d$_6$): δ 5.85 (s, 2H), 7.26 (d, 2H), 7.42 (d, 1H), 7.50 (d, 2H), 7.63 (dd, 1H), 7.81 (d, 1H), 7.95 (d, 1H), 8.47-8.50 (m, 1H), 8.65 (s, 1H), 8.66 (s, 2H), 9.24 (s, 1H), 9.33 (s, 1H).

Example 8-8

1-(2-(3-acetyl-1H-pyrazol-1-yl)-5-(trifluoromethyl)phenyl)-3-(2-(4-(2-amino-5-chloropyridin-3-yl)phenoxy)pyrimidin-5-yl)urea TLC: Rf 0.34 (Hexane:Ethyl Acetate=1:2);
$^1$H-NMR (DMSO-d$_6$): δ 2.58 (s, 3H), 5.85 (s, 2H), 7.05 (d, 1H), 7.26 (d, 2H), 7.42 (d, 1H), 7.50 (d, 2H), 7.57 (dd, 1H), 7.74 (d, 1H), 7.95 (d, 1H), 8.39 (d, 1H), 8.63 (s, 1H), 8.68 (s, 2H), 8.74 (s, 1H), 9.63 (s, 1H).

Example 8-9

1-(2-(4-(2-amino-5-chloropyridin-3-yl)phenoxy)pyrimidin-5-yl)-3-(2-(3-methyl-1H-pyrazol-1-yl)-5-(trifluoromethyl)phenyl)urea TLC: Rf 0.50 (Ethyl Acetate:Hexane=2:1);
$^1$H-NMR (DMSO-d$_6$): δ 2.37 (s, 3H), 5.85 (s, 2H), 6.45 (d, 1H), 7.27 (d, 2H), 7.43 (d, 1H), 7.47-7.54 (m, 3H), 7.70 (d, 1H), 7.95 (d, 1H), 8.28 (d, 1H), 8.57 (s, 1H), 8.70 (s, 2H), 9.81 (s, 1H), 9.92 (s, 1H).

Example 8-10

1-(2-(4-(2-amino-5-chloropyridin-3-yl)phenoxy)pyrimidin-5-yl)-3-(3-(trifluoromethyl)phenyl)urea

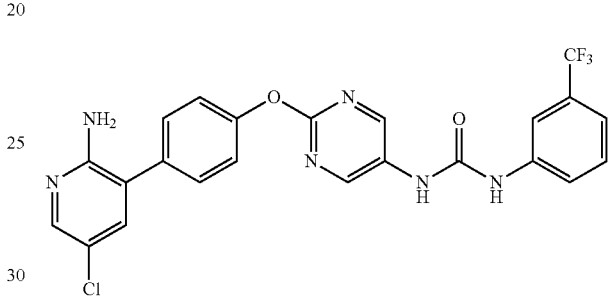

TLC: Rf 0.47 (Hexane:Ethyl Acetate=1:4);
$^1$H-NMR (DMSO-d$_6$): δ 7.27-7.34 (m, 3H), 7.42-7.53 (m, 4H), 7.61-7.66 (m, 1H), 7.88-7.92 (m, 2H), 8.73 (s, 2H).

Example 8-11

1-(2-(4-(2-amino-5-chloropyridin-3-yl)phenoxy)pyrimidin-5-yl)-3-(2-fluoro-5-(trifluoromethyl)phenyl)urea TLC: Rf 0.50 (Hexane:Ethyl Acetate=1:2);
$^1$H-NMR (DMSO-d$_6$): δ 5.85 (s, 2H), 7.26 (d, 2H), 7.38-7.55 (m, 5H), 7.95 (d, 1H), 8.51-8.55 (m, 1H), 8.74 (s, 2H), 9.09 (s, 1H), 9.30 (s, 1H).

Example 8-12

1-(2-(4-(2-amino-5-chloropyridin-3-yl)phenoxy)pyrimidin-5-yl)-3-(2-(4-methyl-1H-pyrazol-1-yl)-5-(trifluoromethyl)phenyl)urea TLC: Rf 0.55 (Ethyl Acetate:Hexane=2:1);
$^1$H-NMR (DMSO-d$_6$): δ 2.15 (s, 3H), 5.85 (s, 2H), 7.26 (d, 2H), 7.42 (d, 1H), 7.49-7.52 (m, 3H), 7.69 (d, 1H), 7.78 (s, 1H), 7.95 (d, 1H), 8.18 (d, 1H), 8.57 (d, 1H), 8.70 (d, 2H), 9.83 (s, 1H), 9.97 (s, 1H).

Example 8-13

1-(2-(4-(2-amino-5-chloropyridin-3-yl)phenoxy)pyrimidin-5-yl)-3-(2-(5-methyl-1H-1,2,3-triazol-1-yl)-5-(trifluoromethyl)phenyl)urea TLC: Rf 0.63 (Ethyl Acetate);
$^1$H-NMR (DMSO-d$_6$): δ 2.19 (s, 3H), 5.84 (d, 2H), 7.26 (d, 2H), 7.42 (d, 2H), 7.50 (d, 2H), 7.61 (d, 1H), 7.84 (s, 1H), 7.94 (d, 1H), 8.29 (s, 1H), 8.64 (s, 1H), 8.66 (s, 2H), 9.45 (s, 1H).

Example 8-14

1-(2-(4-(2-amino-5-chloropyridin-3-yl)phenoxy)pyrimidin-5-yl)-3-(2-methyl-5-(trifluoromethyl)phenyl)urea TLC: Rf 0.30 (Ethyl Acetate:Hexane=2:1);
$^1$H-NMR (DMSO-d$_6$): δ 2.32 (s, 3H), 5.85 (s, 2H), 7.28 (d, 2H), 7.31 (d, 1H), 7.39-7.44 (m, 2H), 7.51 (d, 2H), 7.95 (d, 1H), 8.27 (s, 1H), 8.38 (s, 1H), 8.75 (s, 2H), 9.34 (s, 1H).

Example 8-15

1-(2-(4-(2-amino-5-chloropyridin-3-yl)phenoxy)pyrimidin-5-yl)-3-(2-(3-(1-hydroxyethyl)-1H-pyrazol-1-yl)-5-(trifluoromethyl)phenyl)urea TLC: Rf 0.19 (Hexane:Ethyl Acetate=1:2);
$^1$H-NMR (DMSO-d$_6$): δ 1.44 (d, 3H), 4.92 (quint., 1H), 5.23 (d, 1H), 5.85 (s, 2H), 6.58 (d, 1H), 7.26 (d, 2H), 7.42 (d, 1H), 7.47-7.54 (m, 3H), 7.72 (d, 1H), 7.95 (d, 1H), 8.28-8.31 (m, 1H), 8.50 (d, 1H), 8.69 (s, 2H), 9.69 (s, 1H), 9.85 (s, 1H).

Example 8-16

1-(2-(1H-1,2,4-triazol-1-yl)-5-(trifluoromethyl)phenyl)-3-(2-(4-(2-amino-5-chloropyridin-3-yl)phenoxy)pyrimidin-5-yl)urea TLC: Rf 0.46 (Ethyl Acetate);
$^1$H-NMR (DMSO-d$_6$): δ 5.85 (s, 2H), 7.26 (d, 2H), 7.42 (d, 1H), 7.50 (d, 2H), 7.59 (d, 1H), 7.77 (d, 1H), 7.95 (d, 1H), 8.42 (s, 1H), 8.56 (s, 1H), 8.68 (s, 2H), 8.79 (s, 1H), 9.09 (s, 1H), 9.66 (s, 1H).

Example 8-17

1-(2-(4-(2-amino-5-chloropyridin-3-yl)phenoxy)pyrimidin-5-yl)-3-(4-methyl-3-(trifluoromethyl)phenyl)urea TLC: Rf 0.80 (Ethyl Acetate);
$^1$H-NMR (DMSO-d$_6$): δ 2.36 (d, 3H), 5.85 (s, 2H), 7.26 (dd, 2H), 7.34 (d, 1H), 7.42 (d, 1H), 7.51 (dd, 2H), 7.57 (d, 1H), 7.89 (d, 1H), 7.96 (d, 1H), 8.72 (s, 2H), 8.92 (s, 1H), 9.18 (s, 1H).

Example 8-18

1-(2-(4-(2-amino-5-chloropyridin-3-yl)phenoxy)pyrimidin-5-yl)-3-(3-fluoro-5-(trifluoromethyl)phenyl)urea TLC: Rf 0.26 (Ethyl Acetate:Hexane=1:1);
$^1$H-NMR (DMSO-d$_6$): δ 5.85 (s, 2H), 7.26 (d, 1H), 7.27 (dd, 2H), 7.43 (d, 1H), 7.51 (dd, 2H), 7.53-7.65 (m, 2H), 7.70 (s, 1H), 7.95 (d, 1H), 8.73 (s, 2H), 9.11 (s, 1H), 9.52 (s, 1H).

Example 8-19

1-(2-(4-(2-amino-5-chloropyridin-3-yl)phenoxy)pyrimidin-5-yl)-3-(4-chloro-3-(trifluoromethyl)phenyl)urea TLC: Rf 0.53 (Ethyl Acetate:Hexane=3:1);
$^1$H-NMR (DMSO-d$_6$): δ 5.85 (s, 2H), 7.25 (dd, 2H), 7.42 (dd, 1H), 7.51 (d, 2H), 7.61 (d, 1H), 7.70 (d, 1H), 7.95 (dd, 1H), 8.06 (s, 1H), 8.72 (s, 2H), 9.04 (s, 1H), 9.44 (s, 1H).

Example 8-20

1-(2-(4-(2-amino-5-chloropyridin-3-yl)phenoxy)pyrimidin-5-yl)-3-(2-(5-methyl-1H-pyrazol-1-yl)-5-(trifluoromethyl)phenyl)urea TLC: Rf 0.39 (Ethyl Acetate:Hexane=2:1);
$^1$H-NMR (DMSO-d$_6$): δ 2.20 (s, 3H), 5.84 (s, 2H), 6.40 (s, 1H), 7.26 (d, 2H), 7.41 (d, 1H), 7.52 (d, 2H), 7.53 (d, 1H), 7.55 (d, 1H), 7.75 (d, 1H), 7.94 (d, 1H), 8.40 (s, 1H), 8.61 (s, 1H), 8.67 (s, 2H), 9.73 (s, 1H).

Example 8-21

1-(2-(4-(2-amino-5-chloropyridin-3-yl)phenoxy)pyrimidin-5-yl)-3-(2-(5-methyl-3-(trifluoromethyl)-1H-pyrazol-1-yl)-5-(trifluoromethyl)phenyl)urea TLC: Rf 0.28 (Hexane:Ethyl Acetate=1:2);
$^1$H-NMR (DMSO-d$_6$): δ 2.19 (s, 3H), 5.85 (s, 2H), 6.88 (s, 1H), 7.26 (d, 2H), 7.38-7.43 (m, 1H), 7.46-7.63 (m, 4H), 7.92-7.97 (m, 1H), 8.31 (s, 1H), 8.61 (s, 1H), 8.67 (s, 2H), 9.38 (s, 1H).

Example 8-22

1-(2-(4-(2-amino-5-chloropyridin-3-yl)phenoxy)pyrimidin-5-yl)-3-(3-chloro-5-(trifluoromethyl)phenyl)urea TLC: Rf 0.80 (Ethyl Acetate);
$^1$H-NMR (DMSO-d$_6$): δ 5.86 (s, 2H), 7.27 (d, 2H), 7.43 (s, 2H), 7.51 (d, 2H), 7.84 (s, 2H), 7.95 (d, 1H), 8.73 (s, 2H), 9.15 (s, 1H), 9.51 (s, 1H).

Example 9

The similar procedures as Example 4→Example 5→Example 6→Example 7 were carried out with 3-bromo-5-chloropyridin-2-amine or 3-bromo-5-fluoropyridin-2-amine in place of 3-bromo-5-chloropyridin-2-amine; 2-chloro-5-nitropyridine in place of 2-chloro-5-nitropyrimidine; and the compound produced in Example 3 or a corresponding carbamate compound in place of the compound produced in Example 3 to give the present compounds having the following physical characteristics.

Example 9-1

1-(2-(1H-pyrazol-1-yl)-5-(trifluoromethyl)phenyl-3-(6-(4-(2-amino-5-chloropyridin-3-yl)phenoxy)pyridin-3-yl)urea

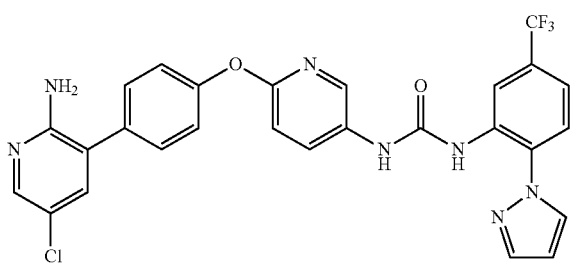 [SMILES: Nc1ncc(Cl)cc1-c1ccc(Oc2ccc(NC(=O)Nc3cc(C(F)(F)F)ccc3-n3cccn3)cn2)cc1]

TLC: Rf 0.62 (Hexane:Ethyl Acetate=1:4);

$^1$H-NMR (DMSO-$d_6$): δ 5.85 (s, 2H), 6.67 (t, 1H), 7.04 (d, 1H), 7.15 (d, 2H), 7.39 (d, 1H), 7.45-7.51 (m, 3H), 7.72 (d, 1H), 7.93-7.94 (m, 2H), 8.00 (dd, 1H), 8.19 (d, 1H), 8.39 (d, 1H), 8.58 (d, 1H), 9.56 (s, 1H), 9.82 (s, 1H).

Example 9-2

1-(2-(1H-1,2,3-triazol-1-yl)-5-(trifluoromethyl)phenyl-3-(6-(4-(2-amino-5-chloropyridin-3-yl)phenoxy)pyridin-3-yl)urea

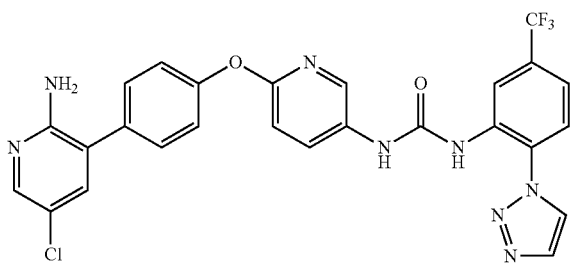 [SMILES: Nc1ncc(Cl)cc1-c1ccc(Oc2ccc(NC(=O)Nc3cc(C(F)(F)F)ccc3-n3ccnn3)cn2)cc1]

TLC: Rf 0.69 (Ethyl Acetate);

$^1$H-NMR (DMSO-$d_6$): δ 5.84 (s, 2H), 7.04 (d, 1H), 7.16 (d, 2H), 7.39 (d, 1H), 7.47 (d, 2H), 7.59 (d, 1H), 7.72 (d, 1H), 7.94 (d, 1H), 7.99 (dd, 1H), 8.10 (d, 1H), 8.15 (d, 1H), 8.59-8.61 (m, 2H), 8.68 (s, 1H), 9.57 (s, 1H).

Example 9-3

1-(2-(1H-pyrazol-1-yl)-5-(trifluoromethyl)phenyl-3-(6-(4-(2-amino-5-fluoropyridin-3-yl)phenoxy)pyridin-3-yl)urea TLC: Rf 0.27 (Hexane:Ethyl Acetate=1:3);

$^1$H-NMR (DMSO-$d_6$): δ 5.55 (s, 2H), 6.67 (t, 1H), 7.04 (d, 1H), 7.16 (d, 2H), 7.34 (dd, 1H), 7.47-7.50 (m, 3H), 7.72 (d, 1H), 7.91-7.94 (m, 2H), 8.01 (dd, 1H), 8.19 (d, 1H), 8.39 (d, 1H), 8.59 (d, 1H), 9.55 (s, 1H), 9.82 (s, 1H).

Example 10

2-(pyridin-3-yl)-5-(trifluoromethyl)aniline

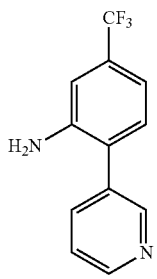 [SMILES: Nc1cc(C(F)(F)F)ccc1-c1cccnc1]

To a solution of 2-bromo-5-(trifluoromethyl)aniline (10 g) and 3-pyridineboronic acid (5.63 g) in acetonitrile (20 mL) were added water (10 mL), sodium carbonate (14.57 g) and bis(triphenylphosphine)palladium (II) dichloride (1.46 g). In an argon atmosphere, the reaction mixture was stirred at 100° C. for 14 hours. The reaction mixture was cooled to room temperature and extracted with ethyl acetate. The organic layer was dried over magnesium sulfate and then concentrated under reduced pressure. The obtained residue was purified on silica gel column chromatography (hexane:ethyl acetate=1:0→0:1), washed with hexane and then dried to give the titled compound having the following physical characteristics (7.62 g).

TLC: Rf 0.56 (Ethyl Acetate:Hexane=3:1);

$^1$H-NMR (DMSO-$d_6$): δ 5.40 (s, 2H), 6.90 (d, 1H), 7.08 (s, 1H), 7.18 (d, 1H), 7.48 (dd, 1H), 7.85 (d, 1H), 8.57 (d, 1H), 8.60 (d, 1H).

Example 11

1-(6-(4-(2-amino-5-chloropyridin-3-yl)phenoxy)pyridin-3-yl)-3-(2-(pyridin-3-yl)-5-(trifluoromethyl)phenyl)urea The similar procedures as Example 3→Example 4→Example 5→Example 6→Example 7 were carried out with 2-chloro-5-nitropyridine in place of 2-chloro-5-nitropyrimidine and the compound produced in Example 10 in place of the compound produced in Example 2 to give the present compound having the following physical characteristics.

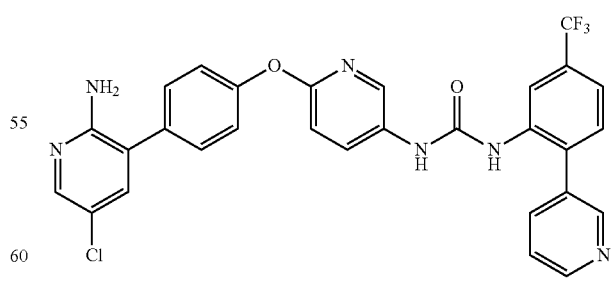

TLC: Rf 0.43 (Ethyl Acetate);

$^1$H-NMR (DMSO-$d_6$): δ 5.80 (s, 2H), 7.04 (d, 1H), 7.16 (s, 2H), 7.41 (d, 1H), 7.47 (s, 1H), 7.50 (s, 2H), 7.54-7.61 (m, 2H), 7.90 (dt, 1H), 7.91 (d, 1H), 7.99 (s, 1H), 8.11-8.15 (m, 2H), 8.43 (s, 1H), 8.64-8.71 (m, 2H), 9.20 (s, 1H).

Example 12

1-(2-(4-(2-amino-5-chloropyridin-3-yl)phenoxy)pyrimidin-5-yl)-3-(2-(pyridin-3-yl)-5-(trifluoromethyl)phenyl)urea The similar procedures as Example 3→Example 7 were carried out with the compound produced in Example 10 in place of the compound produced in Example 2 to give the present compound having the following physical characteristics.

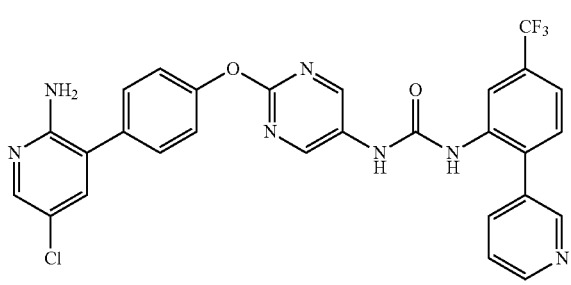 [SMILES: Nc1ncc(Cl)cc1-c1ccc(Oc2ncc(NC(=O)Nc3cc(C(F)(F)F)ccc3-c3cccnc3)cn2)cc1]

TLC: Rf 0.60 (Ethyl Acetate:Methanol=19:1);
$^1$H-NMR (DMSO-$d_6$): δ 5.84 (s, 2H), 7.25 (d, 2H), 7.41 (d, 1H), 7.48-7.58 (m, 5H), 7.89 (dd, 1H), 7.94 (d, 1H), 8.23 (s, 1H), 8.38 (s, 1H), 8.65-8.68 (m, 4H), 9.23 (s, 1H).

Example 13

The similar procedures as Example 10→Example 3→Example 7 were carried out with a corresponding boronic acid compound or a boronate ester compound in place of 3-pyridineboronic acid to give the present compounds having the following physical characteristics.

Example 13-1

1-(2-(4-(2-amino-5-chloropyridin-3-yl)phenoxy)pyrimidin-5-yl)-3-(2-(1-methyl-1H-pyrazol-5-yl)-5-(trifluoromethyl)phenyl)urea

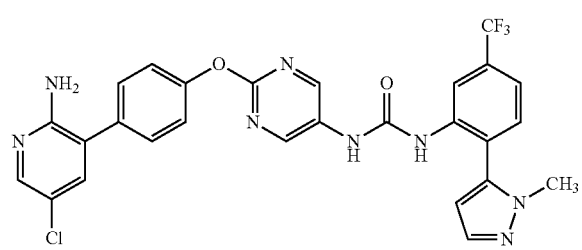 [SMILES: Cn1nccc1-c1ccc(C(F)(F)F)cc1NC(=O)Nc1cnc(Oc2ccc(-c3cc(Cl)cnc3N)cc2)nc1]

TLC: Rf 0.60 (Ethyl Acetate);
$^1$H-NMR (DMSO-$d_6$): δ 3.65 (s, 3H), 5.85 (s, 2H), 6.46 (s, 1H), 7.27 (d, 2H), 7.42 (d, 1H), 7.50-7.52 (m, 4H), 7.62 (s, 1H), 7.95 (d, 1H), 8.09 (s, 1H), 8.56 (s, 1H), 8.68 (s, 2H), 9.49 (s, 1H).

Example 13-2

1-(2-(4-(2-amino-5-chloropyridin-3-yl)phenoxy)pyrimidin-5-yl)-3-(2-(1-methyl-1H-pyrazol-4-yl)-5-(trifluoromethyl)phenyl)urea

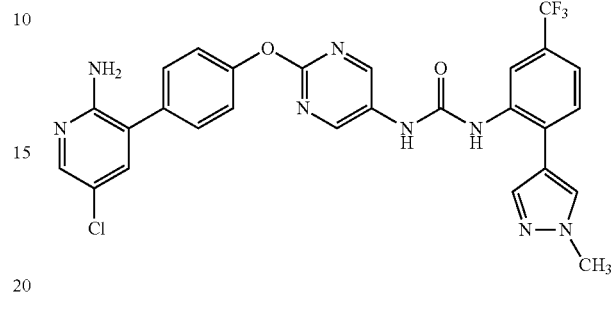

TLC: Rf 0.40 (Ethyl Acetate:Methanol=9:1);
$^1$H-NMR (DMSO-$d_6$): δ 3.92 (s, 3H), 5.85 (s, 2H), 7.25-7.27 (m, 2H), 7.39-7.42 (m, 2H), 7.49-7.51 (m, 3H), 7.76 (s, 1H), 7.95 (d, 1H), 8.10 (s, 1H), 8.24-8.27 (m, 2H), 8.71 (s, 2H), 9.41 (s, 1H).

Example 13-3

1-(2-(4-(2-amino-5-chloropyridin-3-yl)phenoxy)pyrimidin-5-yl)-3-(2-(1-methyl-3-(trifluoromethyl)-1H-pyrazol-5-yl)-5-(trifluoromethyl)phenyl)urea TLC: Rf 0.78 (Ethyl Acetate:Hexane=2:1);
$^1$H-NMR (DMSO-$d_6$): δ 3.73 (s, 3H), 5.85 (s, 2H), 6.96 (s, 1H), 7.26 (d, 2H), 7.42 (d, 1H), 7.51 (d, 2H), 7.53 (d, 1H), 7.58 (d, 1H), 7.95 (d, 1H), 8.28 (s, 1H), 8.53 (s, 1H), 8.68 (s, 2H), 9.32 (s, 1H).

Example 13-4

1-(2-(4-(2-amino-5-chloropyridin-3-yl)phenoxy)pyrimidin-5-yl)-3-(2-(1-methyl-1H-pyrazol-3-yl)-5-(trifluoromethyl)phenyl)urea TLC: Rf 0.48 (Ethyl Acetate);
$^1$H-NMR (DMSO-$d_6$): δ 4.03 (s, 3H), 8.57 (s, 2H), 6.92 (d, 1H), 7.28 (d, 2H), 7.39 (d, 1H), 7.43 (d, 1H), 7.52 (d, 2H), 7.94 (dd, 3H), 8.65 (s, 1H), 8.74 (s, 2H), 9.93 (s, 1H), 10.77 (s, 1H).

Example 14

The similar procedures as Example 6→Example 7 were carried out with 3-bromo-5-fluoropyridin-2-amine in place of 3-bromo-5-chloropyridin-2-amine; and Example 3 or a corresponding carbamate or isocyanate compound in place of Example 3 to give the present compounds having the following physical characteristics.

Example 14-1

1-(2-(4-(2-amino-5-fluoropyridin-3-yl)phenoxy)pyrimidin-5-yl)-3-(2-fluoro-5-(trifluoromethyl)phenyl)urea

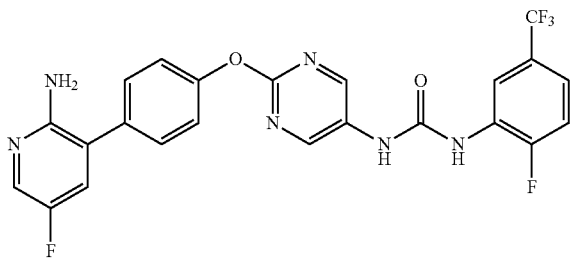 [SMILES: Nc1ncc(F)cc1-c1ccc(Oc2ncc(NC(=O)Nc3cc(C(F)(F)F)ccc3F)cn2)cc1]

TLC: Rf 0.65 (Hexane:Ethyl Acetate=1:9);
$^1$H-NMR (DMSO-$d_6$): δ 5.56 (s, 2H), 7.28 (d, 2H), 7.35-7.54 (m, 5H), 7.93 (d, 1H), 8.51-8.53 (m, 1H), 8.74 (s, 2H), 9.09 (s, 1H), 9.29 (s, 1H).

Example 14-2

1-(2-(4-(2-amino-5-fluoropyridin-3-yl)phenoxy)pyrimidin-5-yl)-3-(3-(trifluoromethyl)phenyl)urea TLC: Rf 0.16 (Ethyl Acetate:Hexane=1:1);
$^1$H-NMR (DMSO-$d_6$): δ 5.56 (s, 2H), 7.27 (d, 2H), 7.33 (d, 1H), 7.38 (dd, 1H), 7.51 (d, 1H), 7.53 (dd, 2H), 7.60 (d, 1H), 7.94 (d, 1H), 7.97 (s, 1H), 8.73 (s, 2H), 8.98 (s, 1H), 9.431 (s, 1H).

Example 14-3

1-(2-(4-(2-amino-5-fluoropyridin-3-yl)phenoxy)pyrimidin-5-yl)-3-(5-(trifluoromethyl)-2-(3-(trifluoromethyl)-1H-pyrazol-1-yl)phenyl)urea

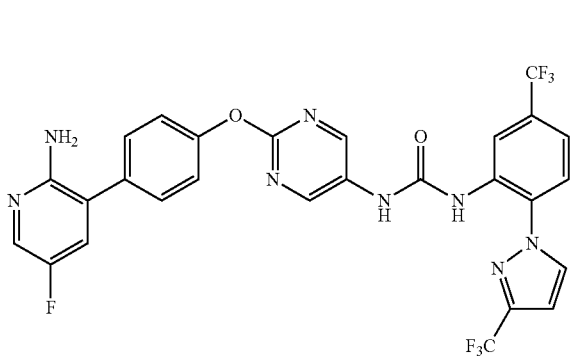 [SMILES: Nc1ncc(F)cc1-c1ccc(Oc2ncc(NC(=O)Nc3cc(C(F)(F)F)ccc3-n3ccc(C(F)(F)F)n3)cn2)cc1]

TLC: Rf 0.74 (Ethyl Acetate:Hexane=2:1);
$^1$H-NMR (DMSO-$d_6$): δ 5.56 (s, 2H), 7.12 (d, 1H), 7.27 (d, 2H), 7.37 (dd, 1H), 7.53 (d, 2H), 7.59 (dd, 1H), 7.71 (d, 1H), 7.94 (d, 1H), 8.47 (s, 2H), 8.58 (s, 1H), 8.67 (s, 2H), 9.48 (s, 1H).

Example 14-4

1-(2-(1H-pyrazol-1-yl)-5-(trifluoromethyl)phenyl)-3-(2-(4-(2-amino-5-fluoropyridin-3-yl)phenoxy)pyrimidin-5-yl)urea TLC: Rf 0.49 (Ethyl Acetate:Hexane=2:1);
$^1$H-NMR (DMSO-$d_6$): δ 5.56 (s, 2H), 6.68 (s, 1H), 7.27 (d, 2H), 7.38 (dd, 1H), 7.53 (d, 3H), 7.75 (d, 1H), 7.92-7.98 (m, 2H), 8.41 (s, 1H), 8.58 (s, 1H), 8.70 (s, 2H), 9.70 (s, 1H), 9.96 (s, 1H).

Example 14-5

1-(2-(1H-1,2,3-triazol-1-yl)-5-(trifluoromethyl)phenyl)-3-(2-(4-(2-amino-5-fluoropyridin-3-yl)phenoxy)pyrimidin-5-yl)urea

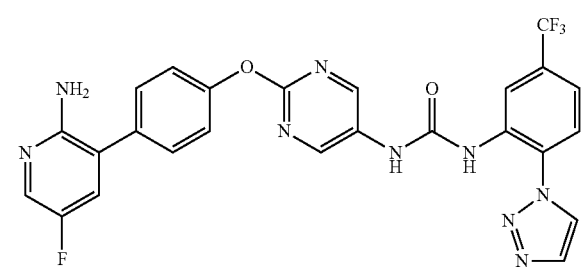 [SMILES: Nc1ncc(F)cc1-c1ccc(Oc2ncc(NC(=O)Nc3cc(C(F)(F)F)ccc3-n3ccnn3)cn2)cc1]

TLC: Rf 0.69 (Ethyl Acetate);
$^1$H-NMR (DMSO-$d_6$): δ 5.55 (s, 2H), 7.27 (d, 2H), 7.37 (dd, 1H), 7.52 (d, 2H), 7.61 (d, 1H), 7.74 (d, 1H), 7.93 (d, 1H), 8.09 (s, 1H), 8.57 (s, 1H), 8.67 (s, 3H), 8.71 (s, 1H), 9.65 (s, 1H).

Example 14-6

1-(2-(4-(2-amino-5-fluoropyridin-3-yl)phenoxy)pyrimidin-5-yl)-3-(2-(pyridin-3-yl)-5-(trifluoromethyl)phenyl)urea

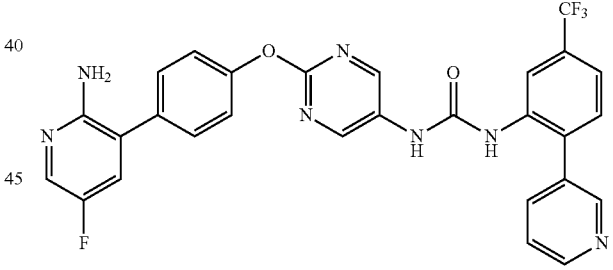

TLC: Rf 0.62 (Ethyl Acetate:Methanol=19:1);
$^1$H-NMR (DMSO-$d_6$): δ 5.55 (s, 2H), 7.25 (d, 2H), 7.36 (dd, 1H), 7.48-7.58 (m, 5H), 7.89 (dd, 1H), 7.93 (d, 1H), 8.24 (s, 1H), 8.38 (s, 1H), 8.64-8.68 (m, 4H), 9.23 (s, 1H).

Example 14-7

1-(2-(4-(2-amino-5-fluoropyridin-3-yl)phenoxy)pyrimidin-5-yl)-3-(2-(4-methyl-1H-1,2,3-triazol-1-yl)-5-(trifluoromethyl)phenyl)urea TLC: Rf 0.33 (Ethyl Acetate:Hexane=3:1);
$^1$H-NMR (DMSO-$d_6$): δ 2.38 (s, 3H), 5.56 (s, 2H), 7.26 (d, 2H), 7.36 (dd, 1H), 7.52 (dd, 2H), 7.60 (d, 1H), 7.69 (d, 1H), 7.94 (d, 1H), 8.34 (d, 1H), 8.59 (d, 1H), 8.68 (d, 2H), 8.76 (s, 1H), 9.69 (s, 1H).

Example 14-8

1-(2-(4-(2-amino-5-fluoropyridin-3-yl)phenoxy)pyrimidin-5-yl)-3-(2-(1-methyl-1H-pyrazol-4-yl)-5-(trifluoromethyl)phenyl)urea

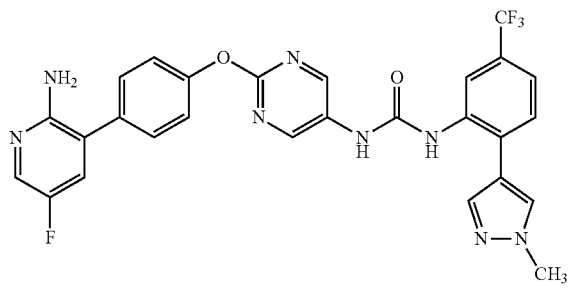 [SMILES: Cn1cc(-c2ccc(C(F)(F)F)cc2NC(=O)Nc2cnc(Oc3ccc(-c4cc(F)cnc4N)cc3)nc2)cn1]

TLC: Rf 0.31 (Ethyl Acetate:Methanol=9:1);
$^1$H-NMR (DMSO-$d_6$): δ 3.92 (s, 3H), 5.56 (s, 2H), 7.27 (d, 2H), 7.35-7.42 (m, 2H), 7.51-7.55 (m, 3H), 7.76 (s, 1H), 7.93 (d, 1H), 8.10 (s, 1H), 8.24 (s, 1H), 8.28 (s, 1H), 8.71 (s, 2H), 9.42 (s, 1H).

Example 14-9

1-(2-(4-(2-amino-5-fluoropyridin-3-yl)phenoxy)pyrimidin-5-yl)-3-(2-(1-methyl-1H-pyrazol-5-yl)-5-(trifluoromethyl)phenyl)urea TLC: Rf 0.50 (Ethyl Acetate);
$^1$H-NMR (DMSO-$d_6$): δ 3.65 (s, 3H), 5.56 (s, 2H), 6.45 (s, 1H), 7.27 (d, 2H), 7.37 (dd, 1H), 7.49-7.54 (m, 4H), 7.62 (s, 1H), 7.94 (d, 1H), 8.09 (s, 1H), 8.56 (s, 1H), 8.68 (s, 2H), 9.49 (s, 1H).

Example 14-10

1-(2-(1H-1,2,4-triazol-1-yl)-5-(trifluoromethyl)phenyl)-3-(2-(4-(2-amino-5-fluoropyridin-3-yl)phenoxy)pyrimidin-5-yl)urea TLC: Rf 0.44 (Ethyl Acetate);
$^1$H-NMR (DMSO-$d_6$): δ 5.56 (s, 2H), 7.27 (d, 2H), 7.36 (dd, 1H), 7.51 (d, 2H), 7.57 (d, 1H), 7.77 (d, 1H), 7.93 (d, 1H), 8.41 (s, 1H), 8.56 (d, 1H), 8.68 (s, 2H), 8.78 (s, 1H), 9.09 (s, 1H), 9.66 (s, 1H).

Example 14-11

1-(2-(4-(2-amino-5-fluoropyridin-3-yl)phenoxy)pyrimidin-5-yl)-3-(2-methyl-5-(trifluoromethyl)phenyl)urea TLC: Rf 0.38 (Ethyl Acetate:Hexane=2:1);
$^1$H-NMR (DMSO-$d_6$): δ 2.32 (s, 3H), 5.56 (s, 2H), 7.25-7.46 (m, 5H), 7.54 (d, 2H), 7.94 (d, 1H), 8.27 (s, 1H), 8.38 (s, 1H), 8.75 (s, 2H), 9.33 (s, 1H).

Example 14-12

1-(2-(4-(2-amino-5-fluoropyridin-3-yl)phenoxy)pyrimidin-5-yl)-3-(2-chloro-5-(trifluoromethyl)phenyl)urea TLC: Rf 0.71 (Hexane:Ethyl Acetate=1:9);
$^1$H-NMR (DMSO-$d_6$): δ 5.56 (s, 2H), 7.28 (d, 2H), 7.36-7.41 (m, 2H), 7.53 (d, 2H), 7.72 (d, 1H), 7.93 (d, 1H), 8.56 (s, 1H), 8.74 (s, 2H), 8.78 (s, 1H), 9.71 (s, 1H).

Example 14-13

1-(2-(4-(2-amino-5-fluoropyridin-3-yl)phenoxy)pyrimidin-5-yl)-3-(2-(4-methyl-1H-pyrazol-1-yl)-5-(trifluoromethyl)phenyl)urea TLC: Rf 0.50 (Ethyl Acetate:Hexane=2:1);
$^1$H-NMR (DMSO-$d_6$): δ 2.15 (s, 3H), 5.56 (s, 2H), 7.26 (d, 2H), 7.36 (dd, 1H), 7.47-7.55 (m, 3H), 7.70 (d, 1H), 7.78 (s, 1H), 7.93 (d, 1H), 8.18 (s, 1H), 8.57 (d, 1H), 8.70 (s, 2H), 9.83 (s, 1H), 9.96 (s, 1H).

Example 14-14

1-(2-(4-(2-amino-5-fluoropyridin-3-yl)phenoxy)pyrimidin-5-yl)-3-(2-(5-methyl-1H-1,2,3-triazol-1-yl)-5-(trifluoromethyl)phenyl)urea TLC: Rf 0.63 (Ethyl Acetate);
$^1$H-NMR (DMSO-$d_6$): δ 2.20 (s, 3H), 5.55 (s, 2H), 7.27 (d, 2H), 7.37 (dd, 1H), 7.53 (d, 2H), 7.62 (d, 2H), 7.84 (s, 1H), 7.94 (d, 1H), 8.30 (s, 1H), 8.65 (s, 1H), 8.67 (s, 2H), 9.46 (s, 1H).

Example 14-15

1-(2-(4-(2-amino-5-fluoropyridin-3-yl)phenoxy)pyrimidin-5-yl)-3-(4-methyl-3-(trifluoromethyl)phenyl)urea TLC: Rf 0.43 (Hexane:Ethyl Acetate=1:4);
$^1$H-NMR (DMSO-$d_6$): δ 2.36 (s, 3H), 5.57 (s, 2H), 7.27 (d, 2H), 7.30-7.42 (m, 2H), 7.50-7.60 (m, 3H), 7.89 (s, 1H), 7.94 (d, 1H), 8.72 (s, 2H), 8.92 (s, 1H), 9.18 (s, 1H).

Example 14-16

1-(2-(4-(2-amino-5-fluoropyridin-3-yl)phenoxy)pyrimidin-5-yl)-3-(2-(3-methyl-1H-pyrazol-1-yl)-5-(trifluoromethyl)phenyl)urea TLC: Rf 0.45 (Ethyl Acetate:Hexane=2:1);
$^1$H-NMR (DMSO-$d_6$): δ 2.37 (s, 3H), 5.56 (s, 2H), 6.45 (s, 1H), 7.28 (d, 2H), 7.38 (dd, 1H), 7.48-7.60 (m, 1H), 7.53 (d, 2H), 7.70 (d, 1H), 7.94 (d, 1H), 8.28 (d, 1H), 8.57 (s, 1H), 8.70 (s, 2H), 9.81 (s, 1H), 9.92 (s, 1H).

Example 14-17

1-(2-(4-(2-amino-5-fluoropyridin-3-yl)phenoxy)pyrimidin-5-yl)-3-(3-fluoro-5-(trifluoromethyl)phenyl)urea TLC: Rf 0.20 (Ethyl Acetate:Hexane=1:1);
$^1$H-NMR (DMSO-$d_6$): δ 5.57 (s, 2H), 7.22-7.33 (m, 3H), 7.38 (dd, 1H), 7.53 (d, 2H), 7.62 (d, 1H), 7.72 (s, 1H), 7.94 (d, 1H), 8.73 (s, 2H), 9.11 (s, 1H), 9.52 (s, 1H).

Example 14-18

1-(2-(4-(2-amino-5-fluoropyridin-3-yl)phenoxy)pyrimidin-5-yl)-3-(4-chloro-3-(trifluoromethyl)phenyl)urea TLC: Rf 0.46 (Ethyl Acetate:Hexane=3:1);
$^1$H-NMR (DMSO-$d_6$): δ 5.56 (s, 2H), 7.26 (d, 2H), 7.38 (dd, 1H), 7.52 (d, 2H), 7.61 (d, 1H), 7.68 (d, 1H), 7.93 (dd, 1H), 8.07 (s, 1H), 8.72 (d, 2H), 9.05 (s, 1H), 9.44 (s, 1H).

Example 14-19

1-(2-(4-(2-amino-5-fluoropyridin-3-yl)phenoxy)pyrimidin-5-yl)-3-(3-chloro-5-(trifluoromethyl)phenyl)urea TLC: Rf 0.80 (Ethyl Acetate);
$^1$H-NMR (DMSO-$d_6$): δ 5.57 (s, 2H), 7.27 (dd, 2H), 7.36 (dd, 1H), 7.43 (s, 1H), 7.53 (dd, 2H), 7.83 (d, 2H), 7.93 (s, 1H), 8.73 (s, 2H), 9.13 (s, 1H), 9.49 (s, 1H).

Example 14-20

1-(2-(4-(2-amino-5-fluoropyridin-3-yl)phenoxy)pyrimidin-5-yl)-3-(2-(5-methyl-1H-pyrazol-1-yl)-5-(trifluoromethyl)phenyl)urea TLC: Rf 0.39 (Ethyl Acetate:Hexane=2:1);
$^1$H-NMR (DMSO-$d_6$): δ 2.20 (s, 3H), 5.50 (s, 2H), 6.40 (s, 1H), 7.27 (d, 2H), 7.37 (dd, 1H), 7.51-7.55 (m, 4H), 7.75 (s, 1H), 7.93 (d, 1H), 8.40 (s, 1H), 8.61 (s, 1H), 8.67 (s, 2H), 9.73 (s, 1H).

Example 15

The similar procedures as Example 4→Example 5→Example 6→Example 7 were carried out with 3-bromo-5-chloropyridin-2-amine or a corresponding amine compound in place of 3-bromo-5-chloropyridin-2-amine; 2-chloro-5-nitropyrimidine or 2-chloro-5-nitropyridine in place of 2-chloro-5-nitropyrimidine; and a corresponding carbamate or isocyanate compound in place of the compound produced in Example 3 to give the present compounds having the following physical characteristics.

Example 15-1

1-(2-(4-(2-amino-5-methylpyridin-3-yl)phenoxy)pyrimidin-5-yl)-3-(3-(trifluoromethyl)phenyl)urea

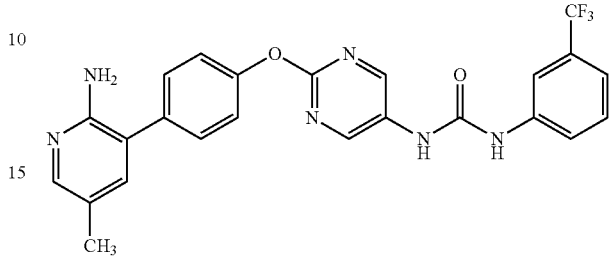

TLC: Rf 0.22 (Ethyl Acetate:Methanol=9:1);
$^1$H-NMR (DMSO-$d_6$): δ 2.16 (s, 3H), 5.47 (s, 2H), 7.21-7.27 (m, 3H), 7.33 (d, 1H), 7.47-7.54 (m, 3H), 7.62 (d, 1H), 7.79 (s, 1H), 7.97 (s, 1H), 8.73 (s, 2H), 8.99 (s, 1H), 9.32 (s, 1H).

Example 15-2

1-(2-(1H-pyrazol-1-yl)-4-(trifluoromethyl)phenyl)-3-(2-(4-(2-amino-5-fluoropyridin-3-yl)phenoxy)pyrimidin-5-yl)urea

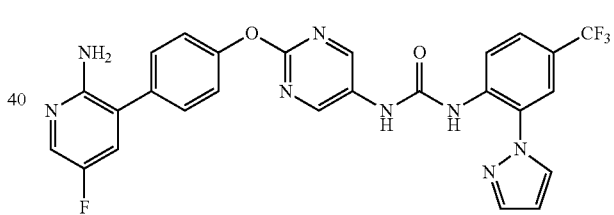

TLC: Rf 0.54 (Ethyl Acetate:Hexane=2:1);
$^1$H-NMR (DMSO-$d_6$): δ 5.56 (s, 2H), 6.66 (d, 1H), 7.27 (d, 2H), 7.36 (dd, 1H), 7.52 (dd, 2H), 7.75 (d, 1H), 7.83 (s, 1H), 7.94 (d, 2H), 8.42-8.44 (m, 2H), 8.70 (s, 2H), 9.57 (s, 1H), 9.97 (s, 1H).

Example 15-3

1-(2-(4-(2-amino-5-fluoropyridin-3-yl)phenoxy)pyrimidin-5-yl)-3-(2-chloro-4-(trifluoromethyl)phenyl)urea TLC: Rf 0.37 (Dichloromethane:Methanol=9:1);
$^1$H-NMR (DMSO-$d_6$): δ 5.56 (s, 2H), 7.29 (d, 2H), 7.38 (dd, 1H), 7.50-7.55 (m, 2H), 7.69 (dd, 1H), 7.89 (d, 1H), 7.94 (d, 1H), 8.43 (d, 1H), 8.75 (s, 2H), 8.80 (s, 1H), 9.77 (s, 1H).

Example 15-4

1-(2-(1H-pyrazol-1-yl)-4-(trifluoromethyl)phenyl)-3-(2-(4-(2-amino-5-chloropyridin-3-yl)phenoxy)pyrimidin-5-yl)urea

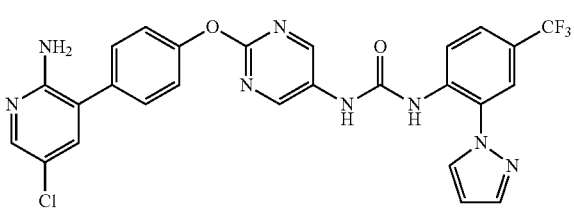 [SMILES: Nc1ncc(Cl)cc1-c1ccc(Oc2ncc(NC(=O)Nc3ccc(C(F)(F)F)cc3-n3cccn3)cn2)cc1]

TLC: Rf 0.40 (Hexane:Ethyl Acetate=1:2);
$^1$H-NMR (DMSO-d$_6$): δ 5.83 (s, 2H), 6.67 (t, 1H), 7.28 (d, 2H), 7.43 (d, 1H), 7.52 (d, 2H), 7.74-7.77 (m, 1H), 7.84 (s, 1H), 7.94-7.97 (m, 2H), 8.43-8.45 (m, 2H), 8.72 (s, 2H), 9.57 (s, 1H), 9.96 (s, 1H).

Example 15-5

1-(2-(4-(2-amino-5-chloropyridin-3-yl)phenoxy)pyrimidin-5-yl)-3-(2-fluoro-4-(trifluoromethyl)phenyl)urea

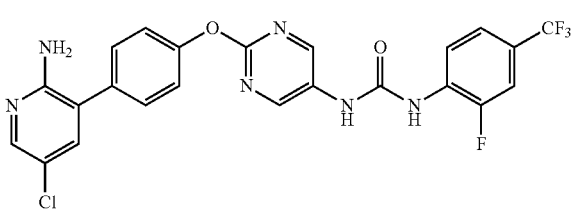 [SMILES: Nc1ncc(Cl)cc1-c1ccc(Oc2ncc(NC(=O)Nc3ccc(C(F)(F)F)cc3F)cn2)cc1]

TLC: Rf 0.45 (Ethyl Acetate:Hexane=2:1);
$^1$H-NMR (DMSO-d$_6$): δ 5.84 (s, 2H), 7.27 (d, 2H), 7.43 (d, 1H), 7.46-7.55 (m, 3H), 7.67 (d, 1H), 7.96 (d, 1H), 8.38 (t, 1H), 8.75 (s, 2H), 9.24 (br, 2H).

Example 15-6

1-(2-(4-(2-amino-5-chloropyridin-3-yl)phenoxy)pyrimidin-5-yl)-3-(2-chloro-4-(trifluoromethyl)phenyl)urea

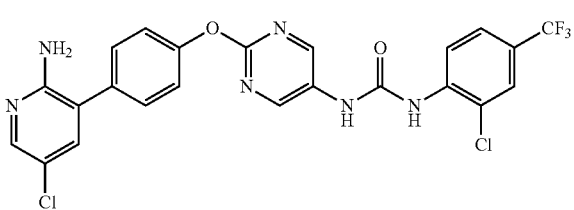 [SMILES: Nc1ncc(Cl)cc1-c1ccc(Oc2ncc(NC(=O)Nc3ccc(C(F)(F)F)cc3Cl)cn2)cc1]

TLC: Rf 0.45 (Hexane:Ethyl Acetate=1:2);
$^1$H-NMR (DMSO-d$_6$): δ 5.85 (s, 2H), 7.28 (d, 2H), 7.43 (d, 1H), 7.52 (d, 2H), 7.69 (dd, 1H), 7.89 (d, 1H), 7.96 (d, 1H), 8.42 (d, 1H), 8.75 (s, 2H), 8.80 (s, 1H), 9.77 (s, 1H).

Example 15-7

1-(2-(4-(2-amino-5-chloropyridin-3-yl)phenoxy)pyrimidin-5-yl)-3-(2,4-dichlorophenyl)urea TLC: Rf 0.59 (Ethyl Acetate:Hexane=2:1);
$^1$H-NMR (DMSO-d$_6$): δ 5.85 (s, 2H), 7.27 (d, 2H), 7.41 (dd, 1H), 7.42 (d, 1H), 7.50 (d, 2H), 7.63 (d, 1H), 7.95 (d, 1H), 8.14 (d, 1H), 8.57 (s, 1H), 8.72 (s, 2H), 9.59 (s, 1H).

Example 15-8

1-(2-(4-(2-amino-5-fluoropyridin-3-yl)phenoxy)pyrimidin-5-yl)-3-(2,4-dichlorophenyl)urea TLC: Rf 0.50 (Ethyl Acetate:Hexane=2:1);
$^1$H-NMR (DMSO-d$_6$): δ 5.56 (s, 2H), 7.27 (d, 2H), 7.35-7.43 (m, 2H), 7.51 (d, 2H), 7.63 (d, 1H), 7.93 (d, 1H), 8.14 (d, 1H), 8.57 (s, 1H), 8.72 (s, 2H), 9.59 (s, 1H).

Example 15-9

1-(2-(4-(2-amino-5-fluoropyridin-3-yl)phenoxy)pyrimidin-5-yl)-3-(2,4,5-trifluorophenyl)urea TLC: Rf 0.40 (Ethyl Acetate);
$^1$H-NMR (DMSO-d$_6$): δ 5.56 (s, 2H), 7.28 (d, 2H), 7.38 (dd, 1H), 7.53 (d, 2H), 7.62-7.66 (m, 1H), 7.94 (d, 1H), 8.08-8.15 (m, 1H), 8.73 (s, 2H), 8.93 (s, 1H), 9.21 (s, 1H).

Example 15-10

1-(2-(4-(2-amino-5-chloropyridin-3-yl)phenoxy)pyrimidin-5-yl)-3-(2,4-difluorophenyl)urea TLC: Rf 0.45 (Ethyl Acetate:Hexane=3:1);
$^1$H-NMR (DMSO-d$_6$): δ 5.85 (s, 2H), 7.04 (t, 1H), 7.26 (d, 2H), 7.31 (dd, 1H), 7.42 (d, 1H), 7.51 (d, 2H), 7.94-8.04 (m, 2H), 8.71-8.72 (m, 3H), 9.16 (s, 1H).

Example 15-11

1-(2-(4-(2-amino-5-chloropyridin-3-yl)phenoxy)pyrimidin-5-yl)-3-(2,5-dichlorophenyl)urea TLC: Rf 0.56 (Ethyl Acetate:Hexane=2:1);
$^1$H-NMR (DMSO-d$_6$): δ 5.85 (s, 2H), 7.12 (dd, 1H), 7.26 (d, 2H), 7.42 (d, 1H), 7.49-7.55 (m, 3H), 7.95-7.97 (m, 1H), 8.26 (d, 1H), 8.64 (s, 1H), 8.74 (d, 2H), 9.68 (s, 1H).

Example 15-12

1-(2-(4-(2-amino-5-chloropyridin-3-yl)phenoxy)pyrimidin-5-yl)-3-(2,5-difluorophenyl)urea TLC: Rf 0.54 (Ethyl Acetate:Hexane=3:1);
$^1$H-NMR (DMSO-d$_6$): δ 5.85 (s, 2H), 6.84 (m, 1H), 7.26-7.32 (m, 3H), 7.42 (d, 1H), 7.51 (dd, 2H), 7.93-8.01 (m, 2H), 8.73 (s, 2H), 8.96 (s, 1H), 9.27 (s, 1H).

Example 15-13

1-(2-(4-(2-amino-5-chloropyridin-3-yl)phenoxy)pyrimidin-5-yl)-3-(3-(difluoromethyl)phenyl)urea TLC: Rf 0.34 (Dichloromethane:Methanol=9:1);
$^1$H-NMR (DMSO-$d_6$): δ 5.85 (s, 2H), 7.00 (t, 1H), 7.17 (d, 1H), 7.25-7.29 (m, 2H), 7.39-7.45 (m, 2H), 7.49-7.53 (m, 3H), 7.78 (s, 1H), 7.95 (d, 1H), 8.73 (s, 2H), 8.91 (s, 1H), 9.17 (s, 1H).

Example 15-14

1-(2-(4-(2-amino-5-chloropyridin-3-yl)phenoxy)pyrimidin-5-yl)-3-(4-fluorophenyl)urea TLC: Rf 0.50 (Ethyl Acetate:Hexane=3:1);
$^1$H-NMR (DMSO-$d_6$): δ 5.84 (s, 2H), 7.06-7.13 (m, 2H), 7.25 (d, 2H), 7.42 (d, 1H), 7.46-7.51 (m, 4H), 7.94 (d, 1H), 8.71 (d, 2H), 9.40 (br, 2H).

Example 15-15

1-(2-(4-(2-amino-5-fluoropyridin-3-yl)phenoxy)pyrimidin-5-yl)-3-(2,5-dichlorophenyl)urea TLC: Rf 0.50 (Ethyl Acetate:Hexane=2:1);
$^1$H-NMR (DMSO-$d_6$): δ 5.56 (s, 2H), 7.12 (dd, 1H), 7.28 (d, 2H), 7.37 (dd, 1H), 7.49 (d, 1H), 7.53 (d, 2H), 7.94 (d, 1H), 8.25 (d, 1H), 8.64 (s, 1H), 8.73 (s, 2H), 9.68 (s, 1H).

Example 15-16

1-(2-(4-(2-aminopyridin-3-yl)phenoxy)pyrimidin-5-yl)-3-(2-(pyridin-3-yl)-5-(trifluoromethyl)phenyl)urea

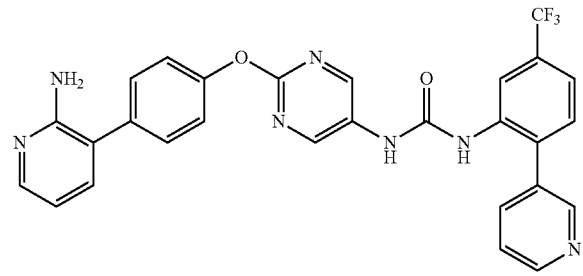 [SMILES: Nc1ncccc1-c1ccc(Oc2ncc(NC(=O)Nc3cc(C(F)(F)F)ccc3-c3cccnc3)cn2)cc1]

TLC: Rf 0.47 (Ethyl Acetate:Methanol=19:1);
$^1$H-NMR (DMSO-$d_6$): δ 5.57 (s, 2H), 6.66 (t, 1H), 7.24 (d, 2H), 7.34 (d, 1H), 7.46-7.58 (m, 6H), 7.89 (d, 1H), 7.94 (d, 1H), 8.24 (s, 1H), 8.38 (s, 1H), 8.65-8.68 (m, 3H), 9.24 (s, 1H).

Example 15-17

1-(2-(4-(2-amino-5-chloropyridin-3-yl)phenoxy)pyrimidin-5-yl)-3-(3,4-difluorophenyl)urea TLC: Rf 0.79 (Ethyl Acetate:Hexane=3:1);
$^1$H-NMR (DMSO-$d_6$): δ 5.85 (s, 2H), 7.13-7.16 (m, 1H), 7.26 (d, 2H), 7.30-7.40 (m, 1H), 7.42 (d, 1H), 7.51 (d, 2H), 7.59-7.67 (m, 1H), 7.95 (d, 1H), 8.71 (s, 2H), 8.93 (s, 1H), 9.16 (s, 1H).

Example 15-18

1-(2-(4-(2-amino-5-chloropyridin-3-yl)phenoxy)pyrimidin-5-yl)-3-(2-(3-methyl-1H-pyrazol-1-yl)-4-(trifluoromethyl)phenyl)urea TLC: Rf 0.23 (Hexane:Ethyl Acetate=1:1);
$^1$H-NMR (DMSO-$d_6$): δ 2.36 (s, 3H), 5.85 (s, 2H), 6.43 (d, 1H), 7.27 (d, 2H), 7.42 (d, 1H), 7.50 (d, 2H), 7.70 (d, 1H), 7.76 (s, 1H), 7.95 (d, 1H), 8.29 (d, 1H), 8.40 (d, 1H), 8.70 (s, 2H), 9.63 (s, 1H), 9.92 (s, 1H).

Example 15-19

1-(2-(4-(2-amino-5-cyclopropylpyridin-3-yl)phenoxy)pyrimidin-5-yl)-3-(3-(trifluoromethyl)phenyl)urea

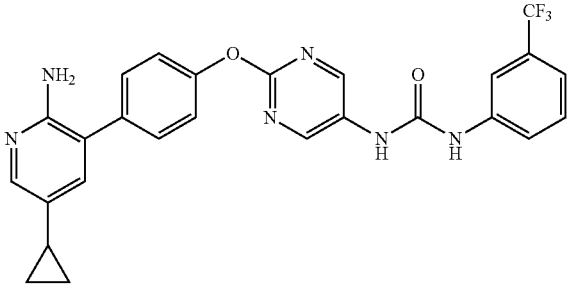 [SMILES: Nc1ncc(C2CC2)cc1-c1ccc(Oc2ncc(NC(=O)Nc3cccc(C(F)(F)F)c3)cn2)cc1]

TLC: Rf 0.54 (Ethyl Acetate:Methanol=9:1);
$^1$H-NMR (DMSO-$d_6$): δ 0.59-0.64 (m, 2H), 0.81-0.87 (m, 2H), 1.77-1.86 (m, 1H), 5.36 (s, 2H), 7.01 (d, 1H), 7.25 (d, 2H), 7.32 (d, 1H), 7.47-7.54 (m, 3H), 7.62 (d, 1H), 7.80 (d, 1H), 7.97 (s, 1H), 8.72 (s, 2H), 8.99 (s, 1H), 9.32 (s, 1H).

Example 15-20

1-(2-(4-(2-amino-5-methylpyridin-3-yl)phenoxy)pyrimidin-5-yl)-3-(2-(pyridin-3-yl)-5-(trifluoromethyl)phenyl)urea TLC: Rf 0.53 (Ethyl Acetate:Methanol:Aqueous Ammonia=9:1:0.5);
$^1$H-NMR (DMSO-$d_6$): δ 2.15 (s, 3H), 5.34 (s, 2H), 7.20-7.24 (m, 3H), 7.46-7.58 (m, 5H), 7.78 (s, 1H), 7.87-7.90 (m, 1H), 8.24 (s, 1H), 8.38 (s, 1H), 8.64-8.68 (m, 4H), 9.24 (s, 1H).

Example 15-21

1-(2-(4-(2-amino-5-chloropyridin-3-yl)phenoxy)pyrimidin-5-yl)-3-(2-(pyridin-3-yl)-4-(trifluoromethyl)phenyl)urea TLC: Rf 0.51 (Ethyl Acetate);
$^1$H-NMR (DMSO-$d_6$): δ 5.84 (s, 2H), 7.26 (d, 2H), 7.42 (d, 1H), 7.51-7.56 (m, 5H), 7.76 (s, 1H), 7.90 (d, 1H), 7.95 (d, 1H), 8.24 (s, 1H), 8.27 (d, 1H), 8.66-8.68 (m, 2H), 9.28 (s, 1H).

Example 15-22

1-(2-(4-(2-amino-5-fluoropyridin-3-yl)phenoxy)pyrimidin-5-yl)-3-(3-(difluoromethyl)phenyl)urea TLC: Rf 0.33 (Dichloromethane:Methanol=9:1);
$^1$H-NMR (DMSO-d$_6$): δ 5.57 (s, 2H), 7.00 (t, 1H), 7.17 (d, 1H), 7.26-7.29 (m, 2H), 7.36-7.45 (m, 2H), 7.51-7.55 (m, 3H), 7.78 (s, 1H), 7.94 (d, 1H), 8.73 (s, 2H), 8.91 (s, 1H), 9.17 (s, 1H).

Example 15-23

1-(2-(4-(2-amino-5-chloropyridin-3-yl)phenoxy)pyrimidin-5-yl)-3-(4-(trifluoromethyl)phenyl)urea TLC: Rf 0.82 (Ethyl Acetate);
$^1$H-NMR (DMSO-d$_6$): δ 5.85 (s, 2H), 7.27 (d, 2H), 7.42 (d, 1H), 7.51 (d, 2H), 7.64 (d, 4H), 7.95 (d, 1H), 8.73 (s, 2H), 8.98 (s, 1H), 9.37 (s, 1H).

Example 15-24

1-(2-(4-(2-aminopyridin-3-yl)phenoxy)pyrimidin-5-yl)-3-(3-(trifluoromethyl)phenyl)urea TLC: Rf 0.20 (Ethyl Acetate:Methanol=19:1);
$^1$H-NMR (DMSO-d$_6$): δ 5.58 (s, 2H), 6.60 (dd, 1H), 7.25-7.37 (m, 4H), 7.47-7.63 (m, 4H), 7.94-7.97 (m, 2H), 8.73 (s, 2H), 9.00 (s, 1H), 9.33 (s, 1H).

Example 15-25

1-(2-(4-(2-amino-5-chloropyridin-3-yl)phenoxy)pyrimidin-5-yl)-3-(4-(trifluoromethyl)-2-(3-(trifluoromethyl)-1H-pyrazol-1-yl)-phenyl)urea TLC: Rf 0.39 (Hexane:Ethyl Acetate=1:1);
$^1$H-NMR (DMSO-d$_6$): δ 5.85 (s, 2H), 7.11 (d, 1H), 7.26 (d, 2H), 7.42 (d, 1H), 7.50 (d, 2H), 7.81 (s, 1H), 7.85-7.88 (m, 1H), 7.95 (d, 1H), 8.36 (d, 1H), 8.47 (s, 1H), 8.53 (s, 1H), 8.67 (s, 2H), 9.50 (s, 1H).

Example 15-26

1-(2-(4-(2-aminopyridin-3-yl)phenoxy)pyrimidin-5-yl)-3-(2-(3,4-dimethylphenyl)-5-(trifluoromethyl)pyridin-3-yl)urea

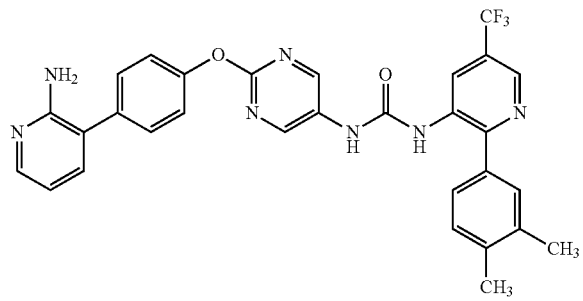 [SMILES: Cc1ccc(-c2ncc(C(F)(F)F)cc2NC(=O)Nc2cnc(Oc3ccc(-c4cccnc4N)cc3)nc2)cc1C]

TLC: Rf 0.29 (Hexane:Ethyl Acetate=1:4);
$^1$H-NMR (DMSO-d$_6$): δ 2.31 (s, 6H), 5.57 (s, 2H), 6.66 (dd, 1H), 7.25 (d, 2H), 7.31-7.42 (m, 4H), 7.48 (d, 2H), 7.95 (dd, 1H), 8.35 (s, 1H), 8.68-8.72 (m, 3H), 8.78 (s, 1H), 9.51 (s, 1H).

Example 15-27

1-(2-(4-(2-amino-5-fluoropyridin-3-yl)phenoxy)pyrimidin-5-yl)-3-(2,4-difluorophenyl)urea TLC: Rf 0.40 (Ethyl Acetate:Hexane=2:1);
$^1$H-NMR (DMSO-d$_6$): δ 5.55 (s, 2H), 7.00-7.09 (m, 1H), 7.27 (d, 2H), 7.28-7.39 (m, 2H), 7.52 (d, 2H), 7.93 (d, 1H), 7.96-8.02 (m, 1H), 8.70 (s, 1H), 8.71 (s, 2H), 9.15 (s, 1H).

Example 15-28

1-(2-(4-(2-amino-5-chloropyridin-3-yl)phenoxy)pyrimidin-5-yl)-3-(2-fluorophenyl)urea TLC: Rf 0.50 (Ethyl Acetate:Hexane=3:1);
$^1$H-NMR (DMSO-d$_6$): δ 5.85 (s, 2H), 7.03-7.06 (m, 1H), 7.12 (t, 1H), 7.20-7.24 (m, 1H), 7.28 (d, 2H), 7.42 (d, 1H), 7.50 (dd, 2H), 7.95 (d, 1H), 8.04 (t, 1H), 8.73 (s, 2H), 9.15 (br, 2H).

Example 15-29

1-(2-(4-(2-amino-5-chloropyridin-3-yl)phenoxy)pyrimidin-5-yl)-3-(2,4,6-trifluorophenyl)urea TLC: Rf 0.60 (Hexane:Ethyl Acetate=1:9);
$^1$H-NMR (DMSO-d$_6$): δ 5.85 (s, 2H), 7.24-7.30 (m, 4H), 7.42 (d, 1H), 7.49 (d, 2H), 7.94 (d, 1H), 8.34 (s, 1H), 8.70 (s, 2H), 9.22 (s, 1H).

Example 15-30

1-(2-(4-(2-amino-5-fluoropyridin-3-yl)phenoxy)pyrimidin-5-yl)-3-(2-(pyridin-3-yl)-4-(trifluoromethyl)phenyl)urea TLC: Rf 0.50 (Ethyl Acetate);
$^1$H-NMR (DMSO-d$_6$): δ 5.56 (d, 2H), 7.27 (d, 2H), 7.36 (dd, 1H), 7.52 (d, 2H), 7.53-7.55 (m, 2H), 7.70 (d, 1H), 7.89-7.94 (m, 2H), 8.24 (s, 1H), 8.28 (d, 1H), 8.66 (s, 2H), 8.67-8.69 (m, 2H), 9.29 (s, 1H).

Example 15-31

1-(2-(4-(2-amino-5-chloropyridin-3-yl)phenoxy)pyrimidin-5-yl)-3-(3-chloro-4-(trifluoromethyl)phenyl)urea TLC: Rf 0.40 (Ethyl Acetate:Hexane=2:1);
$^1$H-NMR (DMSO-d$_6$): δ 5.85 (s, 2H), 7.27 (d, 2H), 7.42 (d, 1H), 7.46-7.55 (m, 3H), 7.74 (d, 1H), 7.89 (d, 1H), 7.95 (d, 1H), 8.72 (s, 2H), 9.09 (s, 1H), 9.55 (s, 1H).

Example 15-32

1-(2-(4-(2-amino-5-fluoropyridin-3-yl)phenoxy)pyrimidin-5-yl)-3-(3,4-difluorophenyl)urea TLC: Rf 0.73 (Ethyl Acetate);
$^1$H-NMR (DMSO-d$_6$): δ 5.56 (s, 2H), 7.13-7.17 (m, 1H), 7.26 (d, 2H), 7.29 (d, 1H), 7.38 (dd, 1H), 7.52 (d, 2H), 7.59-7.67 (m, 1H), 7.93 (d, 1H), 8.70 (s, 2H), 8.93 (s, 1H), 9.16 (s, 1H).

Example 15-33

1-(2-(4-(2-amino-5-fluoropyridin-3-yl)phenoxy)pyrimidin-5-yl)-3-(2-fluoro-4-(trifluoromethyl)phenyl)urea TLC: Rf 0.45 (Ethyl Acetate:Hexane=2:1);
$^1$H-NMR (DMSO-$d_6$): δ 5.56 (s, 2H), 7.29 (d, 2H), 7.38 (dd, 1H), 7.52-7.56 (m, 3H), 7.69-7.76 (m, 1H), 7.94 (d, 1H), 8.32-8.42 (m, 1H), 8.75 (s, 2H), 9.12 (d, 1H), 9.33 (s, 1H).

Example 15-34

1-(2-(4-(2-amino-5-fluoropyridin-3-yl)phenoxy)pyrimidin-5-yl)-3-(2,5-difluorophenyl)urea TLC: Rf 0.80 (Ethyl Acetate);
$^1$H-NMR (DMSO-$d_6$): δ 5.57 (s, 2H), 6.81-6.87 (m, 1H), 7.25-7.58 (m, 2H), 7.29 (d, 1H), 7.38 (dd, 1H), 7.53 (d, 2H), 7.92-8.00 (m, 2H), 8.73 (s, 2H), 8.96 (s, 1H), 9.26 (s, 1H).

Example 15-35

1-(2-(4-(2-amino-5-fluoropyridin-3-yl)phenoxy)pyrimidin-5-yl)-3-(3-chloro-4-(trifluoromethyl)phenyl)urea TLC: Rf 0.40 (Ethyl Acetate:Hexane=2:1);
$^1$H-NMR (DMSO-$d_6$): δ 5.57 (s, 2H), 7.28 (d, 2H), 7.39 (dd, 1H), 7.53 (d, 3H), 7.75 (d, 1H), 7.94 (dd, 2H), 8.73 (s, 2H), 9.11 (s, 1H), 9.57 (s, 1H).

Example 15-36

1-(2-(4-(2-amino-5-fluoropyridin-3-yl)phenoxy)pyrimidin-5-yl)-3-(4-(trifluoromethyl)phenyl)urea TLC: Rf 0.80 (Ethyl Acetate);
$^1$H-NMR (DMSO-$d_6$): δ 5.58 (s, 2H), 7.27 (d, 2H), 7.38 (dd, 1H), 7.54 (d, 2H), 7.61-7.68 (m, 4H), 7.93 (d, 1H), 8.73 (s, 2H), 8.99 (s, 1H), 9.37 (s, 1H).

Example 15-37

1-(2-(4-(2-amino-5-chloropyridin-3-yl)phenoxy)pyrimidin-5-yl)-3-(2-(5-methyl-1H-pyrazol-1-yl)-4-(trifluoromethyl)phenyl)urea TLC: Rf 0.54 (Hexane:Ethyl Acetate=1:4);
$^1$H-NMR (DMSO-$d_6$): δ 2.18 (s, 3H), 5.85 (s, 2H), 6.40 (s, 1H), 7.26 (d, 2H), 7.41 (d, 1H), 7.50 (d, 2H), 7.65 (d, 1H), 7.74 (d, 1H), 7.82 (d, 1H), 7.95 (d, 1H), 8.31 (d, 1H), 8.47 (d, 1H), 8.67 (s, 2H), 9.75 (s, 1H).

Example 15-38

1-(2-(4-(2-amino-5-chloropyridin-3-yl)phenoxy)pyrimidin-5-yl)-3-(3,5-difluorophenyl)urea TLC: Rf 0.68 (Ethyl Acetate);
$^1$H-NMR (DMSO-$d_6$): δ 5.85 (s, 2H), 6.81-6.87 (m, 1H), 7.19 (dd, 2H), 7.27 (d, 2H), 7.42 (d, 1H), 7.50 (d, 1H), 7.52 (d, 2H), 7.96 (d, 1H), 8.71 (s, 2H), 9.03 (s, 1H), 9.36 (s, 1H).

Example 15-39

1-(2-(4-(2-amino-5-fluoropyridin-3-yl)phenoxy)pyrimidin-5-yl)-3-(2,4,6-trifluorophenyl)urea TLC: Rf 0.59 (Hexane:Ethyl Acetate=1:9);
$^1$H-NMR (DMSO-$d_6$): δ 5.56 (s, 2H), 7.25-7.30 (m, 4H), 7.37 (dd, 1H), 7.52 (d, 2H), 7.93 (d, 1H), 8.35 (s, 1H), 8.70 (s, 2H), 9.24 (s, 1H).

Example 15-40

1-(6-(4-(2-amino-5-chloropyridin-3-yl)phenoxy)pyridin-3-yl)-3-(2-chloro-4-(trifluoromethyl)phenyl)urea

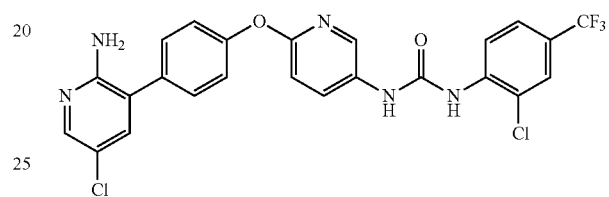

TLC: Rf 0.64 (Hexane:Ethyl Acetate=1:3);
$^1$H-NMR (DMSO-$d_6$): δ 5.84 (s, 2H), 7.08 (d, 1H), 7.16-7.20 (m, 2H), 7.20 (d, 1H), 7.39-7.41 (m, 1H), 7.47-7.51 (m, 2H), 7.68 (dd, 1H), 7.87 (d, 1H), 7.95 (d, 1H), 8.03 (dd, 1H), 8.24 (d, 1H), 8.45 (d, 1H), 8.68 (s, 1H), 9.70 (s, 1H).

Example 15-41

1-(2-(4-(2-amino-5-fluoropyridin-3-yl)phenoxy)pyrimidin-5-yl)-3-(3,5-difluorophenyl)urea TLC: Rf 0.68 (Ethyl Acetate);
$^1$H-NMR (DMSO-$d_6$): δ 5.56 (s, 2H), 6.81 (t, 1H), 7.20 (dd, 2H), 7.28 (d, 2H), 7.38 (dd, 1H), 7.53 (d, 2H), 7.94 (d, 1H), 8.72 (s, 2H), 9.02 (s, 1H), 9.35 (s, 1H).

Example 15-42

1-(2-(4-(2-amino-5-fluoropyridin-3-yl)phenoxy)pyrimidin-5-yl)-3-(2,3,4-trifluorophenyl)urea TLC: Rf 0.50 (Ethyl Acetate:Hexane=2:1);
$^1$H-NMR (DMSO-$d_6$): δ 5.56 (s, 2H), 7.28 (d, 3H), 7.38 (dd, 1H), 7.53 (d, 2H), 7.76-7.80 (m, 1H), 7.94 (s, 1H), 8.72 (s, 2H), 8.91 (s, 1H), 9.20 (s, 1H).

Example 15-43

1-(2-(4-(2-amino-5-fluoropyridin-3-yl)phenoxy)pyrimidin-5-yl)-3-(2,3-difluorophenyl)urea TLC: Rf 0.49 (Ethyl Acetate);
$^1$H-NMR (DMSO-$d_6$): δ 5.56 (s, 2H), 7.05-7.16 (m, 2H), 7.29 (d, 2H), 7.38 (dd, 1H), 7.53 (d, 2H), 7.63-7.66 (m, 1H), 7.87 (t, 1H), 7.94 (d, 1H), 8.73 (s, 1H), 8.96 (s, 1H), 9.26 (s, 1H).

Example 15-44

1-(6-(4-(2-amino-5-fluoropyridin-3-yl)phenoxy)pyridin-3-yl)-3-(2-chloro-4-(trifluoromethyl)phenyl)urea TLC: Rf 0.52 (Hexane:Ethyl Acetate=1:3);
$^1$H-NMR (DMSO-$d_6$): δ 5.55 (s, 2H), 7.08 (d, 1H), 7.18 (d, 2H), 7.34 (dd, 1H), 7.50 (d, 2H), 7.68 (d, 1H), 7.87 (s, 1H), 7.93 (d, 1H), 8.04 (dd, 1H), 8.24 (d, 1H), 8.45 (d, 1H), 8.68 (s, 1H), 9.70 (s, 1H).

Example 15-45

1-(2-(4-(2-amino-5-fluoropyridin-3-yl)phenoxy)pyrimidin-5-yl)-3-(2,6-difluorophenyl)urea TLC: Rf 0.75 (Ethyl Acetate);
$^1$H-NMR (DMSO-$d_6$): δ 5.55 (s, 2H), 7.12-7.28 (m, 2H), 7.27 (d, 2H), 7.36 (dd, 2H), 7.53 (d, 2H), 7.93 (d, 1H), 8.42 (s, 1H), 8.71 (s, 2H), 9.18 (s, 1H).

Example 15-46

1-(2-(4-(2-amino-5-fluoropyridin-3-yl)phenoxy)pyrimidin-5-yl)-3-(2,3,5,6-tetrafluorophenyl)urea TLC: Rf 0.50 (Ethyl Acetate:Hexane=2:1);
$^1$H-NMR (DMSO-$d_6$): δ 5.56 (s, 2H), 7.28 (d, 2H), 7.38 (dd, 1H), 7.53 (d, 2H), 7.74-7.88 (m, 1H), 7.94 (d, 1H), 8.72 (s, 2H), 8.89 (s, 1H), 9.33 (s, 1H).

Example 15-47

1-(2-(4-(2-aminopyridin-3-yl)phenoxy)pyrimidin-5-yl)-3-(3-(tert-butyl)-1-(o-tolyl)-1H-pyrazol-5-yl)urea

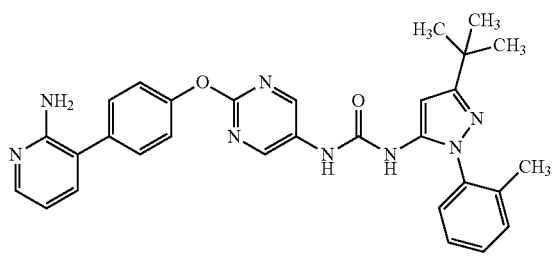 [SMILES: Cc1ccccc1-n1nc(C(C)(C)C)cc1NC(=O)Nc1cnc(Oc2ccc(-c3cccnc3N)cc2)nc1]

TLC: Rf 0.35 (Ethyl Acetate);
$^1$H-NMR (DMSO-$d_6$): δ 1.26 (s, 9H), 1.99 (s, 3H), 5.57 (s, 2H), 6.34 (s, 1H), 6.66 (dd, 1H), 7.20-7.50 (m, 9H), 7.94 (dd, 1H), 8.39 (s, 1H), 8.64 (s, 2H), 9.07 (s, 1H).

Example 15-48

1-(2-(4-(2-amino-5-chloropyridin-3-yl)phenoxy)pyrimidin-5-yl)-3-(3-(tert-butyl)-1-(o-tolyl)-1H-pyrazol-5-yl)urea TLC: Rf 0.71 (Ethyl Acetate:Methanol=9:1);
$^1$H-NMR (DMSO-$d_6$): δ 1.26 (s, 9H), 1.99 (s, 3H), 5.84 (s, 2H), 6.34 (s, 1H), 7.25 (d, 2H), 7.31-7.43 (m, 5H), 7.50 (d, 2H), 7.95 (d, 1H), 8.39 (s, 1H), 8.64 (s, 2H), 9.07 (s, 1H).

Example 15-49

1-(2-(4-(2-aminopyridin-3-yl)phenoxy)pyrimidin-5-yl)-3-(3-(tert-butyl)-1-(2,3-dihydro-1H-inden-5-yl)-1H-pyrazol-5-yl)urea

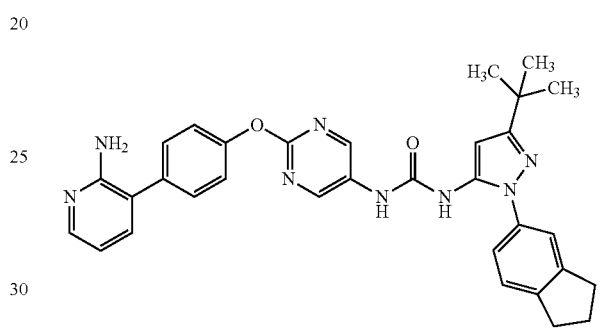

TLC: Rf 0.68 (Ethyl Acetate:Methanol=10:1);
$^1$H-NMR (DMSO-$d_6$): δ 1.25 (s, 9H), 2.06 (quint., 2H), 2.85-2.94 (m, 4H), 5.56 (s, 2H), 6.33 (s, 1H), 6.62-6.69 (m, 1H), 7.19-7.27 (m, 3H), 7.30-7.37 (m, 3H), 7.47 (d, 2H), 7.92-7.96 (m, 1H), 8.56 (s, 1H), 8.66 (s, 2H), 9.18 (s, 1H).

Example 15-50

1-(2-(4-(2-amino-5-methylpyridin-3-yl)phenoxy)pyrimidin-5-yl)-3-(3-(tert-butyl)-1-(o-tolyl)-1H-pyrazol-5-yl)urea TLC: Rf 0.67 (Ethyl Acetate:Methanol=9:1);
$^1$H-NMR (DMSO-$d_6$): δ 1.26 (s, 9H), 1.99 (s, 3H), 2.15 (s, 3H), 5.33 (s, 2H), 6.34 (s, 1H), 7.20-7.24 (m, 3H), 7.31-7.48 (m, 6H), 7.78 (s, 1H), 8.39 (s, 1H), 8.64 (s, 2H), 9.06 (s, 1H).

Example 15-51

1-(2-{4-[2-amino-5-(trifluoromethyl)-3-pyridinyl]phenoxy}-5-pyrimidinyl)-3-[2-(1H-pyrazol-1-yl)-5-(trifluoromethyl)phenyl]urea Purity (LC-MS/ELSD): 100% (Retention Time: 1.01 minutes);
MASS (ESI, Pos.): 601 (M+H)$^+$;
$^1$H-NMR (DMSO-$d_6$): δ 6.49 (s, 2H), 6.67-6.69 (m, 1H), 7.26-7.30 (m, 2H), 7.50-7.56 (m, 4H), 7.76 (d, 1H), 7.95 (d, 1H), 8.26 (d, 1H), 8.41 (d, 1H), 8.58 (d, 1H), 8.70 (s, 2H), 9.71 (s, 1H), 9.97 (s, 1H).

Example 15-52

1-(2-{4-[2-amino-5-(trifluoromethyl)-3-pyridinyl]phenoxy}-5-pyrimidinyl)-3-{5-(trifluoromethyl)-2-[3-(trifluoromethyl)-1H-pyrazol-1-yl]phenyl}urea

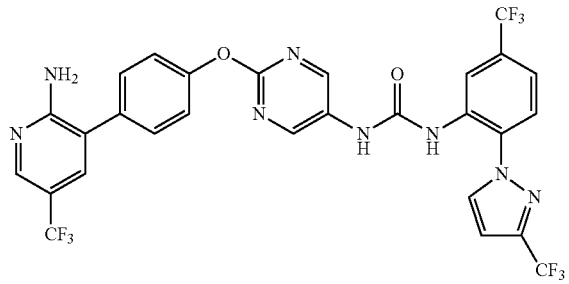 [SMILES: Nc1ncc(C(F)(F)F)cc1-c1ccc(Oc2ncc(NC(=O)Nc3cc(C(F)(F)F)ccc3-n3ccc(C(F)(F)F)n3)cn2)cc1]

Purity (LC-MS/ELSD): 100% (Retention Time: 1.07 minutes);

MASS (ESI, Pos.): 669 (M+H)$^+$;

$^1$H-NMR (DMSO-d$_6$): δ 6.48 (s, 2H), 7.12 (d, 1H), 7.28 (d, 2H), 7.50-7.60 (m, 4H), 7.71 (d, 1H), 8.27 (s, 1H), 8.48 (s, 2H), 8.59 (s, 1H), 8.67 (s, 2H), 9.48 (s, 1H).

Example 15-53

1-{2-[4-(2-amino-5-chloro-3-pyridinyl)phenoxy]-5-pyrimidinyl}-3-[2-(2H-1,2,3-triazol-2-yl)-5-(trifluoromethyl)phenyl]urea Purity (LC-MS/ELSD): 100% (Retention Time: 1.00 minute);

MASS (ESI, Pos.): 568 (M+H)$^+$;

$^1$H-NMR (DMSO-d$_6$): δ 5.86 (s, 2H), 7.25-7.30 (m, 2H), 7.43 (d, 1H), 7.49-7.53 (m, 2H), 7.59 (dd, 1H), 7.95 (d, 1H), 8.07 (d, 1H), 8.33 (s, 2H), 8.65 (d, 1H), 8.72 (s, 2H), 9.67 (s, 1H), 10.03 (s, 1H).

Example 15-54

1-{2-[4-(2-amino-5-chloro-3-pyridinyl)phenoxy]-5-pyrimidinyl}-3-[5-chloro-2-(2H-1,2,3-triazol-2-yl)phenyl]urea Purity (LC-MS/ELSD): 100% (Retention Time: 0.97 minutes);

MASS (ESI, Pos.): 534 (M+H)$^+$;

$^1$H-NMR (DMSO-d$_6$): δ 5.86 (s, 2H), 7.25-7.31 (m, 3H), 7.43 (d, 1H), 7.49-7.53 (m, 2H), 7.80 (d, 1H), 7.95 (d, 1H), 8.26 (s, 2H), 8.32 (d, 1H), 8.70 (s, 2H), 9.37 (s, 1H), 9.93 (s, 1H).

Example 15-55

1-{2-[4-(2-amino-5-chloro-3-pyridinyl)phenoxy]-5-pyrimidinyl}-3-[4-(trifluoromethyl)-2-biphenylyl]urea

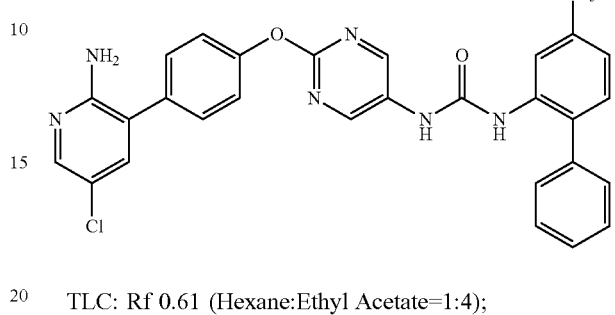

TLC: Rf 0.61 (Hexane:Ethyl Acetate=1:4);

$^1$H-NMR (DMSO-d$_6$): δ 5.85 (s, 2H), 7.26 (d, 2H), 7.40-7.60 (m, 10H), 7.95 (d, 1H), 8.09 (s, 1H), 8.04 (s, 1H), 8.66 (s, 2H), 9.39 (s, 1H).

Example 15-56

1-{2-[4-(2-amino-5-chloro-3-pyridinyl)phenoxy]-5-pyrimidinyl}-3-[2-(2-methyl-3-pyridinyl)-5-(trifluoromethyl)phenyl]urea TLC: Rf 0.58 (Ethyl Acetate:Methanol=19:1);

$^1$H-NMR (DMSO-d$_6$): δ 2.25 (s, 3H), 5.85 (s, 2H), 7.23-7.31 (m, 2H), 7.35-7.56 (m, 6H), 7.60-7.68 (m, 1H), 7.88 (s, 1H), 7.94-7.98 (m, 1H), 8.52-8.56 (m, 1H), 8.58-8.62 (m, 1H), 8.65 (s, 2H), 9.29 (s, 1H).

Example 15-57

1-{2-[4-(2-amino-5-chloro-3-pyridinyl)phenoxy]-5-pyrimidinyl}-3-[5-phenyl-2-(trifluoromethyl)-4-pyridinyl]urea TLC: Rf 0.38 (Hexane:Ethyl Acetate=1:4);

$^1$H-NMR (DMSO-d$_6$): δ 5.86 (s, 2H), 7.25-7.31 (m, 2H), 7.42 (d, 1H), 7.50-7.66 (m, 7H), 7.95 (d, 1H), 8.43-8.46 (m, 2H), 8.69 (s, 2H), 8.75 (s, 1H), 9.74 (s, 1H).

Example 15-58

1-{2-[4-(2-amino-5-fluoro-3-pyridinyl)phenoxy]-5-pyrimidinyl}-3-[4-(trifluoromethyl)-2-biphenylyl]urea

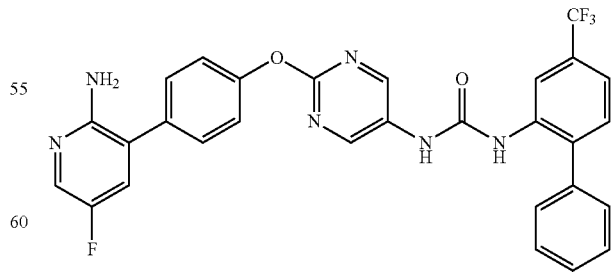

TLC: Rf 0.60 (Hexane:Ethyl Acetate=1:4);

$^1$H-NMR (DMSO-d$_6$): δ 5.57 (s, 2H), 7.23-7.29 (m, 2H), 7.34-7.58 (m, 10H), 7.92-7.96 (m, 1H), 8.09 (s, 1H), 8.41 (s, 1H), 8.66 (s, 2H), 9.39 (s, 1H).

Example 15-59

1-{2-[4-(2-amino-5-chloro-3-pyridinyl)phenoxy]-5-pyrimidinyl}-3-[2-(4-fluoro-1H-pyrazol-1-yl)-5-(trifluoromethyl)phenyl]urea TLC: Rf 0.56 (Hexane:Ethyl Acetate=1:4);
$^1$H-NMR (DMSO-$d_6$): δ 5.86 (s, 2H), 7.24-7.32 (m, 2H), 7.42 (d, 1H), 7.48-7.58 (m, 3H), 7.67-7.73 (m, 1H), 7.95 (d, 1H), 8.03-8.07 (m, 1H), 8.56-8.60 (m, 2H), 8.70 (s, 2H), 9.27 (s, 1H), 9.85 (s, 1H).

Example 15-60

1-{2-[4-(2-amino-5-fluoro-3-pyridinyl)phenoxy]-5-pyrimidinyl}-3-[2-(4-fluoro-1H-pyrazol-1-yl)-5-(trifluoromethyl)phenyl]urea TLC: Rf 0.50 (Hexane:Ethyl Acetate=1:4);
$^1$H-NMR (DMSO-$d_6$): δ 5.57 (s, 2H), 7.26-7.32 (m, 2H), 7.38 (dd, 1H), 7.51-7.59 (m, 3H), 7.66-7.73 (m, 1H), 7.94 (d, 1H), 8.03-8.07 (m, 1H), 8.55-8.60 (m, 2H), 8.70 (s, 2H), 9.27 (s, 1H), 9.85 (s, 1H).

Example 15-61

1-{2-[4-(2-amino-5-chloro-3-pyridinyl)phenoxy]-5-pyrimidinyl}-3-[2-phenyl-5-(trifluoromethyl)-3-pyridinyl]urea TLC: Rf 0.43 (Hexane:Ethyl Acetate=1:3);
$^1$H-NMR (DMSO-$d_6$): δ 5.86 (s, 2H), 7.26 (d, 2H), 7.42 (d, 1H), 7.49-7.70 (m, 7H), 7.95 (d, 1H), 8.43 (s, 1H), 8.68 (s, 2H), 8.73 (s, 1H), 8.76 (s, 1H), 9.47 (s, 1H).

Example 15-62

1-{2-[4-(2-amino-5-chloro-3-pyridinyl)phenoxy]-5-pyrimidinyl}-3-[3',4'-dimethyl-4-(trifluoromethyl)-2-biphenylyl]urea TLC: Rf 0.72 (Hexane:Ethyl Acetate=1:3);
$^1$H-NMR (DMSO-$d_6$): δ 2.29 (s, 6H), 5.85 (s, 2H), 7.12-7.55 (m, 10H), 7.95 (d, 1H), 8.01 (s, 1H), 8.44 (s, 1H), 8.66 (s, 2H), 9.44 (s, 1H).

Example 15-63

1-{2-[4-(2-amino-5-chloro-3-pyridinyl)phenoxy]-5-pyrimidinyl}-3-[2-(4-chloro-1H-pyrazol-1-yl)-5-(trifluoromethyl)phenyl]urea

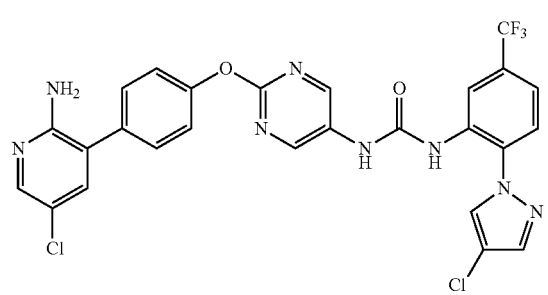 [SMILES: Nc1ncc(Cl)cc1-c1ccc(Oc2ncc(NC(=O)Nc3cc(C(F)(F)F)ccc3-n3cc(Cl)cn3)cn2)cc1]

TLC: Rf 0.43 (Chloroform:Methanol=19:1);
$^1$H-NMR (DMSO-$d_6$): δ 5.86 (s, 2H), 7.24-7.30 (m, 2H), 7.42 (d, 1H), 7.47-7.57 (m, 3H), 7.70 (d, 1H), 7.95 (d, 1H), 8.07 (s, 1H), 8.57 (d, 1H), 8.63 (s, 1H), 8.70 (s, 2H), 9.11 (s, 1H), 9.81 (s, 1H).

Example 15-64

1-{2-[4-(2-amino-5-chloro-3-pyridinyl)phenoxy]-5-pyrimidinyl}-3-[4'-methyl-4-(trifluoromethyl)-2-biphenylyl]urea TLC: Rf 0.63 (Methylene Chloride:Ethyl Acetate:Methanol=8:4:1);
$^1$H-NMR (DMSO-$d_6$): δ 2.39 (s, 3H), 5.86 (brs, 2H), 7.26 (d, 2H), 7.29-7.49 (m, 7H), 7.50 (d, 2H), 7.95 (d, 1H), 8.05 (s, 1H), 8.43 (s, 1H), 8.67 (s, 2H), 9.42 (s, 1H).

Example 15-65

1-{2-[4-(2-amino-5-fluoro-3-pyridinyl)phenoxy]-5-pyrimidinyl}-3-[4'-methyl-4-(trifluoromethyl)-2-biphenylyl]urea TLC: Rf 0.55 (Methylene Chloride:Ethyl Acetate:Methanol=8:4:1);
$^1$H-NMR (DMSO-$d_6$): δ 2.39 (s, 3H), 5.56 (brs, 2H), 7.26 (d, 2H), 7.29-7.48 (m, 7H), 7.52 (d, 2H), 7.94 (d, 1H), 8.05 (s, 1H), 8.43 (s, 1H), 8.67 (s, 2H), 9.42 (s, 1H).

Example 15-66

1-{2-[4-(2-amino-5-chloro-3-pyridinyl)phenoxy]-5-pyrimidinyl}-3-[3'-methyl-4-(trifluoromethyl)-2-biphenylyl]urea TLC: Rf 0.58 (Methylene Chloride:Ethyl Acetate:Methanol=8:4:1);
$^1$H-NMR (DMSO-$d_6$): δ 2.39 (s, 3H), 5.86 (brs, 2H), 7.19-7.55 (m, 11H), 7.95 (d, 1H), 8.04 (s, 1H), 8.43 (s, 1H), 8.66 (s, 2H), 9.43 (s, 1H).

Example 15-67

1-{2-[4-(2-amino-5-fluoro-3-pyridinyl)phenoxy]-5-pyrimidinyl}-3-[3'-methyl-4-(trifluoromethyl)-2-biphenylyl]urea TLC: Rf 0.53 (Methylene Chloride:Ethyl Acetate:Methanol=8:4:1);
$^1$H-NMR (DMSO-$d_6$): δ 2.38 (s, 3H), 5.57 (brs, 2H), 7.19-7.48 (m, 9H), 7.52 (d, 2H), 7.94 (d, 1H), 8.04 (s, 1H), 8.44 (s, 1H), 8.66 (s, 2H), 9.43 (s, 1H).

Example 15-68

1-{2-[4-(2-amino-5-chloro-3-pyridinyl)phenoxy]-5-pyrimidinyl}-3-{2-[4-(difluoromethyl)-1H-pyrazol-1-yl]-5-(trifluoromethyl)phenyl}urea TLC: Rf 0.20 (Hexane:Ethyl Acetate:Methanol=6:4:0.4);
$^1$H-NMR (DMSO-$d_6$): δ 5.85 (s, 2H), 7.16 (t, 1H), 7.26 (d, 2H), 7.41 (d, 1H), 7.48-7.57 (m, 3H), 7.74 (d, 1H), 7.94 (d, 1H), 8.17 (s, 1H), 8.55 (s, 1H), 8.69 (s, 2H), 8.70 (s, 1H), 9.19 (s, 1H), 9.85 (s, 1H).

Example 15-69

1-{2-[4-(2-amino-5-fluoro-3-pyridinyl)phenoxy]-5-pyrimidinyl}-3-{2-[4-(difluoromethyl)-1H-pyrazol-1-yl]-5-(trifluoromethyl)phenyl}urea TLC: Rf 0.16 (Hexane:Ethyl Acetate:Methanol=6:4:0.4);
$^1$H-NMR (DMSO-$d_6$): δ 5.56 (s, 2H), 7.16 (t, 1H), 7.26 (d, 2H), 7.36 (dd, 1H), 7.49-7.57 (m, 3H), 7.74 (d, 1H), 7.92 (d, 1H), 8.18 (s, 1H), 8.55 (d, 1H), 8.69 (s, 2H), 8.70 (s, 1H), 9.19 (s, 1H), 9.85 (s, 1H).

Example 15-70

1-{2-[4-(2-amino-5-chloro-3-pyridinyl)phenoxy]-5-pyrimidinyl}-3-{5-chloro-2-[4-(difluoromethyl)-1H-pyrazol-1-yl]phenyl}urea TLC: Rf 0.17 (Hexane:Ethyl Acetate:Methanol=6:4:0.4);
$^1$H-NMR (DMSO-$d_6$): δ 5.85 (s, 2H), 7.14 (t, 1H), 7.22-7.29 (m, 3H), 7.41 (d, 1H), 7.47-7.53 (m, 3H), 7.94 (d, 1H), 8.12 (s, 1H), 8.24 (d, 1H), 8.58 (s, 1H), 8.68 (s, 2H), 8.91 (s, 1H), 9.78 (s, 1H).

Example 15-71

1-{2-[4-(2-amino-5-chloro-3-pyridinyl)phenoxy]-5-pyrimidinyl}-3-{5-chloro-2-[3-(trifluoromethyl)-1H-pyrazol-1-yl]phenyl}urea

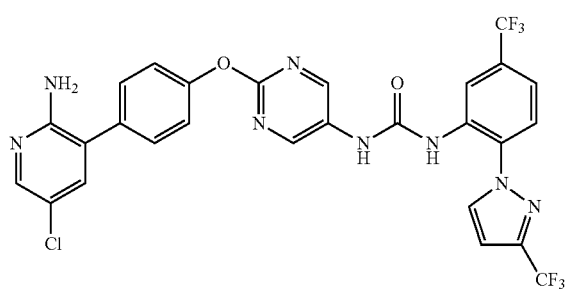 [SMILES: Nc1ncc(Cl)cc1-c1ccc(Oc2ncc(NC(=O)Nc3cc(C(F)(F)F)ccc3-n3ccc(C(F)(F)F)n3)cn2)cc1]

TLC: Rf 0.21 (Hexane:Ethyl Acetate:Methanol=6:4:0.4);
$^1$H-NMR (DMSO-$d_6$): δ 5.85 (s, 2H), 7.07 (s, 1H), 7.22-7.31 (m, 3H), 7.39-7.53 (m, 4H), 7.94 (d, 1H), 8.18 (s, 1H), 8.37 (d, 2H), 8.65 (s, 2H), 9.43 (s, 1H).

Example 15-72

1-{2-[4-(2-amino-5-chloro-3-pyridinyl)phenoxy]-5-pyrimidinyl}-3-{5-chloro-2-[3-(trifluoromethyl)-1H-pyrazol-1-yl]phenyl}urea TLC: Rf 0.29 (Hexane:Ethyl Acetate=2:3);
$^1$H-NMR (DMSO-$d_6$): δ 1.25 (t, 3H), 2.69 (q, 2H), 5.86 (s, 2H), 7.20-7.55 (m, 11H), 7.95 (d, 1H), 8.09 (s, 1H), 8.40 (s, 1H), 8.66 (s, 2H), 9.40 (s, 1H).

Example 15-73

1-{2-[4-(2-amino-5-chloro-3-pyridinyl)phenoxy]-5-pyrimidinyl}-3-[3'-ethyl-4-(trifluoromethyl)-2-biphenylyl]urea TLC: Rf 0.32 (Hexane:Ethyl Acetate=2:3);
$^1$H-NMR (DMSO-$d_6$): δ 1.22 (t, 3H), 2.68 (q, 2H), 5.85 (s, 2H), 7.24-7.55 (m, 11H), 7.94 (d, 1H), 8.06 (d, 1H), 7.38-7.42 (m, 1H), 8.65 (s, 2H), 9.41 (s, 1H).

Example 15-74

1-{2-[4-(2-amino-5-fluoro-3-pyridinyl)phenoxy]-5-pyrimidinyl}-3-[3'-ethyl-4-(trifluoromethyl)-2-biphenylyl]urea TLC: Rf 0.33 (Hexane:Ethyl Acetate=2:3);
$^1$H-NMR (DMSO-$d_6$): δ 1.22 (t, 3H), 2.68 (q, 2H), 5.57 (s, 2H), 7.24-7.56 (m, 11H), 7.94 (d, 1H), 8.07 (s, 1H), 8.39 (s, 1H), 8.66 (s, 2H), 9.41 (s, 1H).

Example 15-75

1-{2-[4-(2-amino-5-chloro-3-pyridinyl)phenoxy]-5-pyrimidinyl}-3-[2-methoxy-4-(trifluoromethyl)phenyl]urea Purity (LC-MS/ELSD): 100% (Retention Time: 0.94 minutes);
MASS (ESI, Pos.): 531 (M+H)$^+$;
$^1$H-NMR (DMSO-$d_6$): δ 3.97 (s, 3H), 5.86 (s, 2H), 7.25-7.33 (m, 4H), 7.43 (d, 1H), 7.49-7.56 (m, 2H), 7.96 (d, 1H), 8.32 (d, 1H), 8.70 (s, 1H), 8.73 (s, 2H), 9.66 (s, 1H).

Example 15-76

1-{2-[4-(2-amino-5-chloro-3-pyridinyl)phenoxy]-5-pyrimidinyl}-3-[2-(methylsulfonyl)-4-(trifluoromethyl)phenyl]urea Purity (LC-MS/ELSD): 100% (Retention Time: 0.90 minutes);
MASS (ESI, Pos.): 579 (M+H)$^+$;
$^1$H-NMR (DMSO-$d_6$): δ 3.42 (s, 3H), 5.87 (s, 2H), 7.26-7.33 (m, 2H), 7.43 (d, 1H), 7.47-7.57 (m, 2H), 7.96 (dd, 1H), 8.04-8.12 (m, 2H), 8.50 (d, 1H), 8.76 (s, 2H), 9.04 (s, 1H), 10.36 (s, 1H).

Example 15-77

1-{2-[4-(2-amino-5-chloro-3-pyridinyl)phenoxy]-5-pyrimidinyl}-3-[2,4-bis(trifluoromethyl)phenyl]urea

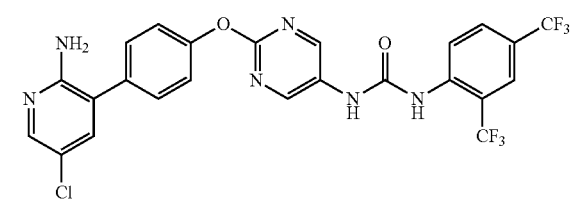 [SMILES: Nc1ncc(Cl)cc1-c1ccc(Oc2ncc(NC(=O)Nc3ccc(C(F)(F)F)cc3C(F)(F)F)cn2)cc1]

Purity (LC-MS/ELSD): 100% (Retention Time: 0.98 minutes);
MASS (ESI, Pos.): 569 (M+H)$^+$;
$^1$H-NMR (DMSO-$d_6$): δ 5.86 (s, 2H), 7.26-7.34 (m, 2H), 7.42-7.44 (m, 1H), 7.49-7.56 (m, 2H), 7.95-7.99 (m, 2H), 8.04 (d, 1H), 8.33 (d, 1H), 8.56 (s, 1H), 8.75 (s, 2H), 9.80 (s, 1H).

Example 15-78

1-{2-[4-(2-amino-5-chloro-3-pyridinyl)phenoxy]-5-pyrimidinyl}-3-(5-chloro-2-methylphenyl)urea Purity (LC-MS/ELSD): 100% (Retention Time: 0.88 minutes);
MASS (ESI, Pos.): 481 (M+H)+;
$^1$H-NMR (DMSO-$d_6$): δ 2.22 (s, 3H), 5.86 (s, 2H), 7.01 (dd, 1H), 7.20 (d, 1H), 7.25-7.32 (m, 2H), 7.43 (d, 1H), 7.48-7.55 (m, 2H), 7.95-7.99 (m, 2H), 8.26 (s, 1H), 8.74 (s, 2H), 9.30 (s, 1H).

Example 15-79

1-{2-[4-(2-amino-5-chloro-3-pyridinyl)phenoxy]-5-pyrimidinyl}-3-(5-chloro-2-methylphenyl)urea TLC: Rf 0.32 (Chloroform:Methanol=19:1);
$^1$H-NMR (DMSO-$d_6$): δ 5.86 (s, 2H), 7.23-7.30 (m, 2H), 7.42 (d, 1H), 7.46-7.56 (m, 3H), 7.70 (d, 1H), 7.95 (d, 1H), 8.06 (s, 1H), 8.56 (d, 1H), 8.62 (s, 1H), 8.69 (s, 2H), 9.11 (s, 1H), 9.81 (s, 1H).

Example 15-80

1-{2-[4-(2-amino-5-chloro-3-pyridinyl)phenoxy]-5-pyrimidinyl}-3-{5-(difluoromethyl)-2-[3-(trifluoromethyl)-1H-pyrazol-1-yl]phenyl}urea TLC: Rf 0.47 (Hexane:Ethyl Acetate=1:2);
$^1$H-NMR (DMSO-$d_6$): δ 5.85 (s, 2H), 7.08 (d, 1H), 7.13 (t, 1H), 7.25 (d, 2H), 7.39-7.44 (m, 2H), 7.50 (d, 2H), 7.60 (d, 1H), 7.94 (d, 1H), 8.28 (s, 1H), 8.40-8.43 (d, 1H), 8.46 (s, 1H), 8.66 (s, 2H), 9.42 (s, 1H).

Example 15-81

1-{2-[4-(2-amino-5-chloro-3-pyridinyl)phenoxy]-5-pyrimidinyl}-3-{4-chloro-2-[3-(trifluoromethyl)-1H-pyrazol-1-yl]phenyl}urea TLC: Rf 0.51 (Hexane:Ethyl Acetate=1:2);
$^1$H-NMR (DMSO-$d_6$): δ 5.84 (s, 2H), 7.05 (d, 1H), 7.24 (d, 2H), 7.40 (d, 1H), 7.52 (d, 2H), 7.53-7.61 (m, 2H), 7.94 (d, 1H), 8.01 (d, 1H), 8.35 (s, 1H), 8.37-8.42 (m, 1H), 8.63 (s, 2H), 9.35 (s, 1H).

Example 15-82

1-(2-{4-[2-amino-5-(trifluoromethyl)-3-pyridinyl]phenoxy}-5-pyrimidinyl)-3-{2-[3-(difluoromethyl)-1H-pyrazol-1-yl]-5-(trifluoromethyl)phenyl}urea Purity (LC-MS/ELSD): 100% (Retention Time: 1.04 minutes);
MASS (ESI, Pos.): 651 (M+H)+;
$^1$H-NMR (DMSO-$d_6$): δ 6.48 (s, 2H), 6.93 (d, 1H), 7.14 (t, 1H), 7.26-7.33 (m, 2H), 7.49-7.60 (m, 4H), 7.73 (d, 1H), 8.27 (d, 1H), 8.45 (d, 1H), 8.54 (d, 1H), 8.69 (s, 2H), 8.95 (s, 1H), 9.66 (s, 1H).

Example 15-83

1-(2-{4-[2-amino-5-(trifluoromethyl)-3-pyridinyl]phenoxy}-5-pyrimidinyl)-3-{5-(trifluoromethyl)-2-[3-(trifluoromethyl)-1H-1,2,4-triazol-1-yl]phenyl}urea Purity (LC-MS/ELSD): 100% (Retention Time: 1.02 minutes);
MASS (ESI, Pos.): 670 (M+H)+;
$^1$H-NMR (DMSO-$d_6$): δ 6.48 (s, 2H), 7.25-7.32 (m, 2H), 7.48-7.58 (m, 3H), 7.72 (dd, 1H), 7.82 (d, 1H), 8.27 (d, 1H), 8.49 (d, 1H), 8.66-8.69 (m, 3H), 9.24 (s, 1H), 9.33 (s, 1H).

Example 15-84

1-[2-(3-acetyl-1H-pyrazol-1-yl)-5-(trifluoromethyl)phenyl]-3-(2-{4-[2-amino-5-(trifluoromethyl)-3-pyridinyl]phenoxy}-5-pyrimidinyl)urea

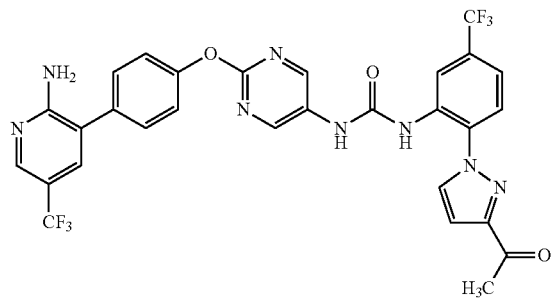 [SMILES: CC(=O)c1ccn(-c2ccc(C(F)(F)F)cc2NC(=O)Nc2cnc(Oc3ccc(-c4cc(C(F)(F)F)cnc4N)cc3)nc2)n1]

Purity (LC-MS/ELSD): 100% (Retention Time: 1.01 minutes);
MASS (ESI, Pos.): 643 (M+H)+;
$^1$H-NMR (DMSO-$d_6$): δ 2.59 (s, 3H), 6.48 (s, 2H), 7.04-7.07 (m, 1H), 7.24-7.32 (m, 2H), 7.48-7.62 (m, 4H), 7.75 (d, 1H), 8.25-8.29 (m, 1H), 8.40 (d, 1H), 8.63 (d, 1H), 8.68 (s, 2H), 8.75 (s, 1H), 9.64 (s, 1H).

Example 15-85

1-(2-{4-[2-amino-5-(trifluoromethyl)-3-pyridinyl]phenoxy}-5-pyrimidinyl)-3-[2-(2-methyl-3-pyridinyl)-5-(trifluoromethyl)phenyl]urea Purity (LC-MS/ELSD): 100% (Retention Time: 0.84 minutes);
MASS (ESI, Pos.): 626 (M+H)+;
$^1$H-NMR (DMSO-$d_6$): δ 2.25 (s, 3H), 6.48 (s, 2H), 7.23-7.57 (m, 8H), 7.63 (dd, 1H), 7.88 (s, 1H), 8.27 (d, 1H), 8.53 (s, 1H), 8.59 (dd, 1H), 8.65 (s, 2H), 9.29 (s, 1H).

Example 15-86

1-(2-{4-[2-amino-5-(trifluoromethyl)-3-pyridinyl]phenoxy}-5-pyrimidinyl)-3-[2-(4-fluoro-1H-pyrazol-1-yl)-5-(trifluoromethyl)phenyl]urea Purity (LC-MS/ELSD): 100% (Retention Time: 1.02 minutes);
MASS (ESI, Pos.): 619 (M+H)+;
$^1$H-NMR (DMSO-$d_6$): δ 6.49 (s, 2H), 7.26-7.33 (m, 2H), 7.48-7.58 (m, 4H), 7.68 (d, 1H), 8.03-8.07 (m, 1H), 8.26-

8.30 (m, 1H), 8.56-8.63 (m, 2H), 8.70 (s, 2H), 9.27 (s, 1H), 9.85 (s, 1H).

Example 15-87

1-(2-{4-[2-amino-5-(trifluoromethyl)-3-pyridinyl]phenoxy}-5-pyrimidinyl)-3-[2-(4-chloro-1H-pyrazol-1-yl)-5-(trifluoromethyl)phenyl]urea

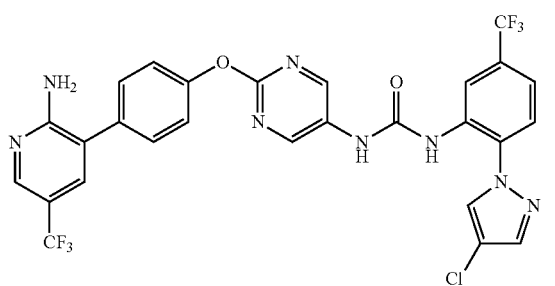 [SMILES: Nc1ncc(C(F)(F)F)cc1-c1ccc(Oc2ncc(NC(=O)Nc3cc(C(F)(F)F)ccc3-n3cc(Cl)cn3)cn2)cc1]

Purity (LC-MS/ELSD): 100% (Retention Time: 1.06 minutes);
MASS (ESI, Pos.): 635 (M+H)$^+$;
$^1$H-NMR (DMSO-d$_6$): δ 6.49 (s, 2H), 7.26-7.32 (m, 2H), 7.50-7.59 (m, 4H), 7.70 (d, 1H), 8.07-8.09 (m, 1H), 8.26-8.30 (m, 1H), 8.57 (d, 1H), 8.63-8.64 (m, 1H), 8.69 (s, 2H), 9.11 (s, 1H), 9.81 (s, 1H).

Example 15-88

1-(2-{4-[2-amino-5-(trifluoromethyl)-3-pyridinyl]phenoxy}-5-pyrimidinyl)-3-[2-chloro-4-(trifluoromethyl)phenyl]urea Purity (LC-MS/ELSD): 100% (Retention Time: 1.04 minutes);
MASS (ESI, Pos.): 569 (M+H)$^+$;
$^1$H-NMR (DMSO-d$_6$): δ 6.49 (s, 2H), 7.27-7.34 (m, 2H), 7.50-7.60 (m, 3H), 7.70 (dd, 1H), 7.89-7.93 (m, 1H), 8.26-8.31 (m, 1H), 8.43 (d, 1H), 8.75 (s, 2H), 8.81 (s, 1H), 9.78 (s, 1H).

Example 15-89

1-(2-{4-[2-amino-5-(trifluoromethyl)-3-pyridinyl]phenoxy}-5-pyrimidinyl)-3-[2-chloro-5-(trifluoromethyl)phenyl]urea Purity (LC-MS/ELSD): 100% (Retention Time: 1.02 minutes);
MASS (ESI, Pos.): 569 (M+H)$^+$;
$^1$H-NMR (DMSO-d$_6$): δ 6.49 (s, 2H), 7.26-7.34 (m, 2H), 7.40 (dd, 1H), 7.50-7.59 (m, 3H), 7.73 (d, 1H), 8.26-8.30 (m, 1H), 8.56 (d, 1H), 8.75 (s, 2H), 8.79 (s, 1H), 9.72 (s, 1H).

Example 15-90

1-(2-{4-[2-amino-5-(trifluoromethyl)-3-pyridinyl]phenoxy}-5-pyrimidinyl)-3-[2-fluoro-5-(trifluoromethyl)phenyl]urea Purity (LC-MS/ELSD): 100% (Retention Time: 0.98 minutes);
MASS (ESI, Pos.): 553 (M+H)$^+$;
$^1$H-NMR (DMSO-d$_6$): δ 6.49 (s, 2H), 7.26-7.33 (m, 2H), 7.38-7.59 (m, 5H), 8.26-8.30 (m, 1H), 8.52 (dd, 1H), 8.75 (s, 2H), 9.11 (s, 1H), 9.31 (s, 1H).

Example 15-91

1-(2-{4-[2-amino-5-(trifluoromethyl)-3-pyridinyl]phenoxy}-5-pyrimidinyl)-3-(2,5-dichlorophenyl)urea Purity (LC-MS/ELSD): 100% (Retention Time: 1.01 minutes);
MASS (ESI, Pos.): 535 (M+H)$^+$;
$^1$H-NMR (DMSO-d$_6$): δ 6.49 (s, 2H), 7.12 (dd, 1H), 7.27-7.34 (m, 2H), 7.50-7.59 (m, 4H), 8.26-8.30 (m, 2H), 8.65 (s, 1H), 8.74 (s, 2H), 9.68 (s, 1H).

Example 15-92

1-(2-{4-[2-amino-5-(trifluoromethyl)-3-pyridinyl]phenoxy}-5-pyrimidinyl)-3-(2,4-dichlorophenyl)urea Purity (LC-MS/ELSD): 100% (Retention Time: 1.00 minute);
MASS (ESI, Pos.): 535 (M+H)$^+$;
$^1$H-NMR (DMSO-d$_6$): δ 6.49 (s, 2H), 7.27-7.33 (m, 2H), 7.39 (dd, 1H), 7.50-7.59 (m, 3H), 7.64 (d, 1H), 8.14 (d, 1H), 8.27-8.30 (m, 1H), 8.59 (s, 1H), 8.73 (s, 2H), 9.60 (s, 1H).

Example 15-93

1-(2-{4-[2-amino-5-(trifluoromethyl)-3-pyridinyl]phenoxy}-5-pyrimidinyl)-3-[2-methyl-5-(trifluoromethyl)phenyl]urea Purity (LC-MS/ELSD): 100% (Retention Time: 0.98 minutes);
MASS (ESI, Pos.): 549 (M+H)$^+$;
$^1$H-NMR (DMSO-d$_6$): δ 2.32 (s, 3H), 6.49 (s, 2H), 7.27-7.34 (m, 3H), 7.42 (d, 1H), 7.50-7.59 (m, 3H), 8.26-8.30 (m, 2H), 8.39 (s, 1H), 8.75 (s, 2H), 9.34 (s, 1H).

Example 15-94

1-{2-[4-(2-amino-5-chloro-3-pyridinyl)phenoxy]-5-pyrimidinyl}-3-[2-isopropyl-5-(trifluoromethyl)phenyl]urea TLC: Rf 0.67 (Ethyl Acetate);
$^1$H-NMR (DMSO-d$_6$): δ 1.22 (d, 6H), 3.21 (m, 1H), 5.86 (s, 2H), 7.25-7.31 (m, 2H), 7.39-7.56 (m, 5H), 7.95 (d, 1H), 8.12-8.15 (m, 1H), 8.43 (s, 1H), 8.74 (s, 2H), 9.28 (s, 1H).

Example 15-95

1-{2-[4-(2-amino-5-chloro-3-pyridinyl)phenoxy]-5-pyrimidinyl}-3-[2-ethyl-5-(trifluoromethyl)phenyl]urea TLC: Rf 0.35 (Ethyl Acetate);
$^1$H-NMR (DMSO-d$_6$): δ 1.20 (t, 3H), 2.69 (q, 2H), 5.86 (s, 2H), 7.25-7.31 (m, 2H), 7.33-7.46 (m, 3H), 7.48-7.56 (m,

Example 15-96

1-{2-[4-(2-amino-5-fluoro-3-pyridinyl)phenoxy]-5-pyrimidinyl}-3-[2-(methylsulfonyl)-5-(trifluoromethyl)phenyl]urea

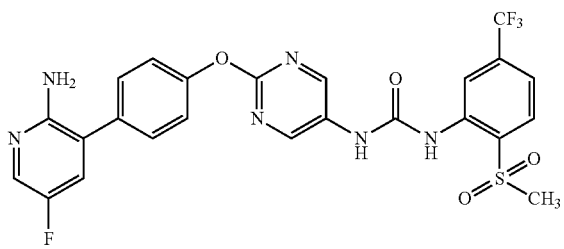 [SMILES: CS(=O)(=O)c1ccc(C(F)(F)F)cc1NC(=O)Nc1cnc(Oc2ccc(-c3cc(F)cnc3N)cc2)nc1]

TLC: Rf 0.44 (Chloroform:Methanol=19:1);
$^1$H-NMR (DMSO-d$_6$): δ 3.38 (s, 3H), 5.57 (s, 2H), 7.25-7.31 (m, 2H), 7.37 (dd, 1H), 7.48-7.56 (m, 2H), 7.61-7.67 (m, 1H), 7.93 (d, 1H), 8.04-8.09 (m, 1H), 8.61-8.65 (m, 1H), 8.75 (s, 2H), 8.97 (s, 1H), 10.30 (s, 1H).

Example 15-97

1-(2-{4-[2-amino-5-(trifluoromethyl)-3-pyridinyl]phenoxy}-5-pyrimidinyl)-3-[2-(methylsulfonyl)-4-(trifluoromethyl)phenyl]urea TLC: Rf 0.31 (Chloroform:Methanol=19:1);
$^1$H-NMR (DMSO-d$_6$): δ 3.42 (s, 3H), 6.49 (s, 2H), 7.27-7.33 (m, 2H), 7.49-7.58 (m, 3H), 8.03-8.11 (m, 2H), 8.25-8.30 (m, 1H), 8.50 (d, 1H), 8.76 (s, 2H), 9.04 (s, 1H), 10.36 (s, 1H).

Example 15-98

1-(2-{4-[2-amino-5-(trifluoromethyl)-3-pyridinyl]phenoxy}-5-pyrimidinyl)-3-[2-(methylsulfonyl)-5-(trifluoromethyl)phenyl]urea

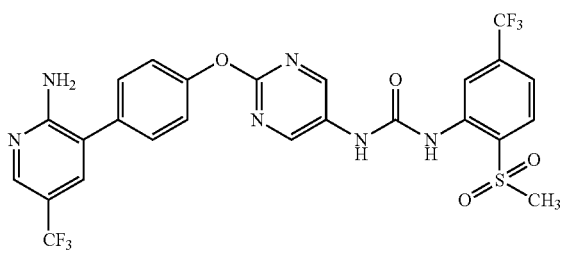 [SMILES: CS(=O)(=O)c1ccc(C(F)(F)F)cc1NC(=O)Nc1cnc(Oc2ccc(-c3cc(C(F)(F)F)cnc3N)cc2)nc1]

TLC: Rf 0.32 (Chloroform:Methanol=19:1);
$^1$H-NMR (DMSO-d$_6$): δ 3.38 (s, 3H), 6.49 (s, 2H), 7.24-7.32 (m, 2H), 7.48-7.58 (m, 3H), 7.64 (d, 1H), 8.06 (d, 1H), 8.24-8.29 (m, 1H), 8.61-8.64 (m, 1H), 8.75 (s, 2H), 8.97 (s, 1H), 10.30 (s, 1H).

Example 15-99

1-{2-[4-(2-amino-5-fluoro-3-pyridinyl)phenoxy]-5-pyrimidinyl}-3-[2-(4-chloro-1H-pyrazol-1-yl)-5-(trifluoromethyl)phenyl]urea TLC: Rf 0.28 (Hexane:Ethyl Acetate=1:2);
$^1$H-NMR (DMSO-d$_6$): δ 5.56 (s, 2H), 7.27 (d, 2H), 7.36 (dd, 1H), 7.51-7.57 (m, 3H), 7.68-7.74 (m, 1H), 7.93 (d, 1H), 8.06 (s, 1H), 8.56 (s, 1H), 8.62 (s, 1H), 8.69 (s, 2H), 9.10 (s, 1H), 9.80 (s, 1H).

Example 15-100

1-{2-[4-(2-amino-5-chloro-3-pyridinyl)phenoxy]-5-pyrimidinyl}-3-[3-methyl-5-(trifluoromethyl)phenyl]urea Purity (LC-MS/ELSD): 100% (Retention Time: 0.94 minutes);
MASS (ESI, Pos.): 515 (M+H)$^+$;
$^1$H-NMR (DMSO-d$_6$): δ 2.36 (s, 3H), 5.86 (s, 2H), 7.15 (s, 1H), 7.26 (d, 2H), 7.40-7.45 (m, 2H), 7.50 (d, 2H), 7.76 (s, 1H), 7.95 (d, 1H), 8.73 (s, 2H), 8.98 (s, 1H), 9.23 (s, 1H).

Example 15-101

1-{2-[4-(2-amino-5-chloro-3-pyridinyl)phenoxy]-5-pyrimidinyl}-3-[2-methyl-4-(trifluoromethyl)phenyl]urea Purity (LC-MS/ELSD): 100% (Retention Time: 0.93 minutes);
MASS (ESI, Pos.): 515 (M+H)$^+$;
$^1$H-NMR (DMSO-d$_6$): δ 2.32 (s, 3H), 5.86 (s, 2H), 7.27 (d, 2H), 7.45 (d, 1H), 7.47-7.54 (m, 3H), 7.56 (s, 1H), 7.95 (d, 1H), 8.14 (d, 1H), 8.40 (s, 1H), 8.75 (s, 2H), 9.39 (s, 1H).

Example 15-102

1-{2-[4-(2-amino-5-chloro-3-pyridinyl)phenoxy]-5-pyrimidinyl}-3-[2,5-bis(trifluoromethyl)phenyl]urea Purity (LC-MS/ELSD): 100% (Retention Time: 0.97 minutes);
MASS (ESI, Pos.): 569 (M+H)$^+$;
$^1$H-NMR (DMSO-d$_6$): δ 5.86 (s, 2H), 7.27 (d, 2H), 7.42 (d, 1H), 7.50 (d, 2H), 7.63 (d, 1H), 7.90-7.97 (m, 2H), 8.41 (s, 1H), 8.57 (s, 1H), 8.74 (s, 2H), 9.73 (s, 1H).

Example 15-103

1-{2-[4-(2-amino-5-chloro-3-pyridinyl)phenoxy]-5-pyrimidinyl}-3-[2-methoxy-5-(trifluoromethyl)phenyl]urea Purity (LC-MS/ELSD): 100% (Retention Time: 0.93 minutes);
MASS (ESI, Pos.): 531 (M+H)$^+$;
$^1$H-NMR (DMSO-d$_6$): δ 3.96 (s, 3H), 5.86 (s, 2H), 7.17-7.37 (m, 4H), 7.42 (d, 1H), 7.50 (d, 2H), 7.95 (d, 1H), 8.48 (d, 1H), 8.66 (s, 1H), 8.72 (s, 2H), 9.60 (s, 1H).

Example 15-104

1-{2-[4-(2-amino-5-chloro-3-pyridinyl)phenoxy]-5-pyrimidinyl}-3-[2-(methylsulfonyl)-5-(trifluoromethyl)phenyl]urea

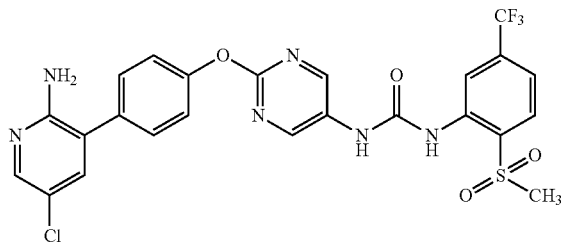 [SMILES: CS(=O)(=O)c1ccc(C(F)(F)F)cc1NC(=O)Nc1cnc(Oc2ccc(-c3cc(Cl)cnc3N)cc2)nc1]

Purity (LC-MS/ELSD): 100% (Retention Time: 0.91 minutes);

MASS (ESI, Pos.): 579 (M+H)$^+$;

$^1$H-NMR (DMSO-$d_6$): δ 3.38 (s, 3H), 5.87 (s, 2H), 7.25-7.31 (m, 2H), 7.43 (d, 1H), 7.48-7.54 (m, 2H), 7.62-7.67 (m, 1H), 7.96 (d, 1H), 8.07 (d, 1H), 8.61-8.65 (m, 1H), 8.75 (s, 2H), 8.97 (s, 1H), 10.31 (s, 1H).

Example 15-105

2-{[(2-{4-[2-amino-5-(trifluoromethyl)-3-pyridinyl]phenoxy}-5-pyrimidinyl)carbamoyl]amino}-N,N-dimethyl-4-(trifluoromethyl)benzenesulfonamide

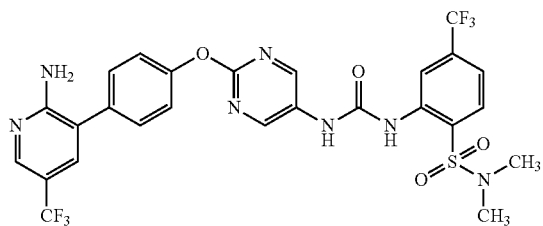 [SMILES: CN(C)S(=O)(=O)c1ccc(C(F)(F)F)cc1NC(=O)Nc1cnc(Oc2ccc(-c3cc(C(F)(F)F)cnc3N)cc2)nc1]

TLC: Rf 0.64 (Hexane:Ethyl Acetate=1:4);

$^1$H-NMR (DMSO-$d_6$): δ 2.76 (s, 6H), 6.49 (s, 2H), 7.27-7.35 (m, 2H), 7.50-7.65 (m, 4H), 7.94 (d, 1H), 8.26-8.30 (m, 1H), 8.61 (s, 1H), 8.74 (s, 2H), 8.99 (s, 1H), 10.31 (s, 1H).

Example 15-106

1-{2-[4-(2-amino-5-chloro-3-pyridinyl)phenoxy]-5-pyrimidinyl}-3-[3'-(hydroxymethyl)-4-(trifluoromethyl)-2-biphenylyl]urea Purity (LC-MS/ELSD): 100% (Retention Time: 0.95 minutes);

MASS (ESI, Pos.): 607 (M+H)$^+$;

$^1$H-NMR (DMSO-$d_6$): δ 4.59 (d, 2H), 5.28 (t, 1H), 5.86 (s, 2H), 7.22-7.33 (m, 3H), 7.36 (s, 1H), 7.37-7.53 (m, 7H), 7.93-7.98 (m, 1H), 8.06 (s, 1H), 8.42 (s, 1H), 8.66 (s, 2H), 9.42 (s, 1H).

Example 15-107

1-{2-[4-(2-amino-5-fluoro-3-pyridinyl)phenoxy]-5-pyrimidinyl}-3-[3'-(hydroxymethyl)-4-(trifluoromethyl)-2-biphenylyl]urea Purity (LC-MS/ELSD): 99% (Retention Time: 0.88 minutes);

MASS (ESI, Pos.): 591 (M+H)$^+$;

$^1$H-NMR (DMSO-$d_6$): δ 4.58 (d, 2H), 5.28 (t, 1H), 5.57 (s, 2H), 7.22-7.32 (m, 3H), 7.35-7.56 (m, 8H), 7.94 (d, 1H), 8.06 (s, 1H), 8.42 (s, 1H), 8.66 (s, 2H), 9.42 (s, 1H).

Example 15-108

1-{2-[4-(2-amino-5-chloro-3-pyridinyl)phenoxy]-5-pyrimidinyl}-3-[3'-(1-hydroxyethyl)-4-(trifluoromethyl)-2-biphenylyl]urea Purity (LC-MS/ELSD): 100% (Retention Time: 0.98 minutes);

MASS (ESI, Pos.): 621 (M+H)$^+$;

$^1$H-NMR (DMSO-$d_6$): δ 1.36 (d, 3H), 4.74-4.93 (m, 1H), 5.21 (d, 1H), 5.86 (s, 2H), 7.22-7.36 (m, 3H), 7.38-7.56 (m, 8H), 7.95 (d, 1H), 8.09 (s, 1H), 8.37 (s, 1H), 8.66 (s, 2H), 9.40 (s, 1H).

Example 15-109

1-{2-[4-(2-amino-5-fluoro-3-pyridinyl)phenoxy]-5-pyrimidinyl}-3-[3'-(1-hydroxyethyl)-4-(trifluoromethyl)-2-biphenylyl]urea Purity (LC-MS/ELSD): 100% (Retention Time: 0.91 minutes);

MASS (ESI, Pos.): 605 (M+H)$^+$;

$^1$H-NMR (DMSO-$d_6$): δ 1.36 (d, 3H), 4.74-4.93 (m, 1H), 5.21 (d, 1H), 5.57 (s, 2H), 7.22-7.57 (m, 11H), 7.94 (d, 1H), 8.09 (s, 1H), 8.37 (s, 1H), 8.66 (s, 2H), 9.40 (s, 1H).

Example 15-110

1-(2-{4-[2-amino-5-(trifluoromethyl)-3-pyridinyl]phenoxy}-5-pyrimidinyl)-3-[2-(ethylsulfonyl)-5-(trifluoromethyl)phenyl]urea TLC: Rf 0.59 (Hexane:Ethyl Acetate=1:4);

$^1$H-NMR (DMSO-$d_6$): δ 1.15 (t, 3H), 3.45 (q, 2H), 6.48 (s, 2H), 7.27 (d, 2H), 7.51 (d, 2H), 7.55 (d, 1H), 7.62 (d, 1H), 8.02 (d, 1H), 8.24-8.28 (m, 1H), 8.64 (s, 1H), 8.74 (s, 2H), 9.00 (s, 1H), 10.32 (s, 1H).

Example 15-111

1-{2-[4-(2-amino-5-chloro-3-pyridinyl)phenoxy]-5-pyrimidinyl}-3-[5-chloro-2-(methylsulfonyl)phenyl]urea TLC: Rf 0.38 (Chloroform:Methanol=19:1);

$^1$H-NMR (DMSO-$d_6$): δ 3.33 (s, 3H), 5.86 (s, 2H), 7.25-7.31 (m, 2H), 7.36 (dd, 1H), 7.43 (d, 1H), 7.48-7.55 (m,

2H), 7.85 (d, 1H), 7.96 (dd, 1H), 8.33 (d, 1H), 8.75 (s, 2H), 8.88 (s, 1H), 10.26 (s, 1H).

Example 15-112

1-(2-{4-[2-amino-5-(trifluoromethyl)-3-pyridinyl]phenoxy}-5-pyrimidinyl)-3-[5-fluoro-2-(methylsulfonyl)phenyl]urea Purity (LC-MS/ELSD): 100% (Retention Time: 0.92 minutes);
MASS (ESI, Pos.): 563 (M+H)$^+$;
$^1$H-NMR (DMSO-d$_6$): δ 3.31 (s, 3H), 6.49 (s, 2H), 7.09-7.19 (m, 1H), 7.29 (d, 2H), 7.50-7.60 (m, 3H), 7.92 (dd, 1H), 8.11 (dd, 1H), 8.25-8.32 (m, 1H), 8.75 (s, 2H), 8.95 (s, 1H), 10.29 (s, 1H).

Example 15-113

2-{[(2-{4-[2-amino-5-(trifluoromethyl)-3-pyridinyl]phenoxy}-5-pyrimidinyl)carbamoyl]amino}-4-fluoro-N,N-dimethylbenzenesulfonamide Purity (LC-MS/ELSD): 100% (Retention Time: 0.98 minutes);
MASS (ESI, Pos.): 592 (M+H)$^+$;
$^1$H-NMR (DMSO-d$_6$): δ 2.70 (s, 6H), 6.49 (s, 2H), 7.09-7.18 (m, 1H), 7.28 (d, 2H), 7.48-7.59 (m, 3H), 7.80 (dd, 1H), 8.11 (dd, 1H), 8.25-8.30 (m, 1H), 8.74 (s, 2H), 8.98 (s, 1H), 10.29 (s, 1H).

Example 15-114

1-{2-[4-(2-amino-5-fluoro-3-pyridinyl)phenoxy]-5-pyrimidinyl}-3-[2-(methylthio)-5-(trifluoromethyl)phenyl]urea TLC: Rf 0.25 (Hexane:Ethyl Acetate=1:2);
$^1$H-NMR (DMSO-d$_6$): δ 2.53 (s, 3H), 5.56 (s, 2H), 7.26 (d, 2H), 7.35-7.43 (m, 2H), 7.49-7.56 (m, 3H), 7.92 (d, 1H), 8.18 (d, 1H), 8.44 (s, 1H), 8.73 (s, 2H), 9.64 (s, 1H).

Example 15-115

1-(2-{4-[2-amino-5-(trifluoromethyl)-3-pyridinyl]phenoxy}-5-pyrimidinyl)-3-[2-(methylsulfinyl)-5-(trifluoromethyl)phenyl]urea TLC: Rf 0.34 (Ethyl Acetate);
$^1$H-NMR (DMSO-d$_6$): δ 2.88 (s, 3H), 6.47 (s, 2H), 7.27 (d, 2H), 7.48-7.57 (m, 3H), 7.65 (d, 1H), 7.90 (d, 1H), 8.26 (s, 2H), 8.73 (s, 2H), 9.25 (s, 1H), 9.68 (s, 1H).

Example 15-116

1-{2-[4-(2-amino-5-fluoro-3-pyridinyl)phenoxy]-5-pyrimidinyl}-3-[2-(methylsulfinyl)-5-(trifluoromethyl)phenyl]urea TLC: Rf 0.32 (Ethyl Acetate);
$^1$H-NMR (DMSO-d$_6$): δ 2.88 (s, 3H), 5.56 (s, 2H), 7.27 (d, 2H), 7.36 (dd, 1H), 7.52 (d, 2H), 7.65 (d, 1H), 7.88-7.94 (m, 2H), 8.26 (s, 1H), 8.73 (s, 2H), 9.24 (s, 1H), 9.68 (s, 1H).

Example 15-117

1-(2-{4-[2-amino-5-(trifluoromethyl)-3-pyridinyl]phenoxy}-5-pyrimidinyl)-3-[5-chloro-2-(methylsulfinyl)phenyl]urea TLC: Rf 0.43 (Ethyl Acetate:Methanol=19:1);
$^1$H-NMR (DMSO-d$_6$): δ 2.86 (s, 3H), 6.48 (s, 2H), 7.27 (d, 2H), 7.35 (dd, 1H), 7.51 (d, 2H), 7.55 (d, 1H), 7.67 (d, 1H), 8.00 (d, 1H), 8.25-8.29 (m, 1H), 8.73 (s, 2H), 9.24 (s, 1H), 9.69 (s, 1H).

Example 15-118

1-{2-[4-(2-amino-5-chloro-3-pyridinyl)phenoxy]-5-pyrimidinyl}-3-[3'-(2-hydroxy-2-propanyl)-4-(trifluoromethyl)-2-biphenylyl]urea Purity (LC-MS/ELSD): 100% (Retention Time: 1.00 minute);
MASS (ESI, Pos.): 635 (M+H)$^+$;
$^1$H-NMR (DMSO-d$_6$): δ 1.45 (s, 6H), 5.07 (s, 1H), 5.85 (s, 2H), 7.21-7.33 (m, 3H), 7.40-7.60 (m, 8H), 7.95 (d, 1H), 8.10 (s, 1H), 8.34 (s, 1H), 8.65 (s, 2H), 9.38 (s, 1H).

Example 15-119

1-(2-{4-[2-amino-5-(trifluoromethyl)-3-pyridinyl]phenoxy}-5-pyrimidinyl)-3-[3'-(2-hydroxy-2-propanyl)-4-(trifluoromethyl)-2-biphenylyl]urea Purity (LC-MS/ELSD): 100% (Retention Time: 1.06 minutes);
MASS (ESI, Pos.): 669 (M+H)$^+$;
$^1$H-NMR (DMSO-d$_6$): δ 1.45 (s, 6H), 5.07 (s, 1H), 6.48 (s, 2H), 7.22-7.34 (m, 3H), 7.41-7.60 (m, 8H), 8.10 (s, 1H), 8.25-8.29 (m, 1H), 8.34 (s, 1H), 8.65 (s, 2H), 9.39 (s, 1H).

Example 15-120

1-{2-[4-(2-amino-5-chloro-3-pyridinyl)phenoxy]-5-pyrimidinyl}-3-[5-chloro-2-(1H-pyrazol-1-yl)phenyl]urea TLC: Rf 0.43 (Hexane:Ethyl Acetate=3: 7);
$^1$H-NMR (DMSO-d$_6$): δ 5.87 (s, 2H), 6.63-6.64 (m, 1H), 7.23 (d, 1H), 7.24-7.28 (m, 2H), 7.40-7.55 (m, 4H), 7.91 (d, 1H), 7.96 (d, 1H), 8.27 (d, 1H), 8.30 (d, 1H), 8.70 (s, 2H), 9.40 (s, 1H), 9.91 (s, 1H).

Example 15-121

1-{2-[4-(2-amino-5-chloro-3-pyridinyl)phenoxy]-5-pyrimidinyl}-3-[4-chloro-2-(1H-pyrazol-1-yl)phenyl]urea TLC: Rf 0.52 (Hexane:Ethyl Acetate=3: 7);
$^1$H-NMR (DMSO-d$_6$): δ 5.86 (s, 2H), 6.61-6.65 (m, 1H), 7.26 (d, 2H), 7.41-7.47 (m, 2H), 7.52 (d, 2H), 7.64 (d, 1H), 7.91 (d, 1H), 7.96 (d, 1H), 8.14 (d, 1H), 8.36 (d, 1H), 8.69 (s, 2H), 9.37 (s, 1H), 9.85 (s, 1H).

Example 15-122

1-{2-[4-(2-amino-5-chloro-3-pyridinyl)phenoxy]-5-pyrimidinyl}-3-[2-(1H-1,2,3-triazol-1-yl)-4-(trifluoromethyl)phenyl]urea Purity (LC-MS/ELSD): 100% (Retention Time: 0.87 minutes);

MASS (ESI, Pos.): 568 (M+H)$^+$;

$^1$H-NMR (DMSO-d$_6$): δ 5.86 (s, 2H), 7.26 (d, 2H), 7.42 (d, 1H), 7.50 (d, 2H), 7.89-7.92 (m, 2H), 7.95 (d, 1H), 8.09 (s, 1H), 8.45 (d, 1H), 8.68-8.70 (m, 4H), 9.69 (brs, 1H).

Example 15-123

1-{6-[4-(2-amino-5-chloro-3-pyridinyl)phenoxy]-3-pyridinyl}-3-[2-fluoro-5-(trifluoromethyl)phenyl]urea Purity (LC-MS/ELSD): 100% (Retention Time: 0.99 minutes);

MASS (ESI, Pos.): 518 (M+H)$^+$;

$^1$H-NMR (DMSO-d$_6$): δ 5.85 (s, 2H), 7.07 (d, 1H), 7.17 (d, 2H), 7.39-7.53 (m, 5H), 7.94 (d, 1H), 8.05 (dd, 1H), 8.22 (d, 1H), 8.56 (dd, 1H), 8.96 (d, 1H), 9.25 (s, 1H).

Example 15-124

1-{6-[4-(2-amino-5-chloro-3-pyridinyl)phenoxy]-3-pyridinyl}-3-[2-(1H-pyrazol-1-yl)-4-(trifluoromethyl)phenyl]urea

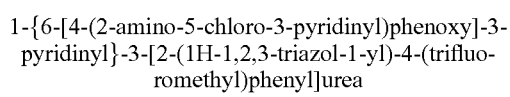

Purity (LC-MS/ELSD): 100% (Retention Time: 1.01 minutes);

MASS (ESI, Pos.): 566 (M+H)$^+$;

$^1$H-NMR (DMSO-d$_6$): δ 5.85 (s, 2H), 6.65 (t, 1H), 7.05 (d, 1H), 7.16 (d, 2H), 7.40 (d, 1H), 7.47 (d, 2H), 7.74 (d, 1H), 7.81 (d, 1H), 7.93-8.00 (m, 3H), 8.22 (d, 1H), 8.42-8.44 (m, 2H), 9.42 (s, 1H), 9.84 (s, 1H).

Example 15-125

1-{6-[4-(2-amino-5-chloro-3-pyridinyl)phenoxy]-3-pyridinyl}-3-[2-(1H-1,2,3-triazol-1-yl)-4-(trifluoromethyl)phenyl]urea Purity (LC-MS/ELSD): 100% (Retention Time: 0.93 minutes);

MASS (ESI, Pos.): 567 (M+H)$^+$;

$^1$H-NMR (DMSO-d$_6$): δ 5.85 (s, 2H), 7.04 (d, 1H), 7.16 (d, 2H), 7.40 (d, 1H), 7.47 (d, 2H), 7.59 (dd, 1H), 7.72 (d, 1H), 7.94 (d, 1H), 7.99 (dd, 1H), 8.10 (d, 1H), 8.15 (d, 1H), 8.59-8.61 (m, 2H), 8.69 (s, 1H), 9.57 (s, 1H).

Example 15-126

1-{2-[4-(2-amino-5-chloro-3-pyridinyl)phenoxy]-5-pyrimidinyl}-3-[5-chloro-2-(3-pyridinyl)phenyl]urea Purity (LC-MS/ELSD): 98% (Retention Time: 0.79 minutes);

MASS (ESI, Pos.): 544 (M+H)$^+$;

$^1$H-NMR (DMSO-d$_6$): δ 5.86 (s, 2H), 7.23-7.30 (m, 4H), 7.42 (d, 1H), 7.49-7.55 (m, 3H), 7.80-7.85 (m, 1H), 7.95 (d, 1H), 8.08 (d, 1H), 8.14 (s, 1H), 8.56-8.65 (m, 4H), 9.21 (s, 1H).

Example 15-127

1-{2-[4-(2-amino-3-pyridinyl)phenoxy]-5-pyrimidinyl}-3-[2-(1H-pyrazol-1-yl)-5-(trifluoromethyl)phenyl]urea Purity (LC-MS/ELSD): 100% (Retention Time: 0.76 minutes);

MASS (ESI, Pos.): 533 (M+H)$^+$;

$^1$H-NMR (DMSO-d$_6$): δ 5.58 (s, 2H), 6.64-6.68 (m, 2H), 7.26 (d, 2H), 7.35 (dd, 1H), 7.47-7.54 (m, 3H), 7.75 (d, 1H), 7.93-7.95 (m, 2H), 8.42 (d, 1H), 8.59 (d, 1H), 8.70 (s, 2H), 9.60-10.08 (br, 2H).

Example 15-128

1-(2-{4-[2-amino-5-(trifluoromethyl)-3-pyridinyl]phenoxy}-5-pyrimidinyl)-3-[2-(3-pyridinyl)-5-(trifluoromethyl)phenyl]urea Purity (LC-MS/ELSD): 100% (Retention Time: 0.90 minutes);

MASS (ESI, Pos.): 612 (M+H)$^+$;

$^1$H-NMR (DMSO-d$_6$): δ 6.48 (s, 2H), 7.24-7.29 (m, 2H), 7.50-7.58 (m, 6H), 7.86-7.91 (m, 1H), 8.25-8.28 (m, 2H), 8.38 (d, 1H), 8.62-8.71 (m, 4H), 9.25 (s, 1H).

Example 15-129

1-(2-{4-[2-amino-5-(trifluoromethyl)-3-pyridinyl]phenoxy}-5-pyrimidinyl)-3-[2-(1H-1,2,3-triazol-1-yl)-5-(trifluoromethyl)phenyl]urea Purity (LC-MS/ELSD): 100% (Retention Time: 0.93 minutes);

MASS (ESI, Pos.): 602 (M+H)$^+$;

$^1$H-NMR (DMSO-d$_6$): δ 6.48 (s, 2H), 7.28 (d, 2H), 7.50-7.56 (m, 3H), 7.61 (dd, 1H), 7.74 (d, 1H), 8.10 (s, 1H), 8.27 (d, 1H), 8.58 (d, 1H), 8.69-8.73 (m, 4H), 9.67 (s, 1H).

Example 15-130

1-{6-[4-(2-amino-5-chloro-3-pyridinyl)phenoxy]-3-pyridinyl}-3-{5-(trifluoromethyl)-2-[3-(trifluoromethyl)-1H-pyrazol-1-yl]phenyl}urea Purity (LC-MS/ELSD): 100% (Retention Time: 1.08 minutes);

MASS (ESI, Pos.): 634 (M+H)$^+$;

$^1$H-NMR (DMSO-d$_6$): δ 5.85 (s, 2H), 7.04 (d, 1H), 7.14-7.18 (m, 3H), 7.40 (d, 1H), 7.45-7.49 (m, 2H), 7.56 (dd,

1H), 7.69 (d, 1H), 7.94 (d, 1H), 7.98 (dd, 1H), 8.16 (d, 1H), 8.45 (s, 1H), 8.47 (d, 1H), 8.51 (d, 1H), 9.40 (s, 1H).

Example 15-131

1-{6-[4-(2-amino-5-fluoro-3-pyridinyl)phenoxy]-3-pyridinyl}-3-{5-(trifluoromethyl)-2-[3-(trifluoromethyl)-1H-pyrazol-1-yl]phenyl}urea Purity (LC-MS/ELSD): 100% (Retention Time: 1.01 minutes);

MASS (ESI, Pos.): 618 (M+H)$^+$;

$^1$H-NMR (DMSO-d$_6$): δ 5.55 (s, 2H), 7.04 (d, 1H), 7.14-7.18 (m, 3H), 7.41 (dd, 1H), 7.46-7.51 (m, 2H), 7.55 (dd, 1H), 7.68 (d, 1H), 7.92 (d, 1H), 7.97 (dd, 1H), 8.15 (d, 1H), 8.44 (s, 1H), 8.46-8.47 (m, 1H), 8.51 (d, 1H), 9.39 (s, 1H).

Example 15-132

1-{2-[4-(2-amino-5-chloro-3-pyridinyl)phenoxy]-5-pyrimidinyl}-3-[3-(1H-pyrazol-1-yl)-5-(trifluoromethyl)phenyl]urea Purity (LC-MS/ELSD): 100% (Retention Time: 0.93 minutes);

MASS (ESI, Pos.): 567 (M+H)$^+$;

$^1$H-NMR (DMSO-d$_6$): δ 5.87 (s, 2H), 6.58-6.59 (m, 1H), 7.28 (d, 2H), 7.43 (d, 1H), 7.49-7.54 (m, 2H), 7.80-7.84 (m, 3H), 8.00 (d, 1H), 8.25 (s, 1H), 8.63 (d, 1H), 8.75 (s, 2H), 9.09 (s, 1H), 9.55 (s, 1H).

Example 15-133

1-{2-[4-(2-amino-5-chloro-3-pyridinyl)phenoxy]-5-pyrimidinyl}-3-[3-(3-pyridinyl)-5-(trifluoromethyl)phenyl]urea Purity (LC-MS/ELSD): 100% (Retention Time: 0.82 minutes);

MASS (ESI, Pos.): 578 (M+H)$^+$;

$^1$H-NMR (DMSO-d$_6$): δ 5.87 (s, 2H), 7.28 (d, 2H), 7.43 (d, 1H), 7.50-7.55 (m, 3H), 7.66 (s, 1H), 7.95-7.96 (m, 2H), 8.01 (s, 1H), 8.09-8.13 (m, 1H), 8.62-8.64 (m, 1H), 8.75 (s, 2H), 8.90 (d, 1H), 9.13 (s, 1H), 9.44 (s, 1H).

Example 15-134

1-{6-[4-(2-amino-5-chloro-3-pyridinyl)phenoxy]-3-pyridinyl}-3-[2-(4-methyl-1H-1,2,3-triazol-1-yl)-5-(trifluoromethyl)phenyl]urea Purity (LC-MS/ELSD): 100% (Retention Time: 0.96 minutes);

MASS (ESI, Pos.): 581 (M+H)$^+$;

$^1$H-NMR (DMSO-d$_6$): δ 2.39 (s, 3H), 5.84 (s, 2H), 7.04 (d, 1H), 7.14-7.17 (m, 2H), 7.39 (d, 1H), 7.45-7.48 (m, 2H), 7.56 (dd, 1H), 7.67 (d, 1H), 7.93 (d, 1H), 7.99 (dd, 1H), 8.15 (d, 1H), 8.38 (d, 1H), 8.61-8.62 (m, 2H), 9.59 (s, 1H).

Example 15-135

1-{2-[4-(2-amino-5-chloro-3-pyridinyl)phenoxy]-5-pyrimidinyl}-3-[5-chloro-2-(1H-1,2,3-triazol-1-yl)phenyl]urea Purity (LC-MS/ELSD): 98% (Retention Time: 0.85 minutes);

MASS (ESI, Pos.): 534 (M+H)$^+$;

$^1$H-NMR (DMSO-d$_6$): δ 5.86 (s, 2H), 7.24-7.29 (m, 2H), 7.32 (dd, 1H), 7.42 (d, 1H), 7.48-7.53 (m, 3H), 7.95 (d, 1H), 8.06 (d, 1H), 8.27 (d, 1H), 8.51 (s, 1H), 8.59 (d, 1H), 8.67 (s, 2H), 9.60 (s, 1H).

Example 15-136

1-{2-[4-(2-amino-5-chloro-3-pyridinyl)phenoxy]-5-pyrimidinyl}-3-[2-(5-methyl-3-pyridinyl)-5-(trifluoromethyl)phenyl]urea TLC: Rf 0.58 (Ethyl Acetate:Methanol=19:1);

$^1$H-NMR (DMSO-d$_6$): δ 2.38 (s, 3H), 5.86 (s, 2H), 7.24-7.31 (m, 2H), 7.40-7.54 (m, 5H), 7.70-7.74 (m, 1H), 7.95 (d, 1H), 8.20 (s, 1H), 8.40-8.47 (m, 2H), 8.51-8.55 (m, 1H), 8.66 (s, 2H), 9.28 (s, 1H).

Example 15-137

1-{2-[4-(2-amino-5-fluoro-3-pyridinyl)phenoxy]-5-pyrimidinyl}-3-[2-(5-methyl-3-pyridinyl)-5-(trifluoromethyl)phenyl]urea TLC: Rf 0.45 (Ethyl Acetate:Methanol=19:1);

$^1$H-NMR (DMSO-d$_6$): δ 2.38 (s, 3H), 5.57 (s, 2H), 7.22-7.31 (m, 2H), 7.37 (dd, 1H), 7.43-7.58 (m, 4H), 7.68-7.75 (m, 1H), 7.93 (d, 1H), 8.20 (s, 1H), 8.40-8.46 (m, 2H), 8.51-8.55 (m, 1H), 8.66 (s, 2H), 9.29 (s, 1H).

Example 15-138

1-{2-[4-(2-amino-5-fluoro-3-pyridinyl)phenoxy]-5-pyrimidinyl}-3-[2-(2-methyl-3-pyridinyl)-5-(trifluoromethyl)phenyl]urea TLC: Rf 0.18 (Ethyl Acetate:Methanol=19:1);

$^1$H-NMR (DMSO-d$_6$): δ 2.25 (s, 3H), 5.56 (s, 2H), 7.22-7.30 (m, 2H), 7.33-7.56 (m, 6H), 7.59-7.66 (m, 1H), 7.87 (s, 1H), 7.93 (d, 1H), 8.53 (s, 1H), 8.56-8.61 (m, 1H), 8.65 (s, 2H), 9.28 (s, 1H).

Example 15-139

1-{2-[4-(2-amino-5-fluoro-3-pyridinyl)phenoxy]-5-pyrimidinyl}-3-[5-phenyl-2-(trifluoromethyl)-4-pyridinyl]urea TLC: Rf 0.44 (Hexane:Ethyl Acetate=1:4);

$^1$H-NMR (DMSO-d$_6$): δ 5.57 (s, 2H), 7.25-7.32 (m, 2H), 7.37 (dd, 1H), 7.50-7.65 (m, 7H), 7.94 (d, 1H), 8.42-8.47 (m, 2H), 8.69 (s, 2H), 8.75 (s, 1H), 9.74 (s, 1H).

Example 15-140

1-{2-[4-(2-amino-5-chloro-3-pyridinyl)phenoxy]-5-pyrimidinyl}-3-[2-(6-methyl-3-pyridinyl)-5-(trifluoromethyl)phenyl]urea TLC: Rf 0.68 (Ethyl Acetate:Methanol=9:1);
$^1$H-NMR (DMSO-$d_6$): δ 2.55 (s, 3H), 5.85 (s, 2H), 7.26 (d, 2H), 7.42-7.53 (m, 6H), 7.76 (dd, 1H), 7.95 (d, 1H), 8.20 (s, 1H), 8.42 (s, 1H), 8.50 (d, 1H), 8.67 (s, 2H), 9.28 (s, 1H).

Example 15-141

1-{2-[4-(2-amino-5-fluoro-3-pyridinyl)phenoxy]-5-pyrimidinyl}-3-[2-phenyl-5-(trifluoromethyl)-3-pyridinyl]urea TLC: Rf 0.43 (Hexane:Ethyl Acetate=1:3);
$^1$H-NMR (DMSO-$d_6$): δ 5.57 (s, 2H), 7.27 (d, 2H), 7.38 (dd, 1H), 7.51-7.69 (m, 7H), 7.94 (d, 1H), 8.43 (s, 1H), 8.68 (s, 2H), 8.73 (s, 1H), 8.76 (s, 1H), 9.47 (s, 1H).

Example 15-142

1-{2-[4-(2-amino-5-fluoro-3-pyridinyl)phenoxy]-5-pyrimidinyl}-3-[3',4'-dimethyl-4-(trifluoromethyl)-2-biphenylyl]urea TLC: Rf 0.79 (Hexane:Ethyl Acetate=1:3);
$^1$H-NMR (DMSO-$d_6$): δ 2.29 (s, 6H), 5.56 (s, 2H), 7.13-7.56 (m, 10H), 7.93 (d, 1H), 8.01 (s, 1H), 8.45 (s, 1H), 8.67 (s, 1H), 9.45 (s, 1H).

Example 15-143

1-{2-[4-(2-amino-5-fluoro-3-pyridinyl)phenoxy]-5-pyrimidinyl}-3-[2-(6-methyl-3-pyridinyl)-5-(trifluoromethyl)phenyl]urea TLC: Rf 0.69 (Ethyl Acetate:Methanol=9:1);
$^1$H-NMR (DMSO-$d_6$): δ 2.55 (s, 3H), 5.56 (s, 2H), 7.26 (d, 2H), 7.35-7.57 (m, 6H), 7.77 (dd, 1H), 7.94 (d, 1H), 8.20 (s, 1H), 8.42 (s, 1H), 8.50 (d, 1H), 8.70 (s, 2H), 9.28 (s, 1H).

Example 15-144

1-{2-[4-(2-amino-5-chloro-3-pyridinyl)phenoxy]-5-pyrimidinyl}-3-[2'-methyl-4-(trifluoromethyl)-2-biphenylyl]urea TLC: Rf 0.59 (Methylene chloride:Ethyl Acetate:Methanol=8:4:1);
$^1$H-NMR (DMSO-$d_6$): δ 2.04 (s, 3H), 5.86 (brs, 2H), 7.16-7.46 (m, 9H), 7.50 (d, 2H), 7.72 (s, 1H), 7.95 (d, 1H), 8.53 (s, 1H), 8.65 (s, 2H), 9.45 (s, 1H).

Example 15-145

1-{2-[4-(2-amino-5-fluoro-3-pyridinyl)phenoxy]-5-pyrimidinyl}-3-[2'-methyl-4-(trifluoromethyl)-2-biphenylyl]urea TLC: Rf 0.56 (Methylene chloride:Ethyl Acetate:Methanol=8:4:1);
$^1$H-NMR (DMSO-$d_6$): δ 2.04 (s, 3H), 5.56 (brs, 2H), 7.16-7.48 (m, 9H), 7.52 (d, 2H), 7.72 (s, 1H), 7.93 (d, 1H), 8.53 (s, 1H), 8.65 (s, 2H), 9.45 (s, 1H).

Example 15-146

1-{2-[4-(2-amino-5-chloro-3-pyridinyl)phenoxy]-5-pyrimidinyl}-3-[2'-ethyl-4-(trifluoromethyl)-2-biphenylyl]urea TLC: Rf 0.51 (Hexane:Ethyl Acetate=1:2);
$^1$H-NMR (DMSO-$d_6$): δ 0.99 (t, 3H), 2.21-2.50 (m, 2H), 5.85 (s, 2H), 7.16 (d, 1H), 7.15-7.51 (m, 10H), 7.66 (s, 1H), 7.94 (d, 1H), 8.53 (s, 1H), 8.64 (s, 2H), 9.47 (s, 1H).

Example 15-147

1-{2-[4-(2-amino-5-fluoro-3-pyridinyl)phenoxy]-5-pyrimidinyl}-3-[2'-ethyl-4-(trifluoromethyl)-2-biphenylyl]urea TLC: Rf 0.50 (Hexane:Ethyl Acetate=1:2);
$^1$H-NMR (DMSO-$d_6$): δ 0.99 (t, 3H), 2.21-2.50 (m, 2H), 5.56 (s, 2H), 7.16 (d, 1H), 7.22-7.56 (m, 10H), 7.66 (s, 1H), 7.93 (d, 1H), 8.53 (s, 1H), 8.64 (s, 2H), 9.47 (s, 1H).

Example 15-148

1-{2-[4-(2-amino-5-fluoro-3-pyridinyl)phenoxy]-5-pyrimidinyl}-3-{5-chloro-2-[4-(difluoromethyl)-1H-pyrazol-1-yl]phenyl}urea TLC: Rf 0.16 (Hexane:Ethyl Acetate:Methanol=6:4:0.4);
$^1$H-NMR (DMSO-$d_6$): δ 5.56 (s, 2H), 7.13 (t, 1H), 7.20-7.29 (m, 3H), 7.36 (dd, 1H), 7.46-7.57 (m, 3H), 7.92 (d, 1H), 8.11 (s, 1H), 8.23 (d, 1H), 8.58 (s, 1H), 8.67 (s, 2H), 8.90 (s, 1H), 9.77 (s, 1H).

Example 15-149

1-{2-[4-(2-amino-5-fluoro-3-pyridinyl)phenoxy]-5-pyrimidinyl}-3-{5-chloro-2-[3-(trifluoromethyl)-1H-pyrazol-1-yl]phenyl}urea TLC: Rf 0.20 (Hexane:Ethyl Acetate:Methanol=6:4:0.4);
$^1$H-NMR (DMSO-$d_6$): δ 5.56 (s, 2H), 7.07 (s, 1H), 7.20-7.32 (m, 3H), 7.37 (dd, 1H), 7.43-7.57 (m, 3H), 7.92 (d, 1H), 8.18 (s, 1H), 8.37 (s, 2H), 8.65 (s, 2H), 9.43 (s, 1H).

Example 15-150

1-{2-[4-(2-amino-5-chloro-3-pyridinyl)phenoxy]-5-pyrimidinyl}-3-[5-chloro-2-(4-fluoro-1H-pyrazol-1-yl)phenyl]urea TLC: Rf 0.45 (Hexane:Ethyl Acetate=1:2);
$^1$H-NMR (DMSO-$d_6$): δ 5.85 (s, 2H), 7.19-7.30 (m, 3H), 7.38-7.54 (m, 4H), 7.91-7.99 (m, 2H), 8.24 (d, 1H), 8.42 (d, 1H), 8.69 (s, 2H), 8.94 (s, 1H), 9.76 (s, 1H).

Example 15-151

1-{2-[4-(2-amino-5-fluoro-3-pyridinyl)phenoxy]-5-pyrimidinyl}-3-[5-chloro-2-(4-fluoro-1H-pyrazol-1-yl)phenyl]urea TLC: Rf 0.39 (Hexane:Ethyl Acetate=1:2);
$^1$H-NMR (DMSO-$d_6$): δ 5.56 (s, 2H), 7.19-7.30 (m, 3H), 7.36 (dd, 1H), 7.44 (d, 1H), 7.51 (d, 2H), 7.92 (d, 1H), 7.95 (d, 1H), 8.24 (d, 1H), 8.42 (d, 1H), 8.68 (s, 2H), 8.94 (s, 1H), 9.75 (s, 1H).

Example 15-152

1-{2-[4-(2-amino-5-fluoro-3-pyridinyl)phenoxy]-5-pyrimidinyl}-3-[4'-ethyl-4-(trifluoromethyl)-2-biphenylyl]urea TLC: Rf 0.31 (Hexane:Ethyl Acetate=2:3);
$^1$H-NMR (DMSO-$d_6$): δ 1.24 (t, 3H), 2.69 (q, 2H), 5.57 (s, 2H), 7.24-7.31 (m, 2H), 7.34-7.56 (m, 9H), 7.93 (d, 1H), 8.09 (s, 1H), 8.41 (s, 1H), 8.67 (s, 2H), 9.41 (s, 1H).

Example 15-153

1--{2-[4-(2-amino-5-chloro-3-pyridinyl)phenoxy]-5-pyrimidinyl}-3-[5-fluoro-2-(3-pyridinyl)phenyl]urea TLC: Rf 0.51 (Ethyl Acetate:Methanol=9:1);
$^1$H-NMR (DMSO-$d_6$): δ 5.86 (s, 2H), 7.02 (dt, 1H), 7.24-7.31 (m, 3H), 7.42 (d, 1H), 7.49-7.55 (m, 3H), 7.82 (dt, 1H), 7.88 (dd, 1H), 7.95 (d, 1H), 8.12 (s, 1H), 8.58-8.65 (m, 4H), 9.23 (s, 1H).

Example 15-154

1-{2-[4-(2-amino-5-chloro-3-pyridinyl)phenoxy]-5-pyrimidinyl}-3-[3,4-bis(trifluoromethyl)phenyl]urea Purity (LC-MS/ELSD): 100% (Retention Time: 0.99 minutes);
MASS (ESI, Pos.): 569 (M+H)$^+$;
$^1$H-NMR (DMSO-$d_6$): δ 5.87 (s, 2H), 7.25-7.31 (m, 2H), 7.43 (d, 1H), 7.49-7.55 (m, 2H), 7.86-7.98 (m, 3H), 8.20 (s, 1H), 8.74 (s, 2H), 9.16 (s, 1H), 9.77 (s, 1H).

Example 15-155

1-{2-[4-(2-amino-5-chloro-3-pyridinyl)phenoxy]-5-pyrimidinyl}-3-[3-methyl-4-(trifluoromethyl)phenyl]urea Purity (LC-MS/ELSD): 100% (Retention Time: 0.94 minutes);
MASS (ESI, Pos.): 515 (M+H)$^+$;
$^1$H-NMR (DMSO-$d_6$): δ 2.39 (s, 3H), 5.87 (s, 2H), 7.25-7.32 (m, 2H), 7.42-7.61 (m, 6H), 7.95 (d, 1H), 8.73 (s, 2H), 8.98 (s, 1H), 9.28 (s, 1H).

Example 15-156

1-{2-[4-(2-amino-5-chloro-3-pyridinyl)phenoxy]-5-pyrimidinyl}-3-[3-fluoro-4-(trifluoromethyl)phenyl]urea Purity (LC-MS/ELSD): 100% (Retention Time: 0.93 minutes);
MASS (ESI, Pos.): 519 (M+H)$^+$;
$^1$H-NMR (DMSO-$d_6$): δ 5.87 (s, 2H), 7.25-7.32 (m, 2H), 7.33-7.39 (m, 1H), 7.43 (d, 1H), 7.48-7.51 (m, 2H), 7.63-7.74 (m, 2H), 7.96 (d, 1H), 8.73 (s, 2H), 9.10 (s, 1H), 9.62 (s, 1H).

Example 15-157

1-{2-[4-(2-amino-5-chloro-3-pyridinyl)phenoxy]-5-pyrimidinyl}-3-[3-fluoro-4-(trifluoromethyl)phenyl]urea Purity (LC-MS/ELSD): 100% (Retention Time: 0.90 minutes);
MASS (ESI, Pos.): 531 (M+H)$^+$;
$^1$H-NMR (DMSO-$d_6$): δ 3.84 (s, 3H), 5.86 (s, 2H), 7.07-7.15 (m, 1H), 7.25-7.32 (m, 2H), 7.41-7.56 (m, 5H), 7.95 (d, 1H), 8.73 (s, 2H), 8.98 (s, 1H), 9.38 (s, 1H).

Example 15-158

1-{2-[4-(2-amino-5-chloro-3-pyridinyl)phenoxy]-5-pyrimidinyl}-3-[2,3-difluoro-4-(trifluoromethyl)phenyl]urea Purity (LC-MS/ELSD): 100% (Retention Time: 0.95 minutes);
MASS (ESI, Pos.): 537 (M+H)$^+$;
$^1$H-NMR (DMSO-$d_6$): δ 5.86 (s, 2H), 7.25-7.32 (m, 2H), 7.43 (d, 1H), 7.48-7.61 (m, 3H), 7.94-7.98 (m, 1H), 8.13-8.21 (m, 1H), 8.75 (s, 2H), 9.36 (s, 2H).

Example 15-159

1-{2-[4-(2-amino-5-chloro-3-pyridinyl)phenoxy]-5-pyrimidinyl}-3-[4-methoxy-3-(trifluoromethyl)phenyl]urea Purity (LC-MS/ELSD): 100% (Retention Time: 0.87 minutes);
MASS (ESI, Pos.): 531 (M+H)$^+$;
$^1$H-NMR (DMSO-$d_6$): δ 3.84 (s, 3H), 5.87 (s, 2H), 7.19-7.31 (m, 3H), 7.43 (d, 1H), 7.49-7.54 (m, 2H), 7.60 (dd, 1H), 7.80 (d, 1H), 7.95 (d, 1H), 8.71 (s, 2H), 8.90 (s, 1H), 9.03 (s, 1H).

Example 15-160

1-{2-[4-(2-amino-5-chloro-3-pyridinyl)phenoxy]-5-pyrimidinyl}-3-[3-methoxy-5-(trifluoromethyl)phenyl]urea Purity (LC-MS/ELSD): 100% (Retention Time: 0.91 minutes);
MASS (ESI, Pos.): 531 (M+H)$^+$;
$^1$H-NMR (DMSO-$d_6$): δ 3.80 (s, 3H), 5.87 (s, 2H), 6.83-6.90 (m, 1H), 7.24-7.31 (m, 3H), 7.41-7.45 (m, 1H), 7.46-7.55 (m, 3H), 7.94-7.97 (m, 1H), 8.72 (s, 2H), 8.98 (s, 1H), 9.31 (s, 1H).

Example 15-161

1-{2-[4-(2-amino-5-fluoro-3-pyridinyl)phenoxy]-5-pyrimidinyl}-3-[3,4-bis(trifluoromethyl)phenyl]urea Purity (LC-MS/ELSD): 100% (Retention Time: 0.92 minutes);
MASS (ESI, Pos.): 553 (M+H)$^+$;
$^1$H-NMR (DMSO-$d_6$): δ 5.58 (s, 2H), 7.25-7.33 (m, 2H), 7.38 (dd, 1H), 7.51-7.58 (m, 2H), 7.85-7.99 (m, 3H), 8.19-8.23 (m, 1H), 8.74 (s, 2H), 9.17 (s, 1H), 9.78 (s, 1H).

Example 15-162

1-{2-[4-(2-amino-5-fluoro-3-pyridinyl)phenoxy]-5-pyrimidinyl}-3-[3-methyl-4-(trifluoromethyl)phenyl]urea Purity (LC-MS/ELSD): 100% (Retention Time: 0.87 minutes);
MASS (ESI, Pos.): 499 (M+H)$^+$;
$^1$H-NMR (DMSO-d$_6$): δ 2.40 (s, 3H), 5.58 (s, 2H), 7.25-7.60 (m, 8H), 7.94-7.96 (m, 1H), 8.73 (s, 2H), 8.98 (s, 1H), 9.28 (s, 1H).

Example 15-163

1-{2-[4-(2-amino-5-fluoro-3-pyridinyl)phenoxy]-5-pyrimidinyl}-3-[3-fluoro-4-(trifluoromethyl)phenyl]urea Purity (LC-MS/ELSD): 100% (Retention Time: 0.86 minutes);
MASS (ESI, Pos.): 503 (M+H)$^+$;
$^1$H-NMR (DMSO-d$_6$): δ 5.58 (s, 2H), 7.25-7.43 (m, 4H), 7.50-7.58 (m, 2H), 7.63-7.75 (m, 2H), 7.94 (d, 1H), 8.73 (s, 2H), 9.10 (s, 1H), 9.61 (s, 1H).

Example 15-164

1-{2-[4-(2-amino-5-fluoro-3-pyridinyl)phenoxy]-5-pyrimidinyl}-3-[2-methoxy-4-(trifluoromethyl)phenyl]urea Purity (LC-MS/ELSD): 100% (Retention Time: 0.87 minutes);
MASS (ESI, Pos.): 515 (M+H)$^+$;
$^1$H-NMR (DMSO-d$_6$): δ 3.97 (s, 3H), 5.57 (s, 2H), 7.25-7.57 (m, 7H), 7.94 (d, 1H), 8.29-8.36 (m, 1H), 8.69-8.75 (m, 3H), 9.66 (s, 1H).

Example 15-165

1-{2-[4-(2-amino-5-fluoro-3-pyridinyl)phenoxy]-5-pyrimidinyl}-3-[3-methoxy-4-(trifluoromethyl)phenyl]urea Purity (LC-MS/ELSD): 100% (Retention Time: 0.83 minutes);
MASS (ESI, Pos.): 515 (M+H)$^+$;
$^1$H-NMR (DMSO-d$_6$): δ 3.83 (s, 3H), 5.57 (s, 2H), 7.07-7.14 (m, 1H), 7.25-7.32 (m, 2H), 7.35-7.57 (m, 5H), 7.93 (d, 1H), 8.72 (s, 2H), 8.97 (s, 1H), 9.37 (s, 1H).

Example 15-166

1-{2-[4-(2-amino-5-fluoro-3-pyridinyl)phenoxy]-5-pyrimidinyl}-3-[4-fluoro-3-(trifluoromethyl)phenyl]urea Purity (LC-MS/ELSD): 88% (Retention Time: 0.83 minutes);
MASS (ESI, Pos.): 503 (M+H)$^+$;
$^1$H-NMR (DMSO-d$_6$): δ 5.58 (s, 2H), 7.25-7.32 (m, 2H), 7.35-7.58 (m, 4H), 7.65-7.75 (m, 1H), 7.92-8.00 (m, 2H), 8.72 (s, 2H), 9.01 (s, 1H), 9.31 (s, 1H).

Example 15-167

1-{2-[4-(2-amino-5-fluoro-3-pyridinyl)phenoxy]-5-pyrimidinyl}-3-[4-methoxy-3-(trifluoromethyl)phenyl]urea Purity (LC-MS/ELSD): 100% (Retention Time: 0.80 minutes);
MASS (ESI, Pos.): 515 (M+H)$^+$;
$^1$H-NMR (DMSO-d$_6$): δ 3.84 (s, 3H), 5.58 (s, 2H), 7.19-7.31 (m, 3H), 7.38 (dd, 1H), 7.50-7.57 (m, 2H), 7.58-7.65 (m, 1H), 7.78-7.83 (m, 1H), 7.93-7.96 (m, 1H), 8.72 (s, 2H), 8.90 (s, 1H), 9.03 (s, 1H).

Example 15-168

1-{2-[4-(2-amino-5-fluoro-3-pyridinyl)phenoxy]-5-pyrimidinyl}-3-[3-methoxy-5-(trifluoromethyl)phenyl]urea Purity (LC-MS/ELSD): 100% (Retention Time: 0.84 minutes);
MASS (ESI, Pos.): 515 (M+H)$^+$;
$^1$H-NMR (DMSO-d$_6$): δ 3.80 (s, 3H), 5.57 (s, 2H), 6.86 (s, 1H), 7.25-7.58 (m, 7H), 7.94 (d, 1H), 8.72 (s, 2H), 8.98 (s, 1H), 9.31 (s, 1H).

Example 15-169

1-{2-[4-(2-amino-5-chloro-3-pyridinyl)phenoxy]-5-pyrimidinyl}-3-[2,6-difluoro-3-(trifluoromethyl)phenyl]urea Purity (LC-MS/ELSD): 100% (Retention Time: 0.84 minutes);
MASS (ESI, Pos.): 537 (M+H)$^+$;
$^1$H-NMR (DMSO-d$_6$): δ 5.86 (s, 2H), 7.24-7.30 (m, 2H), 7.37-7.55 (m, 4H), 7.71-7.82 (m, 1H), 7.95 (d, 1H), 8.67 (brs, 1H), 8.72 (s, 2H), 9.38 (brs, 1H).

Example 15-170

1-{2-[4-(2-amino-5-fluoro-3-pyridinyl)phenoxy]-5-pyrimidinyl}-3-[2,6-difluoro-3-(trifluoromethyl)phenyl]urea Purity (LC-MS/ELSD): 100% (Retention Time: 0.77 minutes);
MASS (ESI, Pos.): 521 (M+H)$^+$;
$^1$H-NMR (DMSO-d$_6$): δ 5.57 (s, 2H), 7.24-7.31 (m, 2H), 7.35-7.56 (m, 4H), 7.71-7.82 (m, 1H), 7.92-7.96 (m, 1H), 8.66 (s, 1H), 8.72 (s, 2H), 9.37 (s, 1H).

Example 15-171

1-{2-[4-(2-amino-5-chloro-3-pyridinyl)phenoxy]-5-pyrimidinyl}-3-[3,5-bis(trifluoromethyl)phenyl]urea Purity (LC-MS/ELSD): 100% (Retention Time: 1.00 minute);

MASS (ESI, Pos.): 569 (M+H)$^+$;

$^1$H-NMR (DMSO-d$_6$): δ 5.87 (s, 2H), 7.25-7.31 (m, 2H), 7.42-7.45 (m, 1H), 7.49-7.55 (m, 2H), 7.65-7.70 (m, 1H), 7.95-7.98 (m, 1H), 8.15 (s, 2H), 8.74 (s, 2H), 9.21 (s, 1H), 9.68 (s, 1H).

Example 15-172

1-{2-[4-(2-amino-5-chloro-3-pyridinyl)phenoxy]-5-pyrimidinyl}-3-[3,5-bis(trifluoromethyl)phenyl]urea Purity (LC-MS/ELSD): 100% (Retention Time: 0.89 minutes);

MASS (ESI, Pos.): 485 (M+H)$^+$;

$^1$H-NMR (DMSO-d$_6$): δ 5.86 (s, 2H), 7.05-7.13 (m, 1H), 7.25-7.37 (m, 3H), 7.43 (d, 1H), 7.48-7.56 (m, 2H), 7.95 (d, 1H), 8.20 (dd, 1H), 8.74 (s, 2H), 8.97 (s, 1H), 9.28 (s, 1H).

Example 15-173

1-{2-[4-(2-amino-5-chloro-3-pyridinyl)phenoxy]-5-pyrimidinyl}-3-[3,5-bis(trifluoromethyl)phenyl]urea Purity (LC-MS/ELSD): 100% (Retention Time: 0.96 minutes);

MASS (ESI, Pos.): 501 (M+H)$^+$;

$^1$H-NMR (DMSO-d$_6$): δ 5.86 (s, 2H), 7.20 (t, 1H), 7.25-7.31 (m, 2H), 7.43 (d, 1H), 7.49-7.56 (m, 4H), 7.95 (d, 1H), 8.72 (s, 2H), 9.09 (s, 1H), 9.33 (s, 1H).

Example 15-174

1-{2-[4-(2-amino-5-chloro-3-pyridinyl)phenoxy]-5-pyrimidinyl}-3-(3-chloro-5-methylphenyl)urea Purity (LC-MS/ELSD): 100% (Retention Time: 0.91 minutes);

MASS (ESI, Pos.): 481 (M+H)$^+$;

$^1$H-NMR (DMSO-d$_6$): δ 3.32 (s, 3H), 5.86 (s, 2H), 6.86-6.90 (s, 1H), 7.10-7.15 (m, 1H), 7.24-7.31 (m, 2H), 7.42-7.55 (m, 4H), 7.95 (d, 1H), 8.72 (s, 2H), 8.92 (s, 1H), 9.06 (s, 1H).

Example 15-175

1-{2-[4-(2-amino-5-chloro-3-pyridinyl)phenoxy]-5-pyrimidinyl}-3-(3-chloro-5-fluorophenyl)urea Purity (LC-MS/ELSD): 100% (Retention Time: 0.90 minutes);

MASS (ESI, Pos.): 485 (M+H)$^+$;

$^1$H-NMR (DMSO-d$_6$): δ 5.86 (s, 2H), 6.98-7.06 (m, 1H), 7.25-7.55 (m, 7H), 7.95 (d, 1H), 8.72 (s, 2H), 9.06 (s, 1H), 9.36 (s, 1H).

Example 15-176

1-{2-[4-(2-amino-5-chloro-3-pyridinyl)phenoxy]-5-pyrimidinyl}-3-(5-chloro-2-methoxyphenyl)urea Purity (LC-MS/ELSD): 100% (Retention Time: 0.90 minutes);

MASS (ESI, Pos.): 497 (M+H)$^+$;

$^1$H-NMR (DMSO-d$_6$): δ 3.88 (s, 3H), 5.86 (s, 2H), 6.98-7.08 (m, 2H), 7.25-7.32 (m, 2H), 7.43 (d, 1H), 7.49-7.55 (m, 2H), 7.95 (d, 1H), 8.18 (d, 1H), 8.56 (s, 1H), 8.72 (s, 2H), 9.59 (s, 1H).

Example 15-177

1-{2-[4-(2-amino-5-chloro-3-pyridinyl)phenoxy]-5-pyrimidinyl}-3-(3-chloro-5-methoxyphenyl)urea Purity (LC-MS/ELSD): 100% (Retention Time: 0.87 minutes);

MASS (ESI, Pos.): 497 (M+H)$^+$;

$^1$H-NMR (DMSO-d$_6$): δ 3.74 (s, 3H), 5.86 (s, 2H), 6.60-6.66 (m, 1H), 6.95-7.00 (m, 1H), 7.15-7.20 (m, 1H), 7.24-7.30 (m, 2H), 7.43 (d, 1H), 7.45-7.55 (m, 2H), 7.95 (d, 1H), 8.71 (s, 2H), 8.93 (s, 1H), 9.13 (s, 1H).

Example 15-178

1-{2-[4-(2-amino-5-chloro-3-pyridinyl)phenoxy]-5-pyrimidinyl}-3-[5-chloro-2-(trifluoromethyl)phenyl]urea Purity (LC-MS/ELSD): 100% (Retention Time: 0.94 minutes);

MASS (ESI, Pos.): 535 (M+H)$^+$;

$^1$H-NMR (DMSO-d$_6$): δ 5.86 (s, 2H), 7.25-7.31 (m, 2H), 7.34-7.40 (m, 1H), 7.43 (d, 1H), 7.49-7.55 (m, 2H), 7.72 (d, 1H), 7.95 (d, 1H), 8.10-8.14 (m, 1H), 8.42 (brs, 1H), 8.74 (s, 2H), 9.67 (brs, 1H).

Example 15-179

1-{2-[4-(2-amino-5-chloro-3-pyridinyl)phenoxy]-5-pyrimidinyl}-3-(2,3-dichlorophenyl)urea Purity (LC-MS/ELSD): 100% (Retention Time: 0.91 minutes);

MASS (ESI, Pos.): 501 (M+H)$^+$;

$^1$H-NMR (DMSO-d$_6$): δ 5.86 (s, 2H), 7.25-7.55 (m, 7H), 7.96 (d, 1H), 8.08-8.15 (m, 1H), 8.66 (s, 1H), 8.74 (s, 2H), 9.65 (s, 1H).

Example 15-180

1-{2-[4-(2-amino-5-chloro-3-pyridinyl)phenoxy]-5-pyrimidinyl}-3-(4-chloro-2-methoxyphenyl)urea Purity (LC-MS/ELSD): 100% (Retention Time: 0.89 minutes);
MASS (ESI, Pos.): 497 (M+H)$^+$;
$^1$H-NMR (DMSO-d$_6$): δ 3.90 (s, 3H), 5.86 (s, 2H), 6.96 (dd, 1H), 7.10 (d, 1H), 7.25-7.31 (m, 2H), 7.42 (d, 1H), 7.48-7.55 (m, 2H), 7.95 (d, 1H), 8.09 (d, 1H), 8.45 (s, 1H), 8.71 (s, 2H), 9.52 (s, 1H).

Example 15-181

1-{2-[4-(2-amino-5-chloro-3-pyridinyl)phenoxy]-5-pyrimidinyl}-3-(4-chloro-2-methylphenyl)urea Purity (LC-MS/ELSD): 100% (Retention Time: 0.87 minutes);
MASS (ESI, Pos.): 481 (M+H)$^+$;
$^1$H-NMR (DMSO-d$_6$): δ 2.23 (s, 3H), 5.86 (s, 2H), 7.18-7.31 (m, 4H), 7.42 (d, 1H), 7.48-7.55 (m, 2H), 7.80 (d, 1H), 7.95 (d, 1H), 8.22 (s, 1H), 8.72 (s, 2H), 9.21 (s, 1H).

Example 15-182

1-{2-[4-(2-amino-5-chloro-3-pyridinyl)phenoxy]-5-pyrimidinyl}-3-(4-chloro-2-fluorophenyl)urea Purity (LC-MS/ELSD): 100% (Retention Time: 0.87 minutes);
MASS (ESI, Pos.): 485 (M+H)$^+$;
$^1$H-NMR (DMSO-d$_6$): δ 5.86 (s, 2H), 7.20-7.55 (m, 7H), 7.95 (d, 1H), 8.09 (t, 1H), 8.73 (s, 2H), 8.56 (s, 1H), 9.22 (s, 1H).

Example 15-183

1-{2-[4-(2-amino-5-chloro-3-pyridinyl)phenoxy]-5-pyrimidinyl}-3-[4-chloro-2-(methylsulfonyl)phenyl]urea Purity (LC-MS/ELSD): 100% (Retention Time: 0.85 minutes);
MASS (ESI, Pos.): 545 (M+H)$^+$;
$^1$H-NMR (DMSO-d$_6$): δ 3.36 (s, 3H), 5.86 (s, 2H), 7.25-7.32 (m, 2H), 7.43 (d, 1H), 7.49-7.56 (m, 2H), 7.75-7.84 (m, 2H), 7.96 (d, 1H), 8.21 (d, 1H), 8.74 (s, 2H), 8.79 (s, 1H), 10.18 (s, 1H).

Example 15-184

1-{2-[4-(2-amino-5-chloro-3-pyridinyl)phenoxy]-5-pyrimidinyl}-3-[4-chloro-3-(methylsulfonyl)phenyl]urea Purity (LC-MS/ELSD): 100% (Retention Time: 0.75 minutes);
MASS (ESI, Pos.): 545 (M+H)$^+$;
$^1$H-NMR (DMSO-d$_6$): δ 3.35 (s, 3H), 5.87 (s, 2H), 7.25-7.32 (m, 2H), 7.43 (d, 1H), 7.49-7.55 (m, 2H), 7.63 (d, 1H), 7.78 (dd, 1H), 7.95-7.96 (m, 1H), 8.27 (d, 1H), 8.73 (s, 2H), 9.00 (s, 1H), 9.56 (s, 1H).

Example 15-185

1-{2-[4-(2-amino-5-chloro-3-pyridinyl)phenoxy]-5-pyrimidinyl}-3-[4-chloro-2-(trifluoromethyl)phenyl]urea Purity (LC-MS/ELSD): 100% (Retention Time: 0.93 minutes);
MASS (ESI, Pos.): 535 (M+H)$^+$;
$^1$H-NMR (DMSO-d$_6$): δ 5.86 (s, 2H), 7.25-7.31 (m, 2H), 7.42-7.45 (m, 1H), 7.49-7.55 (m, 2H), 7.71-7.79 (m, 2H), 7.95-8.01 (m, 2H), 8.38 (s, 1H), 8.74 (s, 2H), 9.57 (s, 1H).

Example 15-186

1-{2-[4-(2-amino-5-chloro-3-pyridinyl)phenoxy]-5-pyrimidinyl}-3-[2-(2,3-dihydro-1H-inden-5-yl)-5-(trifluoromethyl)phenyl]urea

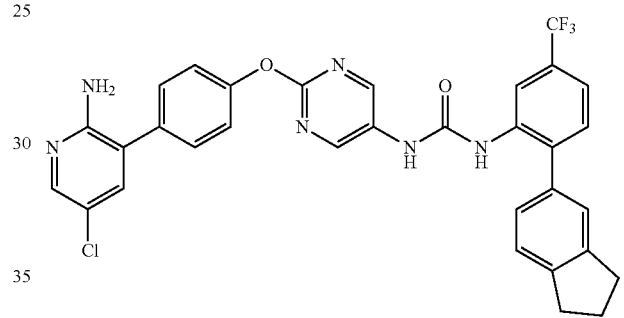

TLC: Rf 0.49 (Hexane:Ethyl Acetate=1:2);
$^1$H-NMR (DMSO-d$_6$): δ 2.00-2.10 (m, 2H), 2.93 (t, 4H), 5.85 (s, 2H), 7.17 (dd, 1H), 7.25-7.27 (m, 3H), 7.37-7.44 (m, 4H), 7.50 (d, 2H), 7.95 (d, 1H), 8.04 (s, 1H), 8.45 (s, 1H), 8.67 (s, 2H), 9.45 (s, 1H).

Example 15-187

1-{2-[4-(2-amino-5-fluoro-3-pyridinyl)phenoxy]-5-pyrimidinyl}-3-[2-(2,3-dihydro-1H-inden-5-yl)-5-(trifluoromethyl)phenyl]urea TLC: Rf 0.44 (Hexane:Ethyl Acetate=1:2);
$^1$H-NMR (DMSO-d$_6$): δ 2.00-2.10 (m, 2H), 2.93 (t, 4H), 5.57 (s, 2H), 7.16 (dd, 1H), 7.25-7.28 (m, 3H), 7.35-7.44 (m, 4H), 7.52 (d, 2H), 7.93 (d, 1H), 8.04 (s, 1H), 8.45 (s, 1H), 8.67 (s, 2H), 9.45 (s, 1H).

Example 15-188

1-{2-[4-(2-amino-5-chloro-3-pyridinyl)phenoxy]-5-pyrimidinyl}-3-[2-(2,3-dihydro-1-benzofuran-5-yl)-5-(trifluoromethyl)phenyl]urea TLC: Rf 0.28 (Hexane:Ethyl Acetate=1:2);
$^1$H-NMR (DMSO-d$_6$): δ 3.25 (t, 2H), 4.60 (t, 2H), 5.85 (s, 2H), 6.91 (d, 1H), 7.14 (dd, 1H), 7.24-7.29 (m, 3H), 7.37-7.42 (m, 3H), 7.50 (d, 2H), 7.95 (d, 1H), 8.03 (s, 1H), 8.44 (s, 1H), 8.67 (s, 2H), 9.45 (s, 1H).

Example 15-189

1-{2-[4-(2-amino-5-fluoro-3-pyridinyl)phenoxy]-5-pyrimidinyl}-3-[2-(2,3-dihydro-1-benzofuran-5-yl)-5-(trifluoromethyl)phenyl]urea TLC: Rf 0.24 (Hexane:Ethyl Acetate=1:2);
$^1$H-NMR (DMSO-$d_6$): δ 3.25 (t, 2H), 4.60 (t, 2H), 5.57 (s, 2H), 6.91 (d, 1H), 7.14 (dd, 1H), 7.25-7.29 (m, 3H), 7.35-7.42 (m, 3H), 7.53 (d, 2H), 7.94 (d, 1H), 8.03 (s, 1H), 8.45 (s, 1H), 8.68 (s, 2H), 9.45 (s, 1H).

Example 15-190

1-{2-[4-(2-amino-5-fluoro-3-pyridinyl)phenoxy]-5-pyrimidinyl}-3-{5-(difluoromethyl)-2-[3-(trifluoromethyl)-1H-pyrazol-1-yl]phenyl}urea TLC: Rf 0.40 (Hexane:Ethyl Acetate=1:2);
$^1$H-NMR (DMSO-$d_6$): δ 5.56 (s, 2H), 7.08 (d, 1H), 7.13 (t, 1H), 7.26 (d, 2H), 7.32-7.45 (m, 2H), 7.51 (d, 2H), 7.60 (d, 1H), 7.92 (d, 1H), 8.28 (s, 1H), 8.41 (s, 1H), 8.45 (s, 1H), 8.65 (s, 2H), 9.42 (s, 1H).

Example 15-191

1-{2-[4-(2-amino-5-fluoro-3-pyridinyl)phenoxy]-5-pyrimidinyl}-3-{4-chloro-2-[3-(trifluoromethyl)-1H-pyrazol-1-yl]phenyl}urea TLC: Rf 0.45 (Hexane:Ethyl Acetate=1:2);
$^1$H-NMR (DMSO-$d_6$): δ 5.56 (s, 2H), 7.06 (d, 1H), 7.25 (d, 2H), 7.36 (dd, 1H), 7.49-7.62 (m, 4H), 7.92 (d, 1H), 8.02 (d, 1H), 8.35 (s, 1H), 8.38-8.42 (m, 1H), 8.64 (s, 2H), 9.36 (s, 1H).

Example 15-192

1-{2-[4-(2-amino-5-fluoro-3-pyridinyl)phenoxy]-5-pyrimidinyl}-3-[2,3-difluoro-4-(trifluoromethyl)phenyl]urea Purity (LC-MS/ELSD): 93% (Retention Time: 0.89 minutes);
MASS (ESI, Pos.): 521 (M+H)$^+$;
$^1$H-NMR (DMSO-$d_6$): δ 5.57 (s, 2H), 7.26-7.33 (m, 2H), 7.38 (dd, 1H), 7.51-7.62 (m, 3H), 7.94 (d, 1H), 8.13-8.22 (m, 1H), 8.75 (s, 2H), 9.36 (s, 2H).

Example 15-193

1-{2-[4-(2-amino-5-chloro-3-pyridinyl)phenoxy]-5-pyrimidinyl}-3-[3-chloro-2-fluoro-5-(trifluoromethyl)phenyl]urea Purity (LC-MS/ELSD): 100% (Retention Time: 1.00 minute);
MASS (ESI, Pos.): 553 (M+H)$^+$.

Example 15-194

1-(2-{4-[2-amino-5-(trifluoromethyl)-3-pyridinyl]phenoxy}-5-pyrimidinyl)-3-[2-(5-methyl-3-pyridinyl)-5-(trifluoromethyl)phenyl]urea Purity (LC-MS/ELSD): 100% (Retention Time: 0.89 minutes);
MASS (ESI, Pos.): 626 (M+H)$^+$;
$^1$H-NMR (DMSO-$d_6$): δ 2.38 (s, 3H), 6.48 (s, 2H), 7.24-8.54 (m, 13H), 8.66 (s, 2H), 9.29 (s, 1H).

Example 15-195

1-(2-{4-[2-amino-5-(trifluoromethyl)-3-pyridinyl]phenoxy}-5-pyrimidinyl)-3-[4-(trifluoromethyl)-2-biphenylyl]urea Purity (LC-MS/ELSD): 100% (Retention Time: 1.09 minutes);
MASS (ESI, Pos.): 611 (M+H)$^+$;
$^1$H-NMR (DMSO-$d_6$): δ 6.48 (s, 2H), 7.25-7.31 (m, 2H), 7.40-7.59 (m, 10H), 8.09 (s, 1H), 8.26-8.30 (m, 1H), 8.40-8.44 (m, 1H), 8.66 (s, 2H), 9.40 (s, 1H).

Example 15-196

1-(2-{4-[2-amino-5-(trifluoromethyl)-3-pyridinyl]phenoxy}-5-pyrimidinyl)-3-[5-phenyl-2-(trifluoromethyl)-4-pyridinyl]urea Purity (LC-MS/ELSD): 100% (Retention Time: 1.02 minutes);
MASS (ESI, Pos.): 612 (M+H)$^+$;
$^1$H-NMR (DMSO-$d_6$): δ 6.48 (s, 2H), 7.26-7.32 (m, 2H), 7.49-7.66 (m, 8H), 8.27-8.30 (m, 1H), 8.42-8.46 (m, 2H), 8.69 (s, 2H), 8.75 (s, 1H), 9.74 (s, 1H).

Example 15-197

1-(2-{4-[2-amino-5-(trifluoromethyl)-3-pyridinyl]phenoxy}-5-pyrimidinyl)-3-[2-phenyl-5-(trifluoromethyl)-3-pyridinyl]urea Purity (LC-MS/ELSD): 100% (Retention Time: 1.01 minutes);
MASS (ESI, Pos.): 612 (M+H)$^+$;
$^1$H-NMR (DMSO-$d_6$): δ 6.48 (s, 2H), 7.25-7.32 (m, 2H), 7.49-7.70 (m, 8H), 8.26-8.30 (m, 1H), 8.43 (s, 1H), 8.68 (s, 2H), 8.74-8.75 (m, 1H), 8.76-8.78 (m, 1H), 9.47 (s, 1H).

Example 15-198

1-(2-{4-[2-amino-5-(trifluoromethyl)-3-pyridinyl]phenoxy}-5-pyrimidinyl)-3-[3',4'-dimethyl-4-(trifluoromethyl)-2-biphenylyl]urea Purity (LC-MS/ELSD): 100% (Retention Time: 1.17 minutes);
MASS (ESI, Pos.): 639 (M+H)$^+$;
$^1$H-NMR (DMSO-$d_6$): δ 2.29 (s, 6H), 6.48 (s, 2H), 7.12-7.58 (m, 10H), 8.01 (s, 1H), 8.26-8.30 (m, 1H), 8.45-8.48 (m, 1H), 8.67 (s, 2H), 9.46 (s, 1H).

Example 15-199

1-(2-{4-[2-amino-5-(trifluoromethyl)-3-pyridinyl]phenoxy}-5-pyrimidinyl)-3-[2-(6-methyl-3-pyridinyl)-5-(trifluoromethyl)phenyl]urea Purity (LC-MS/ELSD): 98% (Retention Time: 0.84 minutes);
MASS (ESI, Pos.): 626 (M+H)$^+$;
$^1$H-NMR (DMSO-$d_6$): δ 2.55 (s, 3H), 6.48 (s, 2H), 7.25-7.32 (m, 2H), 7.39-7.59 (m, 6H), 7.75-7.80 (m, 1H), 8.19-8.23 (m, 1H), 8.26-8.30 (m, 1H), 8.41-8.44 (m, 1H), 8.49-8.53 (m, 1H), 8.67 (s, 2H), 9.28 (s, 1H).

Example 15-200

1-(2-{4-[2-amino-5-(trifluoromethyl)-3-pyridinyl]phenoxy}-5-pyrimidinyl)-3-[3-(trifluoromethyl)phenyl]urea Purity (LC-MS/ELSD): 100% (Retention Time: 0.96 minutes);
MASS (ESI, Pos.): 535 (M+H)$^+$;
$^1$H-NMR (DMSO-d$_6$): δ 6.49 (s, 2H), 7.26-7.36 (m, 3H), 7.48-7.66 (m, 5H), 7.96-8.00 (m, 1H), 8.27-8.30 (m, 1H), 8.73 (s, 2H), 8.99 (s, 1H), 9.33 (s, 1H).

Example 15-201

1-(2-{4-[2-amino-5-(trifluoromethyl)-3-pyridinyl]phenoxy}-5-pyrimidinyl)-3-[2-fluoro-4-(trifluoromethyl)phenyl]urea Purity (LC-MS/ELSD): 100% (Retention Time: 1.00 minute);
MASS (ESI, Pos.): 553 (M+H)$^+$;
$^1$H-NMR (DMSO-d$_6$): δ 6.49 (s, 2H), 7.26-7.34 (m, 2H), 7.49-7.59 (m, 4H), 7.72 (dd, 1H), 8.26-8.31 (m, 1H), 8.37 (t, 1H), 8.75 (s, 2H), 9.14 (s, 1H), 9.34 (s, 1H).

Example 15-202

1-(2-{4-[2-amino-5-(trifluoromethyl)-3-pyridinyl]phenoxy}-5-pyrimidinyl)-3-[2-fluoro-4-(trifluoromethyl)phenyl]urea TLC: Rf 0.28 (Ethyl Acetate);
$^1$H-NMR (DMSO-d$_6$): δ 1.20 (t, 3H), 2.68 (q, 2H), 5.57 (s, 2H), 7.25-7.46 (m, 5H), 7.51-7.58 (m, 2H), 7.94 (d, 1H), 8.25 (s, 1H), 8.38 (s, 1H), 8.75 (s, 2H), 9.34 (s, 1H).

Example 15-203

1-{2-[4-(2-amino-5-chloro-3-pyridinyl)phenoxy]-5-pyrimidinyl}-3-[2-(6-ethyl-3-pyridinyl)-5-(trifluoromethyl)phenyl]urea TLC: Rf 0.34 (Methylene Chloride:Ethyl Acetate:Methanol=8:4:1);
$^1$H-NMR (DMSO-d$_6$): δ 1.29 (t, 3H), 2.84 (q, 2H), 5.86 (brs, 2H), 7.26 (d, 2H), 7.39-7.54 (m, 6H), 7.80 (dd, 1H), 7.95 (d, 1H), 8.24 (s, 1H), 8.40 (s, 1H), 8.54 (d, 1H), 8.67 (s, 2H), 9.26 (s, 1H).

Example 15-204

1-{2-[4-(2-amino-5-fluoro-3-pyridinyl)phenoxy]-5-pyrimidinyl}-3-[2-(6-ethyl-3-pyridinyl)-5-(trifluoromethyl)phenyl]urea TLC: Rf 0.34 (Methylene Chloride:Ethyl Acetate:Methanol=8:4:1);
$^1$H-NMR (DMSO-d$_6$): δ 1.29 (t, 3H), 2.84 (q, 2H), 5.58 (brs, 2H), 7.26 (d, 2H), 7.37 (dd, 1H), 7.41-7.55 (m, 5H), 7.80 (dd, 1H), 7.94 (d, 1H), 8.24 (s, 1H), 8.40 (s, 1H), 8.54 (d, 1H), 8.67 (s, 2H), 9.26 (s, 1H).

Example 15-205

1-{2-[4-(2-amino-5-chloro-3-pyridinyl)phenoxy]-5-pyrimidinyl}-3-[2-(5-ethyl-3-pyridinyl)-5-(trifluoromethyl)phenyl]urea TLC: Rf 0.33 (Methylene Chloride:Ethyl Acetate:Methanol=8:4:1);
$^1$H-NMR (DMSO-d$_6$): δ 1.23 (t, 3H), 2.70 (q, 2H), 5.86 (brs, 2H), 7.26 (d, 2H), 7.42 (d, 1H), 7.45-7.55 (m, 4H), 7.73 (s, 1H), 7.95 (dd, 1H), 8.23 (s, 1H), 8.38 (s, 1H), 8.47 (d, 1H), 8.54 (d, 1H), 8.65 (s, 2H), 9.27 (s, 1H).

Example 15-206

1-{2-[4-(2-amino-5-fluoro-3-pyridinyl)phenoxy]-5-pyrimidinyl}-3-[2-(5-ethyl-3-pyridinyl)-5-(trifluoromethyl)phenyl]urea TLC: Rf 0.33 (Methylene Chloride:Ethyl Acetate:Methanol=8:4:1);
$^1$H-NMR (DMSO-d$_6$): δ 1.23 (t, 3H), 2.70 (q, 2H), 5.57 (brs, 2H), 7.26 (d, 2H), 7.37 (dd, 1H), 7.47-7.56 (m, 4H), 7.73 (t, 1H), 7.93 (d, 1H), 8.23 (s, 1H), 8.38 (s, 1H), 8.47 (d, 1H), 8.54 (d, 1H), 8.65 (s, 2H), 9.27 (s, 1H).

Example 15-207

1-{2-[4-(2-amino-5-fluoro-3-pyridinyl)phenoxy]-5-pyrimidinyl}-3-[2-isopropyl-5-(trifluoromethyl)phenyl]urea

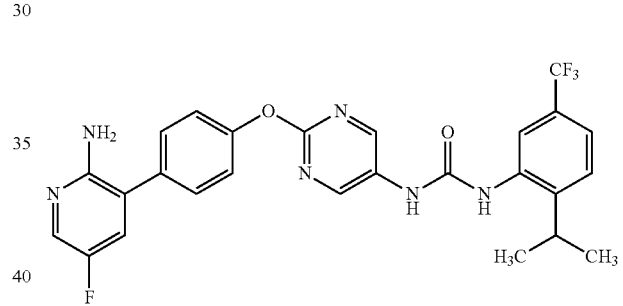

TLC: Rf 0.38 (Ethyl Acetate);
$^1$H-NMR (DMSO-d$_6$): δ 1.22 (d, 6H), 3.14-3.27 (m, 1H), 5.57 (s, 2H), 7.26-7.33 (m, 2H), 7.36-7.57 (m, 5H), 7.94 (d, 1H), 8.12-8.15 (m, 1H), 8.43 (s, 1H), 8.74 (s, 2H), 9.28 (s, 1H).

Example 15-208

1-{2-[4-(2-amino-5-fluoro-3-pyridinyl)phenoxy]-5-pyrimidinyl}-3-[2-(methylsulfonyl)-4-(trifluoromethyl)phenyl]urea TLC: Rf 0.62 (Ethyl Acetate);
$^1$H-NMR (DMSO-d$_6$): δ 3.42 (s, 3H), 5.58 (s, 2H), 7.27-7.34 (m, 2H), 7.38 (dd, 1H), 7.52-7.60 (m, 2H), 7.94 (d, 1H), 8.05-8.12 (m, 2H), 8.46-8.56 (m, 1H), 8.76 (s, 2H), 9.04 (s, 1H), 10.36 (s, 1H).

Example 15-209

1-{2-[4-(2-amino-5-chloro-3-pyridinyl)phenoxy]-5-pyrimidinyl}-3-[2-(4-cyano-1H-pyrazol-1-yl)-5-(trifluoromethyl)phenyl]urea TLC: Rf 0.20 (Hexane:Ethyl Acetate=1:2);
$^1$H-NMR (DMSO-d$_6$): δ 5.85 (s, 2H), 7.26 (d, 2H), 7.41 (dd, 1H), 7.50 (d, 2H), 7.58 (d, 1H), 7.73 (d, 1H), 7.94 (dd, 1H), 8.52 (s, 1H), 8.54 (s, 1H), 8.69 (s, 2H), 8.80 (s, 1H), 9.13 (s, 1H), 9.63 (s, 1H).

Example 15-210

1-{2-[4-(2-amino-5-fluoro-3-pyridinyl)phenoxy]-5-pyrimidinyl}-3-[2-(4-cyano-1H-pyrazol-1-yl)-5-(trifluoromethyl)phenyl]urea TLC: Rf 0.16 (Hexane:Ethyl Acetate=1:2);
$^1$H-NMR (DMSO-d$_6$): δ 5.56 (s, 2H), 7.26 (d, 2H), 7.37 (dd, 1H), 7.52 (d, 2H), 7.58 (d, 1H), 7.73 (d, 1H), 7.92 (d, 1H), 8.52 (s, 1H), 8.54 (s, 1H), 8.68 (s, 2H), 8.80 (s, 1H), 9.13 (s, 1H), 9.63 (s, 1H).

Example 15-211

1-{2-[4-(2-amino-5-chloro-3-pyridinyl)phenoxy]-5-pyrimidinyl}-3-phenylurea

Purity (LC-MS/ELSD): 100% (Retention Time: 0.77 minutes);
MASS (ESI, Pos.): 433 (M+H)$^+$;
$^1$H-NMR (DMSO-d$_6$): δ 5.86 (s, 2H), 6.98 (t, 1H), 7.23-7.32 (m, 4H), 7.41-7.55 (m, 5H), 7.95 (dd, 1H), 8.72 (s, 2H), 8.85 (s, 1H), 8.93 (s, 1H).

Example 15-212

1-{2-[4-(2-amino-5-chloro-3-pyridinyl)phenoxy]-5-pyrimidinyl}-3-[5-(trifluoromethyl)-2-thienyl]urea

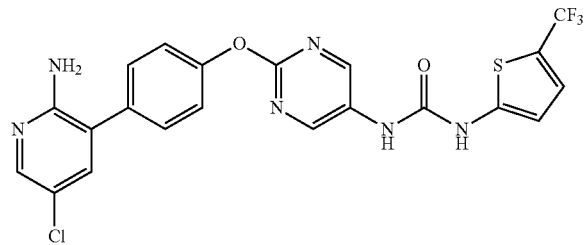 [SMILES: Nc1ncc(Cl)cc1-c1ccc(Oc2ncc(NC(=O)Nc3ccc(C(F)(F)F)s3)cn2)cc1]

Purity (LC-MS/ELSD): 100% (Retention Time: 0.90 minutes);
MASS (ESI, Pos.): 507 (M+H)$^+$;
$^1$H-NMR (DMSO-d$_6$): δ 5.86 (s, 2H), 6.62-6.66 (m, 1H), 7.25-7.32 (m, 2H), 7.38-7.45 (m, 2H), 7.49-7.55 (m, 2H), 7.95 (d, 1H), 8.72 (s, 2H), 9.23 (s, 1H), 10.60 (s, 1H).

Example 15-213

1-{2-[4-(2-amino-5-chloro-3-pyridinyl)phenoxy]-5-pyrimidinyl}-3-[2-(4-morpholinyl)-3-pyridinyl]urea Purity (LC-MS/ELSD): 100% (Retention Time: 0.71 minutes);
MASS (ESI, Pos.): 519 (M+H)$^+$;
$^1$H-NMR (DMSO-d$_6$): δ 2.96-3.03 (m, 4H), 3.80-3.86 (m, 4H), 5.86 (s, 2H), 7.08 (dd, 1H), 7.25-7.32 (m, 2H), 7.43 (d, 1H), 7.48-7.55 (m, 2H), 7.95-8.02 (m, 2H), 8.14 (s, 1H), 8.28 (dd, 1H), 8.74 (s, 2H), 9.71 (s, 1H).

Example 15-214

1-{2-[4-(2-amino-5-chloro-3-pyridinyl)phenoxy]-5-pyrimidinyl}-3-(2,3-dihydro-1-benzofuran-7-yl)urea Purity (LC-MS/ELSD): 100% (Retention Time: 0.80 minutes);
MASS (ESI, Pos.): 475 (M+H)$^+$;
$^1$H-NMR (DMSO-d$_6$): δ 3.22 (t, 2H), 4.60 (t, 2H), 5.86 (s, 2H), 6.76 (t, 1H), 6.89 (d, 1H), 7.24-7.30 (m, 2H), 7.42 (d, 1H), 7.49-7.55 (m, 2H), 7.77 (d, 1H), 7.95-7.98 (m, 1H), 8.35 (s, 1H), 8.71 (s, 2H), 9.24 (s, 1H).

Example 15-215

1-{2-[4-(2-amino-5-chloro-3-pyridinyl)phenoxy]-5-pyrimidinyl}-3-(2,3-dihydro-1-benzofuran-5-yl)urea Purity (LC-MS/ELSD): 100% (Retention Time: 0.75 minutes);
MASS (ESI, Pos.): 475 (M+H)$^+$;
$^1$H-NMR (DMSO-d$_6$): δ 3.14 (t, 2H), 4.47 (t, 2H), 5.86 (s, 2H), 6.67 (d, 1H), 7.06 (dd, 1H), 7.24-7.29 (m, 2H), 7.34-7.38 (m, 1H), 7.42-7.44 (m, 1H), 7.48-7.55 (m, 2H), 7.95-7.98 (m, 1H), 8.65-8.97 (m, 4H).

Example 15-216

2-[({2-[4-(2-amino-5-fluoro-3-pyridinyl)phenoxy]-5-pyrimidinyl}carbamoyl)amino]-N,N-dimethyl-4-(trifluoromethyl)benzenesulfonamide

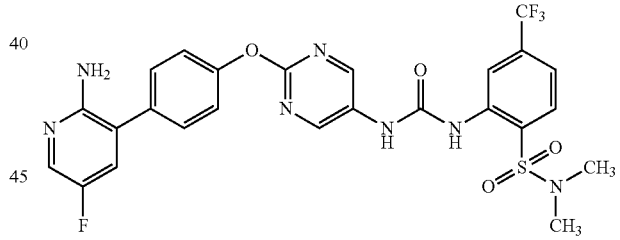

TLC: Rf 0.57 (Hexane:Ethyl Acetate=1:4);
$^1$H-NMR (DMSO-d$_6$): δ 2.76 (s, 6H), 5.57 (s, 2H), 7.26-7.32 (m, 2H), 7.38 (dd, 1H), 7.51-7.64 (m, 3H), 7.92-7.98 (m, 2H), 8.61 (s, 1H), 8.74 (s, 2H), 8.99 (s, 1H), 10.31 (s, 1H).

Example 15-217

1-{2-[4-(2-amino-5-chloro-3-pyridinyl)phenoxy]-5-pyrimidinyl}-3-[2-(methylsulfonyl)phenyl]urea Purity (LC-MS/ELSD): 99% (Retention Time: 0.76 minutes);
MASS (ESI, Pos.): 511 (M+H)$^+$;
$^1$H-NMR (DMSO-d$_6$): δ 3.28 (s, 3H), 5.87 (s, 2H), 7.26-7.34 (m, 3H), 7.42-7.45 (m, 1H), 7.49-7.55 (m, 2H), 7.66-7.73 (m, 1H), 7.85 (dd, 1H), 7.95-7.98 (m, 1H), 8.15 (d, 1H), 8.75 (s, 2H), 8.77 (s, 1H), 10.13 (s, 1H).

Example 15-218

1-{2-[4-(2-amino-5-fluoro-3-pyridinyl)phenoxy]-5-pyrimidinyl}-3-[2-(methylsulfonyl)phenyl] urea Purity (LC-MS/ELSD): 100% (Retention Time: 0.69 minutes);
MASS (ESI, Pos.): 495 (M+H)$^+$;
$^1$H-NMR (DMSO-d$_6$): δ 3.28 (s, 3H), 5.57 (s, 2H), 7.25-7.34 (m, 3H), 7.38 (dd, 1H), 7.51-7.57 (m, 2H), 7.69 (td, 1H), 7.85 (dd, 1H), 7.94 (d, 1H), 8.15 (d, 1H), 8.75 (s, 2H), 8.77 (s, 1H), 10.13 (s, 1H).

Example 15-219

1-(2-{4-[2-amino-5-(trifluoromethyl)-3-pyridinyl]phenoxy}-5-pyrimidinyl)-3-[2-(methylsulfonyl)phenyl]urea Purity (LC-MS/ELSD): 100% (Retention Time: 0.85 minutes);
MASS (ESI, Pos.): 545 (M+H)$^+$;
$^1$H-NMR (DMSO-d$_6$): δ 3.28 (s, 3H), 6.49 (s, 2H), 7.26-7.33 (m, 3H), 7.50-7.59 (m, 3H), 7.69 (td, 1H), 7.85 (dd, 1H), 8.15 (d, 1H), 8.26-8.30 (m, 1H), 8.75-8.81 (m, 3H), 10.13 (s, 1H).

Example 15-220

1-{2-[4-(2-amino-5-fluoro-3-pyridinyl)phenoxy]-5-pyrimidinyl}-3-(5-chloro-2-methylphenyl)urea Purity (LC-MS/ELSD): 100% (Retention Time: 0.82 minutes);
MASS (ESI, Pos.): 465 (M+H)$^+$;
$^1$H-NMR (DMSO-d$_6$): δ 2.22 (s, 3H), 5.57 (s, 2H), 7.00 (dd, 1H), 7.20 (d, 1H), 7.28 (d, 2H), 7.38 (dd, 1H), 7.52 (d, 2H), 7.93 (d, 1H), 7.97 (d, 1H), 8.26 (s, 1H), 8.74 (s, 2H), 9.30 (s, 1H).

Example 15-221

1-(2-{4-[2-amino-5-(trifluoromethyl)-3-pyridinyl]phenoxy}-5-pyrimidinyl)-3-[3'-(hydroxymethyl)-4-(trifluoromethyl)-2-biphenylyl]urea Purity (LC-MS/ELSD): 99% (Retention Time: 1.01 minutes);
MASS (ESI, Pos.): 641 (M+H)$^+$;
$^1$H-NMR (DMSO-d$_6$): δ 4.58 (d, 2H), 5.28 (t, 1H), 6.48 (s, 2H), 7.22-7.58 (m, 11H), 8.06 (s, 1H), 8.27 (s, 1H), 8.42 (s, 1H), 8.66 (s, 2H), 9.42 (s, 1H).

Example 15-222

1-(2-{4-[2-amino-5-(trifluoromethyl)-3-pyridinyl]phenoxy}-5-pyrimidinyl)-3-{5-chloro-2-[3-(trifluoromethyl)-1H-pyrazol-1-yl]phenyl}urea Purity (LC-MS/ELSD): 100% (Retention Time: 1.06 minutes);
MASS (ESI, Pos.): 635 (M+H)$^+$;
$^1$H-NMR (DMSO-d$_6$): δ 6.48 (s, 2H), 7.08 (d, 1H), 7.22-7.35 (m, 3H), 7.43-7.59 (m, 4H), 8.18 (d, 1H), 8.23-8.29 (m, 1H), 8.36-8.42 (m, 2H), 8.66 (s, 2H), 9.44 (s, 1H).

Example 15-223

2-{[(2-{4-[2-amino-5-(trifluoromethyl)-3-pyridinyl]phenoxy}-5-pyrimidinyl)carbamoyl]amino}-N-methyl-4-(trifluoromethyl)benzenesulfonamide TLC: Rf 0.36 (Hexane:Ethyl Acetate=1:4);
$^1$H-NMR (DMSO-d$_6$): δ 3.27-3.38 (m, 3H), 6.49 (s, 2H), 7.27-7.34 (m, 2H), 7.49-7.63 (m, 4H), 7.93-7.99 (m, 1H), 8.02-8.13 (m, 1H), 8.28 (s, 1H), 8.56 (s, 1H), 8.75 (s, 2H), 8.90 (s, 1H), 10.23 (s, 1H).

Example 15-224

2-[({2-[4-(2-amino-5-chloro-3-pyridinyl)phenoxy]-5-pyrimidinyl}carbamoyl)amino]-N,N-dimethyl-4-(trifluoromethyl)benzenesulfonamide Purity (LC-MS/ELSD): 100% (Retention Time: 0.98 minutes);
MASS (ESI, Pos.): 608 (M+H)$^+$;
$^1$H-NMR (DMSO-d$_6$): δ 2.76 (s, 6H), 5.87 (s, 2H), 7.28 (d, 2H), 7.43 (d, 1H), 7.52 (d, 2H), 7.60 (d, 1H), 7.92-7.98 (m, 2H), 8.61 (s, 1H), 8.75 (s, 2H), 8.99 (s, 1H), 10.31 (s, 1H).

Example 15-225

1-(2-{4-[2-amino-5-(trifluoromethyl)-3-pyridinyl]phenoxy}-5-pyrimidinyl)-3-[5-methyl-2-(methylsulfonyl)phenyl]urea Purity (LC-MS/ELSD): 100% (Retention Time: 0.92 minutes);
MASS (ESI, Pos.): 559 (M+H)$^+$;
$^1$H-NMR (DMSO-d$_6$): δ 2.37 (s, 3H), 3.24 (s, 3H), 6.49 (s, 2H), 7.12 (d, 1H), 7.28 (d, 2H), 7.52 (d, 2H), 7.55 (d, 1H), 7.73 (d, 1H), 7.99 (s, 1H), 8.26-8.29 (m, 1H), 8.72 (s, 1H), 8.75 (s, 2H), 10.12 (s, 1H).

Example 15-226

1-(2-{4-[2-amino-5-(trifluoromethyl)-3-pyridinyl]phenoxy}-5-pyrimidinyl)-3-[5-chloro-2-(methylsulfonyl)phenyl]urea Purity (LC-MS/ELSD): 100% (Retention Time: 0.97 minutes);
MASS (ESI, Pos.): 579 (M+H)$^+$.

Example 15-227

1-{2-[4-(2-amino-5-chloro-3-pyridinyl)phenoxy]-5-pyrimidinyl}-3-[5-fluoro-2-(methylsulfonyl)phenyl] urea Purity (LC-MS/ELSD): 100% (Retention Time: 0.85 minutes);
MASS (ESI, Pos.): 529 (M+H)$^+$;
$^1$H-NMR (DMSO-d$_6$): δ 3.15 (d, 3H), 5.87 (s, 2H), 7.10-7.19 (m, 1H), 7.28 (d, 2H), 7.43 (d, 1H), 7.52 (d, 2H), 7.92 (dd, 1H), 7.96 (d, 1H), 8.11 (dd, 1H), 8.75 (s, 2H), 8.95 (s, 1H), 10.29 (s, 1H).

Example 15-228

1-(2-{4-[2-amino-5-(trifluoromethyl)-3-pyridinyl]phenoxy}-5-pyrimidinyl)-3-[2-(methylthio)-5-(trifluoromethyl)phenyl]urea TLC: Rf 0.30 (Hexane:Ethyl Acetate=1:2);
$^1$H-NMR (DMSO-$d_6$): δ 2.53 (s, 3H), 6.47 (s, 2H), 7.27 (d, 2H), 7.40 (dd, 1H), 7.48-7.57 (m, 4H), 8.18 (s, 1H), 8.24-8.28 (m, 1H), 8.44 (s, 1H), 8.73 (s, 2H), 9.64 (s, 1H).

Example 15-229

1-{2-[4-(2-amino-5-chloro-3-pyridinyl)phenoxy]-5-pyrimidinyl}-3-[4-fluoro-3-(trifluoromethyl)phenyl]urea Purity (LC-MS/ELSD): 100% (Retention Time: 0.94 minutes);
MASS (ESI, Pos.): 519 (M+H)$^+$;
$^1$H-NMR (DMSO-$d_6$): δ 5.86 (s, 2H), 7.27 (d, 2H), 7.40-7.57 (m, 4H), 7.64-7.72 (m, 1H), 7.94-7.99 (m, 2H), 8.73 (s, 2H), 9.03 (s, 1H), 9.33 (s, 1H).

Example 15-230

1-(2-{4-[2-amino-5-(trifluoromethyl)-3-pyridinyl]phenoxy}-5-pyrimidinyl)-3-[3'-(1-hydroxyethyl)-4-(trifluoromethyl)-2-biphenylyl]urea Purity (LC-MS/ELSD): 100% (Retention Time: 1.05 minutes);
MASS (ESI, Pos.): 655 (M+H)$^+$;
$^1$H-NMR (DMSO-$d_6$): δ 1.36 (d, 3H), 4.79 (quint, 1H), 5.20 (d, 1H), 6.48 (s, 2H), 7.27 (d, 2H), 7.27-7.35 (m, 1H), 7.39-7.58 (m, 8H), 8.09 (s, 1H), 8.27 (d, 1H), 8.37 (s, 1H), 8.66 (s, 2H), 9.40 (s, 1H).

Example 15-231

1-(2-{4-[2-amino-5-(trifluoromethyl)-3-pyridinyl]phenoxy}-5-pyrimidinyl)-3-[5-chloro-2-(methylthio)phenyl]urea TLC: Rf 0.55 (Ethyl Acetate);
$^1$H-NMR (DMSO-$d_6$): δ 2.42 (s, 3H), 6.48 (s, 2H), 7.08-7.14 (m, 1H), 7.27 (d, 2H), 7.43 (d, 1H), 7.51 (d, 2H), 7.55 (d, 1H), 8.06 (d, 1H), 8.25-8.28 (m, 1H), 8.48 (s, 1H), 8.73 (s, 2H), 9.76 (s, 1H).

Example 15-232

1-{2-[4-(2-amino-5-fluoro-3-pyridinyl)phenoxy]-5-pyrimidinyl}-3-[5-chloro-2-(methylthio)phenyl]urea TLC: Rf 0.42 (Ethyl Acetate);
$^1$H-NMR (DMSO-$d_6$): δ 2.42 (s, 3H), 5.57 (s, 2H), 7.10 (dd, 1H), 7.27 (d, 2H), 7.37 (dd, 1H), 7.43 (d, 1H), 7.52 (d, 2H), 7.93 (d, 1H), 8.06 (d, 1H), 8.48 (s, 1H), 8.73 (s, 2H), 9.76 (s, 1H).

Example 15-233

1-{2-[4-(2-amino-5-fluoro-3-pyridinyl)phenoxy]-5-pyrimidinyl}-3-[5-chloro-2-(methylsulfinyl)phenyl]urea TLC: Rf 0.61 (Ethyl Acetate:Methanol=9:1);
$^1$H-NMR (DMSO-$d_6$): δ 2.85 (s, 3H), 6.48 (s, 2H), 7.27 (d, 2H), 7.32-7.41 (m, 3H), 7.53 (d, 2H), 7.67 (d, 1H), 7.93 (d, 1H), 8.00 (d, 1H), 8.73 (s, 2H), 9.23 (s, 1H), 9.69 (s, 1H).

Example 15-234

1-(2-{4-[2-amino-5-(trifluoromethyl)-3-pyridinyl]phenoxy}-5-pyrimidinyl)-3-[2-(1-methyl-1H-pyrazol-5-yl)-5-(trifluoromethyl)phenyl]urea Purity (LC-MS/ELSD): 100% (Retention Time: 1.02 minutes);
MASS (ESI, Pos.): 615 (M+H)$^+$;
$^1$H-NMR (DMSO-$d_6$): δ 3.65 (s, 3H), 6.48 (s, 2H), 7.27 (d, 2H), 7.46-7.61 (m, 6H), 7.62 (d, 1H), 8.10 (s, 1H), 8.27 (d, 1H), 8.56 (s, 1H), 8.68 (s, 2H), 9.50 (s, 1H).

Example 15-235

2-[({2-[4-(2-amino-5-chloro-3-pyridinyl)phenoxy]-5-pyrimidinyl}carbamoyl)amino]-N-ethyl-N-methyl-4-(trifluoromethyl)benzenesulfonamide TLC: Rf 0.65 (Ethyl Acetate);
$^1$H-NMR (DMSO-$d_6$): δ 1.04 (t, 3H), 2.80 (s, 3H), 3.20 (q, 2H), 5.85 (s, 2H), 7.26-7.32 (m, 2H), 7.43 (d, 1H), 7.50-7.55 (m, 2H), 7.57-7.62 (m, 1H), 7.94-8.01 (m, 2H), 8.54-8.58 (m, 1H), 8.75 (s, 2H), 8.92 (s, 1H), 10.30 (s, 1H).

Example 15-236

1-{2-[4-(2-amino-5-chloro-3-pyridinyl)phenoxy]-5-pyrimidinyl}-3-(tetrahydro-2H-pyran-4-yl)urea Purity (LC-MS/ELSD): 100% (Retention Time: 0.65 minutes);
MASS (ESI, Pos.): 441 (M+H)$^+$;
$^1$H-NMR (DMSO-$d_6$): δ 1.32-1.50 (m, 2H), 1.71-1.83 (m, 2H), 3.32-3.42 (m, 2H), 3.60-3.89 (m, 3H), 5.85 (s, 2H), 6.48 (d, 1H), 7.22-7.28 (m, 2H), 7.42 (d, 1H), 7.47-7.54 (m, 2H), 7.95 (d, 1H), 8.54 (s, 1H), 8.65 (s, 2H).

Example 15-237: rel-1-{2-[4-(2-amino-5-chloro-3-pyridinyl)phenoxy]-5-pyrimidinyl}-3-[(1R,2S,5R)-2-isopropyl-5-methylcyclohexyl]urea

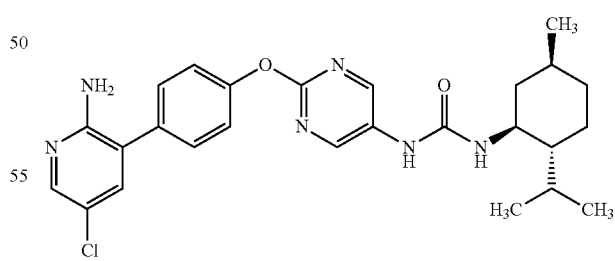

Purity (LC-MS/ELSD): 100% (Retention Time: 1.01 minutes);
MASS (ESI, Pos.): 495 (M+H)$^+$;
$^1$H-NMR (DMSO-$d_6$): δ 0.70-1.15 (m, 12H), 1.32-2.04 (m, 6H), 3.31-3.50 (m, 1H), 5.85 (s, 2H), 6.21 (d, 1H), 7.21-7.28 (m, 2H), 7.42 (d, 1H), 7.47-7.54 (m, 2H), 7.95 (d, 1H), 8.48 (s, 1H), 8.65-8.69 (m, 2H).

Example 15-238

1-{2-[4-(2-amino-5-chloro-3-pyridinyl)phenoxy]-5-pyrimidinyl}-3-(2-hydroxycyclohexyl)urea Purity (LC-MS/ELSD): 100% (Retention Time: 0.67 minutes);
MASS (ESI, Pos.): 455 (M+H)$^+$;
$^1$H-NMR (DMSO-d$_6$): δ 1.00-1.35 (m, 4H), 1.45-1.70 (m, 2H), 1.78-1.97 (m, 2H), 3.15-3.38 (m, 2H), 4.68 (d, 1H), 5.85 (s, 2H), 6.28 (d, 1H), 7.22-7.28 (m, 2H), 7.41 (d, 1H), 7.47-7.54 (m, 2H), 7.94-7.98 (m, 1H), 8.62-8.69 (m, 3H).

Example 15-239

1--{2-[4-(2-amino-5-chloro-3-pyridinyl)phenoxy]-5-pyrimidinyl}-3-(2-hydroxycyclohexyl)urea Purity (LC-MS/ELSD): 100% (Retention Time: 0.65 minutes);
MASS (ESI, Pos.): 455 (M+H)$^+$.

Example 15-240

2-[({2-[4-(2-amino-5-chloro-3-pyridinyl)phenoxy]-5-pyrimidinyl}carbamoyl)amino]-N,N-diethyl-4-(trifluoromethyl)benzenesulfonamide TLC: Rf 0.45 (Chloroform:Methanol=19:1);
$^1$H-NMR (DMSO-d$_6$): δ 1.03 (s, 6H), 3.30 (q, 4H), 5.87 (s, 2H), 7.25-7.31 (m, 2H), 7.43 (d, 1H), 7.49-7.56 (m, 2H), 7.58 (dd, 1H), 7.96 (d, 1H), 8.00 (d, 1H), 8.49 (d, 1H), 8.75 (s, 2H), 8.84 (s, 1H), 10.30 (s, 1H).

Example 15-241

1-{2-[4-(2-amino-5-chloro-3-pyridinyl)phenoxy]-5-pyrimidinyl}-3-[5-chloro-2-(4-cyano-1H-pyrazol-1-yl)phenyl]urea TLC: Rf 0.40 (Hexane:Ethyl Acetate=1:2);
$^1$H-NMR (DMSO-d$_6$): δ 5.85 (s, 2H), 7.23-7.32 (m, 3H), 7.42 (d, 1H), 7.47-7.54 (m, 3H), 7.95 (d, 1H), 8.24 (d, 1H), 8.48 (s, 1H), 8.56 (s, 1H), 8.68 (s, 2H), 9.04 (s, 1H), 9.56 (s, 1H).

Example 15-242

2-[({2-[4-(2-amino-5-chloro-3-pyridinyl)phenoxy]-5-pyrimidinyl}carbamoyl)amino]-N-methylbenzenesulfonamide Purity (LC-MS/ELSD): 100% (Retention Time: 0.80 minutes);
MASS (ESI, Pos.): 526 (M+H)$^+$;
$^1$H-NMR (DMSO-d$_6$): δ 2.46 (s, 3H), 6.04 (brs, 2H), 7.19-7.33 (m, 3H), 7.47-7.65 (m, 4H), 7.72-7.80 (m, 2H), 7.98 (d, 1H), 8.12 (d, 1H), 8.71-8.79 (m, 3H), 10.06 (s, 1H).

Example 15-243

2-[({2-[4-(2-amino-5-chloro-3-pyridinyl)phenoxy]-5-pyrimidinyl}carbamoyl)amino]-N-propyl-4-(trifluoromethyl)benzenesulfonamide Purity (LC-MS/ELSD): 100% (Retention Time: 1.01 minutes);
MASS (ESI, Pos.): 622 (M+H)$^+$;
$^1$H-NMR (DMSO-d$_6$): δ 0.77 (t, 3H), 1.32-1.47 (m, 2H), 2.77-2.88 (m, 2H), 6.15 (brs, 2H), 7.27-7.35 (m, 2H), 7.50-7.62 (m, 4H), 7.96-8.04 (m, 2H), 8.17-8.25 (m, 1H), 8.54 (s, 1H), 8.76 (s, 2H), 8.89 (s, 1H), 10.22 (s, 1H).

Example 15-244

2-[({2-[4-(2-amino-5-chloro-3-pyridinyl)phenoxy]-5-pyrimidinyl}carbamoyl)amino]-N,N-dimethylbenzenesulfonamide Purity (LC-MS/ELSD): 100% (Retention Time: 0.85 minutes);
MASS (ESI, Pos.): 540 (M+H)$^+$;
$^1$H-NMR (DMSO-d$_6$): δ 2.69 (s, 6H), 5.86 (s, 2H), 7.25-7.32 (m, 3H), 7.43 (d, 1H), 7.49-7.56 (m, 2H), 7.62-7.78 (m, 2H), 7.96 (d, 1H), 8.14 (d, 1H), 8.74 (s, 2H), 8.80 (s, 1H), 10.14 (s, 1H).

Example 15-245

2-[({2-[4-(2-amino-5-chloro-3-pyridinyl)phenoxy]-5-pyrimidinyl}carbamoyl)amino]-N-(2-hydroxypropyl)-N-methyl-4-(trifluoromethyl)benzenesulfonamide Purity (LC-MS/ELSD): 100% (Retention Time: 0.97 minutes);
MASS (ESI, Pos.): 652 (M+H)$^+$.

Example 15-246

2-{[(2-{4-[2-amino-5-(trifluoromethyl)-3-pyridinyl]phenoxy}-5-pyrimidinyl)carbamoyl]amino}-N-ethyl-N-methyl-4-(trifluoromethyl)benzenesulfonamide Purity (LC-MS/ELSD): 100% (Retention Time: 1.07 minutes);
MASS (ESI, Pos.): 656 (M+H)$^+$;
$^1$H-NMR (DMSO-d$_6$): δ 1.04 (s, 3H), 2.80 (s, 3H), 3.20 (q, 2H), 6.49 (s, 2H), 7.25-7.32 (m, 2H), 7.50-7.64 (m, 4H), 7.97 (d, 1H), 8.26-8.29 (m, 1H), 8.55 (d, 1H), 8.75 (s, 2H), 8.93 (s, 1H), 10.31 (s, 1H).

Example 15-247

2-{[(2-{4-[2-amino-5-(trifluoromethyl)-3-pyridinyl]phenoxy}-5-pyrimidinyl)carbamoyl]amino}-N,N-diethyl-4-(trifluoromethyl)benzenesulfonamide Purity (LC-MS/ELSD): 100% (Retention Time: 1.09 minutes);
MASS (ESI, Pos.): 670 (M+H)$^+$;
$^1$H-NMR (DMSO-d$_6$): δ 1.03 (s, 6H), 3.27-3.35 (m, 4H), 6.48 (s, 2H), 7.25-7.32 (m, 2H), 7.50-7.61 (m, 4H), 8.00 (d, 1H), 8.27-8.30 (m, 1H), 8.47-8.49 (m, 1H), 8.75 (s, 2H), 8.85 (s, 1H), 10.30 (s, 1H).

Example 15-248

1-(2-{4-[2-amino-5-(trifluoromethyl)-3-pyridinyl]phenoxy}-5-pyrimidinyl)-3-[2-(1-azetidinylsulfonyl)-5-(trifluoromethyl)phenyl]urea Purity (LC-MS/ELSD): 100% (Retention Time: 1.05 minutes);
MASS (ESI, Pos.): 654 (M+H)$^+$;
$^1$H-NMR (DMSO-d$_6$): δ 2.02-2.15 (m, 2H), 3.77-3.82 (m, 4H), 6.49 (s, 2H), 7.25-7.32 (m, 2H), 7.49-7.66 (m, 4H), 7.99 (d, 1H), 8.26-8.29 (m, 1H), 8.68 (d, 1H), 8.75 (s, 2H), 8.94 (s, 1H), 10.35 (s, 1H).

Example 15-249

2-{[(2-{4-[2-amino-5-(trifluoromethyl)-3-pyridinyl]phenoxy}-5-pyrimidinyl)carbamoyl]amino}-N-(2-hydroxypropyl)-N-methyl-4-(trifluoromethyl)benzenesulfonamide LC-MS/ELSD: Retention Time: 1.02 minutes; MASS (ESI, Pos.): 686 (M+H)+.

Example 15-250

1-{2-[4-(2-amino-5-chloro-3-pyridinyl)phenoxy]-5-pyrimidinyl}-3-[2-(3-hydroxy-3-methylbutyl)-5-(trifluoromethyl)phenyl]urea Purity (LC-MS/ELSD): 100% (Retention Time: 0.95 minutes); MASS (ESI, Pos.): 587 (M+H)+;
$^1$H-NMR (DMSO-d$_6$): δ 1.17 (s, 6H), 1.61-1.70 (m, 2H), 2.63-2.75 (m, 2H), 4.37 (s, 1H), 5.86 (s, 2H), 7.27 (d, 2H), 7.32-7.44 (m, 3H), 7.51 (d, 2H), 7.95 (d, 1H), 8.09 (s, 1H), 8.39 (s, 1H), 8.74 (s, 2H), 9.28 (s, 1H).

Example 15-251

1-{2-[4-(2-amino-5-chloro-3-pyridinyl)phenoxy]-5-pyrimidinyl}-3-[2-(3-hydroxy-3-methyl-1-butyn-1-yl)-5-(trifluoromethyl)phenyl]urea Purity (LC-MS/ELSD): 100% (Retention Time: 1.01 minutes);
MASS (ESI, Pos.): 583 (M+H)+;
$^1$H-NMR (DMSO-d$_6$): δ 1.54 (s, 6H), 5.60 (s, 1H), 5.86 (s, 2H), 7.28 (d, 2H), 7.35 (dd, 1H), 7.43 (d, 1H), 7.52 (d, 2H), 7.58 (d, 1H), 7.96 (d, 1H), 8.32 (s, 1H), 8.35 (d, 1H), 8.74 (s, 2H), 9.84 (s, 1H).

Example 16

The similar procedures as Example 6→Example 7 were carried out with 4-amino-5-bromopyrimidine in place of 3-bromo-5-chloropyridin-2-amine, and a corresponding carbamate or isocyanate compound in place of the compound produced in Example 3 to give the present compounds having the following physical characteristics.

Example 16-1

1-(2-(4-(4-aminopyrimidin-5-yl)phenoxy)pyrimidin-5-yl)-3-(2-chloro-5-(trifluoromethyl)phenyl)urea

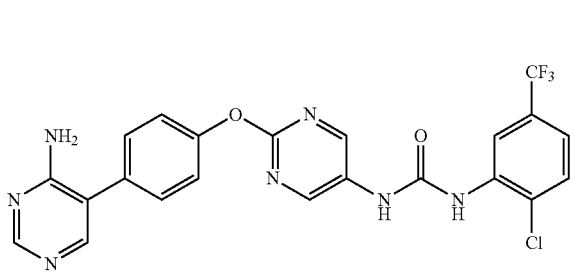 [SMILES: Nc1ncncc1-c1ccc(Oc2ncc(NC(=O)Nc3cc(C(F)(F)F)ccc3Cl)cn2)cc1]

TLC: Rf 0.58 (Ethyl Acetate:Methanol=19:1);
$^1$H-NMR (DMSO-d$_6$): δ 6.66 (s, 2H), 7.29 (d, 2H), 7.40 (d, 1H), 7.48 (d, 2H), 7.75 (d, 1H), 8.03 (s, 1H), 8.36 (s, 1H), 8.57 (s, 1H), 8.75-8.79 (m, 3H), 9.72 (s, 1H).

Example 16-2

1-(2-(4-(4-aminopyrimidin-5-yl)phenoxy)pyrimidin-5-yl)-3-(2-fluoro-5-(trifluoromethyl)phenyl)urea TLC: Rf 0.51 (Ethyl Acetate:Methanol=19:1);
$^1$H-NMR (DMSO-d$_6$): δ 6.67 (s, 2H), 7.28 (d, 2H), 7.43-7.54 (m, 4H), 8.03 (s, 1H), 8.36 (s, 1H), 8.52 (d, 1H), 8.75 (s, 2H), 9.10 (s, 1H), 9.30 (s, 1H).

Example 16-3

1-(2-(4-(4-aminopyrimidin-5-yl)phenoxy)pyrimidin-5-yl)-3-(2-(pyridin-3-yl)-5-(trifluoromethyl)phenyl)urea

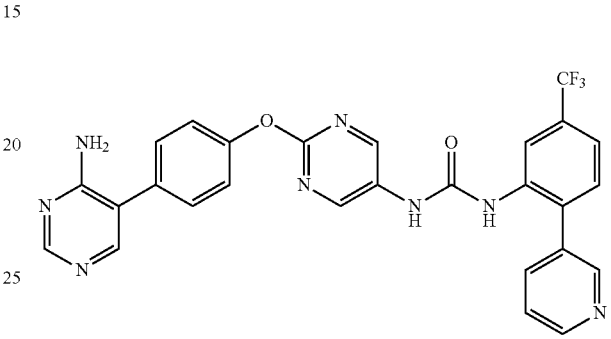

TLC: Rf 0.45 (Ethyl Acetate:Methanol:Aqueous Ammonia=9:1:0.5);
$^1$H-NMR (DMSO-d$_6$): δ 6.66 (s, 2H), 7.26 (d, 2H), 7.45-7.58 (m, 5H), 7.89 (d, 1H), 8.03 (s, 1H), 8.24 (s, 1H), 8.35 (s, 1H), 8.38 (s, 1H), 8.60-8.68 (m, 4H), 9.24 (s, 1H).

Example 16-4

1-(2-(4-(4-aminopyrimidin-5-yl)phenoxy)pyrimidin-5-yl)-3-(3-(trifluoromethyl)phenyl)urea TLC: Rf 0.51 (Ethyl Acetate:Methanol:Aqueous Ammonia=9:1:0.5);
$^1$H-NMR (DMSO-d$_6$): δ 6.67 (s, 2H), 7.27-7.34 (m, 3H), 7.47-7.54 (m, 3H), 7.62 (d, 1H), 7.97 (s, 1H), 8.03 (s, 1H), 8.36 (s, 1H), 8.75 (s, 2H), 8.99 (s, 1H), 9.32 (s, 1H).

Example 16-5

1-(2-(4-(4-aminopyrimidin-5-yl)phenoxy)pyrimidin-5-yl)-3-(2-phenyl-5-(trifluoromethyl)pyridin-3-yl)urea

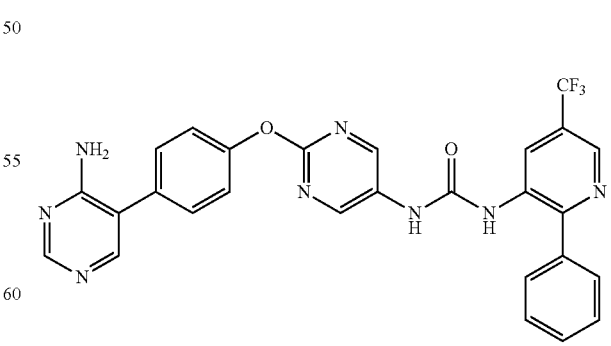

TLC: Rf 0.25 (Ethyl Acetate);
$^1$H-NMR (DMSO-d$_6$): δ 6.65 (s, 2H), 7.26 (d, 2H), 7.45-7.67 (m, 7H), 8.02 (s, 1H), 8.35 (s, 1H), 8.55 (s, 1H), 8.67 (s, 2H), 8.72 (s, 1H), 8.74 (s, 1H), 9.60 (s, 1H).

Example 16-6

1-(2-(4-(4-aminopyrimidin-5-yl)phenoxy)pyrimidin-5-yl)-3-(2-(3,4-dimethylphenyl)-5-(trifluoromethyl)pyridin-3-yl)urea TLC: Rf 0.68 (Ethyl Acetate:Methanol=9:1);
$^1$H-NMR (DMSO-d$_6$): δ 2.31 (s, 6H), 6.65 (s, 2H), 7.25-7.48 (m, 7H), 8.02 (s, 1H), 8.35-8.40 (m, 2H), 8.60-8.65 (m, 3H), 8.77 (s, 1H), 9.55 (s, 1H).

Example 16-7

1-(2-(4-(4-aminopyrimidin-5-yl)phenoxy)pyrimidin-5-yl)-3-(3-(tert-butyl)-1-(2,3-dihydro-1H-inden-5-yl)-1H-pyrazol-5-yl)urea

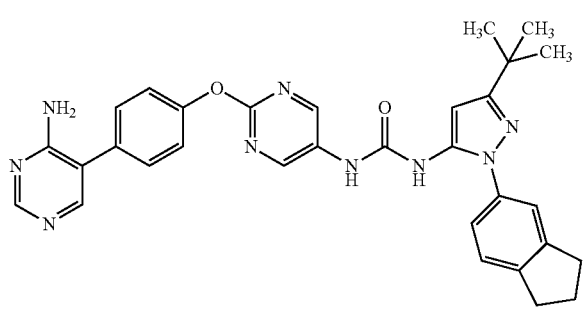 [SMILES: CC(C)(C)c1cc(NC(=O)Nc2cnc(Oc3ccc(-c4cncnc4N)cc3)nc2)n(-c2ccc3c(c2)CCC3)n1]

TLC: Rf 0.49 (Ethyl Acetate:Methanol=10:1);
$^1$H-NMR (DMSO-d$_6$): δ 1.25 (s, 9H), 2.05 (quint., 2H), 2.85-2.95 (m, 4H), 6.33 (s, 1H), 6.65 (s, 2H), 7.18-7.30 (m, 3H), 7.30-7.36 (m, 2H), 7.46 (d, 2H), 8.02 (s, 1H), 8.35 (s, 1H), 8.56 (s, 1H), 8.66 (s, 2H), 9.19 (s, 1H).

Example 16-8

1-(2-(4-(4-aminopyrimidin-5-yl)phenoxy)pyrimidin-5-yl)-3-(3-(tert-butyl)-1-(o-tolyl)-1H-pyrazol-5-yl)urea TLC: Rf 0.48 (Ethyl Acetate:Methanol=9:1);
$^1$H-NMR (DMSO-d$_6$): δ 1.25 (s, 9H), 1.99 (s, 3H), 6.34 (s, 1H), 6.66 (s, 2H), 7.25 (d, 2H), 7.31-7.48 (m, 6H), 8.02 (s, 1H), 8.35 (s, 1H), 8.40 (s, 1H), 8.64 (s, 2H), 9.07 (s, 1H).

Example 17: 3-bromo-5-chloropyrazolo[1,5-a]pyrimidine

A solution of 5-chloropyrazolo[1,5-a]pyrimidine (9 g) in THF (147 mL) was stirred at 5° C. The reaction mixture was added with N-bromosuccinimide (11 g) and stirred at room temperature for 1 hour. The reaction mixture was added with a sodium hydrogen sulfite aqueous solution and stirred for 5 minutes followed by distillation of THF under reduced pressure. The obtained residue was added with a saturated sodium carbonate aqueous solution and extracted with ethyl acetate. The obtained organic layer was washed twice with a saturated sodium carbonate aqueous solution, once with water and once with a saturated sodium chloride aqueous solution. The obtained organic layer was dried over sodium sulfate and filtered followed by distillation of the solvent to give the titled compound having the following physical characteristics (13.6 g).

TLC: Rf 0.40 (Hexane:Ethyl Acetate=4:1);
$^1$H-NMR (DMSO-d$_6$): δ 6.85 (d, 1H), 8.12 (s, 1H), 8.54 (d, 1H).

Example 18: 3-bromo-5-(pyrrolidin-1-yl)pyrazolo[1,5-a]pyrimidine

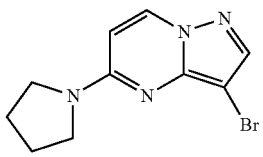 [SMILES: Brc1cnn2ccc(N3CCCC3)nc12]

To a solution of the compound produced in Example 17 (2.5 g) in dimethylsulfoxide (hereinafter abbreviated as DMSO) (20 mL) were added triethylamine (2.25 mL) and pyrrolidine (1.3 mL) and the mixture was stirred at room temperature for 1 hour. The reaction mixture was poured to a sodium hydrogen carbonate aqueous solution and extracted with ethyl acetate. The obtained organic layer was washed with water and a saturated sodium chloride aqueous solution and dried over anhydrous sodium sulfate. The obtained organic layer was filtered followed by distillation of the solvent. The obtained residue was added with tert-butyl methyl ether and filtered to give the titled compound having the following physical characteristics (2.49 g).

TLC: Rf 0.30 (Hexane:Ethyl Acetate=2:1);
$^1$H-NMR (DMSO-d$_6$): δ 1.95-2.12 (br s, 4H), 3.35-3.85 (br s, 4H), 6.14 (d, 1H), 7.80 (s, 1H), 8.18 (d, 1H).

Example 19: 2-(4-(5-(pyrrolidin-1-yl)pyrazolo[1,5-a]pyrimidin-3-yl)phenoxy)pyrimidin-5-amine

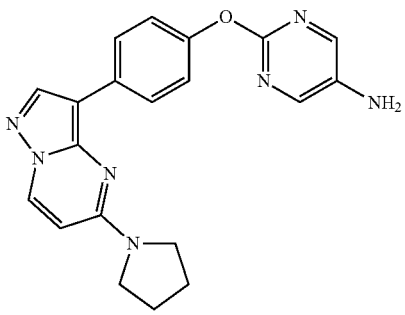 [SMILES: Nc1cnc(Oc2ccc(-c3cnn4ccc(N5CCCC5)nc34)cc2)nc1]

The similar procedure as Example 6 was carried out with the compound produced in Example 18 in place of 3-bromo-5-chloropyridin-2-amine to give the titled compound having the following physical characteristics.

TLC: Rf 0.52 (Dichloromethane:Ethyl Acetate:Methanol=8:4:1);
$^1$H-NMR (DMSO-d$_6$): δ 1.94-2.08 (br s, 4H), 3.40-3.74 (br s, 4H), 5.05-5.35 (br s, 2H), 6.41 (d, 1H), 7.04 (d, 2H), 7.96 (s, 2H), 8.05 (d, 2H), 8.33 (s, 1H), 8.61 (d, 1H).

Example 20: 1-(2-(1H-pyrazol-1-yl)-5-(trifluoromethyl)phenyl)-3-(2-(4-(5-(pyrrolidin-1-yl)pyrazolo[1,5-a]pyrimidin-3-yl)phenoxy)pyrimidin-5-yl)urea

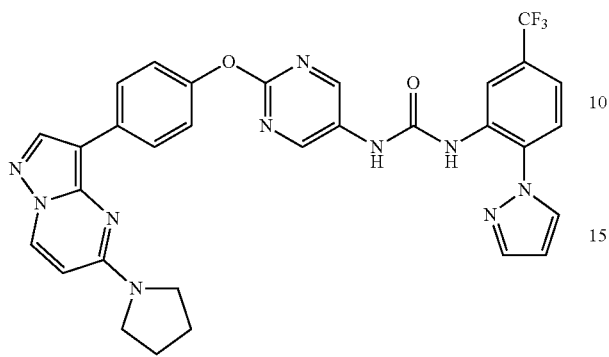

The similar procedure as Example 7 was carried out with the compound produced in Example 19 in place of the compound produced in Example 6 to give the present compound having the following physical characteristics.

TLC: Rf 0.50 (Ethyl Acetate);
$^1$H-NMR (DMSO-$d_6$): δ 1.94-2.08 (br s, 4H), 3.40-3.72 (br s, 4H), 6.42 (d, 1H), 6.67 (dd, 1H), 7.15 (d, 2H), 7.51 (dd, 1H), 7.74 (d, 1H), 7.95 (d, 1H), 8.10 (d, 2H), 8.36 (s, 1H), 8.40 (d, 1H), 8.58 (d, 1H), 8.62 (d, 1H), 8.67 (s, 2H), 9.68 (br s, 1H), 9.92 (br s, 1H).

Example 21

The similar procedure as Example 7 was carried out with the compound produced in Example 19 or a corresponding amine compound in place of the compound produced in Example 19, and the compound produced in Example 3 or a corresponding carbamate or isocyanate compound in place of the compound produced in Example 3 to give the present compounds having the following physical characteristics.

Example 21-1

1-(2-(4-(5-(azetidin-1-yl)pyrazolo[1,5-a]pyrimidin-3-yl)phenoxy)pyrimidin-5-yl)-3-(2-(pyridin-3-yl)-5-(trifluoromethyl)phenyl)urea

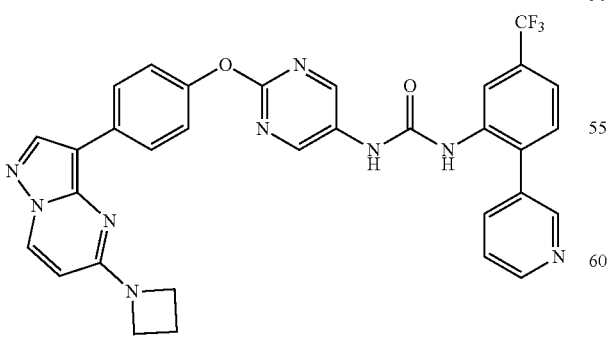

TLC: Rf 0.22 (Chloroform:Methanol=19:1);
$^1$H-NMR (DMSO-$d_6$): δ 2.32-2.42 (m, 2H), 4.12-4.18 (m, 4H), 6.23 (d, 1H), 7.10-7.16 (m, 2H), 7.46-7.58 (m, 3H), 7.86-7.90 (m, 1H), 8.03-8.09 (m, 2H), 8.22 (s, 1H), 8.35-8.39 (m, 2H), 8.60-8.68 (m, 5H), 9.21 (s, 1H).

Example 21-2

1-(2-(4-(5-(azetidin-1-yl)pyrazolo[1,5-a]pyrimidin-3-yl)phenoxy)pyrimidin-5-yl)-3-(2-(1-methyl-1H-pyrazol-5-yl)-5-(trifluoromethyl)phenyl)urea

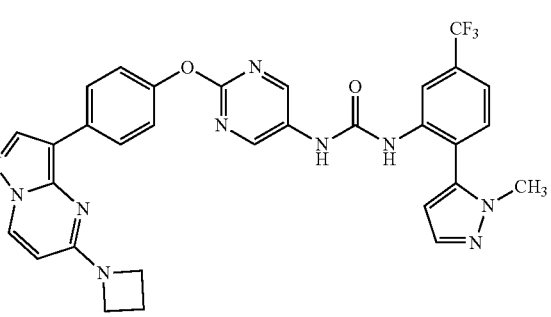

TLC: Rf 0.33 (Ethyl Acetate);
$^1$H-NMR (DMSO-$d_6$): δ 2.37 (t, 2H), 3.65 (s, 3H), 4.15 (t, 4H), 6.23 (d, 1H), 6.44 (d, 1H), 7.14 (d, 2H), 7.48 (d, 2H), 7.61 (d, 1H), 8.04-8.10 (m, 3H), 8.36 (s, 1H), 8.55 (s, 1H), 8.62 (d, 1H), 8.64 (s, 2H), 9.46 (s, 1H).

Example 21-3

1-(2-(4-(5-(azetidin-1-yl)pyrazolo[1,5-a]pyrimidin-3-yl)phenoxy)pyrimidin-5-yl)-3-(2-(3-methyl-1H-pyrazol-1-yl)-5-(trifluoromethyl)phenyl)urea TLC: Rf 0.66 (Ethyl Acetate);
$^1$H-NMR (DMSO-$d_6$): δ 2.35-2.44 (m, 5H), 4.15 (t, 4H), 6.24 (d, 1H), 6.44 (d, 1H), 7.14 (d, 2H), 7.48 (dd, 1H), 7.69 (d, 1H), 8.06 (d, 2H), 8.26 (d, 1H), 8.36 (s, 1H), 8.56 (d, 1H), 8.62 (d, 1H), 8.67 (s, 2H), 9.78 (s, 1H), 9.87 (s, 1H).

Example 21-4

1-(2-(1H-pyrazol-1-yl)-5-(trifluoromethyl)phenyl)-3-(2-(4-(5-(azetidin-1-yl)pyrazolo[1,5-a]pyrimidin-3-yl)phenoxy)pyrimidin-5-yl)urea TLC: Rf 0.47 (Ethyl Acetate);
$^1$H-NMR (DMSO-$d_6$): δ 2.37 (t, 2H), 4.15 (t, 4H), 6.24 (d, 1H), 6.68 (d, 1H), 7.14 (d, 2H), 7.51 (dd, 1H), 7.74 (d, 1H), 7.95 (d, 1H), 8.07 (d, 2H), 8.36 (s, 1H), 8.40 (d, 1H), 8.58-8.67 (m, 4H), 9.68 (s, 1H), 9.92 (s, 1H).

Example 21-5

1-(2-(4-(5-(azetidin-1-yl)pyrazolo[1,5-a]pyrimidin-3-yl)phenoxy)pyrimidin-5-yl)-3-(3-(trifluoromethyl)phenyl)urea

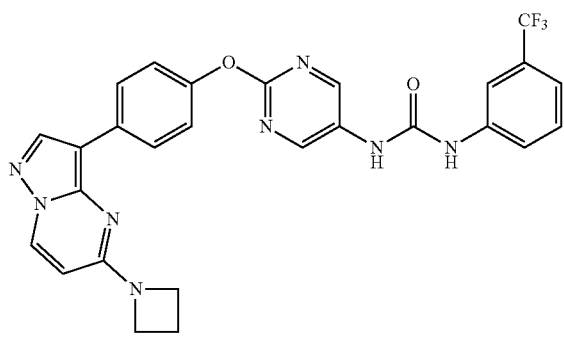 [SMILES: O=C(Nc1cnc(Oc2ccc(-c3cnn4ccc(N5CCC5)nc34)cc2)nc1)Nc1cccc(C(F)(F)F)c1]

TLC: Rf 0.19 (Chloroform:Methanol=19:1);

$^1$H-NMR (DMSO-$d_6$): δ 2.33-2.43 (m, 2H), 4.06-4.12 (m, 4H), 6.25 (d, 1H), 7.13-7.20 (m, 2H), 7.33 (d, 1H), 7.52 (t, 1H), 7.62 (d, 1H), 7.98 (s, 1H), 8.05-8.12 (m, 2H), 8.39 (s, 1H), 8.65 (d, 1H), 8.71 (s, 2H), 8.96 (s, 1H), 9.31 (s, 1H).

Example 21-6

1-(2-(pyridin-3-yl)-5-(trifluoromethyl)phenyl)-3-(2-(4-(5-(pyrrolidin-1-yl)pyrazolo[1,5-a]pyrimidin-3-yl)phenoxy)pyrimidin-5-yl)urea TLC: Rf 0.34 (Ethyl Acetate);

$^1$H-NMR (DMSO-$d_6$): δ 1.94-2.05 (m, 4H), 3.51-3.67 (m, 4H), 6.43 (d, 1H), 7.14 (d, 2H), 7.47-7.58 (m, 3H), 7.89 (dd, 1H), 8.10 (d, 2H), 8.23 (s, 1H), 8.38 (d, 2H), 8.61-8.68 (m, 5H), 9.22 (s, 1H).

Example 21-7

1-(2-(4-(5-(pyrrolidin-1-yl)pyrazolo[1,5-a]pyrimidin-3-yl)phenoxy)pyrimidin-5-yl)-3-(3-(trifluoromethyl)phenyl)urea TLC: Rf 0.68 (Ethyl Acetate);

$^1$H-NMR (DMSO-$d_6$): δ 1.95-2.04 (m, 4H), 3.52-3.65 (m, 4H), 6.44 (d, 1H), 7.24 (d, 2H), 7.46 (d, 1H), 7.57 (t, 2H), 7.72 (d, 1H), 7.93 (s, 1H), 8.16 (d, 2H), 8.36 (s, 1H), 8.64 (d, 1H), 8.76 (s, 2H), 10.23 (s, 1H).

Example 21-8

1-(2-phenyl-5-(trifluoromethyl)pyridin-3-yl)-3-(2-(4-(5-(pyrrolidin-1-yl)pyrazolo[1,5-a]pyrimidin-3-yl)phenoxy)pyrimidin-5-yl)urea TLC: Rf 0.76 (Ethyl Acetate);

$^1$H-NMR (DMSO-$d_6$): δ 1.92-2.05 (m, 4H), 3.52-3.65 (m, 4H), 6.43 (d, 1H), 7.15 (d, 2H), 7.56 (d, 3H), 7.65-7.68 (m, 2H), 8.11 (d, 2H), 8.39 (s, 1H), 8.41 (s, 1H), 8.62 (d, 1H), 8.65 (s, 2H), 8.72 (s, 1H), 8.76 (s, 1H), 9.44 (s, 1H).

Example 21-9

1-(2-(4-(5-methoxypyrazolo[1,5-a]pyrimidin-3-yl)phenoxy)pyrimidin-5-yl)-3-(2-(pyridin-3-yl)-5-(trifluoromethyl)phenyl)urea

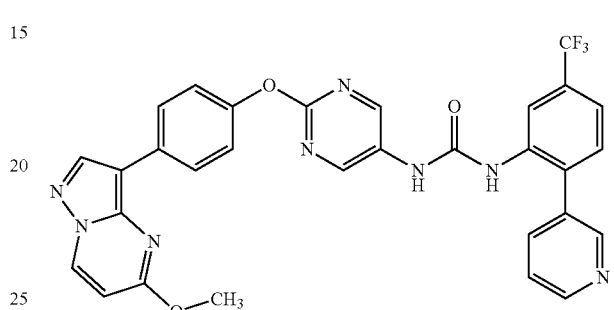

TLC: Rf 0.45 (Ethyl Acetate);

$^1$H-NMR (DMSO-$d_6$): δ 4.03 (s, 3H), 6.61 (d, 1H), 7.21 (d, 2H), 7.46-7.58 (m, 3H), 7.89 (dt, 1H), 8.10 (d, 2H), 8.23 (s, 1H), 8.39 (s, 1H), 8.58 (s, 1H), 8.64-8.68 (m, 4H), 8.93 (d, 1H), 9.23 (s, 1H).

Example 21-10

1-(2-(1H-pyrazol-1-yl)-5-(trifluoromethyl)phenyl)-3-(2-(4-(5-methoxypyrazolo[1,5-a]pyrimidin-3-yl)phenoxy)pyrimidin-5-yl)urea TLC: Rf 0.45 (Chloroform:Methanol=19:1);

$^1$H-NMR (DMSO-$d_6$): δ 4.04 (s, 3H), 6.62 (d, 1H), 6.68 (t, 1H), 7.20-7.26 (m, 2H), 7.53 (dd, 1H), 7.76 (d, 1H), 7.96 (d, 1H), 8.09-8.14 (m, 2H), 8.42 (d, 1H), 8.58-8.61 (m, 2H), 8.70 (s, 2H), 8.94 (d, 1H), 9.71 (s, 1H), 9.96 (s, 1H).

Example 21-11

1-(2-(4-(5-methoxypyrazolo[1,5-a]pyrimidin-3-yl)phenoxy)pyrimidin-5-yl)-3-(3-(trifluoromethyl)phenyl)urea TLC: Rf 0.45 (Hexane:Ethyl Acetate=1:2);

$^1$H-NMR (DMSO-$d_6$): δ 4.04 (s, 3H), 6.62 (d, 1H), 7.21-7.27 (m, 2H), 7.33 (d, 1H), 7.52 (t, 1H), 7.63 (d, 1H), 7.96-8.00 (m, 1H), 8.10-8.15 (m, 2H), 8.59 (s, 1H), 8.72 (s, 2H), 8.94 (d, 1H), 8.99 (s, 1H), 9.32 (s, 1H).

Example 21-12

1-(2-(4-(5-((2-hydroxy-2-methylpropyl)amino)pyrazolo[1,5-a]pyrimidin-3-yl)phenoxy)pyrimidin-5-yl)-3-(3-(trifluoromethyl)phenyl)urea

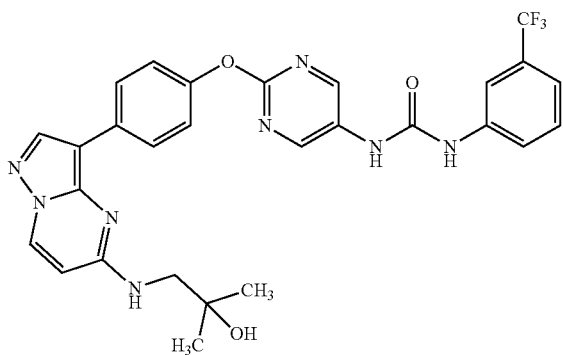 [SMILES: CC(C)(O)CNc1ccn2ncc(-c3ccc(Oc4ncc(NC(=O)Nc5cccc(C(F)(F)F)c5)cn4)cc3)c2n1]

TLC: Rf 0.41 (Chloroform:Methanol=9:1);
$^1$H-NMR (DMSO-$d_6$): δ 1.19 (s, 6H), 3.43 (d, 2H), 4.62 (s, 1H), 6.48 (d, 1H), 7.14-7.20 (m, 2H), 7.33 (d, 1H), 7.48-7.56 (m, 2H), 7.63 (d, 1H), 7.96-8.00 (m, 1H), 8.06-8.12 (m, 2H), 8.31 (s, 1H), 8.47 (d, 1H), 8.71 (s, 2H), 8.97 (s, 1H), 9.32 (s, 1H).

Example 21-13

1-(2-(4-(pyrazolo[1,5-a]pyrimidin-3-yl)phenoxy)pyrimidin-5-yl)-3-(2-(pyridin-3-yl)-5-(trifluoromethyl)phenyl)urea

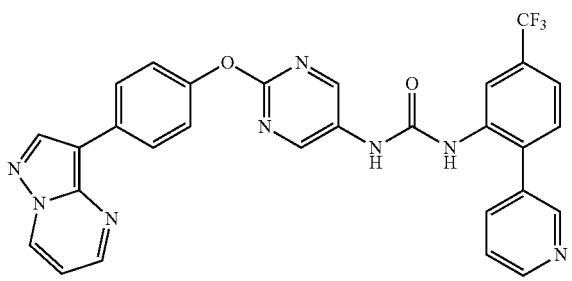 [SMILES: O=C(Nc1cnc(Oc2ccc(-c3cnn4cccnc34)cc2)nc1)Nc1cc(C(F)(F)F)ccc1-c1cccnc1]

TLC: Rf 0.22 (Ethyl Acetate);
$^1$H-NMR (DMSO-$d_6$): δ 7.11 (dd, 1H), 7.24 (d, 2H), 7.47-7.58 (m, 3H), 7.86-7.91 (m, 1H), 8.16 (d, 2H), 8.22 (s, 1H), 8.39 (s, 1H), 8.60-8.68 (m, 5H), 8.76 (s, 1H), 9.16 (dd, 1H), 9.23 (s, 1H).

Example 21-14

1-(2-(4-(pyrazolo[1,5-a]pyrimidin-3-yl)phenoxy)pyrimidin-5-yl)-3-(3-(trifluoromethyl)phenyl)urea TLC: Rf 0.65 (Ethyl Acetate);
$^1$H-NMR (DMSO-$d_6$): δ 7.11 (dd, 1H), 7.25 (d, 2H), 7.32 (d, 1H), 7.51 (t, 1H), 7.61 (d, 1H), 7.97 (s, 1H), 8.17 (d, 2H), 8.66 (dd, 1H), 8.71 (s, 2H), 8.76 (s, 1H), 8.98 (s, 1H), 9.16 (dd, 1H), 9.32 (s, 1H).

Example 21-15

1-(2-(1H-pyrazol-1-yl)-5-(trifluoromethyl)phenyl)-3-(2-(4-(pyrazolo[1,5-a]pyrimidin-3-yl)phenoxy)pyrimidin-5-yl)urea TLC: Rf 0.74 (Ethyl Acetate);
$^1$H-NMR (DMSO-$d_6$): δ 6.67 (t, 1H), 7.11 (dd, 1H), 7.25 (d, 2H), 7.52 (dd, 1H), 7.74 (d, 1H), 7.95 (d, 1H), 8.17 (d, 2H), 8.40 (d, 1H), 8.58 (d, 1H), 8.64-8.70 (m, 3H), 8.75 (s, 1H), 9.15 (dd, 1H), 9.67 (s, 1H), 9.94 (s, 1H).

Example 21-16

1-(2-(1H-1,2,3-triazol-1-yl)-5-(trifluoromethyl)phenyl)-3-(2-(4-(pyrazolo[1,5-a]pyrimidin-3-yl)phenoxy)pyrimidin-5-yl)urea TLC: Rf 0.60 (Ethyl Acetate);
$^1$H-NMR (DMSO-$d_6$): δ 7.10 (dd, 1H), 7.24 (d, 2H), 7.61 (d, 1H), 7.73 (d, 1H), 8.09 (s, 1H), 8.16 (d, 2H), 8.57 (s, 1H), 8.66 (s, 2H), 8.67-8.70 (m, 2H), 8.75 (s, 2H), 9.15 (s, 1H), 9.63 (s, 1H).

Example 21-17

1-(2-fluoro-5-(trifluoromethyl)phenyl)-3-(2-(4-(pyrazolo[1,5-a]pyrimidin-3-yl)phenoxy)pyrimidin-5-yl)urea TLC: Rf 0.65 (Ethyl Acetate);
$^1$H-NMR (DMSO-$d_6$): δ 7.11 (dd, 1H), 7.26 (d, 2H), 7.37-7.44 (m, 1H), 7.46 (t, 1H), 8.17 (d, 2H), 8.51 (dd, 1H), 8.65 (dd, 1H), 8.72 (s, 2H), 8.75 (s, 1H), 9.08 (s, 1H), 9.15 (dd, 1H), 9.28 (s, 1H).

Example 21-18

1-(2-chloro-5-(trifluoromethyl)phenyl)-3-(2-(4-(pyrazolo[1,5-a]pyrimidin-3-yl)phenoxy)pyrimidin-5-yl)urea TLC: Rf 0.69 (Ethyl Acetate);
$^1$H-NMR (DMSO-$d_6$): δ 7.10 (dd, 1H), 7.26 (d, 2H), 7.40 (dd, 1H), 7.72 (d, 1H), 8.17 (d, 2H), 8.56 (d, 1H), 8.66 (dd, 1H), 8.73 (s, 2H), 8.75 (s, 1H), 8.77 (s, 1H), 9.15 (dd, 1H), 9.69 (s, 1H).

Example 21-19

1-(2-methyl-5-(trifluoromethyl)phenyl)-3-(2-(4-(pyrazolo[1,5-a]pyrimidin-3-yl)phenoxy)pyrimidin-5-yl)urea TLC: Rf 0.72 (Ethyl Acetate);
$^1$H-NMR (DMSO-$d_6$): δ 2.32 (s, 3H), 7.11 (dd, 1H), 7.26 (d, 2H), 7.29 (d, 1H), 7.42 (d, 1H), 8.17 (d, 2H), 8.27 (s, 1H), 8.37 (s, 1H), 8.66 (dd, 1H), 8.73 (s, 2H), 8.76 (s, 1H), 9.16 (dd, 1H), 9.31 (s, 1H).

Example 21-20

1-(3-fluoro-5-(trifluoromethyl)phenyl)-3-(2-(4-(pyrazolo[1,5-a]pyrimidin-3-yl)phenoxy)pyrimidin-5-yl)urea TLC: Rf 0.76 (Ethyl Acetate);
$^1$H-NMR (DMSO-$d_6$): δ 7.11 (dd, 1H), 7.20-7.30 (m, 3H), 7.54-7.72 (m, 2H), 8.18 (d, 2H), 8.65-8.76 (m, 4H), 9.09 (s, 1H), 9.16-9.20 (m, 1H), 9.51 (s, 1H).

Example 21-21

1-(4-methyl-3-(trifluoromethyl)phenyl)-3-(2-(4-(pyrazolo[1,5-a]pyrimidin-3-yl)phenoxy)pyrimidin-5-yl)urea TLC: Rf 0.76 (Ethyl Acetate);
$^1$H-NMR (DMSO-$d_6$): δ 2.36 (s, 3H), 7.10 (dd, 1H), 7.25 (d, 2H), 7.33 (d, 1H), 7.52 (dd, 1H), 7.88 (d, 1H), 8.17 (d, 2H), 8.65 (dd, 1H), 8.70 (s, 2H), 8.75 (s, 1H), 8.91 (s, 1H), 9.15 (d, 1H), 9.17 (d, 1H).

Example 21-22

1-(2-phenyl-5-(trifluoromethyl)pyridin-3-yl)-3-(2-(4-(pyrazolo[1,5-a]pyrimidin-3-yl)phenoxy)pyrimidin-5-yl)urea TLC: Rf 0.77 (Ethyl Acetate);
$^1$H-NMR (DMSO-$d_6$): δ 7.11 (dd, 1H), 7.25 (d, 2H), 7.52-7.62 (m, 3H), 7.62-7.69 (m, 2H), 8.17 (d, 2H), 8.41 (s, 1H), 8.62-8.80 (m, 6H), 9.16 (dd, 1H), 9.45 (d, 1H).

Example 21-23

1-(3-(difluoromethyl)phenyl)-3-(2-(4-(pyrazolo[1,5-a]pyrimidin-3-yl)phenoxy)pyrimidin-5-yl)urea TLC: Rf 0.73 (Ethyl Acetate);
$^1$H-NMR (DMSO-$d_6$): δ 7.00 (t, 1H), 7.11 (dd, 1H), 7.18 (d, 1H), 7.26 (d, 2H), 7.42 (t, 1H), 7.52 (d, 1H), 7.77 (s, 1H), 8.17 (d, 2H), 8.66 (dd, 1H), 8.71-8.76 (m, 3H), 8.89 (s, 1H), 9.17 (d, 2H).

Example 21-24

1-(3,5-difluorophenyl)-3-(2-(4-(pyrazolo[1,5-a]pyrimidin-3-yl)phenoxy)pyrimidin-5-yl)urea TLC: Rf 0.74 (Ethyl Acetate);
$^1$H-NMR (DMSO-$d_6$): δ 6.80 (dt, 1H), 7.11 (dd, 1H), 7.19 (dd, 2H), 7.26 (d, 2H), 8.17 (d, 2H), 8.66 (dd, 1H), 8.70 (s, 2H), 8.75 (s, 1H), 9.00 (s, 1H), 9.16 (dd, 1H), 9.30 (s, 1H).

Example 21-25

1-(2-(1H-pyrazol-1-yl)-4-(trifluoromethyl)phenyl)-3-(2-(4-(5-(azetidin-1-yl)pyrazolo[1,5-a]pyrimidin-3-yl)phenoxy)pyrimidin-5-yl)urea

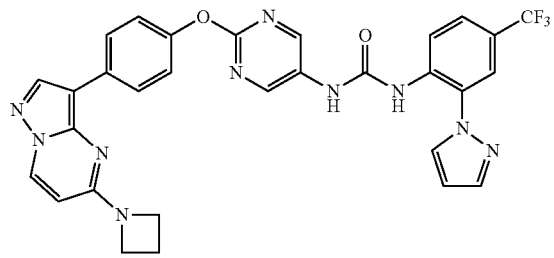 [SMILES: O=C(Nc1cnc(Oc2ccc(-c3cnn4ccc(N5CCC5)nc34)cc2)nc1)Nc1ccc(C(F)(F)F)cc1-n1cccn1]

TLC: Rf 0.63 (Ethyl Acetate);
$^1$H-NMR (DMSO-$d_6$): δ 2.45-2.42 (m, 2H), 4.15 (t, 4H), 6.24 (d, 1H), 6.65 (t, 1H), 7.15 (d, 2H), 7.74 (dd, 1H), 7.82 (d, 1H), 7.93 (d, 1H), 8.60 (d, 2H), 8.36 (s, 1H), 8.43 (dd, 2H), 8.63 (d, 1H), 8.67 (s, 2H), 9.54 (s, 1H), 9.26 (s, 1H).

Example 21-26

1-(2-(4-(5-(azetidin-1-yl)pyrazolo[1,5-a]pyrimidin-3-yl)phenoxy)pyrimidin-5-yl)-3-(2-chloro-4-(trifluoromethyl)phenyl)urea TLC: Rf 0.44 (Hexane:Ethyl Acetate=1:2);
$^1$H-NMR (DMSO-$d_6$): δ 2.36-2.42 (m, 2H), 4.15 (t, 4H), 6.24 (d, 1H), 7.16 (d, 2H), 7.68 (dd, 1H), 7.87 (s, 1H), 8.07 (d, 2H), 8.37 (s, 1H), 8.42 (d, 1H), 8.63 (d, 1H), 8.72 (s, 2H), 8.78 (s, 1H), 9.73 (s, 1H).

Example 21-27

1-(2-(4-(5-(azetidin-1-yl)pyrazolo[1,5-a]pyrimidin-3-yl)phenoxy)pyrimidin-5-yl)-3-phenylurea TLC: Rf 0.20 (Chloroform:Methanol=19:1);
$^1$H-NMR (DMSO-$d_6$): δ 2.33-2.43 (m, 2H), 4.11-4.19 (m, 4H), 6.25 (d, 1H), 6.95-7.02 (m, 1H), 7.13-7.19 (m, 2H), 7.25-7.34 (m, 2H), 7.42-7.47 (m, 2H), 8.06-8.10 (m, 2H), 8.38 (s, 1H), 8.64 (d, 1H), 8.70 (s, 2H), 8.82 (s, 1H), 8.91 (s, 1H).

Example 21-28

1-(2-chloro-4-(trifluoromethyl)phenyl)-3-(2-(4-(5-(pyrrolidin-1-yl)pyrazolo[1,5-a]pyrimidin-3-yl)phenoxy)pyrimidin-5-yl)urea TLC: Rf 0.62 (Dichloromethane:Ethyl Acetate:Methanol=8:4:1);
$^1$H-NMR (DMSO-$d_6$): δ 1.92-2.06 (br s, 4H), 3.40-3.70 (br s, 4H), 6.43 (d, 1H), 7.17 (d, 2H), 7.69 (dd, 1H), 7.88 (d, 1H), 8.12 (d, 2H), 8.37 (s, 1H), 8.43 (d, 1H), 8.63 (d, 1H), 8.72 (s, 2H), 8.79 (s, 1H), 9.75 (s, 1H).

Example 21-29

1-(2-chloro-4-(trifluoromethyl)phenyl)-3-(2-(4-(pyrazolo[1,5-a]pyrimidin-3-yl)phenoxy)pyrimidin-5-yl)urea TLC: Rf 0.80 (Ethyl Acetate);
$^1$H-NMR (DMSO-$d_6$): δ 7.10 (dd, 1H), 7.26 (d, 2H), 7.68 (dd, 1H), 7.87 (s, 1H), 8.17 (d, 2H), 8.42 (d, 1H), 8.66 (dd, 1H), 8.73 (s, 2H), 8.75 (s, 1H), 8.78 (s, 1H), 9.16 (d, 1H), 9.74 (s, 1H).

Example 21-30

1-{2-[4-(5-methoxypyrazolo[1,5-a]pyrimidin-3-yl)phenoxy]-5-pyrimidinyl}-3-[2-(1-methyl-1H-pyrazol-5-yl)-5-(trifluoromethyl)phenyl]urea Purity (LC-MS/ELSD): 100% (Retention Time: 1.01 minutes);
MASS (ESI, Pos.): 602 (M+H)$^+$;
$^1$H-NMR (DMSO-$d_6$): δ 3.65 (s, 3H), 4.03 (s, 3H), 6.45 (d, 1H), 6.61 (d, 1H), 7.22 (d, 2H), 7.46-7.52 (m, 2H), 7.62

(d, 1H), 8.09-8.12 (m, 3H), 8.56 (s, 1H), 8.59 (s, 1H), 8.66 (s, 2H), 8.93 (d, 1H), 9.48 (s, 1H).

Example 21-31

1-{2-[4-(5-methoxypyrazolo[1,5-a]pyrimidin-3-yl)phenoxy]-5-pyrimidinyl}-3-[2-(3-methyl-1H-pyrazol-1-yl)-5-(trifluoromethyl)phenyl]urea $^1$H-NMR (DMSO-$d_6$): δ 2.37 (s, 3H), 4.03 (s, 3H), 6.45 (d, 1H), 6.61 (d, 1H), 7.20-7.25 (m, 2H), 7.48 (dd, 1H), 7.69 (d, 1H), 8.09-8.13 (m, 2H), 8.28 (d, 1H), 8.57 (d, 1H), 8.58 (s, 1H), 8.68 (s, 2H), 8.93 (d, 1H), 9.80 (s, 1H), 9.90 (s, 1H).

Example 21-32

1-{2-[4-(5-methoxypyrazolo[1,5-a]pyrimidin-3-yl)phenoxy]-5-pyrimidinyl}-3-[2-(4-methyl-1H-pyrazol-1-yl)-5-(trifluoromethyl)phenyl]urea Purity (LC-MS/ELSD): 100% (Retention Time: 1.08 minutes);
MASS (ESI, Pos.): 602 (M+H)$^+$;
$^1$H-NMR (DMSO-$d_6$): δ 2.14 (s, 3H), 4.03 (s, 3H), 6.61 (d, 1H), 7.22 (d, 2H), 7.49 (dd, 1H), 7.70 (d, 1H), 7.78 (s, 1H), 8.11 (d, 2H), 8.18 (s, 1H), 8.57-8.58 (m, 2H), 8.69 (s, 2H), 8.93 (d, 1H), 9.83 (s, 1H), 9.95 (s, 1H).

Example 21-33

1-{2-[4-(5-methoxypyrazolo[1,5-a]pyrimidin-3-yl)phenoxy]-5-pyrimidinyl}-3-[2-(3-pyridinyl)-4-(trifluoromethyl)phenyl]urea Purity (LC-MS/ELSD): 100% (Retention Time: 0.92 minutes);
MASS (ESI, Pos.): 599 (M+H)$^+$;
$^1$H-NMR (DMSO-$d_6$): δ 4.03 (s, 3H), 6.61 (d, 1H), 7.19-7.24 (m, 2H), 7.53-7.57 (m, 2H), 7.75 (dd, 1H), 7.88-7.92 (m, 1H), 8.08-8.12 (m, 2H), 8.24-8.29 (m, 2H), 8.58 (s, 1H), 8.64-8.68 (m, 4H), 8.93 (d, 1H), 9.28 (brs, 1H).

Example 21-34

1-[2-chloro-5-(trifluoromethyl)phenyl]-3-{2-[4-(5-methoxypyrazolo[1,5-a]pyrimidin-3-yl)phenoxy]-5-pyrimidinyl}urea Purity (LC-MS/ELSD): 100% (Retention Time: 1.05 minutes);
MASS (ESI, Pos.): 556 (M+H)$^+$;
$^1$H-NMR (DMSO-$d_6$): δ 4.03 (s, 3H), 6.61 (d, 1H), 7.24 (d, 2H), 7.40 (dd, 1H), 7.73 (d, 1H), 8.11 (d, 2H), 8.57-8.59 (d, 2H), 8.73 (s, 2H), 8.78 (s, 1H), 8.94 (d, 1H), 9.70 (s, 1H).

Example 21-35

1-{2-[4-(5-methoxypyrazolo[1,5-a]pyrimidin-3-yl)phenoxy]-5-pyrimidinyl}-3-[2-methyl-5-(trifluoromethyl)phenyl]urea Purity (LC-MS/ELSD): 100% (Retention Time: 1.00 minute);
MASS (ESI, Pos.): 536 (M+H)$^+$;
$^1$H-NMR (DMSO-$d_6$): δ 2.32 (s, 3H), 4.03 (s, 3H), 6.61 (d, 1H), 7.24 (d, 2H), 7.30 (d, 1H), 7.41 (d, 1H), 8.09-8.13 (m, 2H), 8.28 (s, 1H), 8.37 (s, 1H), 8.59 (s, 1H), 8.73 (s, 2H), 8.94 (d, 1H), 9.32 (s, 1H).

Example 21-36

1-(2,4-dichlorophenyl)-3-{2-[4-(5-methoxypyrazolo[1,5-a]pyrimidin-3-yl)phenoxy]-5-pyrimidinyl}urea Purity (LC-MS/ELSD): 100% (Retention Time: 1.03 minutes);
MASS (ESI, Pos.): 522 (M+H)$^+$;
$^1$H-NMR (DMSO-$d_6$): δ 4.03 (s, 3H), 6.61 (d, 1H), 7.23 (d, 2H), 7.39 (dd, 1H), 7.63 (d, 1H), 8.10-8.16 (m, 3H), 8.57 (s, 1H), 8.59 (s, 1H), 8.71 (s, 2H), 8.93 (d, 1H), 9.58 (s, 1H).

Example 21-37

1-(2-{4-[5-(dimethylamino)pyrazolo[1,5-a]pyrimidin-3-yl]phenoxy}-5-pyrimidinyl)-3-[2-(3-pyridinyl)-5-(trifluoromethyl)phenyl]urea

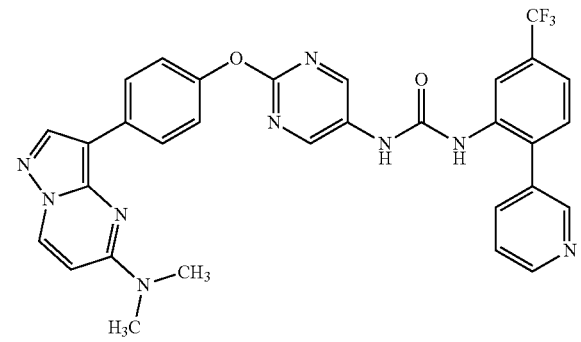 [SMILES: CN(C)c1ccn2ncc(-c3ccc(Oc4ncc(NC(=O)Nc5cc(C(F)(F)F)ccc5-c5cccnc5)cn4)cc3)c2n1]

TLC: Rf 0.32 (Chloroform:Methanol=19:1);
$^1$H-NMR (DMSO-$d_6$): δ 3.19 (s, 6H), 6.62 (d, 1H), 7.12-7.17 (m, 2H), 7.46-7.57 (m, 3H), 7.86-7.90 (m, 1H), 8.06-8.11 (m, 2H), 8.22 (s, 1H), 8.37-8.38 (m, 2H), 8.61-8.68 (m, 5H), 9.21 (s, 1H).

Example 21-38

1-(2-{4-[5-(dimethylamino)pyrazolo[1,5-a]pyrimidin-3-yl]phenoxy}-5-pyrimidinyl)-3-[2-(1H-pyrazol-1-yl)-5-(trifluoromethyl)phenyl]urea

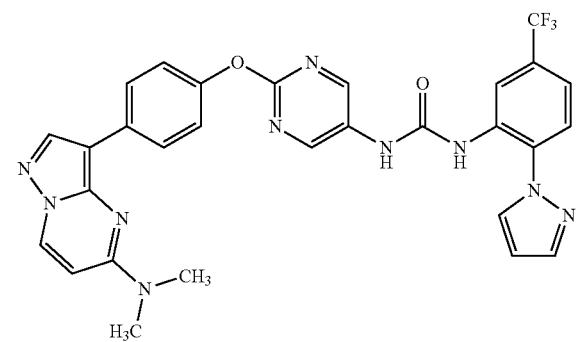 [SMILES: CN(C)c1ccn2ncc(-c3ccc(Oc4ncc(NC(=O)Nc5cc(C(F)(F)F)ccc5-n5cccn5)cn4)cc3)c2n1]

TLC: Rf 0.30 (Chloroform:Methanol=19:1);
$^1$H-NMR (DMSO-$d_6$): δ 3.19 (s, 6H), 6.63 (d, 1H), 6.67-6.68 (m, 1H), 7.14-7.17 (m, 2H), 7.52 (dd, 1H), 7.75 (d, 1H), 7.95 (d, 1H), 8.08-8.11 (m, 2H), 8.39 (s, 1H), 8.41 (d, 1H), 8.59 (d, 1H), 8.64 (d, 1H), 8.68 (s, 2H), 9.69 (s, 1H), 9.93 (s, 1H).

Example 21-39

1-[2-fluoro-5-(trifluoromethyl)phenyl]-3-{2-[4-(5-methoxypyrazolo[1,5-a]pyrimidin-3-yl)phenoxy]-5-pyrimidinyl}urea Purity (LC-MS/ELSD): 100% (Retention Time: 1.01 minutes);
MASS (ESI, Pos.): 540 (M+H)$^+$;
$^1$H-NMR (DMSO-d$_6$): δ 4.03 (s, 3H), 6.61 (d, 1H), 7.21-7.26 (m, 2H), 7.39-7.53 (m, 2H), 8.09-8.14 (m, 2H), 8.53 (dd, 1H), 8.59 (s, 1H), 8.73 (s, 2H), 8.93 (d, 1H), 9.02-9.36 (br s, 2H).

Example 21-40

1-[5-chloro-2-(3-pyridinyl)phenyl]-3-{2-[4-(5-methoxypyrazolo[1,5-a]pyrimidin-3-yl)phenoxy]-5-pyrimidinyl}urea Purity (LC-MS/ELSD): 100% (Retention Time: 0.87 minutes);
MASS (ESI, Pos.): 565 (M+H)$^+$;
$^1$H-NMR (DMSO-d$_6$): δ 4.03 (s, 3H), 6.60 (d, 1H), 7.20-7.30 (m, 4H), 7.53 (dd, 1H), 7.81-7.85 (m, 1H), 8.08-8.12 (m, 4H), 8.55-8.64 (m, 5H), 8.93 (d, 1H), 9.18 (s, 1H).

Example 21-41

1--{2-[4-(5-methoxypyrazolo[1,5-a]pyrimidin-3-yl)phenoxy]-5-pyrimidinyl}-3-{5-(trifluoromethyl)-2-[3-(trifluoromethyl)-1H-pyrazol-1-yl]phenyl}urea Purity (LC-MS/ELSD): 100% (Retention Time: 1.09 minutes);
MASS (ESI, Pos.): 656 (M+H)$^+$;
$^1$H-NMR (DMSO-d$_6$): δ 4.03 (s, 3H), 6.61 (d, 1H), 7.12 (d, 1H), 7.20-7.24 (m, 2H), 7.58 (dd, 1H), 7.10 (d, 1H), 8.09-8.13 (m, 2H), 8.47-8.48 (m, 2H), 8.58 (s, 2H), 8.65 (s, 2H), 8.93 (d, 1H), 9.46 (s, 1H).

Example 21-42

1-{2-[4-(5-ethoxypyrazolo[1,5-a]pyrimidin-3-yl)phenoxy]-5-pyrimidinyl}-3-[2-(3-pyridinyl)-5-(trifluoromethyl)phenyl]urea

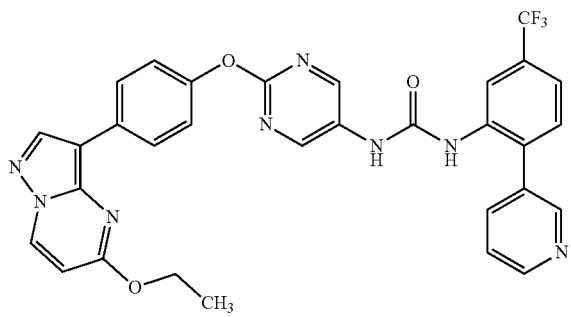 [SMILES: CCOc1ccn2ncc(-c3ccc(Oc4ncc(NC(=O)Nc5cc(C(F)(F)F)ccc5-c5cccnc5)cn4)cc3)c2n1]

Purity (LC-MS/ELSD): 100% (Retention Time: 0.98 minutes);
MASS (ESI, Pos.): 613 (M+H)$^+$;
$^1$H-NMR (DMSO-d$_6$): δ 1.40 (t, 3H), 4.49 (q, 2H), 6.58 (d, 1H), 7.18-7.22 (m, 2H), 7.47-7.58 (m, 3H), 7.87-7.91 (m, 1H), 8.05-8.10 (m, 2H), 8.23 (s, 1H), 8.39 (s, 1H), 8.57 (s, 1H), 8.64-8.68 (m, 4H), 8.92 (d, 1H), 9.23 (s, 1H).

Example 21-43

1-{2-[4-(5-cyclobutylpyrazolo[1,5-a]pyrimidin-3-yl)phenoxy]-5-pyrimidinyl}-3-[2-(3-pyridinyl)-5-(trifluoromethyl)phenyl]urea Purity (LC-MS/ELSD): 99% (Retention Time: 1.03 minutes);
MASS (ESI, Pos.): 623 (M+H)$^+$;
$^1$H-NMR (DMSO-d$_6$): δ 1.85-2.12 (m, 2H), 2.33-2.42 (m, 4H), 3.73-3.84 (m, 1H), 6.97 (d, 1H), 7.24 (d, 2H), 7.47-7.58 (m, 3H), 7.87-7.91 (m, 1H), 8.18-8.23 (m, 3H), 8.39 (s, 1H), 8.64-8.68 (m, 5H), 9.01 (d, 1H), 9.23 (s, 1H).

Example 21-44

1-{2-[4-(5-methoxypyrazolo[1,5-a]pyrimidin-3-yl)phenoxy]-5-pyrimidinyl}-3-[2-(2H-1,2,3-triazol-2-yl)-5-(trifluoromethyl)phenyl]urea Purity (LC-MS/ELSD): 100% (Retention Time: 1.09 minutes);
MASS (ESI, Pos.): 589 (M+H)$^+$;
$^1$H-NMR (DMSO-d$_6$): δ 4.03 (s, 3H), 6.62 (d, 1H), 7.23 (d, 2H), 7.58 (dd, 1H), 8.05-8.13 (m, 3H), 8.33 (s, 2H), 8.59 (s, 1H), 8.65 (d, 1H), 8.70 (s, 2H), 8.93 (d, 1H), 9.66 (s, 1H), 10.00 (s, 1H).

Example 21-45

1-[5-chloro-2-(2H-1,2,3-triazol-2-yl)phenyl]-3-{2-[4-(5-methoxypyrazolo[1,5-a]pyrimidin-3-yl)phenoxy]-5-pyrimidinyl}urea Purity (LC-MS/ELSD): 99% (Retention Time: 1.08 minutes);
MASS (ESI, Pos.): 555 (M+H)$^+$;
$^1$H-NMR (DMSO-d$_6$): δ 4.03 (s, 3H), 6.61 (d, 1H), 7.20-7.25 (m, 2H), 7.29 (dd, 1H), 7.80 (d, 1H), 8.09-8.13 (m, 2H), 8.26 (s, 2H), 8.33 (d, 1H), 8.58 (s, 1H), 8.69 (s, 2H), 8.93 (d, 1H), 9.36 (s, 1H), 9.91 (s, 1H).

Example 21-46

1-(2-{4-[5-(1-azetidinyl)pyrazolo[1,5-a]pyrimidin-3-yl]phenoxy}-5-pyrimidinyl)-3-[4-(trifluoromethyl)-2-biphenylyl]urea TLC: Rf 0.24 (Chloroform:Methanol=19:1);
$^1$H-NMR (DMSO-d$_6$): δ 2.31-2.44 (m, 2H), 4.10-4.19 (m, 4H), 6.24 (d, 1H), 7.10-7.18 (m, 2H), 7.39-7.59 (d, 7H), 8.03-8.12 (m, 3H), 8.37 (s, 1H), 8.41 (s, 1H), 8.60-8.66 (m, 3H), 9.37 (s, 1H).

Example 21-47

1-(2-{4-[5-(1-azetidinyl)pyrazolo[1,5-a]pyrimidin-3-yl]phenoxy}-5-pyrimidinyl)-3-[2-(6-methyl-3-pyridinyl)-5-(trifluoromethyl)phenyl]urea TLC: Rf 0.33 (Chloroform:Methanol=19:1);
$^1$H-NMR (DMSO-d$_6$): δ 2.32-2.43 (m, 2H), 2.55 (s, 3H), 4.10-4.19 (m, 4H), 6.24 (d, 1H), 7.11-7.18 (m, 2H), 7.40-7.51 (m, 3H), 7.76 (dd, 1H), 8.03-8.10 (m, 2H), 8.18 (s, 1H), 8.37 (s, 1H), 8.41-8.43 (m, 1H), 8.51 (d,1H), 8.61-8.69 (m, 3H), 9.25 (s, 1H).

Example 21-48

1-(2-{4-[5-(dimethylamino)pyrazolo[1,5-a]pyrimidin-3-yl]phenoxy}-5-pyrimidinyl)-3-[2-(6-methyl-3-pyridinyl)-5-(trifluoromethyl)phenyl]urea TLC: Rf 0.30 (Methylene chloride:Ethyl acetate:Methanol=8:4:1);
$^1$H-NMR (DMSO-d$_6$): δ 2.55 (s, 3H), 3.19 (s, 6H), 6.63 (d, 1H), 7.15 (d, 2H), 7.38-7.52 (m, 3H), 7.76 (dd, 1H), 8.10 (d, 2H), 8.18 (s, 1H), 8.38 (s, 1H), 8.42 (s, 1H), 8.50 (d, 1H), 8.64 (s, 2H), 8.64 (d, 1H), 9.25 (s, 1H).

Example 21-49

1-(2-{4-[5-(1-azetidinyl)pyrazolo[1,5-a]pyrimidin-3-yl]phenoxy}-5-pyrimidinyl)-3-[4'-methyl-4-(trifluoromethyl)-2-biphenylyl]urea TLC: Rf 0.32 (Chloroform:Methanol=19:1);
$^1$H-NMR (DMSO-d$_6$): δ 2.30-2.45 (m, 5H), 4.10-4.19 (m, 4H), 6.24 (d, 1H), 7.11-7.18 (m, 2H), 7.30-7.47 (m, 6H), 8.01-8.10 (m, 3H), 8.37 (s, 1H), 8.42-8.45 (m, 1H), 8.62-8.66 (m, 3H), 9.39 (s, 1H).

Example 21-50

1-(2-{4-[5-(dimethylamino)pyrazolo[1,5-a]pyrimidin-3-yl]phenoxy}-5-pyrimidinyl)-3-[2-phenyl-5-(trifluoromethyl)-3-pyridinyl]urea Purity (LC-MS/ELSD): 100% (Retention Time: 1.01 minutes);
MASS (ESI, Pos.): 612 (M+H)$^+$;
$^1$H-NMR (DMSO-d$_6$): δ 3.19 (s, 6H), 6.63 (d, 1H), 7.12-7.19 (m, 2H), 7.51-7.68 (m, 5H), 8.05-8.13 (m, 2H), 8.36-8.47 (m, 2H), 8.62-8.67 (m, 3H), 8.71-8.73 (m, 1H), 8.75-8.78 (m, 1H), 9.45 (s, 1H).

Example 21-51

1-(2-{4-[5-(dimethylamino)pyrazolo[1,5-a]pyrimidin-3-yl]phenoxy}-5-pyrimidinyl)-3-[2-(1-methyl-1H-pyrazol-5-yl)-5-(trifluoromethyl)phenyl]urea

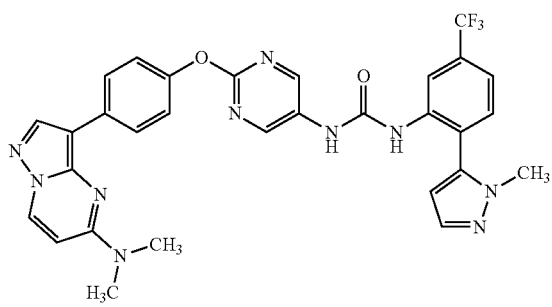 [SMILES: CN(C)c1ccn2ncc(-c3ccc(Oc4ncc(NC(=O)Nc5cc(C(F)(F)F)ccc5-c5ccnn5C)cn4)cc3)c2n1]

Purity (LC-MS/ELSD): 100% (Retention Time: 0.98 minutes);
MASS (ESI, Pos.): 615 (M+H)$^+$;
$^1$H-NMR (DMSO-d$_6$): δ 3.19 (s, 6H), 3.65 (s, 3H), 6.45 (d, 1H), 6.63 (d, 1H), 7.13-7.19 (m, 2H), 7.44-7.54 (m, 2H), 7.62 (d, 1H), 8.06-8.14 (m, 3H), 8.38 (s, 1H), 8.56 (s, 1H), 8.63-8.68 (m, 3H), 9.47 (s, 1H).

Example 21-52

1-(2-{4-[5-(dimethylamino)pyrazolo[1,5-a]pyrimidin-3-yl]phenoxy}-5-pyrimidinyl)-3-[2-(3-methyl-1H-pyrazol-1-yl)-5-(trifluoromethyl)phenyl]urea Purity (LC-MS/ELSD): 100% (Retention Time: 1.04 minutes);
MASS (ESI, Pos.): 615 (M+H)$^+$;
$^1$H-NMR (DMSO-d$_6$): δ 2.37 (s, 3H), 3.19 (s, 6H), 6.45 (d, 1H), 6.63 (d, 1H), 7.14-7.21 (m, 2H), 7.48 (dd, 1H), 7.69 (d, 1H), 8.07-8.14 (m, 2H), 8.28 (d, 1H), 8.39 (s, 1H), 8.57 (d, 1H), 8.63-8.70 (m, 3H), 9.80 (s, 1H), 9.89 (s, 1H).

Example 21-53

1-(2-{4-[5-(dimethylamino)pyrazolo[1,5-a]pyrimidin-3-yl]phenoxy}-5-pyrimidinyl)-3-{5-(trifluoromethyl)-2-[3-(trifluoromethyl)-1H-pyrazol-1-yl]phenyl}urea Purity (LC-MS/ELSD): 100% (Retention Time: 1.07 minutes);
MASS (ESI, Pos.): 669 (M+H)$^+$;
$^1$H-NMR (DMSO-d$_6$): δ 3.19 (s, 6H), 6.63 (d, 1H), 7.10-7.20 (m, 3H), 7.58 (dd, 1H), 7.70 (d, 1H), 8.07-8.14 (m, 2H), 8.38 (s, 1H), 8.45-8.50 (m, 2H), 8.57 (s, 1H), 8.63-8.67 (m, 3H), 9.45 (s, 1H).

Example 21-54

1-[2-(4-chloro-1H-pyrazol-1-yl)-5-(trifluoromethyl)phenyl]-3-(2-{4-[5-(dimethylamino)pyrazolo[1,5-a]pyrimidin-3-yl]phenoxy}-5-pyrimidinyl)urea Purity (LC-MS/ELSD): 100% (Retention Time: 1.06 minutes);
MASS (ESI, Pos.): 635 (M+H)$^+$;
$^1$H-NMR (DMSO-d$_6$): δ 3.19 (s, 6H), 6.63 (d, 1H), 7.14-7.20 (m, 2H), 7.53 (dd, 1H), 7.70 (d, 1H), 8.06-8.14 (m, 3H), 8.39 (s, 1H), 8.56-8.71 (m, 5H), 9.09 (s, 1H), 9.78 (s, 1H).

Example 21-55

1-(2-{4-[5-(dimethylamino)pyrazolo[1,5-a]pyrimidin-3-yl]phenoxy}-5-pyrimidinyl)-3-{5-(trifluoromethyl)-2-[3-(trifluoromethyl)-1H-1,2,4-triazol-1-yl]phenyl}urea Purity (LC-MS/ELSD): 100% (Retention Time: 1.02 minutes);
MASS (ESI, Pos.): 670 (M+H)$^+$;
$^1$H-NMR (DMSO-d$_6$): δ 3.19 (s, 6H), 6.63 (d, 1H), 7.13-7.20 (m, 2H), 7.60-7.65 (m, 1H), 7.81 (d, 1H), 8.05-8.14 (m, 2H), 8.38 (s, 1H), 8.50 (d, 1H), 8.57-8.68 (m, 4H), 9.21 (s, 1H), 9.33 (s, 1H).

Example 21-56

1-[5-chloro-2-(2H-1,2,3-triazol-2-yl)phenyl]-3-(2-{4-[5-(dimethylamino)pyrazolo[1,5-a]pyrimidin-3-yl]phenoxy}-5-pyrimidinyl)urea Purity (LC-MS/ELSD): 100% (Retention Time: 1.02 minutes);
MASS (ESI, Pos.): 568 (M+H)$^+$;
$^1$H-NMR (DMSO-d$_6$): δ 3.19 (s, 6H), 6.63 (d, 1H), 7.13-7.21 (m, 2H), 7.29 (dd, 1H), 7.80 (d, 1H), 8.07-8.14 (m, 2H), 8.26 (s, 2H), 8.32 (d, 1H), 8.38 (s, 1H), 8.64 (d, 1H), 8.68 (s, 2H), 9.36 (s, 1H), 9.90 (s, 1H).

Example 21-57

1-[5-chloro-2-(3-pyridinyl)phenyl]-3-(2-{4-[5-(dimethylamino)pyrazolo[1,5-a]pyrimidin-3-yl]phenoxy}-5-pyrimidinyl)urea Purity (LC-MS/ELSD): 100% (Retention Time: 0.83 minutes);
MASS (ESI, Pos.): 578 (M+H)$^+$;
$^1$H-NMR (DMSO-d$_6$): δ 3.19 (s, 6H), 6.62 (d, 1H), 7.15 (d, 2H), 7.21-7.30 (m, 2H), 7.49-7.55 (m, 1H), 7.80-7.85 (m, 1H), 8.06-8.12 (m, 4H), 8.38 (s, 1H), 8.56-8.66 (m, 5H), 9.17 (s, 1H).

Example 21-58

1-(2-{4-[5-(dimethylamino)pyrazolo[1,5-a]pyrimidin-3-yl]phenoxy}-5-pyrimidinyl)-3-[2-(1H-pyrazol-1-yl)-4-(trifluoromethyl)phenyl]urea Purity (LC-MS/ELSD): 100% (Retention Time: 1.02 minutes);
MASS (ESI, Pos.): 601 (M+H)$^+$;
$^1$H-NMR (DMSO-d$_6$): δ 3.19 (s, 6H), 6.60-6.68 (m, 2H), 7.16 (d, 2H), 7.74 (dd, 1H), 7.80-7.85 (m, 1H), 7.92-7.95 (m, 1H), 8.10 (d, 2H), 8.37-8.46 (m, 3H), 8.61-8.69 (m, 3H), 9.55 (s, 1H), 9.94 (s, 1H).

Example 21-59

1-(2-{4-[5-(dimethylamino)pyrazolo[1,5-a]pyrimidin-3-yl]phenoxy}-5-pyrimidinyl)-3-[2-fluoro-4-(trifluoromethyl)phenyl]urea Purity (LC-MS/ELSD): 100% (Retention Time: 1.00 minute);
MASS (ESI, Pos.): 553 (M+H)$^+$;
$^1$H-NMR (DMSO-d$_6$): δ 3.16 (s, 6H), 6.62 (d, 1H), 7.17 (d, 2H), 7.54 (d, 1H), 7.70 (d, 1H), 8.06-8.16 (m, 2H), 8.32-8.42 (m, 2H), 8.64 (d, 1H), 8.72 (s, 2H), 9.17 (s, 1H), 9.40 (s, 1H).

Example 21-60

1-(2-{4-[5-(dimethylamino)pyrazolo[1,5-a]pyrimidin-3-yl]phenoxy}-5-pyrimidinyl)-3-[3-(trifluoromethyl)phenyl]urea Purity (LC-MS/ELSD): 100% (Retention Time: 0.97 minutes);
MASS (ESI, Pos.): 535 (M+H)$^+$;
$^1$H-NMR (DMSO-d$_6$): δ 3.19 (s, 6H), 6.63 (d, 1H), 7.17 (d, 2H), 7.32 (d, 1H), 7.51 (t, 1H), 7.62 (d, 1H), 7.97 (s, 1H), 8.10 (d, 2H), 8.39 (s, 1H), 8.64 (d, 1H), 8.70 (s, 2H), 8.96 (s, 1H), 9.31 (s, 1H).

Example 21-61

1-[2-chloro-5-(trifluoromethyl)phenyl]-3-(2-{4-[5-(dimethylamino)pyrazolo[1,5-a]pyrimidin-3-yl]phenoxy}-5-pyrimidinyl)urea Purity (LC-MS/ELSD): 100% (Retention Time: 1.03 minutes);
MASS (ESI, Pos.): 569 (M+H)$^+$;
$^1$H-NMR (DMSO-d$_6$): δ 3.19 (s, 6H), 6.63 (d, 1H), 7.17 (d, 2H), 7.39 (d, 1H), 7.72 (d, 1H), 8.11 (d, 2H), 8.39 (s, 1H), 8.57 (d, 1H), 8.65 (d, 1H), 8.72 (s, 2H), 8.78 (s, 1H), 9.69 (s, 1H).

Example 21-62

1-(2-{4-[5-(dimethylamino)pyrazolo[1,5-a]pyrimidin-3-yl]phenoxy}-5-pyrimidinyl)-3-[2-methyl-5-(trifluoromethyl)phenyl]urea TLC: Rf 0.18 (Hexane:Ethyl acetate=1:4);
$^1$H-NMR (DMSO-d$_6$): δ 2.32 (s, 3H), 3.19 (s, 6H), 6.62 (d, 1H), 7.16 (d, 2H), 7.29 (d, 1H), 7.41 (d, 1H), 8.10 (d, 2H), 8.27 (s, 1H), 8.37 (d, 2H), 8.64 (d, 1H), 8.71 (s, 2H), 9.30 (s, 1H).

Example 21-63

1-(2-{4-[5-(dimethylamino)pyrazolo[1,5-a]pyrimidin-3-yl]phenoxy}-5-pyrimidinyl)-3-[2-fluoro-5-(trifluoromethyl)phenyl]urea Purity (LC-MS/ELSD): 100% (Retention Time: 0.99 minutes);
MASS (ESI, Pos.): 553 (M+H)$^+$;
$^1$H-NMR (DMSO-d$_6$): δ 3.19 (s, 6H), 6.62 (d, 1H), 7.16 (d, 2H), 7.36-7.43 (m, 1H), 7.45-7.54 (m, 1H), 8.10 (d, 2H), 8.38 (s, 1H), 8.49-8.56 (m, 1H), 8.64 (d, 1H), 8.71 (s, 2H), 9.08 (s, 1H), 9.27 (s, 1H).

Example 21-64

1-(2,4-dichlorophenyl)-3-(2-{4-[5-(dimethylamino)pyrazolo[1,5-a]pyrimidin-3-yl]phenoxy}-5-pyrimidinyl)urea Purity (LC-MS/ELSD): 100% (Retention Time: 1.01 minutes);
MASS (ESI, Pos.): 535 (M+H)$^+$;
$^1$H-NMR (DMSO-d$_6$): δ 3.19 (s, 6H), 6.62 (d, 1H), 7.16 (d, 2H), 7.38 (dd, 1H), 7.62 (d, 1H), 8.09 (d, 2H), 8.13 (d, 1H), 8.38 (s, 1H), 8.56 (s, 1H), 8.64 (d, 1H), 8.70 (s, 2H), 9.56 (s, 1H).

Example 21-65

1-{2-[4-(5-methylpyrazolo[1,5-a]pyrimidin-3-yl)phenoxy]-5-pyrimidinyl}-3-[2-(3-pyridinyl)-5-(trifluoromethyl)phenyl]urea

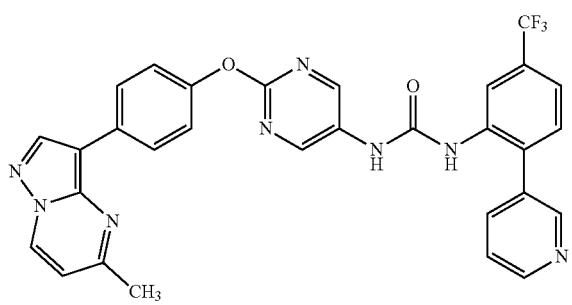 [SMILES: Cc1ccn2ncc(-c3ccc(Oc4ncc(NC(=O)Nc5cc(C(F)(F)F)ccc5-c5cccnc5)cn4)cc3)c2n1]

TLC: Rf 0.43 (Methylene chloride:Methanol=9:1);
$^1$H-NMR (DMSO-$d_6$): δ 2.60 (s, 3H), 6.99 (d, 1H), 7.23 (d, 2H), 7.45-7.59 (m, 3H), 7.89 (d, 1H), 8.14 (d, 2H), 8.23 (s, 1H), 8.39 (s, 1H), 8.61-8.72 (m, 5H), 9.00 (d, 1H), 9.23 (s, 1H).

Example 21-66

1-(2-{4-[5-(ethylamino)pyrazolo[1,5-a]pyrimidin-3-yl]phenoxy}-5-pyrimidinyl)-3-[2-(3-pyridinyl)-5-(trifluoromethyl)phenyl]urea TLC: Rf 0.31 (Chloroform:Methanol=19:1);
$^1$H-NMR (DMSO-$d_6$): δ 1.22 (t, 3H), 3.38-3.47 (m, 2H), 6.26 (d, 1H), 7.11-7.18 (m, 2H), 7.46-7.65 (m, 4H), 7.86-7.92 (m, 1H), 8.04-8.11 (m, 2H), 8.23 (s, 1H), 8.31 (s, 1H), 8.37-8.41 (m, 1H), 8.46 (d, 1H), 8.61-8.69 (m, 4H), 9.22 (s, 1H).

Example 21-67

1-(2-{4-[5-(ethylamino)pyrazolo[1,5-a]pyrimidin-3-yl]phenoxy}-5-pyrimidinyl)-3-[3'-methyl-4-(trifluoromethyl)-2-biphenylyl]urea

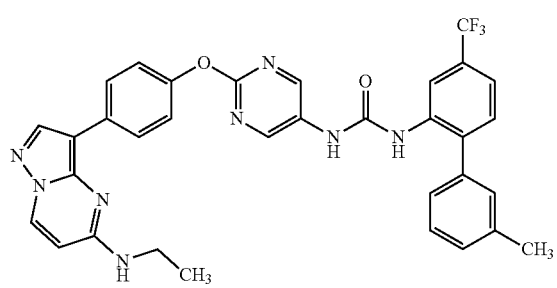 [SMILES: CCNc1ccn2ncc(-c3ccc(Oc4ncc(NC(=O)Nc5cc(C(F)(F)F)ccc5-c5cccc(C)c5)cn4)cc3)c2n1]

TLC: Rf 0.36 (Chloroform:Methanol=19:1);
$^1$H-NMR (DMSO-$d_6$): δ 1.22 (t, 3H), 2.38 (s, 3H), 3.36-3.48 (m, 2H), 6.26 (d, 1H), 7.11-7.46 (m, 8H), 7.60 (t, 1H), 8.00-8.11 (m, 3H), 8.30 (s, 1H), 8.42-8.48 (m, 2H), 8.63 (s, 2H), 9.39 (s, 1H).

Example 21-68

1-(2-{4-[5-(1-azetidinyl)pyrazolo[1,5-a]pyrimidin-3-yl]phenoxy}-5-pyrimidinyl)-3-[2-(methylsulfonyl)-5-(trifluoromethyl)phenyl]urea TLC: Rf 0.43 (Chloroform:Methanol=19:1);
$^1$H-NMR (DMSO-$d_6$): δ 2.32-2.44 (m, 2H), 3.38 (s, 3H), 4.10-4.20 (m, 4H), 6.24 (d, 1H), 7.13-7.20 (m, 2H), 7.61-7.66 (m, 1H), 8.04-8.11 (m, 3H), 8.38 (s, 1H), 8.61-8.67 (m, 2H), 8.73 (s, 2H), 8.96 (s, 1H), 10.27 (s, 1H).

Example 21-69

1-(2-{4-[5-(dimethylamino)pyrazolo[1,5-a]pyrimidin-3-yl]phenoxy}-5-pyrimidinyl)-3-[2-(methylsulfonyl)-5-(trifluoromethyl)phenyl]urea TLC: Rf 0.48 (Ethyl acetate);
$^1$H-NMR (DMSO-$d_6$): δ 3.19 (s, 6H), 3.38 (s, 3H), 6.63 (d, 1H), 7.15-7.22 (m, 2H), 7.61-7.69 (m, 1H), 8.05-8.15 (m, 3H), 8.39 (s, 1H), 8.63-8.68 (m, 2H), 8.73 (s, 2H), 8.96 (s, 1H), 10.27 (s, 1H).

Example 21-70

1-(2-{4-[5-(dimethylamino)pyrazolo[1,5-a]pyrimidin-3-yl]phenoxy}-5-pyrimidinyl)-3-[4-(trifluoromethyl)-2-biphenylyl]urea

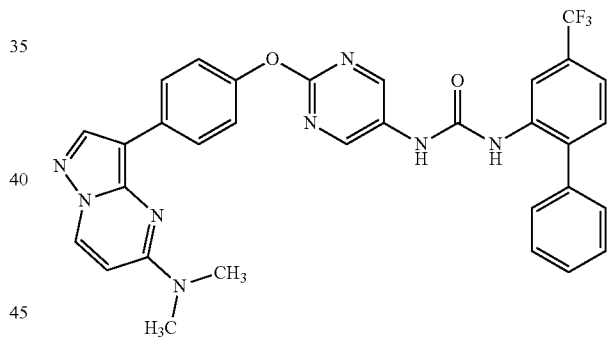

Purity (LC-MS/ELSD): 100% (Retention Time: 1.09 minutes);
MASS (ESI, Pos.): 611 (M+H)$^+$;
$^1$H-NMR (DMSO-$d_6$): δ 3.19 (s, 6H), 6.62 (d, 1H), 7.15 (d, 2H), 7.40-7.58 (m, 7H), 8.06-8.12 (m, 3H), 8.38 (s, 1H), 8.41 (s, 1H), 8.61-8.66 (m, 3H), 9.36 (s, 1H).

Example 21-71

1-(2-{4-[5-(dimethylamino)pyrazolo[1,5-a]pyrimidin-3-yl]phenoxy}-5-pyrimidinyl)-3-[4'-methyl-4-(trifluoromethyl)-2-biphenylyl]urea Purity (LC-MS/ELSD): 100% (Retention Time: 1.13 minutes);
MASS (ESI, Pos.): 625 (M+H)$^+$;
$^1$H-NMR (DMSO-$d_6$): δ 2.39 (s, 3H), 3.19 (s, 6H), 6.62 (d, 1H), 7.15 (d, 2H), 7.28-7.47 (m, 6H), 8.03 (s, 1H), 8.09 (d, 2H), 8.38 (s, 1H), 8.43 (s, 1H), 8.61-8.66 (m, 3H), 9.39 (s, 1H).

Example 21-72

1-(2-{4-[5-(dimethylamino)pyrazolo[1,5-a]pyrimidin-3-yl]phenoxy}-5-pyrimidinyl)-3-[4'-ethyl-4-(trifluoromethyl)-2-biphenylyl]urea Purity (LC-MS/ELSD): 100% (Retention Time: 1.16 minutes);

MASS (ESI, Pos.): 639 (M+H)⁺;

¹H-NMR (DMSO-d₆): δ 1.24 (t, 3H), 2.68 (q, 2H), 3.19 (s, 6H), 6.62 (d, 1H), 7.14 (d, 2H), 7.35-7.49 (m, 6H), 8.03-8.12 (m, 3H), 8.38 (s, 1H), 8.41 (s, 1H), 8.61-8.66 (m, 3H), 9.38 (s, 1H).

Example 21-73

1-(2-{4-[5-(dimethylamino)pyrazolo[1,5-a]pyrimidin-3-yl]phenoxy}-5-pyrimidinyl)-3-[3'-methyl-4-(trifluoromethyl)-2-biphenylyl]urea

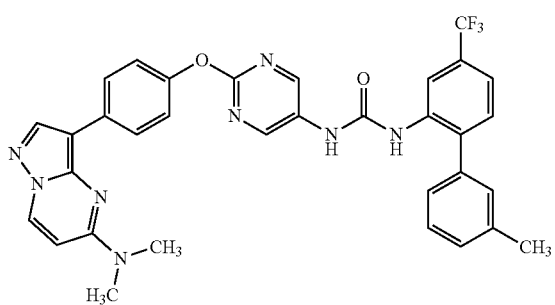 [SMILES: Cc1cccc(-c2ccc(C(F)(F)F)cc2NC(=O)Nc2cnc(Oc3ccc(-c4cnn5ccc(N(C)C)nc45)cc3)nc2)c1]

Purity (LC-MS/ELSD): 100% (Retention Time: 1.13 minutes);

MASS (ESI, Pos.): 625 (M+H)⁺;

¹H-NMR (DMSO-d₆): δ 2.38 (s, 3H), 3.19 (s, 6H), 6.62 (d, 1H), 7.14 (d, 2H), 7.19-7.32 (m, 3H), 7.36-7.47 (m, 3H), 8.02 (s, 1H), 8.09 (s, 1H), 8.11 (s, 1H), 8.38 (s, 1H), 8.44 (s, 1H), 8.64 (s, 2H), 8.66 (s, 1H), 9.40 (s, 1H).

Example 21-74

1-(2-{4-[5-(dimethylamino)pyrazolo[1,5-a]pyrimidin-3-yl]phenoxy}-5-pyrimidinyl)-3-[3'-ethyl-4-(trifluoromethyl)-2-biphenylyl]urea Purity (LC-MS/ELSD): 100% (Retention Time: 1.17 minutes);

MASS (ESI, Pos.): 639 (M+H)⁺;

¹H-NMR (DMSO-d₆): δ 1.22 (t, 3H), 2.68 (q, 2H), 3.19 (s, 6H), 6.62 (d, 1H), 7.15 (d, 2H), 7.22-7.36 (m, 3H), 7.40-7.49 (m, 3H), 8.05 (s, 1H), 8.10 (d, 2H), 8.38 (s, 1H), 8.40 (s, 1H), 8.63 (s, 2H), 8.66 (s, 1H), 9.38 (s, 1H).

Example 21-75

1-(2-{4-[5-(dimethylamino)pyrazolo[1,5-a]pyrimidin-3-yl]phenoxy}-5-pyrimidinyl)-3-[2'-methyl-4-(trifluoromethyl)-2-biphenylyl]urea

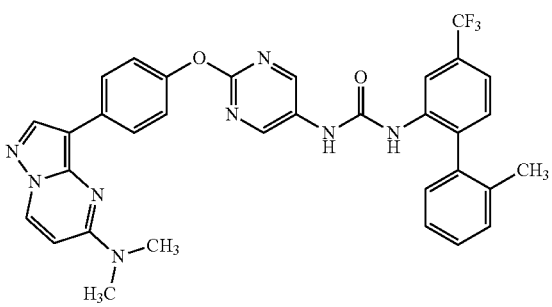 [SMILES: Cc1ccccc1-c1ccc(C(F)(F)F)cc1NC(=O)Nc1cnc(Oc2ccc(-c3cnn4ccc(N(C)C)nc34)cc2)nc1]

Purity (LC-MS/ELSD): 100% (Retention Time: 1.14 minutes);

MASS (ESI, Pos.): 625 (M+H)⁺;

¹H-NMR (DMSO-d₆): δ 2.04 (s, 3H), 3.19 (s, 6H), 6.62 (d, 1H), 7.10-7.22 (m, 3H), 7.26-7.46 (m, 5H), 7.70 (s, 1H), 8.09 (d, 2H), 8.38 (s, 1H), 8.53 (s, 1H), 8.62 (s, 2H), 8.65 (s, 1H), 9.42 (s, 1H).

Example 21-76

1-(2-{4-[5-(dimethylamino)pyrazolo[1,5-a]pyrimidin-3-yl]phenoxy}-5-pyrimidinyl)-3-[3',4'-dimethyl-4-(trifluoromethyl)-2-biphenylyl]urea Purity (LC-MS/ELSD): 100% (Retention Time: 1.17 minutes);

MASS (ESI, Pos.): 639 (M+H)⁺;

¹H-NMR (DMSO-d₆): δ 2.29 (s, 6H), 3.19 (s, 6H), 6.62 (d, 1H), 7.12-7.19 (m, 3H), 7.19-7.22 (m, 1H), 7.30 (d, 1H), 7.36 (d, 1H), 7.42 (dd, 1H), 8.00 (s, 1H), 8.09 (d, 2H), 8.38 (s, 1H), 8.44-8.48 (m, 1H), 8.62-8.67 (m, 3H), 9.42 (s, 1H).

Example 21-77

1-(2-{4-[5-(methylamino)pyrazolo[1,5-a]pyrimidin-3-yl]phenoxy}-5-pyrimidinyl)-3-[2-(methylsulfonyl)-4-(trifluoromethyl)phenyl]urea Purity (LC-MS/ELSD): 100% (Retention Time: 0.93 minutes);

MASS (ESI, Pos.): 599 (M+H)⁺;

¹H-NMR (DMSO-d₆): δ 2.93 (d, 3H), 3.41 (s, 3H), 6.27 (d, 1H), 7.17 (d, 2H), 7.56-7.67 (m, 1H), 8.03-8.17 (m, 4H), 8.32 (s, 1H), 8.43-8.55 (m, 2H), 8.73 (s, 2H), 9.03 (s, 1H), 10.33 (s, 1H).

Example 21-78

1-(2-{4-[5-(methylamino)pyrazolo[1,5-a]pyrimidin-3-yl]phenoxy}-5-pyrimidinyl)-3-[2'-methyl-4-(trifluoromethyl)-2-biphenylyl]urea TLC: Rf 0.38 (Chloroform:Methanol=19:1);

¹H-NMR (DMSO-d₆): δ 2.04 (s, 3H), 2.92 (d, 3H), 6.28 (d, 1H), 7.11-7.45 (m, 8H), 7.56-7.73 (m, 2H), 8.06-8.13 (m,

2H), 8.31 (s, 1H), 8.46 (d, 1H), 8.51-8.54 (m, 1H), 8.62 (s, 2H), 9.42 (s, 1H).

Example 21-79

1-(2-{4-[5-(methylamino)pyrazolo[1,5-a]pyrimidin-3-yl]phenoxy}-5-pyrimidinyl)-3-[2-(3-pyridinyl)-5-(trifluoromethyl)phenyl]urea TLC: Rf 0.30 (Chloroform:Methanol=19:1);
$^1$H-NMR (DMSO-$d_6$): δ 2.92 (d, 3H), 6.27 (d, 1H), 7.11-7.18 (m, 2H), 7.46-7.65 (m, 4H), 7.89 (dt, 1H), 8.06-8.14 (m, 2H), 8.23 (s, 1H), 8.31 (s, 1H), 8.39 (s, 1H), 8.46 (d, 1H), 8.61-8.69 (m, 4H), 9.22 (s, 1H).

Example 21-80

1-(2-{4-[5-(methylamino)pyrazolo[1,5-a]pyrimidin-3-yl]phenoxy}-5-pyrimidinyl)-3-[4-(trifluoromethyl)-2-biphenylyl]urea TLC: Rf 0.42 (Chloroform:Methanol=19:1);
$^1$H-NMR (DMSO-$d_6$): δ 2.92 (d, 3H), 6.26 (d, 1H), 7.11-7.17 (m, 2H), 7.38-7.64 (m, 8H), 8.04-8.12 (m, 3H), 8.31 (s, 1H), 8.39-8.42 (m, 1H), 8.46 (d, 1H), 8.63 (s, 2H), 9.35 (s, 1H).

Example 21-81

1-(2-{4-[5-(dimethylamino)pyrazolo[1,5-a]pyrimidin-3-yl]phenoxy}-5-pyrimidinyl)-3-[2-(methylsulfinyl)-5-(trifluoromethyl)phenyl]urea TLC: Rf 0.14 (Ethyl acetate);
$^1$H-NMR (DMSO-$d_6$): δ 2.89 (s, 3H), 3.19 (s, 6H), 6.62 (d, 1H), 7.15 (d, 2H), 7.64 (d, 1H), 7.90 (d, 1H), 8.09 (d, 2H), 8.26 (s, 1H), 8.38 (s, 1H), 8.63 (d, 2H), 8.70 (s, 2H), 9.22 (s, 1H), 9.65 (s, 1H).

Example 21-82

1-(2-{4-[5-(dimethylamino)pyrazolo[1,5-a]pyrimidin-3-yl]phenoxy}-5-pyrimidinyl)-3-[3'-(1-hydroxyethyl)-4-(trifluoromethyl)-2-biphenylyl]urea Purity (LC-MS/ELSD): 99% (Retention Time: 1.07 minutes);
MASS (ESI, Pos.): 655 (M+H)$^+$;
$^1$H-NMR (DMSO-$d_6$): δ 1.36 (d, 3H), 3.19 (s, 6H), 4.74-4.83 (m, 1H), 5.20-5.23 (m, 1H), 6.62 (d, 1H), 7.15 (d, 2H), 7.27-7.36 (m, 1H), 7.38-7.56 (m, 5H), 8.04-8.26 (m, 3H), 8.37 (s, 1H), 8.38 (s, 1H), 8.63 (s, 2H), 8.66 (s, 1H), 9.36 (s, 1H).

Example 21-83

1-{2-[4-(5-methoxypyrazolo[1,5-a]pyrimidin-3-yl)phenoxy]-5-pyrimidinyl}-3-[2-(1H-pyrazol-1-yl)-4-(trifluoromethyl)phenyl]urea Purity (LC-MS/ELSD): 100% (Retention Time: 1.05 minutes);
MASS (ESI, Pos.): 588 (M+H)$^+$;
$^1$H-NMR (DMSO-$d_6$): δ 4.03 (s, 3H), 6.61 (d, 1H), 6.65-6.66 (m, 1H), 7.20-7.25 (m, 2H), 7.73-7.83 (m, 2H), 7.93 (d, 1H), 8.00-8.13 (m, 2H), 8.41-8.44 (m, 2H), 8.58 (s, 1H), 8.69 (s, 2H), 8.93 (d, 1H), 9.56 (brs, 1H), 9.95 (brs, 1H).

Example 21-84

1-[3-(difluoromethyl)phenyl]-3-{2-[4-(5-methoxypyrazolo[1,5-a]pyrimidin-3-yl)phenoxy]-5-pyrimidinyl}urea Purity (LC-MS/ELSD): 100% (Retention Time: 0.92 minutes);
MASS (ESI, Pos.): 504 (M+H)$^+$;
$^1$H-NMR (DMSO-$d_6$): δ 4.03 (s, 3H), 6.61 (d, 1H), 7.00-7.24 (m, 4H), 7.42 (t, 1H), 7.52 (d, 1H), 7.78 (s, 1H), 8.10-8.13 (m, 2H), 8.59 (s, 1H), 8.71 (s, 2H), 8.90-8.95 (m, 2H), 9.16 (s, 1H).

Example 21-85

1-(2,5-dichlorophenyl)-3-{2-[4-(5-methoxypyrazolo[1,5-a]pyrimidin-3-yl)phenoxy]-5-pyrimidinyl}urea Purity (LC-MS/ELSD): 100% (Retention Time: 1.04 minutes);
MASS (ESI, Pos.): 522 (M+H)$^+$;
$^1$H-NMR (DMSO-$d_6$): δ 4.03 (s, 3H), 6.61 (d, 1H), 7.12 (dd, 1H), 7.21-7.26 (m, 2H), 7.51 (d, 1H), 8.09-8.14 (m, 2H), 8.26 (s, 1H), 8.59 (s, 1H), 8.63 (s, 1H), 8.72 (s, 2H), 8.93 (d, 1H), 9.66 (s, 1H).

Example 21-86

1-(2,5-difluorophenyl)-3-{2-[4-(5-methoxypyrazolo[1,5-a]pyrimidin-3-yl)phenoxy]-5-pyrimidinyl}urea Purity (LC-MS/ELSD): 100% (Retention Time: 0.94 minutes);
MASS (ESI, Pos.): 490 (M+H)$^+$;
$^1$H-NMR (DMSO-$d_6$): δ 4.03 (s, 3H), 6.61 (d, 1H), 6.81-6.89 (m, 1H), 7.21-7.34 (m, 3H), 7.93-8.00 (m, 1H), 8.10-8.14 (m, 2H), 8.59 (s, 1H), 8.72 (s, 2H), 8.92-8.96 (m, 2H), 9.25 (s, 1H).

Example 21-87

1-[2-chloro-4-(trifluoromethyl)phenyl]-3-{2-[4-(5-methoxypyrazolo[1,5-a]pyrimidin-3-yl)phenoxy]-5-pyrimidinyl}urea Purity (LC-MS/ELSD): 100% (Retention Time: 1.06 minutes);
MASS (ESI, Pos.): 556 (M+H)$^+$;
$^1$H-NMR (DMSO-$d_6$): δ 4.03 (s, 3H), 6.61 (d, 1H), 7.22-7.26 (m, 2H), 7.69 (dd, 1H), 7.89 (d, 1H), 8.00-8.14 (m, 2H), 8.43 (d, 1H), 8.59 (s, 1H), 8.73 (s, 2H), 8.79 (s, 1H), 8.93 (d, 1H), 9.76 (s, 1H).

Example 21-88

1-{2-[4-(5-methoxypyrazolo[1,5-a]pyrimidin-3-yl)phenoxy]-5-pyrimidinyl}-3-[2-(4-methyl-1H-1,2,3-triazol-1-yl)-5-(trifluoromethyl)phenyl]urea Purity (LC-MS/ELSD): 100% (Retention Time: 1.00 minute);
MASS (ESI, Pos.): 603 (M+H)$^+$;
$^1$H-NMR (DMSO-$d_6$): δ 2.38 (s, 3H), 4.03 (s, 3H), 6.62 (d, 1H), 7.20-7.24 (m, 2H), 7.58-7.71 (m, 2H), 8.08-8.13 (m, 2H), 8.33 (s, 1H), 8.51-8.60 (m, 2H), 8.67 (s, 2H), 8.75 (s, 1H), 8.93 (d, 1H), 9.68 (s, 1H).

Example 21-89

1-[5-chloro-2-(1H-pyrazol-1-yl)phenyl]-3-{2-[4-(5-methoxypyrazolo[1,5-a]pyrimidin-3-yl)phenoxy]-5-pyrimidinyl}urea Purity (LC-MS/ELSD): 100% (Retention Time: 1.05 minutes);
MASS (ESI, Pos.): 554 (M+H)$^+$;
$^1$H-NMR (DMSO-d$_6$): δ 4.03 (s, 3H), 6.59-6.62 (m, 2H), 7.19-7.24 (m, 3H), 7.51 (d, 1H), 7.89 (d, 1H), 8.08-8.12 (m, 2H), 8.26 (d, 1H), 8.27 (d, 1H), 8.58 (s, 1H), 8.67 (s, 2H), 8.92 (d, 1H), 9.36 (s, 1H), 9.87 (s, 1H).

Example 21-90

1-(2-{4-[5-(3-oxetanyloxy)pyrazolo[1,5-a]pyrimidin-3-yl]phenoxy}-5-pyrimidinyl)-3-[2-(3-pyridinyl)-5-(trifluoromethyl)phenyl]urea Purity (LC-MS/ELSD): 94% (Retention Time: 0.89 minutes);
MASS (ESI, Pos.): 641 (M+H)$^+$;
$^1$H-NMR (DMSO-d$_6$): δ 4.67-4.71 (m, 2H), 4.99 (t, 2H), 5.71-5.79 (m, 1H), 6.69 (d, 1H), 7.21-7.26 (m, 2H), 7.47-7.58 (m, 3H), 7.83-7.91 (m, 1H), 8.00-8.04 (m, 2H), 8.24 (s, 1H), 8.39 (s, 1H), 8.60 (s, 1H), 8.64-8.69 (m, 4H), 9.00 (d, 1H), 9.24 (s, 1H).

Example 21-91

1-[5-chloro-2-(1H-1,2,3-triazol-1-yl)phenyl]-3-{2-[4-(5-methoxypyrazolo[1,5-a]pyrimidin-3-yl)phenoxy]-5-pyrimidinyl}urea Purity (LC-MS/ELSD): 100% (Retention Time: 0.95 minutes);
MASS (ESI, Pos.): 555 (M+H)$^+$;
$^1$H-NMR (DMSO-d$_6$): δ 4.03 (s, 3H), 6.61 (d, 1H), 7.22 (d, 2H), 7.31 (dd, 1H), 7.51 (d, 1H), 8.06-8.12 (m, 3H), 8.27 (d, 1H), 8.49 (s, 1H), 8.59 (s, 1H), 8.65 (s, 2H), 8.70 (s, 1H), 8.93 (d, 1H), 9.58 (s, 1H).

Example 21-92

1-(2-{4-[5-(1-azetidinyl)pyrazolo[1,5-a]pyrimidin-3-yl]phenoxy}-5-pyrimidinyl)-3-{5-(trifluoromethyl)-2-[3-(trifluoromethyl)-1H-pyrazol-1-yl]phenyl}urea Purity (LC-MS/ELSD): 99% (Retention Time: 1.10 minutes);
MASS (ESI, Pos.): 681 (M+H)$^+$;
$^1$H-NMR (DMSO-d$_6$): δ 2.32-2.42 (m, 2H), 4.15 (t, 4H), 6.23 (d, 1H), 7.12-7.17 (m, 3H), 7.58 (dd, 1H), 7.70 (d, 1H), 8.04-8.09 (m, 2H), 8.37 (s, 1H), 8.48 (s, 2H), 8.57 (s, 1H), 8.62-8.65 (m, 3H), 9.45 (s, 1H).

Example 21-93

1-(2-{4-[5-(1-azetidinyl)pyrazolo[1,5-a]pyrimidin-3-yl]phenoxy}-5-pyrimidinyl)-3-[2-(4-methyl-1H-pyrazol-1-yl)-5-(trifluoromethyl)phenyl]urea Purity (LC-MS/ELSD): 98% (Retention Time: 1.10 minutes);
MASS (ESI, Pos.): 627 (M+H)$^+$;
$^1$H-NMR (DMSO-d$_6$): δ 2.15 (s, 3H), 2.32-2.42 (m, 2H), 4.15 (t, 4H), 6.24 (d, 1H), 7.15 (d, 2H), 7.49 (dd, 1H), 7.70 (d, 1H), 7.78 (s, 1H), 8.05-8.09 (m, 2H), 8.18 (s, 1H), 8.37 (s, 1H), 8.58 (d, 1H), 8.62-8.68 (m, 3H), 9.82 (s, 1H), 9.94 (s, 1H).

Example 21-94

1-(2-{4-[5-(1-azetidinyl)pyrazolo[1,5-a]pyrimidin-3-yl]phenoxy}-5-pyrimidinyl)-3-[2-(3-pyridinyl)-4-(trifluoromethyl)phenyl]urea Purity (LC-MS/ELSD): 97% (Retention Time: 0.93 minutes);
MASS (ESI, Pos.): 624 (M+H)$^+$;
$^1$H-NMR (DMSO-d$_6$): δ 2.32-2.42 (m, 2H), 4.15 (t, 4H), 6.24 (d, 1H), 7.11-7.16 (m, 2H), 7.53-7.58 (m, 2H), 7.76 (dd, 1H), 7.88-7.92 (m, 1H), 8.06 (d, 2H), 8.23 (s, 1H), 8.28 (d, 1H), 8.37 (s, 1H), 8.62-8.68 (m, 5H), 9.27 (s, 1H).

Example 21-95

1-(2-{4-[5-(1-azetidinyl)pyrazolo[1,5-a]pyrimidin-3-yl]phenoxy}-5-pyrimidinyl)-3-[5-chloro-2-(1H-pyrazol-1-yl)phenyl]urea Purity (LC-MS/ELSD): 100% (Retention Time: 1.03 minutes);
MASS (ESI, Pos.): 579 (M+H)$^+$;
$^1$H-NMR (DMSO-d$_6$): δ 2.32-2.42 (m, 2H), 4.15 (t, 4H), 6.24 (d, 1H), 6.62 (t, 1H), 7.13-7.17 (m, 2H), 7.22 (dd, 1H), 7.51 (d, 1H), 7.89 (d, 1H), 8.04-8.09 (m, 2H), 8.26 (d, 1H), 8.28 (d, 1H), 8.37 (s, 1H), 8.62-8.66 (m, 3H), 9.37 (s, 1H), 9.87 (s, 1H).

Example 21-96

1-(2-{4-[5-(1-azetidinyl)pyrazolo[1,5-a]pyrimidin-3-yl]phenoxy}-5-pyrimidinyl)-3-[5-chloro-2-(3-pyridinyl)phenyl]urea Purity (LC-MS/ELSD): 100% (Retention Time: 0.86 minutes);
MASS (ESI, Pos.): 590 (M+H)$^+$;
$^1$H-NMR (DMSO-d$_6$): δ 2.32-2.42 (m, 2H), 4.15 (t, 4H), 6.24 (d, 1H), 7.11-7.16 (m, 2H), 7.23 (dd, 1H), 7.28 (d, 1H), 7.53 (dd, 1H), 7.80-7.85 (m, 1H), 8.04-8.12 (m, 4H), 8.37 (s, 1H), 8.59-8.65 (m, 5H), 9.17 (s, 1H).

Example 21-97

1-(2-{4-[5-(1-azetidinyl)pyrazolo[1,5-a]pyrimidin-3-yl]phenoxy}-5-pyrimidinyl)-3-[2-(2H-1,2,3-triazol-2-yl)-5-(trifluoromethyl)phenyl]urea Purity (LC-MS/ELSD): 100% (Retention Time: 1.08 minutes);
MASS (ESI, Pos.): 614 (M+H)$^+$;
$^1$H-NMR (DMSO-d$_6$): δ 2.32-2.42 (m, 2H), 4.15 (t, 4H), 6.24 (d, 1H), 7.13-7.18 (m, 2H), 7.58 (dd, 1H), 8.05-8.09 (m, 3H), 8.32 (s, 2H), 8.38 (s, 1H), 8.62-8.66 (m, 2H), 8.69 (s, 2H), 9.66 (s, 1H), 9.99 (s, 1H).

Example 21-98

1-(2-{4-[5-(1-azetidinyl)pyrazolo[1,5-a]pyrimidin-3-yl]phenoxy}-5-pyrimidinyl)-3-[5-chloro-2-(1H-1,2,3-triazol-1-yl)phenyl]urea Purity (LC-MS/ELSD): 96% (Retention Time: 0.94 minutes);
MASS (ESI, Pos.): 580 (M+H)$^+$;
$^1$H-NMR (DMSO-d$_6$): δ 2.32-2.42 (m, 2H), 4.15 (t, 4H), 6.24 (d, 1H), 7.12-7.17 (m, 2H), 7.31 (dd, 1H), 7.51 (d, 1H), 8.05-8.08 (m, 3H), 8.27 (d, 1H), 8.37 (s, 1H), 8.48 (s, 1H), 8.59-8.65 (m, 4H), 9.57 (s, 1H).

Example 21-99

1-(2-{4-[5-(1-azetidinyl)pyrazolo[1,5-a]pyrimidin-3-yl]phenoxy}-5-pyrimidinyl)-3-[5-chloro-2-(2H-1,2,3-triazol-2-yl)phenyl]urea Purity (LC-MS/ELSD): 100% (Retention Time: 1.06 minutes);
MASS (ESI, Pos.): 580 (M+H)$^+$;
$^1$H-NMR (DMSO-d$_6$): δ 2.32-2.42 (m, 2H), 4.15 (t, 4H), 6.24 (d, 1H), 7.13-7.18 (m, 2H), 7.29 (dd, 1H), 7.80 (d, 1H), 8.05-8.09 (m, 2H), 8.26 (s, 2H), 8.33 (d, 1H), 8.37 (s, 1H), 8.64 (d, 1H), 8.68 (s, 2H), 9.36 (s, 1H), 9.90 (s, 1H).

Example 21-100

1-(2-{4-[5-(1-azetidinyl)pyrazolo[1,5-a]pyrimidin-3-yl]phenoxy}-5-pyrimidinyl)-3-[2-chloro-5-(trifluoromethyl)phenyl]urea Purity (LC-MS/ELSD): 100% (Retention Time: 1.03 minutes);
MASS (ESI, Pos.): 581 (M+H)$^+$;
$^1$H-NMR (DMSO-d$_6$): δ 2.32-2.42 (m, 2H), 4.15 (t, 4H), 6.24 (d, 1H), 7.14-7.19 (m, 2H), 7.40 (dd, 1H), 7.72 (d, 1H), 8.05-8.09 (m, 2H), 8.38 (s, 1H), 8.57 (d, 1H), 8.64 (d, 1H), 8.72 (s, 2H), 8.78 (s, 1H), 9.69 (s, 1H).

Example 21-101

1-(2-{4-[5-(1-azetidinyl)pyrazolo[1,5-a]pyrimidin-3-yl]phenoxy}-5-pyrimidinyl)-3-[2-fluoro-5-(trifluoromethyl)phenyl]urea Purity (LC-MS/ELSD): 100% (Retention Time: 1.00 minute);
MASS (ESI, Pos.): 565 (M+H)$^+$;
$^1$H-NMR (DMSO-d$_6$): δ 2.32-2.42 (m, 2H), 4.15 (t, 4H), 6.24 (d, 1H), 7.13-7.18 (m, 2H), 7.38-7.53 (m, 2H), 8.04-8.09 (m, 2H), 8.37 (s, 1H), 8.52 (dd, 1H), 8.63 (d, 1H), 8.71 (s, 2H), 9.08 (s, 1H), 9.27 (s, 1H).

Example 21-102

1-(2-{4-[5-(1-azetidinyl)pyrazolo[1,5-a]pyrimidin-3-yl]phenoxy}-5-pyrimidinyl)-3-[2-methyl-5-(trifluoromethyl)phenyl]urea Purity (LC-MS/ELSD): 99% (Retention Time: 1.03 minutes);
MASS (ESI, Pos.): 561 (M+H)$^+$;
$^1$H-NMR (DMSO-d$_6$): δ 2.32-2.42 (m, 5H), 4.15 (t, 4H), 6.24 (d, 1H), 7.14-7.18 (m, 2H), 7.29 (dd, 1H), 7.41 (d, 1H), 8.05-8.09 (m, 2H), 8.27 (s, 1H), 8.37-8.38 (m, 2H), 8.64 (d, 1H), 8.72 (s, 2H), 9.31 (s, 1H).

Example 21-103

1-(2-{4-[5-(1-azetidinyl)pyrazolo[1,5-a]pyrimidin-3-yl]phenoxy}-5-pyrimidinyl)-3-(2,5-dichlorophenyl)urea Purity (LC-MS/ELSD): 97% (Retention Time: 1.06 minutes);
MASS (ESI, Pos.): 547 (M+H)$^+$;
$^1$H-NMR (DMSO-d$_6$): δ 2.32-2.42 (m, 2H), 4.15 (t, 4H), 6.24 (d, 1H), 7.10-7.18 (m, 3H), 7.50 (d, 1H), 8.05-8.09 (m, 2H), 8.26 (d, 1H), 8.38 (s, 1H), 8.63-8.71 (m, 4H), 9.66 (s, 1H).

Example 21-104

1-(2-{4-[5-(1-azetidinyl)pyrazolo[1,5-a]pyrimidin-3-yl]phenoxy}-5-pyrimidinyl)-3-(2,4-dichlorophenyl)urea Purity (LC-MS/ELSD): 100% (Retention Time: 1.02 minutes);
MASS (ESI, Pos.): 547 (M+H)$^+$;
$^1$H-NMR (DMSO-d$_6$): δ 2.32-2.42 (m, 2H), 4.15 (t, 4H), 6.24 (d, 1H), 7.13-7.17 (m, 2H), 7.38 (dd, 1H), 7.63 (d, 1H), 8.04-8.09 (m, 2H), 8.14 (d, 1H), 8.37 (s, 1H), 8.56 (brs, 1H), 8.66 (d, 1H), 8.70 (s, 2H), 9.57 (brs, 1H).

Example 21-105

1-(2-{4-[5-(1-azetidinyl)pyrazolo[1,5-a]pyrimidin-3-yl]phenoxy}-5-pyrimidinyl)-3-(2,5-difluorophenyl)urea Purity (LC-MS/ELSD): 100% (Retention Time: 0.93 minutes);
MASS (ESI, Pos.): 515 (M+H)$^+$;
$^1$H-NMR (DMSO-d$_6$): δ 2.32-2.42 (m, 2H), 4.15 (t, 4H), 6.24 (d, 1H), 6.81-6.88 (m, 1H), 7.13-7.18 (m, 2H), 7.25-7.34 (m, 1H), 7.94-8.00 (m, 1H), 8.05-8.09 (m, 2H), 8.38 (s, 1H), 8.64 (d, 1H), 8.70 (s, 2H), 8.95 (s, 1H), 9.25 (s, 1H).

Example 21-106

1-(2-{4-[5-(1-azetidinyl)pyrazolo[1,5-a]pyrimidin-3-yl]phenoxy}-5-pyrimidinyl)-3-[3-(difluoromethyl)phenyl]urea Purity (LC-MS/ELSD): 99% (Retention Time: 0.90 minutes);
MASS (ESI, Pos.): 529 (M+H)$^+$;
$^1$H-NMR (DMSO-d$_6$): δ 2.32-2.42 (m, 2H), 4.15 (t, 4H), 6.24 (d, 1H), 6.81-7.19 (m, 4H), 7.41 (t, 1H), 7.51 (d, 1H), 7.77 (s, 1H), 8.05-8.09 (m, 2H), 8.38 (s, 1H), 8.64 (d, 1H), 8.70 (s, 2H), 8.89 (s, 1H), 9.16 (s, 1H).

Example 21-107

1-{6-[4-(5-methoxypyrazolo[1,5-a]pyrimidin-3-yl)phenoxy]-3-pyridinyl}-3-[2-(3-pyridinyl)-5-(trifluoromethyl)phenyl]urea Purity (LC-MS/ELSD): 100% (Retention Time: 0.96 minutes);
MASS (ESI, Pos.): 598 (M+H)$^+$;
$^1$H-NMR (DMSO-d$_6$): δ 4.02 (s, 3H), 6.60 (d, 1H), 6.99 (d, 1H), 7.10-7.15 (m, 2H), 7.45-7.58 (m, 3H), 7.87-7.91 (m, 1H), 7.97 (dd, 1H), 8.07-8.09 (m, 4H), 8.42 (s, 1H), 8.56 (s, 1H), 8.64-8.69 (m, 2H), 8.92 (d, 1H), 9.16 (s, 1H).

Example 21-108

1-{6-[4-(5-methoxypyrazolo[1,5-a]pyrimidin-3-yl)phenoxy]-3-pyridinyl}-3-[2-(1H-pyrazol-1-yl)-5-(trifluoromethyl)phenyl]urea Purity (LC-MS/ELSD): 100% (Retention Time: 1.08 minutes);
MASS (ESI, Pos.): 587 (M+H)$^+$;
$^1$H-NMR (DMSO-d$_6$): δ 4.02 (s, 3H), 6.60 (d, 1H), 6.66-6.68 (m, 1H), 7.01 (d, 1H), 7.11-7.16 (m, 2H), 7.49 (dd, 1H), 7.73 (d, 1H), 7.94 (d, 1H), 7.99 (dd, 1H), 8.06-8.11 (m, 2H), 8.16 (d, 1H), 8.40 (d, 1H), 8.56 (s, 1H), 8.60 (s, 1H), 8.92 (d, 1H), 9.54 (s, 1H), 9.80 (s, 1H).

Example 21-109

1-{6-[4-(5-methoxypyrazolo[1,5-a]pyrimidin-3-yl)phenoxy]-3-pyridinyl}-3-{5-(trifluoromethyl)-2-[3-(trifluoromethyl)-1H-pyrazol-1-yl]phenyl}urea Purity (LC-MS/ELSD): 100% (Retention Time: 1.13 minutes);
MASS (ESI, Pos.): 655 (M+H)$^+$;
$^1$H-NMR (DMSO-d$_6$): δ 4.02 (s, 3H), 6.60 (d, 1H), 7.01 (d, 1H), 7.12-7.15 (m, 3H), 7.55 (dd, 1H), 7.68 (d, 1H), 7.96 (dd, 1H), 8.07-8.13 (m, 3H), 8.43 (s, 1H), 8.47 (d, 1H), 8.52 (d, 1H), 8.56 (s, 1H), 8.92 (d, 1H), 9.38 (s, 1H).

Example 21-110

1-(2-{4-[5-(dimethylamino)pyrazolo[1,5-a]pyrimidin-3-yl]phenoxy}-5-pyrimidinyl)-3-[2-(4-methyl-1H-pyrazol-1-yl)-5-(trifluoromethyl)phenyl]urea Purity (LC-MS/ELSD): 100% (Retention Time: 1.06 minutes);
MASS (ESI, Pos.): 615 (M+H)$^+$.

Example 21-111

1-(2-{4-[5-(dimethylamino)pyrazolo[1,5-a]pyrimidin-3-yl]phenoxy}-5-pyrimidinyl)-3-[2-(3-pyridinyl)-4-(trifluoromethyl)phenyl]urea Purity (LC-MS/ELSD): 100% (Retention Time: 0.89 minutes);
MASS (ESI, Pos.): 612 (M+H)$^+$;
$^1$H-NMR (DMSO-d$_6$): δ 3.19 (s, 6H), 6.63 (d, 1H), 7.12-7.19 (m, 2H), 7.52-7.60 (m, 2H), 7.75 (dd, 1H), 7.90 (dt, 1H), 8.07-8.13 (m, 2H), 8.22 (s, 1H), 8.28 (d, 1H), 8.38 (s, 1H), 8.62-8.70 (m, 5H), 9.26 (s, 1H).

Example 21-112

1-(2-{4-[5-(dimethylamino)pyrazolo[1,5-a]pyrimidin-3-yl]phenoxy}-5-pyrimidinyl)-3-[2-(methylsulfonyl)-4-(trifluoromethyl)phenyl]urea TLC: Rf 0.50 (Ethyl acetate);
$^1$H-NMR (DMSO-d$_6$): δ 3.32 (s, 6H), 3.41 (s, 3H), 6.63 (d, 1H), 7.15-7.22 (m, 2H), 8.04-8.15 (m, 4H), 8.39 (s, 1H), 8.48-8.55 (m, 1H), 8.65 (d, 1H), 8.73 (s, 2H), 9.03 (s, 1H), 10.33 (s, 1H).

Example 21-113

1-(2-{4-[5-(1-azetidinyl)pyrazolo[1,5-a]pyrimidin-3-yl]phenoxy}-5-pyrimidinyl)-3-[2-(methylsulfonyl)-4-(trifluoromethyl)phenyl]urea TLC: Rf 0.37 (Chloroform:Methanol=19:1);
$^1$H-NMR (DMSO-d$_6$): δ 2.31-2.42 (m, 2H), 3.41 (s, 3H), 4.12-4.18 (m, 4H), 6.24 (d, 1H), 7.10-7.19 (m, 2H), 8.01-8.11 (m, 4H), 8.37 (s, 1H), 8.49 (d, 1H), 8.63 (d, 1H), 8.73 (s, 2H), 9.02 (s, 1H), 10.32 (s, 1H).

Example 21-114

1-(2-{4-[5-(dimethylamino)pyrazolo[1,5-a]pyrimidin-3-yl]phenoxy}-5-pyrimidinyl)-3-[2-(5-methyl-3-pyridinyl)-5-(trifluoromethyl)phenyl]urea Purity (LC-MS/ELSD): 100% (Retention Time: 0.89 minutes);
MASS (ESI, Pos.): 626 (M+H)$^+$;
$^1$H-NMR (DMSO-d$_6$): δ 2.38 (s, 3H), 3.19 (s, 6H), 6.63 (d, 1H), 7.13-7.19 (m, 2H), 7.44-7.53 (m, 2H), 7.69-7.73 (m, 1H), 8.07-8.13 (m, 2H), 8.18 (s, 1H), 8.38 (s, 1H), 8.42-8.45 (m, 2H), 8.51-8.54 (m, 1H), 8.63-8.67 (m, 3H), 9.25 (s, 1H).

Example 21-115

1-(2-{4-[5-(1-azetidinyl)pyrazolo[1,5-a]pyrimidin-3-yl]phenoxy}-5-pyrimidinyl)-3-[2-(5-methyl-3-pyridinyl)-5-(trifluoromethyl)phenyl]urea Purity (LC-MS/ELSD): 99% (Retention Time: 0.90 minutes);
MASS (ESI, Pos.): 638 (M+H)$^+$;
$^1$H-NMR (DMSO-d$_6$): δ 2.32-2.47 (m, 5H), 4.12-4.19 (m, 4H), 6.24 (d, 1H), 7.12-7.18 (m, 2H), 7.43-7.53 (m, 2H), 7.70-7.73 (m, 1H), 8.04-8.10 (m, 2H), 8.18 (s, 1H), 8.37 (s, 1H), 8.42-8.46 (m, 2H), 8.51-8.54 (m, 1H), 8.63-8.66 (m, 3H), 9.26 (s, 1H).

Example 21-116

1-(2-{4-[5-(1-azetidinyl)pyrazolo[1,5-a]pyrimidin-3-yl]phenoxy}-5-pyrimidinyl)-3-[3',4'-dimethyl-4-(trifluoromethyl)-2-biphenylyl]urea Purity (LC-MS/ELSD): 99% (Retention Time: 1.19 minutes);
MASS (ESI, Pos.): 651 (M+H)$^+$;
$^1$H-NMR (DMSO-d$_6$): δ 2.30 (s, 6H), 2.33-2.44 (m, 2H), 4.11-4.19 (m, 4H), 6.24 (d, 1H), 7.12-7.18 (m, 3H), 7.20-7.22 (m, 1H), 7.28-7.46 (m, 3H), 8.00 (s, 1H), 8.04-8.10 (m, 2H), 8.37 (s, 1H), 8.45-8.48 (m, 1H), 8.62-8.66 (m, 3H), 9.42 (s, 1H).

Example 21-117

1-(2-{4-[5-(1-azetidinyl)pyrazolo[1,5-a]pyrimidin-3-yl]phenoxy}-5-pyrimidinyl)-3-[3'-methyl-4-(trifluoromethyl)-2-biphenylyl]urea Purity (LC-MS/ELSD): 100% (Retention Time: 1.15 minutes);
MASS (ESI, Pos.): 637 (M+H)$^+$;
$^1$H-NMR (DMSO-d$_6$): δ 2.32-2.43 (m, 5H), 4.11-4.20 (m, 4H), 6.24 (d, 1H), 7.12-7.18 (m, 2H), 7.20-7.32 (m, 3H), 7.37-7.48 (m, 3H), 8.00-8.11 (m, 3H), 8.37 (s, 1H), 8.43-8.46 (m, 1H), 8.63-8.66 (m, 3H), 9.41 (s, 1H).

Example 21-118

1-(2-{4-[5-(dimethylamino)pyrazolo[1,5-a]pyrimidin-3-yl]phenoxy}-5-pyrimidinyl)-3-[2-(methylsulfonyl)phenyl]urea Purity (LC-MS/ELSD): 100% (Retention Time: 0.86 minutes);
MASS (ESI, Pos.): 545 (M+H)⁺;
¹H-NMR (DMSO-d₆): δ 3.19 (s, 6H), 3.28 (s, 3H), 6.63 (d, 1H), 7.14-7.20 (m, 2H), 7.27 (td, 1H), 7.65-7.71 (m, 1H), 7.85 (dd, 1H), 8.09-8.18 (m, 3H), 8.39 (s, 1H), 8.65 (d, 1H), 8.72-8.78 (m, 3H), 10.09 (s, 1H).

Example 21-119

1-(2-{4-[5-(methylamino)pyrazolo[1,5-a]pyrimidin-3-yl]phenoxy}-5-pyrimidinyl)-3-[2-(methylsulfonyl)-5-(trifluoromethyl)phenyl]urea Purity (LC-MS/ELSD): 100% (Retention Time: 0.92 minutes);
MASS (ESI, Pos.): 599 (M+H)⁺;
¹H-NMR (DMSO-d₆): δ 2.93 (d, 3H), 3.38 (s, 3H), 6.27 (d, 1H), 7.17 (d, 2H), 7.56-7.68 (m, 2H), 8.03-8.18 (m, 3H), 8.32 (s, 1H), 8.47 (d, 1H), 8.63 (s, 1H), 8.73 (s, 2H), 8.96 (s, 1H), 10.28 (s, 1H).

Example 21-120

1-(2-{4-[5-(dimethylamino)pyrazolo[1,5-a]pyrimidin-3-yl]phenoxy}-5-pyrimidinyl)-3-[2-(ethylsulfonyl)-5-(trifluoromethyl)phenyl]urea TLC: Rf 0.24 (Hexane:Ethyl Acetate=1:4);
¹H-NMR (DMSO-d₆): δ 1.14 (t, 3H), 3.18 (s, 6H), 3.45 (q, 2H), 6.61 (d, 1H), 7.16 (d, 2H), 7.62 (dd, 1H), 8.01 (d, 1H), 8.10 (d, 2H), 8.38 (s, 1H), 8.61-8.67 (m, 2H), 8.72 (s, 2H), 8.99 (s, 1H), 10.28 (s, 1H).

Example 21-121

1-(2-{4-[5-(dimethylamino)pyrazolo[1,5-a]pyrimidin-3-yl]phenoxy}-5-pyrimidinyl)-3-[2-(methylthio)-5-(trifluoromethyl)phenyl]urea TLC: Rf 0.28 (Ethyl Acetate);
¹H-NMR (DMSO-d₆): δ 2.53 (s, 3H), 3.19 (s, 6H), 6.62 (d, 1H), 7.16 (d, 2H), 7.40 (dd, 1H), 7.54 (d, 1H), 8.10 (d, 2H), 8.19 (d, 1H), 8.38 (s, 1H), 8.42 (s, 1H), 8.63 (d, 1H), 8.70 (s, 2H), 9.62 (s, 1H).

Example 21-122

1-(2-{4-[5-(dimethylamino)pyrazolo[1,5-a]pyrimidin-3-yl]phenoxy}-5-pyrimidinyl)-3-[5-fluoro-2-(methylsulfonyl)phenyl]urea Purity (LC-MS/ELSD): 100% (Retention Time: 0.93 minutes);
MASS (ESI, Pos.): 599 (M+H)⁺;
¹H-NMR (DMSO-d₆): δ 3.20 (s, 6H), 3.30 (s, 3H), 6.63 (d, 1H), 7.09-7.21 (m, 3H), 7.91 (dd, 1H), 8.08-8.17 (m, 3H), 8.39 (s, 1H), 8.65 (d, 1H), 8.72 (s, 2H), 8.93 (s, 1H), 10.26 (s, 1H).

Example 21-123

2-{[(2-{4-[5-(dimethylamino)pyrazolo[1,5-a]pyrimidin-3-yl]phenoxy}-5-pyrimidinyl)carbamoyl]amino}-N,N-dimethyl-4-(trifluoromethyl)benzenesulfonamide

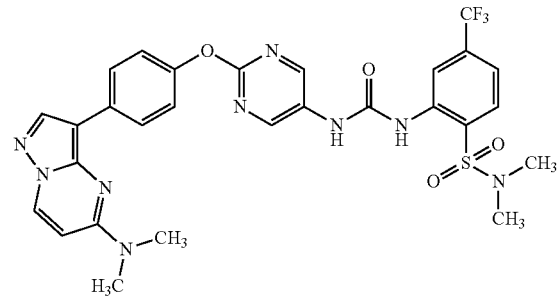 [SMILES: CN(C)c1ccn2ncc(-c3ccc(Oc4ncc(NC(=O)Nc5cc(C(F)(F)F)ccc5S(=O)(=O)N(C)C)cn4)cc3)c2n1]

Purity (LC-MS/ELSD): 100% (Retention Time: 1.04 minutes);
MASS (ESI, Pos.): 642 (M+H)⁺;
¹H-NMR (DMSO-d₆): δ 2.75 (s, 6H), 3.19 (s, 6H), 6.63 (d, 1H), 7.17 (d, 2H), 7.59 (dd, 1H), 7.94 (d, 1H), 8.11 (d, 2H), 8.39 (s, 1H), 8.61 (d, 1H), 8.65 (d, 1H), 8.72 (s, 2H), 8.98 (s, 1H), 10.28 (s, 1H).

Example 21-124

2-{[(2-{4-[5-(1-azetidinyl)pyrazolo[1,5-a]pyrimidin-3-yl]phenoxy}-5-pyrimidinyl)carbamoyl]amino}-N,N-dimethyl-4-(trifluoromethyl)benzenesulfonamide Purity (LC-MS/ELSD): 100% (Retention Time: 1.06 minutes);
MASS (ESI, Pos.): 654 (M+H)⁺;
¹H-NMR (DMSO-d₆): δ 2.31-2.44 (m, 2H), 2.75 (s, 6H), 4.15 (t, 4H), 6.24 (d, 1H), 7.16 (d, 2H), 7.60 (dd, 1H), 7.95 (d, 1H), 8.08 (d, 2H), 8.38 (s, 1H), 8.61 (d, 1H), 8.64 (d, 1H), 8.72 (s, 2H), 8.98 (s, 1H), 10.28 (s, 1H).

Example 21-125

2-{[(2-{4-[5-(dimethylamino)pyrazolo[1,5-a]pyrimidin-3-yl]phenoxy}-5-pyrimidinyl)carbamoyl]amino}-4-fluoro-N,N-dimethylbenzenesulfonamide Purity (LC-MS/ELSD): 100% (Retention Time: 0.98 minutes);
MASS (ESI, Pos.): 592 (M+H)⁺.

Example 21-126

1-(2-{4-[5-(dimethylamino)pyrazolo[1,5-a]pyrimidin-3-yl]phenoxy}-5-pyrimidinyl)-3-[3'-(hydroxymethyl)-4-(trifluoromethyl)-2-biphenylyl]urea Purity (LC-MS/ELSD): 100% (Retention Time: 1.04 minutes);
MASS (ESI, Pos.): 641 (M+H)⁺;
¹H-NMR (DMSO-d₆): δ 3.19 (s, 6H), 4.58 (d, 2H), 5.28 (t, 1H), 6.63 (d, 1H), 7.15 (d, 2H), 7.31 (d, 1H), 7.36 (s, 1H), 7.37-7.56 (m, 4H), 8.04 (s, 1H), 8.10 (d, 2H), 8.38 (s, 1H), 8.42 (s, 1H), 8.62-8.68 (m, 3H), 9.39 (s, 1H).

Example 21-127

1-(2-{4-[5-(1-azetidinyl)pyrazolo[1,5-a]pyrimidin-3-yl]phenoxy}-5-pyrimidinyl)-3-[3'-(hydroxymethyl)-4-(trifluoromethyl)-2-biphenylyl]urea Purity (LC-MS/ELSD): 100% (Retention Time: 1.05 minutes);
MASS (ESI, Pos.): 653 (M+H)$^+$;
$^1$H-NMR (DMSO-d$_6$): δ 2.37 (quint, 2H), 4.15 (t, 4H), 4.58 (d, 2H), 5.30 (t, 1H), 6.24 (s, 1H), 7.14 (d, 2H), 7.24-7.56 (m, 6H), 8.02-8.09 (m, 3H), 8.37 (s, 1H), 8.42 (s, 1H), 8.60-8.63 (m, 3H), 9.38 (s, 1H).

Example 21-128

1-(2-{4-[5-(1-azetidinyl)pyrazolo[1,5-a]pyrimidin-3-yl]phenoxy}-5-pyrimidinyl)-3-[3'-(hydroxyethyl)-4-(trifluoromethyl)-2-biphenylyl]urea Purity (LC-MS/ELSD): 100% (Retention Time: 1.08 minutes);
MASS (ESI, Pos.): 667 (M+H)$^+$;
$^1$H-NMR (DMSO-d$_6$): δ 1.36 (d, 3H), 2.37 (quint, 2H), 4.15 (t, 4H), 4.75-4.82 (m, 1H), 5.21 (d, 1H), 6.24 (d, 1H), 7.14 (d, 2H), 7.29-7.34 (m, 1H), 7.38-7.53 (m, 5H), 8.02-8.10 (m, 3H), 8.37 (s, 2H), 8.62-8.64 (m, 3H), 9.37 (s, 1H).

Example 21-129

1-(2-{4-[5-(dimethylamino)pyrazolo[1,5-a]pyrimidin-3-yl]phenoxy}-5-pyrimidinyl)-3-[3'-(2-hydroxy-2-propanyl)-4-(trifluoromethyl)-2-biphenylyl]urea Purity (LC-MS/ELSD): 100% (Retention Time: 1.06 minutes);
MASS (ESI, Pos.): 669 (M+H)$^+$.

Example 21-130

1-[3'-(hydroxymethyl)-4-(trifluoromethyl)-2-biphenylyl]-3-{2-[4-(5-methylpyrazolo[1,5-a]pyrimidin-3-yl)phenoxy]-5-pyrimidinyl}urea Purity (LC-MS/ELSD): 100% (Retention Time: 1.02 minutes);
MASS (ESI, Pos.): 612 (M+H)$^+$;
$^1$H-NMR (DMSO-d$_6$): δ 2.60 (s, 3H), 4.58 (d, 2H), 5.28 (t, 1H), 6.98 (d, 1H), 7.23 (d, 2H), 7.30 (d, 1H), 7.34-7.56 (m, 5H), 8.05 (s, 1H), 8.14 (d, 2H), 8.42 (d, 1H), 8.65 (s, 2H), 8.66 (s, 1H), 9.00 (d, 1H), 9.40 (s, 1H).

Example 21-131

1-[3'-(1-hydroxyethyl)-4-(trifluoromethyl)-2-biphenylyl]-3-{2-[4-(5-methylpyrazolo[1,5-a]pyrimidin-3-yl)phenoxy]-5-pyrimidinyl}urea Purity (LC-MS/ELSD): 100% (Retention Time: 1.04 minutes);
MASS (ESI, Pos.): 626 (M+H)$^+$;
$^1$H-NMR (DMSO-d$_6$): δ 1.36 (d, 3H), 2.60 (s, 3H), 4.74-4.83 (m, 1H), 5.21 (d, 1H), 6.98 (d, 1H), 7.23 (d, 2H), 7.27-7.35 (m, 1H), 7.39-7.52 (m, 5H), 8.07 (s, 1H), 8.10-8.17 (m, 2H), 8.37 (s, 1H), 8.64 (s, 2H), 8.66 (s, 1H), 9.00 (d, 1H), 9.38 (s, 1H).

Example 21-132

1-[3'-(2-hydroxy-2-propanyl)-4-(trifluoromethyl)-2-biphenylyl]-3-{2-[4-(5-methylpyrazolo[1,5-a]pyrimidin-3-yl)phenoxy]-5-pyrimidinyl}urea Purity (LC-MS/ELSD): 100% (Retention Time: 1.06 minutes);
MASS (ESI, Pos.): 640 (M+H)$^+$;
$^1$H-NMR (DMSO-d$_6$): δ 1.45 (s, 6H), 2.60 (s, 3H), 5.07 (s, 1H), 6.98 (d, 1H), 7.23 (d, 2H), 7.24-7.31 (m, 1H), 7.41-7.59 (m, 5H), 8.08 (s, 1H), 8.11-8.18 (m, 2H), 8.34 (s, 1H), 8.64 (s, 2H), 8.66 (s, 1H), 9.00 (d, 1H), 9.37 (s, 1H).

Example 21-133

1-{2-[4-(5-methylpyrazolo[1,5-a]pyrimidin-3-yl)phenoxy]-5-pyrimidinyl}-3-{5-(trifluoromethyl)-2-[3-(trifluoromethyl)-1H-pyrazol-1-yl]phenyl}urea Purity (LC-MS/ELSD): 100% (Retention Time: 1.09 minutes);
MASS (ESI, Pos.): 640 (M+H)$^+$;
$^1$H-NMR (DMSO-d$_6$): δ 2.60 (s, 3H), 6.98 (d, 1H), 7.12 (d, 1H), 7.23 (d, 2H), 7.58 (dd, 1H), 7.70 (d, 1H), 8.14 (d, 2H), 8.47 (s, 2H), 8.57 (s, 1H), 8.63-8.67 (m, 3H), 9.00 (d, 1H), 9.46 (s, 1H).

Example 21-134

1-[2-(methylsulfonyl)-5-(trifluoromethyl)phenyl]-3-(2-{4-[5-(3-oxetanyloxy)pyrazolo[1,5-a]pyrimidin-3-yl]phenoxy}-5-pyrimidinyl)urea Purity (LC-MS/ELSD): 100% (Retention Time: 0.97 minutes);
MASS (ESI, Pos.): 642 (M+H)$^+$;
$^1$H-NMR (DMSO-d$_6$): δ 3.38 (s, 3H), 4.63-4.76 (m, 2H), 4.96-5.04 (m, 2H), 5.76 (quint, 1H), 6.70 (d, 1H), 7.26 (d, 2H), 7.64 (d, 1H), 7.99-8.11 (m, 3H), 8.59-8.64 (m, 2H), 8.75 (s, 2H), 8.93-9.03 (m, 2H), 10.29 (s, 1H).

Example 22

The similar procedure as Example 7 was carried out with a corresponding amine compound produced with 6-chloroimidazo[1,2-b]pyridazine in place of Example 19 produced with 5-chloropyrazolo[1,5-a]pyrimidine, and the compound produced in Example 3 or a corresponding carbamate or isocyanate compound in place of the compound produced in Example 3 to give the present compounds having the following physical characteristics.

Example 22-1

1-(2-(1H-pyrazol-1-yl)-5-(trifluoromethyl)phenyl)-3-(2-(4-(6-(azetidin-1-yl)imidazo[1,2-b]pyridazin-3-yl)phenoxy)pyrimidin-5-yl)urea

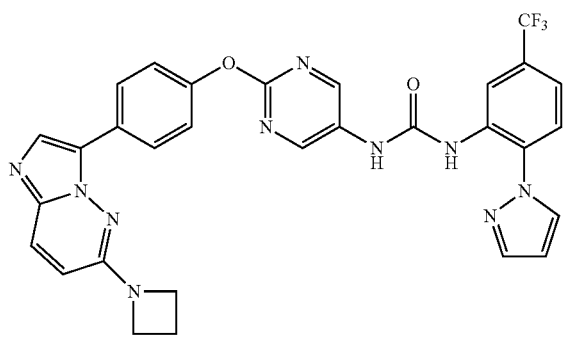 [SMILES: O=C(Nc1cnc(Oc2ccc(-c3cnc4ccc(N5CCC5)nn34)cc2)nc1)Nc1cc(C(F)(F)F)ccc1-n1cccn1]

TLC: Rf 0.50 (Ethyl Acetate:Methanol=9:1);

¹H-NMR (DMSO-d₆): δ 2.32-2.42 (m, 2H), 4.08 (t, 4H), 6.64-6.68 (m, 2H), 7.27 (d, 2H), 7.51 (d, 1H), 7.74 (d, 1H), 7.88 (d, 1H), 7.95 (s, 2H), 8.21 (d, 2H), 8.40 (d, 1H), 8.58 (s, 1H), 8.69 (s, 2H), 9.69 (s, 1H), 9.95 (s, 1H).

Example 22-2

1-(2-(4-(6-(azetidin-1-yl)imidazo[1,2-b]pyridazin-3-yl)phenoxy)pyrimidin-5-yl)-3-(2-(pyridin-3-yl)-5-(trifluoromethyl)phenyl)urea TLC: Rf 0.52 (Ethyl Acetate:Methanol=9:1);

¹H-NMR (DMSO-d₆): δ 2.32-2.42 (m, 2H), 4.08 (t, 4H), 6.66 (d, 1H), 7.24-7.27 (m, 2H), 7.47-7.58 (m, 3H), 7.87-7.95 (m, 3H), 8.20-8.23 (m, 3H), 8.38 (s, 1H), 8.65-8.68 (m, 4H), 9.24 (s, 1H).

Example 22-3

1-(2-(4-(6-(azetidin-1-yl)imidazo[1,2-b]pyridazin-3-yl)phenoxy)pyrimidin-5-yl)-3-(3-(trifluoromethyl)phenyl)urea TLC: Rf 0.28 (Chloroform:Methanol=19:1);

¹H-NMR (DMSO-d₆): δ 2.33-2.43 (m, 2H), 4.06-4.12 (m, 4H), 6.67 (d, 1H), 7.25-7.36 (m, 3H), 7.52 (t, 1H), 7.62 (d, 1H), 7.90 (d, 1H), 7.96-7.99 (m, 2H), 8.19-8.26 (m, 2H), 8.73 (s, 2H), 8.99 (s, 1H), 9.31 (s, 1H).

Example 22-4

1-(2-(4-(6-(azetidin-1-yl)imidazo[1,2-b]pyridazin-3-yl)phenoxy)pyrimidin-5-yl)-3-(2-phenyl-5-(trifluoromethyl)pyridin-3-yl)urea TLC: Rf 0.34 (Chloroform:Methanol=19:1);

¹H-NMR (DMSO-d₆): δ 2.33-2.43 (m, 2H), 4.06-4.11 (m, 4H), 6.68 (d, 1H), 7.25-7.29 (m, 2H), 7.53-7.61 (m, 3H), 7.64-7.69 (m, 2H), 7.90 (d, 1H), 7.97 (s, 1H), 8.20-8.25 (m, 2H), 8.43 (s, 1H), 8.69 (s, 2H), 8.72-8.75 (m, 1H), 8.76-8.79 (m, 1H), 9.47 (s, 1H).

Example 22-5

1-(2-(pyridin-3-yl)-5-(trifluoromethyl)phenyl)-3-(2-(4-(6-(pyrrolidin-1-yl)imidazo[1,2-b]pyridazin-3-yl)phenoxy)pyrimidin-5-yl)urea

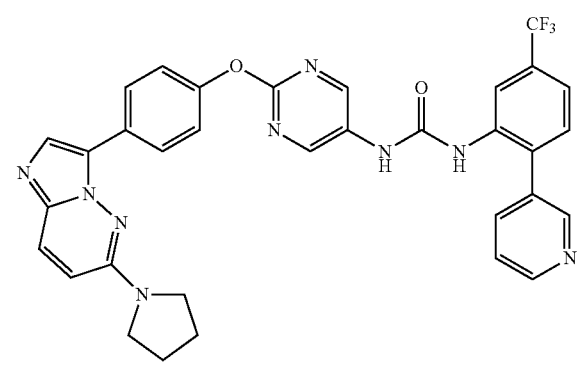 [SMILES: O=C(Nc1cnc(Oc2ccc(-c3cnc4ccc(N5CCCC5)nn34)cc2)nc1)Nc1cc(C(F)(F)F)ccc1-c1cccnc1]

TLC: Rf 0.59 (Ethyl Acetate:Methanol=9:1);

¹H-NMR (DMSO-d₆): δ 1.96-2.01 (m, 4H), 3.47-3.52 (m, 4H), 6.87 (d, 1H), 7.25-7.28 (m, 2H), 7.50-7.58 (m, 3H), 7.85-7.94 (m, 3H), 8.23-8.28 (m, 3H), 8.39 (s, 1H), 8.65-8.68 (m, 4H), 9.24 (s, 1H).

Example 22-6

1-(2-(4-(6-(pyrrolidin-1-yl)imidazo[1,2-b]pyridazin-3-yl)phenoxy)pyrimidin-5-yl)-3-(3-(trifluoromethyl)phenyl)urea TLC: Rf 0.40 (Ethyl Acetate);

¹H-NMR (DMSO-d₆): δ 1.96-2.02 (m, 4H), 3.47-3.54 (m, 4H), 6.88 (d, 1H), 7.26-7.36 (m, 3H), 7.53 (t, 1H), 7.61 (dd, 1H), 7.87 (d, 1H), 7.95-7.99 (m, 2H), 8.28 (d, 2H), 8.73 (s, 2H), 8.98 (s, 1H), 9.31 (s, 1H).

Example 22-7

1-(2-phenyl-5-(trifluoromethyl)pyridin-3-yl)-3-(2-(4-(6-(pyrrolidin-1-yl)imidazo[1,2-b]pyridazin-3-yl)phenoxy)pyrimidin-5-yl)urea TLC: Rf 0.50 (Ethyl Acetate:Methanol=9:1);

¹H-NMR (DMSO-d₆): δ 1.96-2.03 (m, 4H), 3.46-3.55 (m, 4H), 6.87 (d, 1H), 7.27 (d, 2H), 7.52-7.69 (m, 5H), 7.86 (d, 1H), 7.94 (s, 1H), 8.26 (d, 2H), 8.40-8.44 (m, 1H), 8.67-8.78 (m, 4H), 9.45 (s, 1H).

Example 22-8

1-(2-(4-(6-methoxyimidazo[1,2-b]pyridazin-3-yl)phenoxy)pyrimidin-5-yl)-3-(2-(pyridin-3-yl)-5-(trifluoromethyl)phenyl)urea

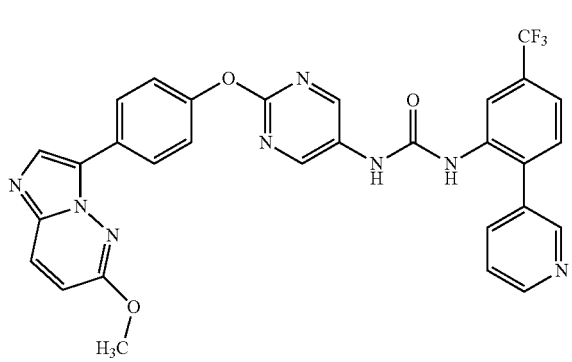 [SMILES: COc1ccc2ncc(-c3ccc(Oc4ncc(NC(=O)Nc5cc(C(F)(F)F)ccc5-c5cccnc5)cn4)cc3)n2n1]

TLC: Rf 0.27 (Ethyl Acetate:Methanol=9:1);

$^1$H-NMR (DMSO-d$_6$): δ 4.01 (s, 3H), 6.95 (d, 1H), 7.29-7.32 (m, 2H), 7.47-7.58 (m, 3H), 7.87-7.91 (m, 1H), 8.07-8.10 (m, 2H), 8.20-8.24 (m, 3H), 8.39 (s, 1H), 8.65-8.69 (m, 4H), 9.25 (s, 1H).

Example 22-9

1-(2-(1H-pyrazol-1-yl)-5-(trifluoromethyl)phenyl)-3-(2-(4-(6-methoxyimidazo[1,2-b]pyridazin-3-yl)phenoxy)pyrimidin-5-yl)urea TLC: Rf 0.68 (Ethyl Acetate:Methanol=9:1);

$^1$H-NMR (DMSO-d$_6$): δ 4.02 (s, 3H), 6.68 (t, 1H), 6.95 (d, 1H), 7.31-7.34 (m, 2H), 7.52 (dd, 1H), 7.75 (d, 1H), 7.96 (d, 1H), 8.07-8.10 (m, 2H), 8.21-8.24 (m, 2H), 8.41 (d, 1H), 7.58 (d, 1H), 8.71 (s, 2H), 9.70 (s, 1H), 9.97 (s, 1H).

Example 22-10

1-(2-(4-(6-methoxyimidazo[1,2-b]pyridazin-3-yl)phenoxy)pyrimidin-5-yl)-3-(3-(trifluoromethyl)phenyl)urea TLC: Rf 0.59 (Ethyl Acetate:Methanol=9:1);

$^1$H-NMR (DMSO-d$_6$): δ 4.02 (s, 3H), 6.95 (d, 1H), 7.31-7.34 (m, 3H), 7.51 (t, 1H), 7.62 (d, 1H), 7.98 (s, 1H), 8.07-8.10 (m, 2H), 8.21-8.24 (m, 2H), 8.74 (s, 2H), 8.99 (s, 1H), 9.31 (s, 1H).

Example 22-11

1-(2-(4-(6-(2-hydroxypropan-2-yl)imidazo[1,2-b]pyridazin-3-yl)phenoxy)pyrimidin-5-yl)-3-(3-(trifluoromethyl)phenyl)urea

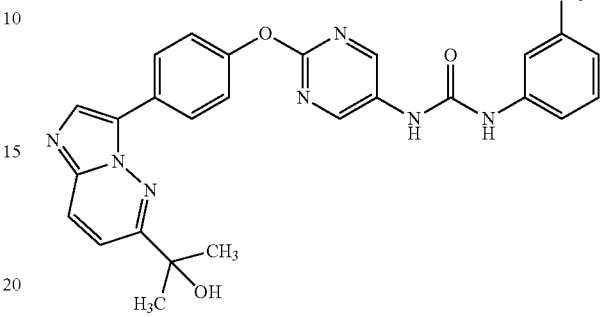

TLC: Rf 0.20 (Chloroform:Methanol=19:1);

$^1$H-NMR (DMSO-d$_6$): δ 1.59 (s, 6H), 5.61 (s, 1H), 7.31-7.38 (m, 3H), 7.50-7.64 (m, 3H), 7.97-8.00 (m, 1H), 8.17 (d, 1H), 8.22-8.28 (m, 3H), 8.75 (s, 2H), 9.00 (s, 1H), 9.32 (s, 1H).

Example 22-12

1-(2-(4-(6-(1-hydroxyethyl)imidazo[1,2-b]pyridazin-3-yl)phenoxy)pyrimidin-5-yl)-3-(3-(trifluoromethyl)phenyl)urea TLC: Rf 0.19 (Chloroform:Methanol=19:1);

$^1$H-NMR (DMSO-d$_6$): δ 1.49 (d, 3H), 4.85-4.93 (m, 1H), 5.74 (d, 1H), 7.31-7.37 (m, 3H), 7.41 (d, 1H), 7.52 (t, 1H), 7.60-7.65 (m, 1H), 7.97-8.00 (m, 1H), 8.18-8.25 (m, 4H), 8.75 (s, 2H), 9.00 (s, 1H), 9.32 (s, 1H).

Example 22-13

1-(2-(4-(6-((2-hydroxy-2-methylpropyl)amino)imidazo[1,2-b]pyridazin-3-yl)phenoxy)pyrimidin-5-yl)-3-(3-(trifluoromethyl)phenyl)urea

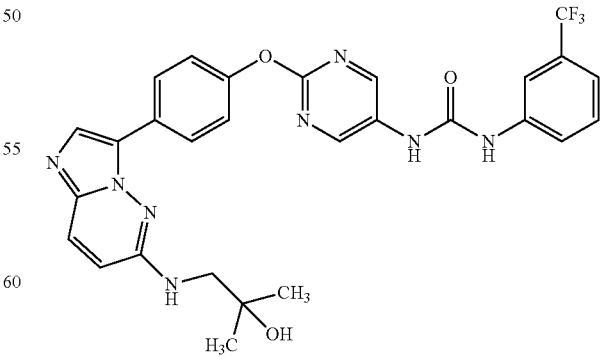

TLC: Rf 0.35 (Ethyl Acetate:Methanol=9:1);

$^1$H-NMR (DMSO-d$_6$): δ 1.19 (s, 6H), 3.27 (d, 2H), 4.57 (s, 1H), 6.87-6.90 (m, 2H), 7.26-7.34 (m, 3H), 7.51 (t, 1H), 7.62 (d, 1H), 7.73 (d, 1H), 7.85 (s, 1H), 7.97 (s, 1H), 8.20-8.25 (m, 2H), 8.73 (s, 2H), 8.98 (s, 1H), 9.31 (s, 1H).

Example 22-14

1-(2-(4-(imidazo[1,2-b]pyridazin-3-yl)phenoxy)pyrimidin-5-yl)-3-(2-(pyridin-3-yl)-5-(trifluoromethyl)phenyl)urea

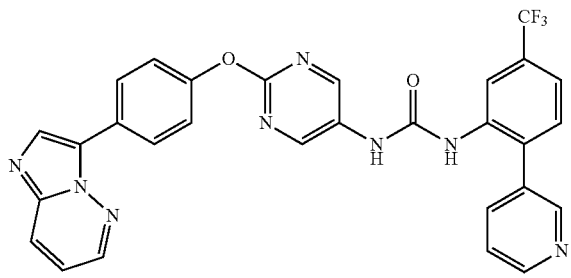 [SMILES: O=C(Nc1cnc(Oc2ccc(-c3cnc4cccnn34)cc2)nc1)Nc1cc(C(F)(F)F)ccc1-c1cccnc1]

TLC: Rf 0.50 (Ethyl Acetate:Methanol=19:1);
<sup>1</sup>H-NMR (DMSO-d<sub>6</sub>): δ 7.26-7.34 (m, 3H), 7.47-7.58 (m, 3H), 7.87-7.93 (m, 1H), 8.15-8.28 (m, 5H), 8.38 (s, 1H), 8.63-8.70(m, 5H), 9.24 (s, 1H).

Example 22-15

1-(2-(1H-1,2,3-triazol-1-yl)-5-(trifluoromethyl)phenyl)-3-(2-(4-(imidazo[1,2-b]pyridazin-3-yl)phenoxy)pyrimidin-5-yl)urea TLC: Rf 0.45 (Ethyl Acetate);
<sup>1</sup>H-NMR (DMSO-d<sub>6</sub>): δ 7.27-7.38 (m, 4H), 7.59-7.65 (m, 1H), 7.74 (d, 1H), 8.10 (s, 1H), 8.16-8.28 (m, 4H), 8.58 (s, 1H), 8.63-8.73 (m, 4H), 9.66 (s, 1H).

Example 22-16

1-(2-(1H-pyrazol-1-yl)-5-(trifluoromethyl)phenyl)-3-(2-(4-(imidazo[1,2-b]pyridazin-3-yl)phenoxy)pyrimidin-5-yl)urea TLC: Rf 0.38 (Hexane:Ethyl Acetate=1:2);
<sup>1</sup>H-NMR (DMSO-d<sub>6</sub>): δ 6.67-6.72 (m, 1H), 7.26-7.40 (m, 3H), 7.50-7.57 (m, 1H), 7.75 (d, 1H), 7.95-8.00 (m, 1H), 8.16-8.30 (m, 4H), 8.40-8.45 (m, 1H), 8.59 (s, 1H), 8.64-8.68 (m, 1H), 8.70 (s, 2H), 9.70 (s, 1H), 9.96 (s, 1H).

Example 22-17

1-(2-chloro-5-(trifluoromethyl)phenyl)-3-(2-(4-(imidazo[1,2-b]pyridazin-3-yl)phenoxy)pyrimidin-5-yl)urea TLC: Rf 0.27 (Ethyl Acetate);
<sup>1</sup>H-NMR (DMSO-d<sub>6</sub>): δ 7.28-7.43 (m, 4H), 7.74 (d, 1H), 8.16-8.27 (m, 4H), 8.56 (dd, 1H), 8.64 (dd, 1H), 8.75 (s, 2H), 8.78 (s, 1H), 9.72 (s, 1H).

Example 22-18

1-(2-fluoro-5-(trifluoromethyl)phenyl)-3-(2-(4-(imidazo[1,2-b]pyridazin-3-yl)phenoxy)pyrimidin-5-yl)urea TLC: Rf 0.30 (Ethyl Acetate);
<sup>1</sup>H-NMR (DMSO-d<sub>6</sub>): δ 7.27-7.54 (m, 5H), 8.16-8.27 (m, 4H), 8.53 (dd, 1H), 8.63 (dd, 1H), 8.75 (s, 2H), 9.08 (s, 1H), 9.31 (s, 1H).

Example 22-19

1-(2-(4-(imidazo[1,2-b]pyridazin-3-yl)phenoxy)pyrimidin-5-yl)-3-(2-methyl-5-(trifluoromethyl)phenyl)urea TLC: Rf 0.43 (Ethyl Acetate);
<sup>1</sup>H-NMR (DMSO-d<sub>6</sub>): δ 2.32 (s, 3H), 7.27-7.41 (m, 6H), 8.17-8.26 (m, 6H), 8.64 (dd, 1H), 8.75 (s, 2H).

Example 22-20

1-(2-(4-(imidazo[1,2-b]pyridazin-3-yl)phenoxy)pyrimidin-5-yl)-3-(3-(trifluoromethyl)phenyl)urea TLC: Rf 0.47 (Ethyl Acetate);
<sup>1</sup>H-NMR (DMSO-d<sub>6</sub>): δ 7.27-7.36 (m, 4H), 7.51 (t, 1H), 7.62 (d, 1H), 7.97 (s, 1H), 8.17-8.26 (m, 4H), 8.64 (d, 1H), 8.74 (s, 2H), 8.99 (s, 1H), 9.31 (s, 1H).

Example 22-21

1-(3-fluoro-5-(trifluoromethyl)phenyl)-3-(2-(4-(imidazo[1,2-b]pyridazin-3-yl)phenoxy)pyrimidin-5-yl)urea TLC: Rf 0.22 (Ethyl Acetate);
<sup>1</sup>H-NMR (DMSO-d<sub>6</sub>): δ 7.22-7.37 (m, 4H), 7.62 (d, 1H), 7.70 (s, 1H), 8.15-8.27 (m, 4H), 8.26 (d, 1H), 8.63 (dd, 1H), 8.73 (s, 2H), 9.12 (s, 1H), 9.52 (s, 1H).

Example 22-22

1-(2-(4-(6-(azetidin-1-yl)imidazo[1,2-b]pyridazin-3-yl)phenoxy)pyrimidin-5-yl)-3-(2-chloro-4-(trifluoromethyl)phenyl)urea TLC: Rf 0.57 (Ethyl Acetate:Methanol=9: 1; CHROMATOREX NH TLC PLATE);
<sup>1</sup>H-NMR (DMSO-d<sub>6</sub>): δ 2.32-2.42 (m, 2H), 4.08 (t, 4H), 6.67 (d, 1H), 7.27-7.30 (m, 2H), 7.69 (dd, 1H), 7.88-7.91 (m, 2H), 7.97 (s, 1H), 8.21-8.24 (m, 2H), 8.44 (d, 1H), 8.75 (s, 2H), 8.82 (br s, 1H), 9.76 (brs, 1H).

Example 22-23

1-(2-chloro-4-(trifluoromethyl)phenyl)-3-(2-(4-(6-methoxyimidazo[1,2-b]pyridazin-3-yl)phenoxy)pyrimidin-5-yl)urea TLC: Rf 0.53 (Ethyl Acetate:Methanol=9:1);
<sup>1</sup>H-NMR (DMSO-d<sub>6</sub>): δ 4.02 (s, 3H), 6.95 (d, 1H), 7.32-7.35 (m, 2H), 7.69 (dd, 1H), 7.89 (d, 1H), 8.07-8.10 (m, 2H), 8.21-8.24 (m, 2H), 8.43 (d, 1H), 8.76 (s, 2H), 8.80 (s, 1H), 9.78 (s, 1H).

Example 22-24

1-(2-chloro-4-(trifluoromethyl)phenyl)-3-(2-(4-(imidazo[1,2-b]pyridazin-3-yl)phenoxy)pyrimidin-5-yl)urea TLC: Rf 0.33 (Ethyl Acetate);
<sup>1</sup>H-NMR (DMSO-d<sub>6</sub>): δ 7.31 (dd, 1H), 7.36 (d, 2H), 7.68 (dd, 1H), 7.88-7.92 (m, 1H), 8.17-8.28 (m, 4H), 8.43 (d, 1H), 8.64 (dd, 1H), 8.75 (s, 2H), 8.79 (s, 1H), 9.78 (s, 1H).

Example 22-25

1-(2-(4-(imidazo[1,2-b]pyridazin-3-yl)phenoxy)pyrimidin-5-yl)-3-(4-(trifluoromethyl)phenyl)urea TLC: Rf 0.20 (Hexane:Ethyl Acetate=1:3);
$^1$H-NMR (DMSO-$d_6$): δ 7.28 (dd, 1H), 7.35 (d, 2H), 7.61-7.69 (m, 4H), 8.16-8.28 (m, 4H), 8.64 (d, 1H), 8.74 (s, 2H), 8.99 (s, 1H), 9.37 (s, 1H).

Example 22-26

1-(2-(4-(6-(azetidin-1-yl)imidazo[1,2-b]pyridazin-3-yl)phenoxy)pyrimidin-5-yl)-3-(3,5-difluorophenyl)urea TLC: Rf 0.25 (Ethyl Acetate);
$^1$H-NMR (DMSO-$d_6$): δ 6.76-6.85 (m, 1H), 7.19 (dd, 2H), 7.27-7.35 (m, 3H), 8.17-8.27 (m, 4H), 8.64 (dd, 1H), 8.72 (s, 2H), 9.15 (s, 1H), 9.46 (s, 1H).

Example 22-27

1-(6-(4-(imidazo[1,2-b]pyridazin-3-yl)phenoxy)pyridin-3-yl)-3-(3-(trifluoromethyl)phenyl)urea

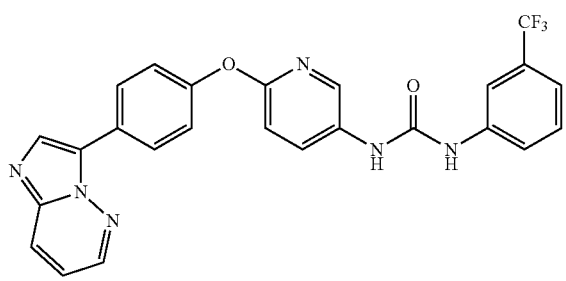 [SMILES: O=C(Nc1ccc(Oc2ccc(-c3cnc4cccnn34)cc2)nc1)Nc1cccc(C(F)(F)F)c1]

TLC: Rf 0.51 (Ethyl Acetate);
$^1$H-NMR (DMSO-$d_6$): δ 7.07 (d, 1H), 7.22-7.31 (m, 4H), 7.50 (t, 1H), 7.59 (d, 1H), 7.97-8.00 (m, 1H), 8.03 (dd, 1H), 8.14-8.25 (m, 5H), 8.63 (dd, 1H), 8.90 (s, 1H), 9.14 (s, 1H).

Example 22-28

1-{2-[4-(6-methoxyimidazo[1,2-b]pyridazin-3-yl)phenoxy]-5-pyrimidinyl}-3-[2-(1-methyl-1H-pyrazol-5-yl)-5-(trifluoromethyl)phenyl]urea Purity (LC-MS/ELSD): 96% (Retention Time: 0.87 minutes);
MASS (ESI, Pos.): 602 (M+H)$^+$;
$^1$H-NMR (DMSO-$d_6$): δ 3.65 (s, 3H), 4.01 (s, 3H), 6.45 (d, 1H), 6.95 (d, 1H), 7.30-7.33 (m, 2H), 7.46-7.52 (m, 2H), 7.62 (d, 1H), 8.07-8.23 (m, 5H), 8.56 (s, 1H), 8.69 (s, 2H), 9.50 (s, 1H).

Example 22-29

1-{2-[4-(6-methoxyimidazo[1,2-b]pyridazin-3-yl)phenoxy]-5-pyrimidinyl}-3-[2-(3-methyl-1H-pyrazol-1-yl)-5-(trifluoromethyl)phenyl]urea Purity (LC-MS/ELSD): 99% (Retention Time: 0.94 minutes);
MASS (ESI, Pos.): 602 (M+H)$^+$;
$^1$H-NMR (DMSO-$d_6$): δ 2.37 (s, 3H), 4.02 (s, 3H), 6.45 (d, 1H), 6.95 (d, 1H), 7.30-7.35 (m, 2H), 7.49 (dd, 1H), 7.70 (d, 1H), 8.07-8.11 (m, 2H), 8.23-8.25 (m, 2H), 8.28 (d, 1H), 8.57 (d, 1H), 8.71 (s, 2H), 9.81 (s, 1H), 9.93 (s, 1H).

Example 22-30

1-{2-[4-(6-methoxyimidazo[1,2-b]pyridazin-3-yl)phenoxy]-5-pyrimidinyl}-3-[2-(4-methyl-1H-pyrazol-1-yl)-5-(trifluoromethyl)phenyl]urea Purity (LC-MS/ELSD): 96% (Retention Time: 0.95 minutes);
MASS (ESI, Pos.): 602 (M+H)$^+$;
$^1$H-NMR (DMSO-$d_6$): δ 2.14 (s, 3H), 4.02 (s, 3H), 6.95 (d, 1H), 7.32 (d, 2H), 7.49 (dd, 1H), 7.70 (d, 1H), 7.79 (s, 1H), 8.07-8.11 (m, 2H), 8.19-8.24 (m, 3H), 8.57 (d, 1H), 8.71 (s, 2H), 9.84 (s, 1H), 9.98 (s, 1H).

Example 22-31

1-{2-[4-(6-methoxyimidazo[1,2-b]pyridazin-3-yl)phenoxy]-5-pyrimidinyl}-3-[2-(3-pyridinyl)-4-(trifluoromethyl)phenyl]urea Purity (LC-MS/ELSD): 100% (Retention Time: 0.78 minutes);
MASS (ESI, Pos.): 599 (M+H)$^+$;
$^1$H-NMR (DMSO-$d_6$): δ 4.01 (s, 3H), 6.95 (d, 1H), 7.31 (d, 2H), 7.54-7.57 (m, 2H), 7.76 (dd, 1H), 7.88-7.92 (m, 1H), 8.07-8.10 (m, 2H), 8.20-8.29 (m, 4H), 8.65-8.69 (m, 4H), 9.30 (s, 1H).

Example 22-32

1-{2-[4-(6-methoxyimidazo[1,2-b]pyridazin-3-yl)phenoxy]-5-pyrimidinyl}-3-[2-methyl-5-(trifluoromethyl)phenyl]urea Purity (LC-MS/ELSD): 100% (Retention Time: 0.87 minutes);
MASS (ESI, Pos.): 536 (M+H)$^+$;
$^1$H-NMR (DMSO-$d_6$): δ 2.32 (s, 3H), 4.02 (s, 3H), 6.95 (d, 1H), 7.29-7.34 (m, 3H), 7.42 (d, 1H), 8.08-8.11 (m, 2H), 8.20-8.25 (m, 2H), 8.28 (s, 1H), 8.38 (s, 1H), 8.75 (s, 2H), 9.34 (s, 1H).

Example 22-33

1-{2-[4-(6-methoxyimidazo[1,2-b]pyridazin-3-yl)phenoxy]-5-pyrimidinyl}-3-{5-(trifluoromethyl)-2-[3-(trifluoromethyl)-1H-pyrazol-1-yl]phenyl}urea Purity (LC-MS/ELSD): 100% (Retention Time: 0.97 minutes);
MASS (ESI, Pos.): 656 (M+H)$^+$;
$^1$H-NMR (DMSO-$d_6$): δ 4.01 (s, 3H), 6.93 (d, 1H), 7.12 (s, 1H), 7.31 (d, 2H), 7.58 (d, 1H), 7.70 (d, 1H), 8.07-8.10

(m, 2H), 8.21 (d, 2H), 8.47 (s, 2H), 8.59 (s, 1H), 8.67 (s, 2H), 9.49 (s, 1H).

Example 22-34

1-{2-[4-(6-ethoxyimidazo[1,2-b]pyridazin-3-yl)phenoxy]-5-pyrimidinyl}-3-[2-(3-pyridinyl)-5-(trifluoromethyl)phenyl]urea

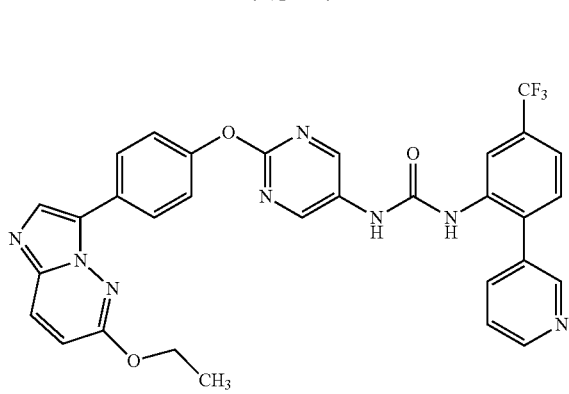 [SMILES: CCOc1ccc2ncc(-c3ccc(Oc4ncc(NC(=O)Nc5cc(C(F)(F)F)ccc5-c5cccnc5)cn4)cc3)n2n1]

Purity (LC-MS/ELSD): 99% (Retention Time: 0.86 minutes);

MASS (ESI, Pos.): 613 (M+H)$^+$;

$^1$H-NMR (DMSO-d$_6$): δ 1.41 (t, 3H), 4.40 (q, 2H), 6.92 (d, 1H), 7.28-7.32 (m, 2H), 7.47-7.58 (m, 3H), 7.87-7.91 (m, 1H), 8.05-8.09 (m, 2H), 8.16-8.20 (m, 2H), 8.24 (s, 1H), 8.38 (s, 1H), 8.64-8.68 (m, 4H), 9.24 (s, 1H).

Example 22-35

1-(2-{4-[6-(3-oxetanyloxy)imidazo[1,2-b]pyridazin-3-yl]phenoxy}-5-pyrimidinyl)-3-[2-(3-pyridinyl)-5-(trifluoromethyl)phenyl]urea Purity (LC-MS/ELSD): 99% (Retention Time: 0.79 minutes);

MASS (ESI, Pos.): 641 (M+H)$^+$;

$^1$H-NMR (DMSO-d$_6$): δ 4.70 (dd, 2H), 4.95 (t, 2H), 5.62-5.71 (m, 1H), 7.02 (d, 1H), 7.32-7.36 (m, 2H), 7.36-7.59 (m, 3H), 7.87-7.91 (m, 1H), 8.06-8.10 (m, 3H), 8.15 (d, 1H), 8.25 (s, 1H), 8.39 (s, 1H), 8.65-8.69 (m, 4H), 9.26 (s, 1H).

Example 22-36

1-{2-[4-(6-methylimidazo[1,2-b]pyridazin-3-yl)phenoxy]-5-pyrimidinyl}-3-[2-(3-pyridinyl)-5-(trifluoromethyl)phenyl]urea Purity (LC-MS/ELSD): 100% (Retention Time: 0.76 minutes);

MASS (ESI, Pos.): 583 (M+H)$^+$;

$^1$H-NMR (DMSO-d$_6$): δ 2.59 (s, 3H), 7.19 (d, 1H), 7.29-7.34 (m, 2H), 7.47-7.58 (m, 3H), 7.87-7.91 (m, 1H), 8.09 (d, 1H), 8.16-8.24 (m, 4H), 8.39 (s, 1H), 8.64-8.69 (m, 4H), 9.25 (s, 1H).

Example 22-37

1-[2-fluoro-5-(trifluoromethyl)phenyl]-3-(2-{4-[6-(3-oxetanyloxy)imidazo[1,2-b]pyridazin-3-yl]phenoxy}-5-pyrimidinyl)urea

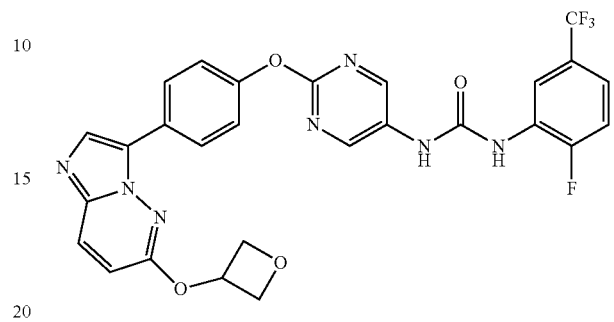

TLC: Rf 0.31 (Chloroform:Methanol=19:1);

$^1$H-NMR (DMSO-d$_6$): δ 4.70 (dd, 2H), 4.96 (dd, 2H), 5.63-5.71 (m, 1H), 7.03 (d, 1H), 7.34-7.55 (m, 4H), 8.06-8.13 (m, 3H), 8.15 (d, 1H), 8.53 (dd, 1H), 8.76 (s, 2H), 9.13 (s, 1H), 9.32 (s, 1H).

Example 22-38

1-[3'-(2-hydroxy-2-propanyl)-4-(trifluoromethyl)-2-biphenylyl]-3-(2-{4-[6-(3-oxetanyloxy)imidazo[1,2-b]pyridazin-3-yl]phenoxy}-5-pyrimidinyl)urea Purity (LC-MS/ELSD): 100% (Retention Time: 0.94 minutes);

MASS (ESI, Pos.): 698 (M+H)$^+$;

$^1$H-NMR (DMSO-d$_6$): δ 1.45 (s, 6H), 4.70 (dd, 2H), 4.95 (dd, 2H), 5.07 (s, 1H), 5.61-5.72 (m, 1H), 7.02 (d, 1H), 7.29 (d, 1H), 7.35(d, 2H), 7.41-7.60 (m, 5H), 8.03-8.19 (m, 5H), 8.34 (s, 1H), 8.67 (s, 2H), 9.39 (s, 1H).

Example 22-39

1-{2-[4-(6-methoxyimidazo[1,2-b]pyridazin-3-yl)phenoxy]-5-pyrimidinyl}-3-[2-(1H-pyrazol-1-yl)-4-(trifluoromethyl)phenyl]urea Purity (LC-MS/ELSD): 98% (Retention Time: 0.91 minutes);

MASS (ESI, Pos.): 588 (M+H)$^+$;

$^1$H-NMR (DMSO-d$_6$): δ 4.01 (s, 3H), 6.65-6.66 (m, 1H), 6.95 (d, 1H), 7.32 (d, 2H), 7.75 (d, 1H), 7.83 (s, 1H), 7.94 (d, 1H), 8.07-8.11 (m, 2H), 8.22 (d, 2H), 8.41-8.44 (m, 2H), 8.71 (s, 2H), 9.57 (s, 1H), 9.98 (s, 1H).

Example 22-40

1-[3-(difluoromethyl)phenyl]-3-{2-[4-(6-methoxyimidazo[1,2-b]pyridazin-3-yl)phenoxy]-5-pyrimidinyl}urea Purity (LC-MS/ELSD): 100% (Retention Time: 0.77 minutes);

MASS (ESI, Pos.): 504 (M+H)$^+$;

$^1$H-NMR (DMSO-d$_6$): δ 4.02 (s, 3H), 6.82-7.19 (m, 3H), 7.31-7.35 (m, 2H), 7.42 (t, 1H), 7.52 (d, 1H), 7.78 (s, 1H), 8.08-8.11 (m, 2H), 8.20-8.25 (m, 2H), 8.74 (s, 2H), 8.92 (s, 1H), 9.17 (s, 1H).

Example 22-41

1-[2-chloro-5-(trifluoromethyl)phenyl]-3-{2-[4-(6-methoxyimidazo[1,2-b]pyridazin-3-yl)phenoxy]-5-pyrimidinyl}urea Purity (LC-MS/ELSD): 100% (Retention Time: 0.91 minutes);
MASS (ESI, Pos.): 556 (M+H)$^+$;
$^1$H-NMR (DMSO-d$_6$): δ 4.02 (s, 3H), 6.95 (d, 1H), 7.31-7.36 (m, 2H), 7.40 (dd, 1H), 7.73 (d, 1H), 8.08-8.11 (m, 2H), 8.21-8.25 (m, 2H), 8.57 (d, 1H), 8.76 (s, 2H), 8.79 (s, 1H), 9.72 (s, 1H).

Example 22-42

1-[2-fluoro-5-(trifluoromethyl)phenyl]-3-{2-[4-(6-methoxyimidazo[1,2-b]pyridazin-3-yl)phenoxy]-5-pyrimidinyl}urea Purity (LC-MS/ELSD): 100% (Retention Time: 0.87 minutes);
MASS (ESI, Pos.): 540 (M+H)$^+$;
$^1$H-NMR (DMSO-d$_6$): δ 4.02 (s, 3H), 6.95 (d, 1H), 7.31-7.36 (m, 2H), 7.38-7.54 (m, 2H), 8.08-8.11 (m, 2H), 8.20-8.25 (m, 2H), 8.53 (dd, 1H), 8.75 (s, 2H), 9.10 (d, 1H), 9.31 (s, 1H).

Example 22-43

1-(2,5-dichlorophenyl)-3-{2-[4-(6-methoxyimidazo[1,2-b]pyridazin-3-yl)phenoxy]-5-pyrimidinyl}urea Purity (LC-MS/ELSD): 100% (Retention Time: 0.89 minutes);
MASS (ESI, Pos.): 522 (M+H)$^+$;
$^1$H-NMR (DMSO-d$_6$): δ 4.02 (s, 3H), 6.95 (d, 1H), 7.11 (dd, 1H), 7.31-7.35 (m, 2H), 7.50 (d, 1H), 8.07-8.10 (m, 2H), 8.20-8.26 (m, 3H), 8.64 (s, 1H), 8.74 (s, 2H), 9.68 (s, 1H).

Example 22-44

1-(2,4-dichlorophenyl)-3-{2-[4-(6-methoxyimidazo[1,2-b]pyridazin-3-yl)phenoxy]-5-pyrimidinyl}urea Purity (LC-MS/ELSD): 100% (Retention Time: 0.89 minutes);
MASS (ESI, Pos.): 522 (M+H)$^+$;
$^1$H-NMR (DMSO-d$_6$): δ 4.02 (s, 3H), 6.95 (d, 1H), 7.31-7.35 (m, 2H), 7.39 (dd, 1H), 7.64 (d, 1H), 8.07-8.11 (m, 2H), 8.14 (d, 1H), 8.20-8.25 (m, 2H), 8.58 (s, 1H), 8.74 (s, 2H), 9.60 (s, 1H).

Example 22-45

1-(2,5-difluorophenyl)-3-{2-[4-(6-methoxyimidazo[1,2-b]pyridazin-3-yl)phenoxy]-5-pyrimidinyl}urea Purity (LC-MS/ELSD): 100% (Retention Time: 0.79 minutes);
MASS (ESI, Pos.): 490 (M+H)$^+$;
$^1$H-NMR (DMSO-d$_6$): δ 4.02 (s, 3H), 6.81-6.90 (m, 1H), 6.95 (d, 1H), 7.26-7.35 (m, 3H), 7.94-8.00 (m, 1H), 8.08-8.12 (m, 2H), 8.20-8.25 (m, 2H), 8.74 (s, 2H), 8.97 (s, 1H), 9.28 (s, 1H).

Example 22-46

1-{2-[4-(6-methoxyimidazo[1,2-b]pyridazin-3-yl)phenoxy]-5-pyrimidinyl}-3-[2-(4-methyl-1H-1,2,3-triazol-1-yl)-5-(trifluoromethyl)phenyl]urea Purity (LC-MS/ELSD): 99% (Retention Time: 0.86 minutes);
MASS (ESI, Pos.): 603 (M+H)$^+$;
$^1$H-NMR (DMSO-d$_6$): δ 2.38 (s, 3H), 4.01 (s, 3H), 6.95 (d, 1H), 7.30-7.34 (m, 2H), 7.59 (dd, 1H), 7.70 (d, 1H), 8.07-8.10 (m, 2H), 8.20-8.24 (m, 2H), 8.39 (s, 1H), 8.60 (s, 1H), 8.69 (s, 2H), 8.76 (s, 1H), 9.70 (s, 1H).

Example 22-47

1-[5-chloro-2-(1H-pyrazol-1-yl)phenyl]-3-{2-[4-(6-methoxyimidazo[1,2-b]pyridazin-3-yl)phenoxy]-5-pyrimidinyl}urea Purity (LC-MS/ELSD): 100% (Retention Time: 0.88 minutes);
MASS (ESI, Pos.): 554 (M+H)$^+$;
$^1$H-NMR (DMSO-d$_6$): δ 4.01 (s, 3H), 6.61-6.63 (m, 1H), 6.94 (d, 1H), 7.22 (dd, 1H), 7.30-7.34 (m, 2H), 7.51 (d, 1H), 7.89 (d, 1H), 8.07-8.10 (m, 2H), 8.19-8.24 (m, 2H), 8.26 (d, 1H), 8.27 (d, 1H), 8.69 (s, 2H), 9.37 (s, 1H), 9.89 (s, 1H).

Example 22-48

1-[5-chloro-2-(3-pyridinyl)phenyl]-3-{2-[4-(6-methoxyimidazo[1,2-b]pyridazin-3-yl)phenoxy]-5-pyrimidinyl}urea Purity (LC-MS/ELSD): 77% (Retention Time: 0.75 minutes);
MASS (ESI, Pos.): 565 (M+H)$^+$;
$^1$H-NMR (DMSO-d$_6$): δ 4.02 (s, 3H), 6.95 (d, 1H), 7.22-7.34 (m, 4H), 7.54 (dd, 1H), 7.80-7.85 (m, 1H), 8.07-8.23 (m, 6H), 8.59-8.66 (m, 4H), 9.20 (brs, 1H).

Example 22-49

1-{6-[4-(6-methoxyimidazo[1,2-b]pyridazin-3-yl)phenoxy]-3-pyridinyl}-3-[2-(3-pyridinyl)-5-(trifluoromethyl)phenyl]urea Purity (LC-MS/ELSD): 98% (Retention Time: 0.83 minutes);
MASS (ESI, Pos.): 598 (M+H)$^+$;
$^1$H-NMR (DMSO-d$_6$): δ 4.00 (s, 3H), 6.94 (d, 1H), 7.05 (d, 1H), 7.18-7.23 (m, 2H), 7.45-7.59 (m, 3H), 7.87-7.91 (m, 1H), 8.00 (dd, 1H), 8.06-8.21 (m, 6H), 8.42 (s, 1H), 8.64-8.69 (m, 2H), 9.18 (s, 1H).

Example 22-50

1-{6-[4-(6-methoxyimidazo[1,2-b]pyridazin-3-yl)phenoxy]-3-pyridinyl}-3-[2-(1H-pyrazol-1-yl)-5-(trifluoromethyl)phenyl]urea Purity (LC-MS/ELSD): 100% (Retention Time: 0.95 minutes);
MASS (ESI, Pos.): 587 (M+H)$^+$;
$^1$H-NMR (DMSO-d$_6$): δ 4.01 (s, 3H), 6.67-6.68 (m, 1H), 6.94 (d, 1H), 7.07 (d, 1H), 7.19-7.24 (m, 2H), 7.50 (dd, 1H), 7.73 (d, 1H), 7.95 (d, 1H), 8.00-8.10 (m, 3H), 8.18-8.21 (m, 3H), 8.40 (d, 1H), 8.59 (s, 1H), 9.56 (s, 1H), 9.83 (s, 1H).

Example 22-51

1-{6-[4-(6-methoxyimidazo[1,2-b]pyridazin-3-yl)phenoxy]-3-pyridinyl}-3-{5-(trifluoromethyl)-2-[3-(trifluoromethyl)-1H-pyrazol-1-yl]phenyl}urea Purity (LC-MS/ELSD): 100% (Retention Time: 1.01 minutes);
MASS (ESI, Pos.): 655 (M+H)$^+$;
$^1$H-NMR (DMSO-d$_6$): δ 4.01 (s, 3H), 6.94 (d, 1H), 7.07 (d, 1H), 7.13 (d, 1H), 7.19-7.24 (m, 2H), 7.55 (dd, 1H), 7.69 (d, 1H), 7.99 (dd, 1H), 8.01-8.21 (m, 5H), 8.45-8.52 (m, 3H), 9.40 (s, 1H).

Example 22-52

1-(2-{4-[6-(3-oxetanyloxy)imidazo[1,2-b]pyridazin-3-yl]phenoxy}-5-pyrimidinyl)-3-[3-(trifluoromethyl)phenyl]urea Purity (LC-MS/ELSD): 100% (Retention Time: 0.84 minutes);
MASS (ESI, Pos.): 564 (M+H)$^+$;
$^1$H-NMR (DMSO-d$_6$): δ 4.68-4.72 (m, 2H), 4.93-4.98 (m, 2H), 5.63-5.72 (m, 1H), 7.02 (d, 1H), 7.31-7.40 (m, 3H), 7.51 (t, 1H), 7.61 (d, 1H), 7.96-8.00 (m, 1H), 8.07-8.17 (m, 4H), 8.74 (s, 2H), 9.00 (s, 1H), 9.32 (s, 1H).

Example 22-53

1-[2-chloro-5-(trifluoromethyl)phenyl]-3-(2-{4-[6-(3-oxetanyloxy)imidazo[1,2-b]pyridazin-3-yl]phenoxy}-5-pyrimidinyl)urea Purity (LC-MS/ELSD): 100% (Retention Time: 0.90 minutes);
MASS (ESI, Pos.): 598 (M+H)$^+$;
$^1$H-NMR (DMSO-d$_6$): δ 4.68-4.73 (m, 2H), 4.93-4.99 (m, 2H), 5.63-5.72 (m, 1H), 7.03 (d, 1H), 7.35-7.43 (m, 3H), 7.73 (d, 1H), 8.07-8.17 (m, 4H), 8.57 (d, 1H), 8.76 (s, 2H), 8.80 (s, 1H), 9.73 (s, 1H).

Example 22-54

1-[2-methyl-5-(trifluoromethyl)phenyl]-3-(2-{4-[6-(3-oxetanyloxy)imidazo[1,2-b]pyridazin-3-yl]phenoxy}-5-pyrimidinyl)urea Purity (LC-MS/ELSD): 100% (Retention Time: 0.86 minutes);
MASS (ESI, Pos.): 578 (M+H)$^+$;
$^1$H-NMR (DMSO-d$_6$): δ 2.32 (s, 3H), 4.67-4.74 (m, 2H), 4.93-4.99 (m, 2H), 5.63-5.71 (m, 1H), 7.03 (d, 1H), 7.27-7.45 (m, 4H), 8.07-8.18 (m, 4H), 8.27-8.30 (m, 1H), 8.39 (s, 1H), 8.76 (s, 2H), 9.35 (s, 1H).

Example 22-55

1-(2,4-dichlorophenyl)-3-(2-{4-[6-(3-oxetanyloxy)imidazo[1,2-b]pyridazin-3-yl]phenoxy}-5-pyrimidinyl)urea Purity (LC-MS/ELSD): 100% (Retention Time: 0.87 minutes);
MASS (ESI, Pos.): 564 (M+H)$^+$;
$^1$H-NMR (DMSO-d$_6$): δ 4.67-4.74 (m, 2H), 4.92-5.00 (m, 2H), 5.63-5.72 (m, 1H), 7.03 (d, 1H), 7.34-7.43 (m, 3H), 7.64 (dd, 1H), 8.06-8.19 (m, 5H), 8.59 (s, 1H), 8.75 (s, 2H), 9.61 (s, 1H).

Example 22-56

1-(5-chloro-2-methylphenyl)-3-(2-{4-[6-(3-oxetanyloxy)imidazo[1,2-b]pyridazin-3-yl]phenoxy}-5-pyrimidinyl)urea Purity (LC-MS/ELSD): 100% (Retention Time: 0.84 minutes);
MASS (ESI, Pos.): 544 (M+H)$^+$;
$^1$H-NMR (DMSO-d$_6$): δ 2.22 (s, 3H), 4.70 (dd, 2H), 4.96 (dd, 2H), 5.63-5.72 (m, 1H), 6.98-7.05 (m, 2H), 7.20 (d, 1H), 7.36 (d, 2H), 7.98 (d, 1H), 8.05-8.19 (m, 4H), 8.27 (s, 1H), 8.75 (s, 2H), 9.31 (s, 1H).

Example 22-57

1-(2,5-difluorophenyl)-3-(2-{4-[6-(3-oxetanyloxy)imidazo[1,2-b]pyridazin-3-yl]phenoxy}-5-pyrimidinyl)urea Purity (LC-MS/ELSD): 99% (Retention Time: 0.81 minutes);
MASS (ESI, Pos.): 532 (M+H)$^+$;
$^1$H-NMR (DMSO-d$_6$): δ 4.70 (dd, 2H), 4.96 (dd, 2H), 5.62-5.72 (m, 1H), 6.81-6.92 (m, 1H), 7.03 (d, 1H), 7.23-7.32 (m, 1H), 7.38 (d, 2H), 7.93-8.01 (m, 1H), 8.04-8.19 (m, 4H), 8.75 (s, 2H), 8.98 (s, 1H), 9.29 (s, 1H).

Example 22-58

1-[5-methyl-2-(methylsulfonyl)phenyl]-3-(2-{4-[6-(3-oxetanyloxy)imidazo[1,2-b]pyridazin-3-yl]phenoxy}-5-pyrimidinyl)urea Purity (LC-MS/ELSD): 100% (Retention Time: 0.77 minutes);
MASS (ESI, Pos.): 588 (M+H)$^+$;
$^1$H-NMR (DMSO-d$_6$): δ 2.37 (s, 3H), 3.24 (s, 3H), 4.71 (dd, 2H), 4.96 (dd, 2H), 5.62-5.72 (m, 1H), 7.03 (d, 1H), 7.12 (d, 1H), 7.37 (d, 2H), 7.73 (d, 1H), 7.99 (s, 1H), 8.05-8.20 (m, 4H), 8.73 (s, 1H), 8.77 (s, 2H), 10.13 (s, 1H).

Example 22-59

1-[5-chloro-2-(methylsulfonyl)phenyl]-3-(2-{4-[6-(3-oxetanyloxy)imidazo[1,2-b]pyridazin-3-yl]phenoxy}-5-pyrimidinyl)urea Purity (LC-MS/ELSD): 100% (Retention Time: 0.83 minutes);
MASS (ESI, Pos.): 608 (M+H)$^+$;
$^1$H-NMR (DMSO-d$_6$): δ 3.32 (s, 3H), 4.70 (dd, 2H), 4.95 (dd, 2H), 5.63-5.71 (m, 1H), 7.03 (d, 1H), 7.23-7.31 (m, 3H), 7.85 (d, 1H), 8.03-8.19 (m, 4H), 8.33 (d, 1H), 8.77 (s, 2H), 8.88 (s, 1H), 10.14 (s, 1H).

Example 22-60

1-[5-fluoro-2-(methylsulfonyl)phenyl]-3-(2-{4-[6-(3-oxetanyloxy)imidazo[1,2-b]pyridazin-3-yl]phenoxy}-5-pyrimidinyl)urea Purity (LC-MS/ELSD): 99% (Retention Time: 0.79 minutes);
MASS (ESI, Pos.): 592 (M+H)$^+$;
$^1$H-NMR (DMSO-d$_6$): δ 3.32 (s, 3H), 4.71 (dd, 2H), 4.96 (dd, 2H), 5.62-5.72 (m, 1H), 7.03 (d, 1H), 7.20-7.30 (m, 1H), 7.37 (d, 2H), 7.92 (dd, 1H), 8.03-8.20 (m, 5H), 8.76 (s, 2H), 8.95 (s, 1H), 10.30 (s, 1H).

Example 22-61

1-[2-(methylsulfonyl)-5-(trifluoromethyl)phenyl]-3-(2-{4-[6-(3-oxetanyloxy)imidazo[1,2-b]pyridazin-3-yl]phenoxy}-5-pyrimidinyl)urea Purity (LC-MS/ELSD): 98% (Retention Time: 0.87 minutes);
MASS (ESI, Pos.): 642 (M+H)$^+$;
$^1$H-NMR (DMSO-d$_6$): δ 3.39 (s, 3H), 4.70 (dd, 2H), 4.95 (dd, 2H), 5.62-5.73 (m, 1H), 7.03 (d, 1H), 7.37 (d, 2H), 7.64 (d, 1H), 8.03-8.20 (m, 5H), 8.63 (s, 1H), 8.77 (s, 2H), 8.98 (s, 1H), 10.32 (s, 1H).

Example 22-62

1-[2-(methylsulfonyl)phenyl]-3-(2-{4-[6-(3-oxetanyloxy)imidazo[1,2-b]pyridazin-3-yl]phenoxy}-5-pyrimidinyl)urea Purity (LC-MS/ELSD): 93% (Retention Time: 0.73 minutes);
MASS (ESI, Pos.): 574 (M+H)$^+$;
$^1$H-NMR (DMSO-d$_6$): δ 3.28 (s, 3H), 4.70 (dd, 2H), 4.96 (dd, 2H), 5.62-5.73 (m, 1H), 7.03 (d, 1H), 7.25-7.33 (m, 1H), 7.37 (d, 2H), 7.62-7.72 (m, 1H), 7.85 (dd, 1H), 8.04-8.20 (m, 5H), 8.77 (s, 3H), 10.14 (s, 1H).

Example 22-63

2-[({2-[4-(6-ethoxyimidazo[1,2-b]pyridazin-3-yl)phenoxy]-5-pyrimidinyl}carbamoyl)amino]-N,N-dimethyl-4-(trifluoromethyl)benzenesulfonamide Purity (LC-MS/ELSD): 100% (Retention Time: 0.99 minutes);
MASS (ESI, Pos.): 643 (M+H)$^+$;
$^1$H-NMR (DMSO-d$_6$): δ 1.41 (t, 3H), 2.76 (s, 6H), 4.42 (q, 2H), 6.92 (d, 1H), 7.33 (d, 2H), 7.60 (dd, 1H), 7.94 (d, 1H), 8.05-8.10 (m, 2H), 8.20 (d, 2H), 8.61 (s, 1H), 8.75 (s, 2H), 8.99 (s, 1H), 10.31 (s, 1H).

Example 22-64

1-{2-[4-(6-ethoxyimidazo[1,2-b]pyridazin-3-yl)phenoxy]-5-pyrimidinyl}-3-[2-(methylsulfonyl)-5-(trifluoromethyl)phenyl]urea Purity (LC-MS/ELSD): 100% (Retention Time: 0.94 minutes);
MASS (ESI, Pos.): 614 (M+H)$^+$;
$^1$H-NMR (DMSO-d$_6$): δ 1.41 (t, 3H), 3.38 (s, 3H), 4.42 (q, 2H), 6.93 (d, 1H), 7.33 (d, 2H), 7.64 (d, 1H), 8.03-8.26 (m, 3H), 8.20 (d, 2H), 8.63 (s, 1H), 8.76 (s, 2H), 8.97 (s, 1H), 10.31 (s, 1H).

Example 22-65

1-[5-chloro-2-(methylsulfonyl)phenyl]-3-{2-[4-(6-ethoxyimidazo[1,2-b]pyridazin-3-yl)phenoxy]-5-pyrimidinyl}urea Purity (LC-MS/ELSD): 100% (Retention Time: 0.91 minutes);
MASS (ESI, Pos.): 580 (M+H)$^+$;
$^1$H-NMR (DMSO-d$_6$): δ 1.43 (t, 3H), 3.32 (s, 3H), 4.45 (q, 2H), 7.26 (d, 1H), 7.35-7.41 (m, 3H), 7.85 (d, 1H), 8.18 (d, 2H), 8.27 (d, 1H), 8.33 (d, 1H), 8.40 (s, 1H), 8.77 (s, 2H), 8.89 (s, 1H), 10.33 (s, 1H).

Example 22-66

1-[3'-(hydroxymethyl)-4-(trifluoromethyl)-2-biphenylyl]-3-(2-{4-[6-(3-oxetanyloxy)imidazo[1,2-b]pyridazin-3-yl]phenoxy}-5-pyrimidinyl)urea Purity (LC-MS/ELSD): 99% (Retention Time: 1.07 minutes);
MASS (ESI, Pos.): 670 (M+H)$^+$;
$^1$H-NMR (DMSO-d$_6$): δ 4.58 (d, 2H), 4.70 (dd, 2H), 4.95 (dd, 2H), 5.29 (t, 1H), 5.67 (quint, 1H), 7.03 (d, 1H), 7.27-7.56 (m, 8H), 8.04-8.15 (m, 4H), 8.15 (d, 1H), 8.42 (d, 1H), 8.68 (s, 2H), 9.43 (s, 1H).

Example 22-67

1-[3'-(1-hydroxyethyl)-4-(trifluoromethyl)-2-biphenylyl]-3-(2-{4-[6-(3-oxetanyloxy)imidazo[1,2-b]pyridazin-3-yl]phenoxy}-5-pyrimidinyl)urea Purity (LC-MS/ELSD): 99% (Retention Time: 0.94 minutes);
MASS (ESI, Pos.): 684 (M+H)$^+$;
$^1$H-NMR (DMSO-d$_6$): δ 1.36 (d, 3H), 4.70 (dd, 2H), 4.76-4.83 (m, 1H), 4.95 (dd, 2H), 5.21 (d, 1H), 5.67 (quint, 1H), 7.02 (d, 1H), 7.27-7.56 (m, 8H), 8.03-8.13 (m, 4H), 8.15 (d, 1H), 8.37 (s, 1H), 8.67 (s, 2H), 9.41 (s, 1H).

Example 23

The similar procedure as Example 7 was carried out with a corresponding amine compound produced with a corresponding bicyclic heterocycle compound in place of Example 19 produced with 5-chloropyrazolo[1,5-a]pyrimidine, and the compound produced in Example 3 or a corresponding carbamate or isocyanate compound in place of the compound produced in Example 3 to give the present compounds having the following physical characteristics.

Example 23-1

1-(2-(4-(6-methoxyimidazo[1,2-a]pyridin-3-yl)phenoxy)pyrimidin-5-yl)-3-(3-(trifluoromethyl)phenyl)urea

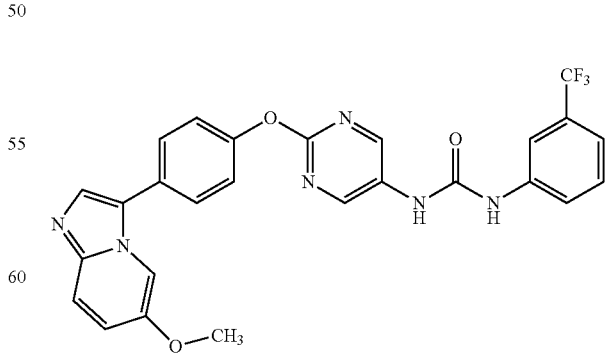

TLC: Rf 0.52 (Ethyl acetate:Methanol=9:1);
$^1$H-NMR (DMSO-d$_6$): δ 3.81 (s, 3H), 7.10 (dd, 1H), 7.30-7.37 (m, 3H), 7.52 (t, 1H), 7.54-7.65 (m, 2H), 7.71 (s, 1H), 7.73-7.77 (m, 2H), 7.98-8.03 (m, 2H), 8.75 (s, 2H), 9.00 (s, 1H), 9.32 (s, 1H).

Example 23-2

1-(2-(4-(6-(2-hydroxypropan-2-yl)imidazo[1,2-a]pyridin-3-yl)phenoxy)pyrimidin-5-yl)-3-(3-(trifluoromethyl)phenyl)urea TLC: Rf 0.26 (Chloroform:Methanol=19:1);
$^1$H-NMR (DMSO-$d_6$): δ 1.48 (s, 6H), 5.30 (s, 1H), 7.30-7.43 (m, 4H), 7.49-7.74 (m, 6H), 7.95-7.99 (m, 1H), 8.50-8.53 (m, 1H), 8.75 (s, 2H), 9.00 (s, 1H), 9.32 (s, 1H).

Example 23-3

1-(2-(1H-pyrazol-1-yl)-5-(trifluoromethyl)phenyl)-3-(2-(4-(imidazo[1,2-a]pyridin-3-yl)phenoxy)pyrimidin-5-yl)urea TLC: Rf 0.59 (Ethyl acetate:Methanol=9:1);
$^1$H-NMR (DMSO-$d_6$): δ 6.67 (t, 1H), 6.96 (t, 1H), 7.27-7.37 (m, 3H), 7.51 (d, 1H), 7.64-7.77 (m, 5H), 7.95 (s, 1H), 8.41 (d, 1H), 8.55-8.58 (m, 2H), 8.71 (s, 2H), 9.70 (s, 1H), 9.97 (s, 1H).

Example 23-4

1-(2-(4-(imidazo[1,2-a]pyridin-3-yl)phenoxy)pyrimidin-5-yl)-3-(2-(pyridin-3-yl)-5-(trifluoromethyl)phenyl)urea TLC: Rf 0.27 (Ethyl acetate);
$^1$H-NMR (DMSO-$d_6$): δ 6.95-7.00 (m, 1H), 7.27-7.36 (m, 3H), 7.48-7.60 (m, 3H), 7.64-7.72 (m, 3H), 7.77 (s, 1H), 7.88 (dt, 1H), 8.24 (s, 1H), 8.39 (s, 1H), 8.56 (d, 1H), 8.65-8.69 (m, 4H), 9.25 (s, 1H).

Example 23-5

1-(2-(4-(imidazo[1,2-a]pyridin-3-yl)phenoxy)pyrimidin-5-yl)-3-(3-(trifluoromethyl)phenyl)urea TLC: Rf 0.46 (Ethyl acetate);
$^1$H-NMR (DMSO-$d_6$): δ 6.95-7.05 (m, 1H), 7.28-7.38 (m, 4H), 7.52 (t, 1H), 7.60-7.74 (m, 4H), 7.78 (s, 1H), 7.98 (s, 1H), 8.57 (d, 1H), 8.74 (s, 2H), 9.02 (s, 1H), 9.34 (s, 1H).

Example 23-6

1-(2-(4-(imidazo[1,2-a]pyridin-3-yl)phenoxy)pyrimidin-5-yl)-3-(2-phenyl-5-(trifluoromethyl)pyridin-3-yl)urea TLC: Rf 0.29 (Ethyl acetate);
$^1$H-NMR (DMSO-$d_6$): δ 6.95-7.01 (m, 1H), 7.27-7.37 (m, 3H), 7.54-7.78 (m, 9H), 8.43 (s, 1H), 8.56 (s, 2H), 8.70 (s, 2H), 8.73 (s, 1H), 8.76 (d, 1H), 9.48 (s, 1H).

Example 23-7

1-(2-(4-(1H-pyrrolo[2,3-b]pyridin-5-yl)phenoxy)pyrimidin-5-yl)-3-(2-(pyridin-3-yl)-5-(trifluoromethyl)phenyl)urea

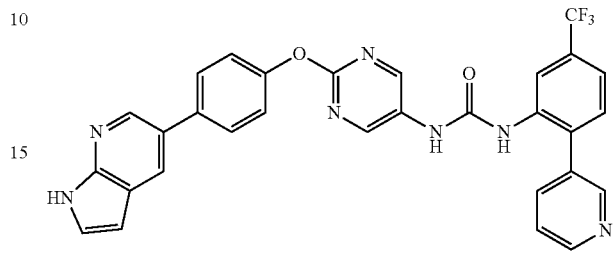

TLC: Rf 0.23 (Ethyl acetate);
$^1$H-NMR (DMSO-$d_6$): δ 6.49 (d, 1H), 7.26 (d, 2H), 7.47-7.58 (m, 4H), 7.73 (d, 2H), 7.90 (d, 1H), 8.19-8.25 (m, 2H), 8.39 (s, 1H), 8.49-8.51 (m, 1H), 8.65-8.68 (m, 4H), 9.24 (s, 1H), 11.7 (s, 1H).

Example 23-8

1-(2-(4-(1H-pyrrolo[2,3-b]pyridin-5-yl)phenoxy)pyrimidin-5-yl)-3-(3-(trifluoromethyl)phenyl)urea TLC: Rf 0.60 (Ethyl acetate);
$^1$H-NMR (DMSO-$d_6$): δ 6.49-6.50 (m, 1H), 7.26-7.36 (m, 3H), 7.46-7.54 (m, 2H), 7.62 (d, 1H), 7.74 (d, 2H), 7.97 (s, 1H), 8.21 (s, 1H), 8.50-8.53 (m, 1H), 8.73 (s, 2H), 8.98 (s, 1H), 9.31 (s, 1H), 11.7 (s, 1H).

Example 23-9

1-(2-(4-(6-amino-1H-pyrrolo[2,3-b]pyridin-5-yl)phenoxy)pyrimidin-5-yl)-3-(2-(pyridin-3-yl)-5-(trifluoromethyl)phenyl)urea

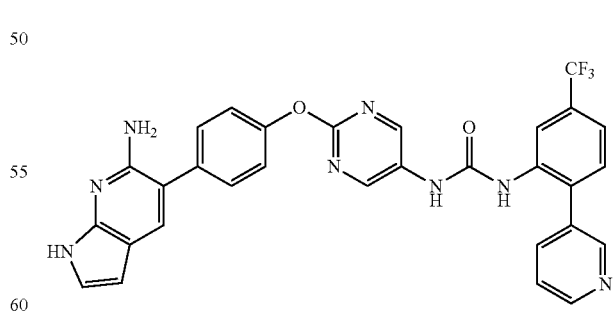

TLC: Rf 0.35 (Ethyl acetate);
$^1$H-NMR (DMSO-$d_6$): δ 5.19 (s, 2H), 6.20-6.24 (m, 1H), 6.99 (t, 1H), 7.23 (d, 2H), 7.46-7.58 (m, 6H), 7.88-7.92 (m, 1H), 8.23 (s, 1H), 8.38 (s, 1H), 8.63-8.68 (m, 4H), 9.23 (s, 1H), 10.9 (s, 1H).

Example 23-10

1-(2-(4-(imidazo[1,2-a]pyrazin-3-yl)phenoxy)pyrimidin-5-yl)-3-(2-(pyridin-3-yl)-5-(trifluoromethyl)phenyl)urea

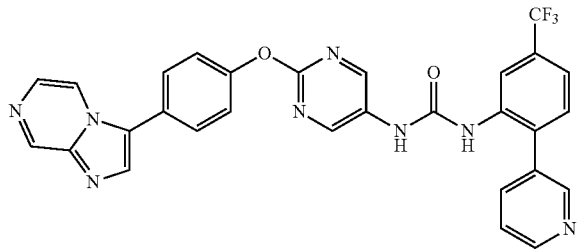 [SMILES: O=C(Nc1cnc(Oc2ccc(-c3cnc4cnccn34)cc2)nc1)Nc1cc(C(F)(F)F)ccc1-c1cccnc1]

TLC: Rf 0.34 (Dichloromethane:Methanol=9:1);
$^1$H-NMR (DMSO-d$_6$): δ 7.38 (d, 2H), 7.46-7.59 (m, 3H), 7.78 (d, 2H), 7.85-7.91 (m, 1H), 7.92 (d, 1H), 8.06 (s, 1H), 8.24 (s, 1H), 8.38 (s, 1H), 8.58-8.69 (m, 5H), 9.13 (d, 1H), 9.25 (s, 1H).

Example 23-11

1-(2-(4-(pyrazolo[1,5-a]pyridin-3-yl)phenoxy)pyrimidin-5-yl)-3-(2-(pyridin-3-yl)-5-(trifluoromethyl)phenyl)urea

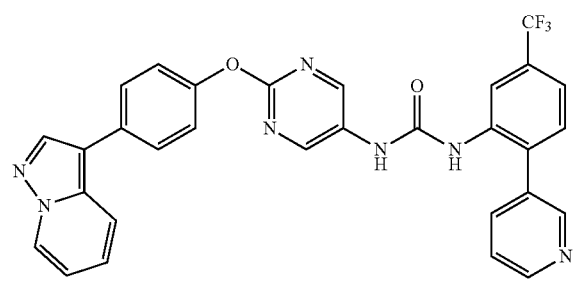

TLC: Rf 0.29 (Ethyl acetate);
$^1$H-NMR (DMSO-d$_6$): δ 6.94 (t, 1H), 7.74-7.35 (m, 3H), 7.46-7.58 (m, 3H), 7.71 (d, 2H), 7.89 (d, 1H), 7.96 (d, 1H), 8.23 (s, 1H), 8.36-8.38 (m, 2H), 8.64-8.74 (m, 5H), 9.22 (s, 1H).

Example 23-12

1-(2-(4-(1H-pyrazolo[3,4-b]pyridin-5-yl)phenoxy)pyrimidin-5-yl)-3-(2-(pyridin-3-yl)-5-(trifluoromethyl)phenyl)urea

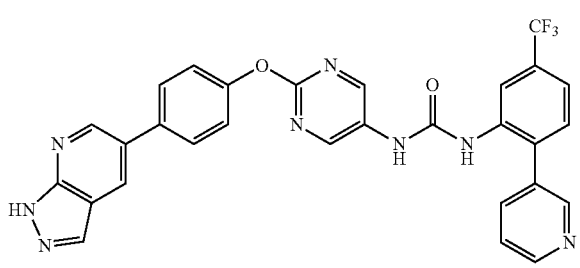 [SMILES: O=C(Nc1cnc(Oc2ccc(-c3cnc4[nH]ncc4c3)cc2)nc1)Nc1cc(C(F)(F)F)ccc1-c1cccnc1]

TLC: Rf 0.23 (Ethyl acetate);
$^1$H-NMR (DMSO-d$_6$): δ 7.29 (d, 2H), 7.47-7.58 (m, 3H), 7.79 (d, 2H), 7.87-7.93 (m, 1H), 8.18-8.21 (m, 1H), 8.24 (s, 1H), 8.38 (s, 1H), 8.47 (d, 1H), 8.64-8.68 (m, 4H), 8.83 (d, 1H), 9.23 (s, 1H), 13.7 (s, 1H).

PHARMACOLOGICAL EXPERIMENT EXAMPLES

Pharmacological Experiment Example 1

Measurement of TrkA Kinase-Inhibiting Activity Using Human TrkA-Expressing Cells TrkA kinase-inhibiting activity in cell systems was measured using CHO-K1 cells expressing human TrkA and NFAT-bla (CellSenser™ TrkA-NFAT-bla CHO-K1 cells, Invitrogen).

On the day before the assay, CellSenser™ TrkA-NFAT-bla CHO-K1 cells were suspended in an assay medium (Opti-MEM1 Reduced Serum Medium (Invitrogen) containing 0.5% dialysed fetal bovine serum (Invitrogen), 0.1 mM nonessential amino acids (Invitrogen), 1 mM sodium pyruvate (Invitrogen) and antibiotics (100 U/mL penicillin and 100 μg/mL streptomycin (Invitrogen))) and plated at a density of 2.4×10$^4$ cells/40 μL/well in a 96-well clear bottom plate (Corning, Catalogue No.: 3882). In some wells were added only the assay medium at 40 μL/well (Cell-free). On the day of the assay, 10 mM of the present compound (DMSO solution) was distributed in a 96-well plate (Costar, Catalogue No.: 3363) and serially diluted with DMSO with the geometrical ratio of 3. The serial dilutions were diluted with the assay medium to 100-fold to prepare a solution of the present compound with a 10-fold concentration (DMSO concentration: 1%). To the plate where cells were plated was added the present compound at 5 μL/well and the plate was incubated in a CO$_2$ incubator with 5% CO$_2$, 95% Air at 37° C. for 30 minutes. For a control and a blank, the assay medium containing 1% DMSO was added at 5 μL/well in place of the solution of the present compound. Subsequently the assay medium containing NGF (Mouse 2.5s, Natural, Invitrogen) was added to the plate at 5 μL/well (final concentration of NGF: 50 ng/ml) and the plate was incubated in a CO$_2$ incubator with 5% CO$_2$, 95% Air at 37° C. for 5 hours. For the blank group, the assay medium was added in place of NGF at 5 μL/well. A reporter assay detection reagent (10 μL/well) was added to the plate which was then incubated in the dark at room temperature for 120 minutes. The reporter assay detection reagent was prepared from LiveBLAzer™-FRET B/G Loading Kit (Invitrogen). On the Analyst GT (Molecular Devices Japan, K.K.) the wells were irradiated with excitation light at 405 nm and the fluorescence intensities at 460 nm and 530 nm were measured. The time resolved fluorescence resonance energy transfer (TR-FRET) ratio of each well was calculated according to the following Equation 1:

$$\text{TR-FRET ratio} = (A_{460X} - A_{460F})/(A_{530X} - A_{530F}) \quad \text{[Eq. 1]}$$

wherein:
$A_{460X}$: the fluorescence intensity at 460 nm of the present compound, control or blank;
$A_{460F}$: the fluorescence intensity at 460 nm of the Cell-free;
$A_{530X}$: the fluorescence intensity at 530 nm of the present compound, control or blank; and
$A_{530F}$: the fluorescence intensity at 530 nm of the Cell-free.

The TR-FRET inhibition rate (%) of the present compound was calculated according to the following Equation 2:

$$\text{Inhibition rate (\%)} = \{1 - (A_X - A_B)/(A_C - A_B)\} \times 100 \quad [\text{Eq. 2}]$$

wherein $A_X$: the TR-FRET ratio when the present compound is added;

$A_B$: the TR-FRET of the blank; and $A_C$: the TR-FRET of the control.

The $IC_{50}$ value by the present compound was calculated from the inhibition curve based on the inhibition rate of the present compound at respective concentrations.

As a result, it was found that the present compounds had $IC_{50}$ values of 0.5 μM or lower and had TrkA-inhibiting activity. $IC_{50}$ values of some of the present compounds are shown in the following Table 1 or 2.

TABLE 1

| Example | TrkA-inhibiting activity (IC50; μM) |
|---|---|
| 7 | 0.001 |
| 8-1 | 0.001 |
| 8-2 | 0.002 |
| 8-4 | 0.001 |
| 9-1 | 0.003 |
| 9-2 | 0.001 |
| 11 | 0.001 |
| 13-1 | 0.002 |
| 14-5 | 0.001 |
| 14-6 | 0.001 |
| 15-4 | 0.001 |
| 15-5 | 0.003 |
| 15-6 | 0.002 |
| 15-52 | 0.004 |
| 15-55 | 0.004 |
| 15-58 | 0.002 |
| 15-63 | 0.002 |
| 15-71 | 0.002 |
| 15-77 | 0.002 |
| 15-87 | 0.001 |
| 15-96 | 0.0004 |
| 15-98 | 0.0008 |
| 15-104 | 0.0005 |
| 15-105 | 0.004 |

TABLE 2

| Example | TrkA-inhibiting activity (IC50; μM) |
|---|---|
| 21-1 | 0.001 |
| 21-2 | 0.001 |
| 21-9 | 0.001 |
| 21-13 | 0.001 |
| 21-37 | 0.001 |
| 21-51 | 0.001 |
| 21-65 | 0.0007 |
| 21-67 | 0.004 |
| 21-70 | 0.002 |
| 21-73 | 0.003 |
| 21-75 | 0.004 |
| 22-8 | 0.001 |
| 22-9 | 0.001 |
| 22-34 | 0.001 |
| 23-3 | 0.001 |
| 23-7 | 0.002 |
| 23-10 | 0.001 |
| 23-11 | 0.001 |
| 23-12 | 0.001 |

Pharmacological Experiment Example 2

Enzyme-Inhibiting Activity Test of Kinases Other than Trk (Selectivity Experiment)

A test substance (the present compound) was dissolved in dimethylsulfoxide to prepare a 100-fold concentration of the test concentration, 3 μM. The solution was further diluted to 25-fold with an assay buffer (20 mM HEPES, 0.01% Triton X-100, 2 mM DTT, pH 7.5) to obtain a test substance solution. In a similar manner a positive control substance solution was prepared with a positive control substance.

A 4-times concentration solution (5 μL) of the test substance prepared with the assay buffer, 5 μL of a 4-times concentration solution of substrate/ATP/metal (Mg) and 10 μL of a 2-times concentration solution of kinase were mixed in a well of a polypropylene 384-well plate and allowed to react at room temperature for 1 hour. The reaction was terminated by adding 60 μL of a Termination Buffer (QuickScout Screening Assist MSA; Carna Biosciences). The substrate peptide and the phosphorylated peptide in the reaction solution were separated and quantified. The kinase reaction was assessed from the product ratio (P/(P+S)) calculated from the height (S) of the peak of the substrate peptide and the height (P) of the peak of the phosphorylated peptide. Other kinases used in the kinase selectivity experiments were, for example, b-Raf and KDR. The following Table 3 indicates substrates, substrate concentrations, ATP concentrations and positive control substances used in respective kinase enzyme inhibition activity tests.

TABLE 3

| Kinase | Substrate Name | (nM) | ATP (μM) | Positive control |
|---|---|---|---|---|
| b-Raf | MAP2K1 | 1 | 1000 | ZM336372 |
| KDR | CSKtide | 1000 | 75 | Staurosporine |

The inhibition rate was calculated from the average signal intensity of the test wells containing respective test substances provided that the average signal intensity of control wells each containing all reaction components was 0% inhibition and the average signal intensity of background wells (without addition of the enzyme) was 100% inhibition. As a result, the present compounds at a concentration of 3 μM had the inhibition rates of kinases as shown in the following Table 4.

TABLE 4

| | Inhibition rate (%) | |
|---|---|---|
| Example | b-Raf | KDR |
| 7 | 40 | 0 |
| 8-1 | 6.5 | 0 |
| 8-2 | 21 | 0 |
| 13-1 | 33 | 7.5 |
| 14-5 | 13 | 0 |
| 14-6 | 45 | 1.7 |
| 15-4 | 0 | 0 |
| 15-6 | 37 | 0 |
| 15-52 | 20 | 0 |
| 15-55 | 30 | 0 |
| 15-58 | 30 | 0 |
| 15-63 | 43 | 0 |
| 15-71 | 40 | 0 |
| 15-77 | 32 | 0 |

TABLE 4-continued

| Example | Inhibition rate (%) b-Raf | KDR |
|---|---|---|
| 15-87 | 34 | 0 |
| 15-96 | 22 | 2 |
| 15-98 | 23 | 8 |
| 15-104 | 53 | 18 |
| 15-105 | 26 | 0 |
| 21-1 | 36 | 1.5 |
| 21-2 | 30 | 1 |
| 21-37 | 50 | 16 |
| 21-51 | 49 | 9 |
| 21-65 | 58 | 19 |
| 21-67 | 19 | 0 |
| 21-70 | 19 | 0 |
| 21-73 | 21 | 0 |
| 21-75 | 41 | 0 |
| 22-34 | 56 | 19 |

From this result, it is demonstrated that the present compounds show low inhibition of kinases other than TrkA, e.g., b-Raf and KDR, while exhibit strong inhibition of TrkA. In other words, the present compounds have TrkA inhibition as strong as $IC_{50}$ of 0.5 μM or less according to the result from Pharmacological Example 1, while the present compounds inhibit kinases other than TrkA only at 0% to about 58% even at the concentration of 3 μM according to the result from Pharmacological Example 2. Thus it is demonstrated that the present compounds have high selectivity towards TrkA inhibition and have excellent kinase selectivity.

Pharmacological Experiment Example 3

Inhibition of Rat NGF-Induced Vascular Hyper Permeability

TrkA-inhibiting activity of the present compound was evaluted in vivo. The present compound dissolved in a medium was orally administered (adminstered volume: 5 mL/kg) to male CD(SD)IGS rats (7- to 9-week old, Charles River laboratories Japan, Inc.) shaved on the back. A medium was orally administered (adminstered volume: 5 mL/kg) to the control and normal groups. After 6, 12 or 14 hours of administration, 3 μg/mL of a NGF (Mouse 2.5s, Natural, Invitrogen) solution prepared in 0.1% BSA (Sigma-Aldrich)-containing saline was intracutaneously administered (dose; 50 μL/site) at 3 sites on the back of animals under halothane anesthesia. For the normal group, 0.1% BSA-containing saline was intracutaneously administered (dose; 50 μL/site) at 3 sites on the back. Immediately after intracutaneous administration, 1% Evans Blue (Tokyo Chemical Industry Co., Ltd.) was administered intravenously from tail (adminstered volume: 3 mL/kg). After 10 minutes of administration, the animals were sacrificed by bleeding due to incision of the abdominal aorta. The sites of intracutaneous administration on the back (3 sites) were excised and the skin samples were respectively transferred to the wells in a 48-well plate (Asahi Glass Co., Ltd.). Formamide (0.8 mL/well) was added to the plate and the plate was sealed and incubated overnight at 60° C. The formamide extraction solution (200 μL) was transferred to a 96-well plate and the absorbance (wavelength: 620 nm) of Evans Blue extracted in formamide was measured on an absorbance microplate reader (SpectraMAX 190, Molecular Devices Japan, K.K.). Standard samples of Evans Blue dissolved in formamide (0, 0.78, 1.56, 3.13, 6.25, 12.5, 25 and 50 μg/mL) were measured at the same time for the absorbance (wavelength: 620 nm) to generate a calibration curve. Based on the calibration curve and the absorbances of samples, the concentrations of Evans Blue in the sample was calculated. The concentrations of Evans Blue for three skin samples collected from one aminal were averaged to obtain the vale for the animal. The rate of inhibition for rat NGF-induced vascular hyper permeability of the present compound was calculated according to the following Equation:

$$\text{Inhibition rate (\%)} = \{1 - (A_X - A_N)/(A_C - A_N)\} \times 100 \qquad [\text{Eq. 3}]$$

wherein $A_X$: the concentration of Evans Blue of the test compound (an average value of 3 samples from one animal);

$A_N$: the concentration of Evans Blue of the normal group (an average value of 3 samples from one animal);

$A_C$: the concentration of Evans Blue of the control group (an average value of 3 samples from one animal).

As a result, the present compound (3 mg/kg; 6 hours after administration) had the rate of inhibition for rat NGF-induced vascular hyper permeability of about 70%, and it was found that the present compounds strongly inhibited vascular hyper permeability even after a long period of time.

For example, some of the present compounds (1 mg/kg; 14 or 12 hours after administration) had inhibition rate of rat NGF-induced vascular hyper permeability as shown in the following Tables 5 and 6.

TABLE 5

| Example | Inhibition rate of vascular hyper permeability (%) (time after administration (h)) |
|---|---|
| 7 | 97% (14 h) |
| 8-1 | 94% (14 h) |
| 8-2 | 100% (14 h) |
| 8-4 | 96% (14 h) |
| 9-1 | 86% (14 h) |
| 9-2 | 100% (14 h) |
| 11 | 100% (14 h) |
| 13-1 | 100% (14 h) |
| 14-5 | 93% (14 h) |
| 14-6 | 78% (14 h) |
| 15-4 | 100% (14 h) |
| 15-5 | 92% (14 h) |
| 15-6 | 95% (14 h) |
| 15-52 | 96% (14 h) |
| 15-55 | 94% (14 h) |
| 15-58 | 100% (14 h) |
| 15-63 | 99% (14 h) |
| 15-71 | 100% (14 h) |
| 15-77 | 100% (14 h) |
| 15-87 | 86% (14 h) |
| 15-96 | 90% (14 h) |
| 15-98 | 80% (14 h) |
| 15-104 | 100% (14 h) |
| 15-105 | 100% (14 h) |

TABLE 6

| Example | Inhibition rate of vascular hyper permeability (%) (time after administration (h)) |
|---|---|
| 21-1 | 87% (14 h) |
| 21-2 | 100% (14 h) |
| 21-9 | 100% (14 h) |
| 21-13 | 100% (12 h) |
| 21-37 | 98% (14 h) |
| 21-51 | 95% (14 h) |
| 21-65 | 92% (14 h) |

TABLE 6-continued

| Example | Inhibition rate of vascular hyper permeability (%) (time after administration (h)) |
|---|---|
| 21-67 | 90% (14 h) |
| 21-70 | 100% (14 h) |
| 21-73 | 92% (14 h) |
| 21-75 | 100% (14 h) |
| 22-8 | 100% (14 h) |
| 22-9 | 100% (14 h) |
| 22-34 | 91% (14 h) |

Pharmacological Experiment Example 4

Analgesic Effect on Sodium Monoiodoacetate-Induced Model Rats

Using model rats induced with sodium monoiodoacetate (hereinafter abbreviated as MIA) (Sigma-Aldrich Japan), the present compounds were evaluated for the analgesic effect thereof.

(1) Generation of MIA-Induced Model Rats

Under isoflurane anaesthesia, rats were shaved on around knees of right hind limbs and 25 μL solution of 120 mg/mL MIA was administered into the right hind limb knee joint using a syringe (BD Lo-Dose, Beckton Dickinson Japan) with a 29 G needle. To a normal control group, 25 μL of saline was administered.

(2) Group Organisation and Grouping

The groups included were a normal control group, a disease control group, a test substance group and a tramadol or morphine group. Other than the normal control group, rats were grouped so that the right hind limb weight load ratio (the measurement of the ratio is described hereinbelow) of model rats 14 days after induction with MIA generated according to the method as described in the above (1) was equivalent between all groups.

(3) Administration of Test Substances, Tramadol or Morphine

The present compounds which are the test substances were respectively dissolved in Wellsolve (Celeste Corporation) to prepare the solutions with concentrations of 0.1, 0.3 and 1 mg/mL. The prepared 0.1, 0.3 or 1 mg/mL solution was diluted 5-fold with distilled water to prepare 0.02, 0.06 or 0.2 mg/mL solution (final concentration of Wellsolve: 20%). The positive control drug, tramadol, was dissolved in saline to prepare a solution of 2 mg/mL. Alternatively the positive control drug, morphine, was dissolved in saline to prepare a solution of 0.6 mg/mL. From day 14 to day 23 after induction with MIA, a test substance solution (0.1, 0.3 or 1 mg/kg) was orally administered to the test substance group twice a day over 10 days. On day 24 after induction with MIA, the test substance solution was further orally administered 3 hours before the measurement of the right hind limb weight load ratio and saline was subcutaneously administered 1 hour before the measurement. The tramadol group or the morphine group orally received 20% Wellsolve twice a day over 10 days from day 14 to day 23 after induction with MIA. On day 24 after induction with MIA, 20% Wellsolve was further orally administered 3 hours before the measurement of the right hind limb weight load ratio and a tramadol solution (10 mg/kg) or a morphine solution (3 mg/kg) was subcutaneously administered 1 hour before the measurement. The normal control group and the disease control group received 20% Wellsolve twice a day over 10 days from day 14 to day 23 after induction with MIA. On day 24 after induction with MIA, 20% Wellsolve was further orally administered 3 hours before the measurement of the right hind limb weight load ratio and saline was subcutaneously administered 1 hour before the measurement.

(4) Measurement of Right Hind Limb Weight Load Ratio

The weight load on right and left hind limbs was measured with the Linton Incapacitance Tester (MJS Technology INC., UK). Namely, a rat was transferred into a cage of the Linton Incapacitance Tester and adjusted so that right and left hind limbs were respectively on each of a pair of gravimetric sensors. After confirming that the rat was balanced on left and right and forward and back, the weight load of left and right hind limbs was respectively measured for 3 seconds. The measurement was repeated 3 times per rat. In order to obtain stable results, rats were conditioned in the cage for 20 minutes or longer per day over 5 or more days between the day of induction with MIA and day 14 after induction. Further, rats were also conditioned in the cage immediately before the measurement for about 10 minutes. The weight load of right and left hind limbs was measured before grouping on day 14 after induction with MIA and day 24 after induction for the normal control group, the disease control group, the test substance group (3 hours after administration), the tramadol group (1 hour after administration) and the morphine group (1 hour after administration). Based on the averages of right and left hind limb weight loads, the right hind limb weight load ratio with respect to the weight load of both hind limbs was calculated according to the following Equation 4. The measurement was carried out in a blind manner. The percent improvement for the present compounds which are the test substances was calculated based on the right hind limb weight load ratio of each group at day 24 after induction with MIA according to the following Equation 5, thereby evaluating analgesic effect of the test substances (present compounds).

$$\text{Right hind limb weight load ratio } B(\%) = \{A_R/(A_R + A_L) \times 100\} \quad \text{[Eq. 4]}$$

wherein:

$A_R$: weight load of right hind limb (average of three measurements per rat); and $A_L$: weight load of left hind limb (average of three measurements per rat).

$$\text{Percent improvement of test substance } (\%) = \{1-(B_T-B_C)/(B_N-B_C)\} \times 100 \quad \text{[Eq. 5]}$$

wherein:

$B_C$: average of the normal control group;

$B_N$: average of the disease control group; and $B_T$: average of the test substance group.

As a result, the present compounds had percent improvement that was equivalent to or higher than that of tramadol and morphine which are commonly used as analgesic agents. Accordingly, it was found that the present compounds had analgesic effect that was equivalent or superior to tramadol and morphine.

Examples of the analgesic effect (percent improvement) of some of the present compounds on MIA-induced model rats are shown in the following Table 7 (the results obtained with the positive control drug of tramadol) and Table 8 (the results obtained with the positive control drug of morphine).

TABLE 7

| Example | Percent improvement (%) |
|---|---|
| 7 | 61 |
| 8-1 | 60 |
| 14-5 | 47 |

TABLE 7-continued

| | Percent improvement (%) |
|---|---|
| 15-6 | 51 |
| 21-9 | 64 |
| 21-13 | 66 |
| Positive control drug | |
| Tramadol | 43 |

TABLE 8

| | Percent improvement (%) |
|---|---|
| Example | |
| 14-6 | 53 |
| 15-52 | 60 |
| 15-55 | 62 |
| 15-63 | 53 |
| 15-77 | 55 |
| 15-87 | 57 |
| 15-98 | 57 |
| 15-104 | 54 |
| 21-37 | 67 |
| 21-51 | 68 |
| 21-70 | 61 |
| 21-73 | 62 |
| Positive control drug | |
| Morphine | 54 |

FORMULATION EXAMPLES

Formulation Example 1

The following components were mixed and compressed to tablets according to a conventional method to give 10,000 tablets containing 10 mg of the active ingredient per tablet.

| | |
|---|---|
| 1-(2-(4-(2-amino-5-chloropyridin-3-yl)phenoxy)pyrimidin-5-yl)-3-(2-(4-methyl-1H-1,2,3-triazol-1-yl)-5-(trifluoromethyl)phenyl)urea | 100 g |
| Calcium carboxymethylcellulose (disintegrating agent) | 20 g |
| Magnesium stearate (lubricant) | 10 g |
| Microcrystalline cellulose | 870 g |

Formulation Example 2

The following components were mixed according to a conventional method, filtered through a dust filter, distributed to ampoules at 5 ml and thermally sterilized in an autoclave to obtain 10,000 ampoules containing 20 mg of the active ingredient per ampoule.

| | |
|---|---|
| 1-(2-(4-(2-amino-5-chloropyridin-3-yl)phenoxy)pyrimidin-5-yl)-3-(2-(4-methyl-1H-1,2,3-triazol-1-yl)-5-(trifluoromethyl)phenyl)urea | 200 g |
| Mannitol | 20 g |
| Distilled water | 50 L |

INDUSTRIAL APPLICABILITY

The present compound has Trk-inhibiting activity and thus is useful for prophylaxis and/or therapy of diseases to which Trk is involved, for example, pain, pruritus, lower urinary tract dysfunction, asthma, allergic rhinitis, inflammatory bowel disease and Chagas disease.

The invention claimed is:

1. A method for treating a cancer, comprising administering, to a patient, an effective amount of 1-{2-[4-(2-amino-5-chloro-3-pyridinyl)phenoxy]-5-pyrimidinyl}-3-[2-(methylsulfonyl)-5-(trifluoromethyl)phenyl]urea or a salt thereof; and wherein the cancer is a cancer expressing a Trk receptor.

2. The method according to claim 1, wherein the cancer is neuroblastoma, prostate cancer or pancreatic cancer.

* * * * *